(12) United States Patent
Jakob et al.

(10) Patent No.: US 12,358,907 B2
(45) Date of Patent: Jul. 15, 2025

(54) SUBSTITUTED PYRROLIDINE AMIDES III

(71) Applicant: GRÜNENTHAL GMBH, Aachen (DE)

(72) Inventors: Florian Jakob, Aachen (DE); Jo Alen, Averbode (BE); Sebastian Krüger, Aachen (DE); Daniela Friebe, Düsseldorf (DE); Stephanie Hennen, Aachen (DE); Philipp Barbie, Berlin (DE)

(73) Assignee: GRÜNENTHAL GMBH, Aachen (DE)

( * ) Notice: Subject to any disclaimer, the term of this patent is extended or adjusted under 35 U.S.C. 154(b) by 909 days.

(21) Appl. No.: 17/422,257

(22) PCT Filed: Jan. 13, 2020

(86) PCT No.: PCT/EP2020/050626
§ 371 (c)(1),
(2) Date: Jul. 12, 2021

(87) PCT Pub. No.: WO2020/144375
PCT Pub. Date: Jul. 16, 2020

(65) Prior Publication Data
US 2022/0089573 A1 Mar. 24, 2022

(30) Foreign Application Priority Data

Jan. 11, 2019 (EP) .................................... 19151406
Jan. 17, 2019 (EP) .................................... 19152282
Jun. 19, 2019 (EP) .................................... 19181203

(51) Int. Cl.
| | |
|---|---|
| *C07D 417/14* | (2006.01) |
| *C07D 401/14* | (2006.01) |
| *C07D 403/10* | (2006.01) |
| *C07D 403/12* | (2006.01) |
| *C07D 403/14* | (2006.01) |
| *C07D 409/14* | (2006.01) |
| *C07D 413/14* | (2006.01) |
| *C07D 471/04* | (2006.01) |

(52) U.S. Cl.
CPC ......... *C07D 417/14* (2013.01); *C07D 401/14* (2013.01); *C07D 403/10* (2013.01); *C07D 403/12* (2013.01); *C07D 403/14* (2013.01); *C07D 409/14* (2013.01); *C07D 413/14* (2013.01); *C07D 471/04* (2013.01)

(58) Field of Classification Search
CPC .. C07D 417/14; C07D 401/14; C07D 403/10; C07D 403/12; C07D 403/14; C07D 409/14; C07D 413/14; C07D 471/04; A61P 29/00; A61P 25/00
See application file for complete search history.

(56) References Cited

U.S. PATENT DOCUMENTS

| | | |
|---|---|---|
| 7,666,879 B2 | 2/2010 | Barda et al. |
| 8,420,694 B2 | 4/2013 | Hasuoka |
| 9,302,988 B2 | 4/2016 | Schunk et al. |
| 9,951,086 B2 | 4/2018 | Bothe et al. |
| 10,189,796 B2 | 1/2019 | Kawashima et al. |
| 10,435,379 B2 | 10/2019 | Kawashima et al. |
| 10,626,106 B2 | 4/2020 | Jakob et al. |
| 10,793,556 B2 | 10/2020 | Kuehnert et al. |
| 10,807,988 B2 | 10/2020 | Kuehnert et al. |
| 10,829,480 B2 | 11/2020 | Kuehnert et al. |
| 2006/0069269 A1 | 3/2006 | Amrein et al. |
| 2007/0265326 A1 | 11/2007 | Biggadike et al. |
| 2008/0249091 A1 | 10/2008 | Peleman et al. |
| 2009/0124607 A1 | 5/2009 | Bladh et al. |
| 2009/0170898 A1 | 7/2009 | Bengtsson et al. |
| 2010/0076026 A1 | 3/2010 | Benson et al. |
| 2011/0003797 A1 | 1/2011 | Dankulich et al. |
| 2017/0349607 A1 | 12/2017 | Seitzberg et al. |

(Continued)

FOREIGN PATENT DOCUMENTS

| | | |
|---|---|---|
| CN | 104755459 A | 7/2015 |
| JP | 2009-512687 A | 3/2009 |

(Continued)

OTHER PUBLICATIONS

Christopher M. Yates et al., Structure Guided Design of 5-Arylindazole Glucocorticoid Receptor Agonists and Antagonists, Journal of Medicinal Chemistry, 2010, 53(11), pp. 4531-4544, DOI: 10. 1021/jm100447c.

(Continued)

*Primary Examiner* — Joseph K McKane
*Assistant Examiner* — Quincy McKoy
(74) *Attorney, Agent, or Firm* — Norris Mclaughlin, P.A.

(57) ABSTRACT

The invention relates to compounds according to general formula (I),

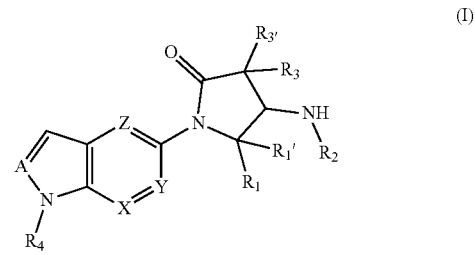

which act as modulators of the glucocorticoid receptor and can be used in the treatment and/or prophylaxis of disorders which are at least partially mediated by the glucocorticoid receptor.

18 Claims, No Drawings

(56) References Cited

U.S. PATENT DOCUMENTS

| | | | |
|---|---|---|---|
| 2018/0244633 A1 | 8/2018 | Kawashima et al. | |
| 2019/0106393 A1 | 4/2019 | Kawashima et al. | |
| 2019/0185455 A1 | 6/2019 | Jakob et al. | |
| 2019/0185470 A1 | 6/2019 | Jakob et al. | |
| 2019/0359577 A1 | 11/2019 | Kawashima et al. | |
| 2020/0223840 A1* | 7/2020 | Jakob | C07D 403/04 |
| 2022/0127264 A1* | 4/2022 | Jakob | A61P 19/02 |

FOREIGN PATENT DOCUMENTS

| | | |
|---|---|---|
| WO | 2006/091671 A1 | 8/2006 |
| WO | 2006/108699 A1 | 10/2006 |
| WO | 2007/114763 A1 | 10/2007 |
| WO | 2007/122165 A1 | 11/2007 |
| WO | 2008/043789 A1 | 4/2008 |
| WO | 2008/063116 A1 | 5/2008 |
| WO | 2008/076048 A1 | 6/2008 |
| WO | 2009/020234 A2 | 2/2009 |
| WO | 2009/035067 A1 | 3/2009 |
| WO | 2009/142569 A1 | 11/2009 |
| WO | 2009/142571 A1 | 11/2009 |
| WO | 2015/091426 A1 | 6/2015 |
| WO | 2015/099196 A1 | 7/2015 |
| WO | 2016/046260 A1 | 3/2016 |
| WO | 2017/034006 A1 | 3/2017 |
| WO | 2017/121647 A1 | 7/2017 |
| WO | 2017/121648 A1 | 7/2017 |
| WO | 2017/121650 A1 | 7/2017 |
| WO | 2019/121606 A1 | 6/2019 |
| WO | 2019/121611 A1 | 6/2019 |

OTHER PUBLICATIONS

Keller, P. A. (2008). Pyridines and their Benzo Derivatives: Synthesis. Comprehensive Heterocyclic Chemistry III, 217-308. Recuperado de doi: 10.1016/b978-008044992-0.00605-2.
Perrino, M. et al. (2010). A novel route to substituted poly (vinyl pyrrolidone) s via simple functionalization of 1-vinyl-2-pyrrolidone in the 3-position by ring-opening reactions. European polymer journal, 46(7), 1557-1562.
Antilla, Jon C. et al., "Copper-Diamine-Catalyzed N-Arylation of Pyrroles, Pyrazoles, Indazoles, Imidazoles, and Triazoles"; J. Org. Chem. 2004, 69, pp. 5578-5587.
Badet, B. et al., "Basic Elimination of Sulfonum Salts, Neighbouring Group Influence on Regioselectivity"; Tetrahedron Letters, vol. 24, No. 30, pp. 4331-4334 1983.
Bianchi, Luca, et al., "Acquivion PFSA as a Novel Solid and Reusable Acid Catalyst in the Synthesis of 2-Pyrrolidin-2-ones in Flow"; ACS Sustainable Chem. Eng. 2015, 3, pp. 1873-1880.
Buttgereit, F. et al., "Novel glucocorticoids: where are we now and where do we want to go?", Clin Exp Rheumatol 2015, 33 (Suppl. 92): S-29-S33.
Buttgereit, Frank, et al., "Polymyalgia Rheumatica and Giant Cell Arteritis A Systematic Review", JAMA 2016; 315 (22): pp. 2442-2458.
De Bosscher, Karolien et al., "Activation of the Glucocorticoid Receptor in Acute Inflammation: the SEDIGRAM Concept"; Trends in Pharmacological Sciences, Jan. 2016, vol. 37, No. 1.
Du, Yao, et al., "Asymmetric Reductive Mannich Reaction to Ketimines Catalyzed by a Cu(I) Complex"; J. Am. Chem. Soc. 2008, 130, pp. 16146-16147.
Fischer, Carolin et al., "Palladium- and copper-mediated N-aryl bond formation reactions for the synthesis of biological active compounds"; Beilstein J. Org. Chem. 2011, 7, pp. 59-74.
Greene, Theodora W., et al., "Protection for the Amino Group", Protective Groups in Organic Synthesis, Third Edition, 1999; pp. 494-653.
Greene, et al. "Protection for Amides", Protective Groups in Organic Synthesis, 2007, 4th Edition, 99. 905-906.

Hapgood, Janet P. et al., "Glucocorticoid-independent modulation of GR activity: Implications for immunotherapy"; Pharmacology & Therapeutics 165 (2016) pp. 93-113.
Hartmann, Kerstin et al., "Molecular actions of glucocorticoids in cartilage and bone during health, disease, and steroid therapy"; Physiol Rev. 96: pp. 409-447, 2016.
Klapars, Artis et al., "A General and Efficient Copper Catalyst for the Amidation of Aryl Halides and the N-Arylation of Nitrogen Heterocycles"; J. Am. Chem. Soc. 2001, 123, pp. 7727-7729.
Liu, Dora, et al., "A practical guide to the monitoring and management of the complications of systemic corticosteroid therapy"; Allergy, Asthma & Clinical Immunology 2013, 9:30.
Ma, Bin, et al., "A modified Curtius reaction: an efficient and simple method for direct isolation of free amine"; Tetrahedron Letters 51 (2010) pp. 385-386.
Maldaner, Adriano O. et al., "Stereoselective Alkylation of N-Boc-2-Pyrrolidinones and N-Boc-2-Piperidinones. Synthesis and Characterization of Disubstituted Lactams"; Tetrahedron 55 (1999) pp. 13321-13332.
March CHP. 16—Acyl Substitution Reactions Advanced Organic Chemistry, 2006, 6th Edition, p. 1427-1474.
March, et al. "Reductions", Advanced Organic Chemistry, 2006, Chapter 19, pp. 1811-1869.
Pelletier, Sophie M. C., et al., "Nitro-Mannich/Lactamization Cascades for the Direct Stereoselective Synthesis of Pyrrolidin-2-ones"; Organic Letters 2009, vol. 11, No. 20, pp. 4512-4515.
Pelletier, Sophie M. C., et al., "Diastereoselective Synthesis of 1,3,5-Trisubstituted 4-Notropyrrolidin-2-ones via a Nitro-Mannich/Lactamization Cascade"; Organic Letters 2011, vol. 13, No. 24, pp. 6406-6409.
Qiao, Jennifer X. et al., "Copper-Promoted Carbon-Heteroatom Bond Cross-Coupling with Boronic Acids and Derivatives", Synthesis 2011, No. 6, pp. 0829-0856.
Ruiz-Castillo, Paula, et al., "Applications of Palladium-Catalyzd C-N Cross-Coupling Reactions"; Chem. Rev. 2016, 116, pp. 12564-12649.
Sambiago, Carol, et al., "Copper catalysed Ullmann type chemistry: from mechanistic aspects to modern development"; Chem. Soc. Rev. 2014, 43; pp. 3525-3550.
Senra, Jaqueline D., et al., "Recent Progress in Transition-Metal-Catalyzed C—N Cross-Couplings: Emerging Approaches Towards Sustainability"; Current Organic Synthesis, 2011, 8, pp. 53-78.
Smiley, R. A. , et al., "The Preparation of 2,2-Dialkyl-3-nitropropionic Acids"; Journal of Chemical and Engineering Data, vol. 11, No. 4, Oct. 1966.
Surry, David S. , et al., "Diamine ligands in copper-catalyzed reactions"; Chem. Sci. 2010, 1, pp. 13-31.
Surry, David S., et al., "Dialkylbiaryl phosphines in Pd-catalyzed amination: a user's guide"; Chem. Sci., 2011, 2, pp. 27-50.
Wei, Jingqiang et al., "Diastereoselective Synthesis of y-Lactams by a One-Pot, Four-Component Reaction"; Organic Letters, 2007, vol. 9, No. 20, pp. 4077-4080.
Liu, Yu-Xiu, et al., "Studies on the Synthesis and Bioactivities of 4-Amino Derivatives of Tetramic Acid"; J. Heterocyclic Chem. 51, pp. E25-E33, 2014.
March, et al. "E. Hydrogen on Both Sides", Chapter 15, Reactions in Which Hydrogen Adds to One Side, pp. 1053-1247 (2006).
Bisol, Tula B., et al., "Nucleophilic Ring-Openng of Epoxide and Aziriding Acetates for the Stereodivergent Synthesis of β-hydroxy and β-Hydroxy and β-Amino y-Lactams"; J. Org. Chem., 2011, 76, pp. 948-962.
Pohmakotr, Manat, et al., "Highly Diastereoselective Synthesis of B-Carboxy-y-lactams and Their Ethyl Esters via Sc(OTf)3-Catalyzed Imino Mukaiyama-Aldol Type Reaction of 2,5-Bis(trimethylsilyloxy)furan with Imines"; J. Org. Chem. 2007, 72, pp. 5016-5019.
Biggs-Houck, James E., et al., "Carbon-Carbon Bond-Forming Reactions of α-Thioaryl Carbonyl Compounds for the Synthesis of Complex Heterocyclic Molecules"; J. Org. Chem. 2012, 77, pp. 160-172.

* cited by examiner

SUBSTITUTED PYRROLIDINE AMIDES III

This application is a 371 of PCT/EP2020/050626, filed Jan. 13, 2020, which claims foreign priority benefit under 35 U.S.C. § 119 of European Patent Application No. 19181203.1, filed Jun. 19, 2019; European Patent Application No. 19152282.0, filed Jan. 17, 2019; and European Patent Application No. 19151406.6, filed Jan. 11, 2019, the disclosures of which are incorporated herein by reference.

The invention relates to compounds according to general formula (I)

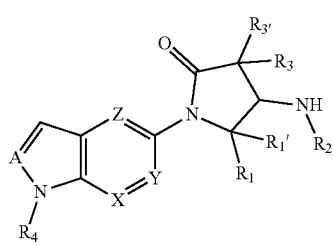

which act as modulators of the glucocorticoid receptor and can be used in the treatment and/or prophylaxis of disorders which are at least partially mediated by the glucocorticoid receptor.

Glucocorticoids (GC) exert strong anti-inflammatory, immunosuppressive and disease-modifying therapeutic effects mediated by the glucocorticoid receptor (GR). They have been widely used to treat inflammatory and immune diseases for decades and still represent the most effective therapy in those conditions. However, chronic GC treatment of inflammatory diseases such as asthma, rheumatoid arthritis, inflammatory bowel disease, chronic obstructive pulmonary disease, acute respiratory distress syndrome, cystic fibrosis, osteoarthritis, polymyalgia rheumatica and giant cell arteritis is hampered by GC-associated adverse effects. These undesired side effects include insulin resistance, diabetes, hypertension, glaucoma, depression, osteoporosis, adrenal suppression and muscle wasting with osteoporosis and diabetes being the most severe ones from the physician's point of view (Hapgood J P. et al., Pharmacol Ther. 2016 September; 165: 93-113; Buttgereit F. el al, Clin Exp Rheumatol. 2015 July-August; 33(4 Suppl 92):S29-33; Hartmann K. et al, Physiol Rev. 2016 April; 96(2):409-47).

One example of an oral glucocorticoid is prednisone which is frequently prescribed for the treatment of several inflammatory disorders (De Bosscher K et al., Trends Pharmacol Sci. 2016 January; 37(1):4-16; Buttgereit F. et al., *JAMA*. 2016; 315(22):2442-2458). As GC cause adrenal suppression, prednisolone withdrawal symptoms can be severe if the drug is discontinued abruptly when all the signs of the disease have disappeared. Thus gradual GC tapering to physiological doses is frequently part of treatment protocols to reduce the risk of relapse and other withdrawal symptoms (Liu D. et al., Allergy Asthma Clin Immunol. 2013 Aug. 15; 9(1):30). Therefore, there is high medical need for novel potent anti-inflammatory drugs with less adverse effects.

Recent research has focused on the development of partial agonists or selective glucocorticoid receptor modulators which activate the pathways for the inhibition of inflammation but avoid targeting the pathways that lead to the GC-associated adverse effects. Most of these effects have been demonstrated to be mediated by different GR-dependent genomic mechanisms termed transactivation and transrepression. The anti-inflammatory actions of GC are mainly attributable to the transrepression of inflammatory genes while certain side effects are predominantly mediated via transactivation of several genes. According to the nature of a ligand the GR can be selectively modulated in a specific conformation which favors transrepression over transactivation resulting in an improved therapeutic benefit (De Bosscher K et al., Trends Pharmacol Sci. 2016 January; 37(1):4-16). The concept of such dissociating ligands was already defined about two decades ago and several compounds have been identified and were evaluated in preclinical and clinical testing but none of them has as yet been approved for clinical use.

Compounds which are active as modulators of the glucocorticoid receptor are also known e.g. from WO 2007/122165, WO 2008/076048 and WO 2008/043789, WO 2009/035067, WO 2009/142571, WO 2016/046260, and WO 2017/034006.

It was an object of the invention to provide novel compounds which are modulators of the glucocorticoid receptor and which preferably have advantages over the compounds of the prior art. The novel compounds should in particular be suitable for use in the treatment and/or prophylaxis of disorders or diseases which are at least partially mediated by the glucocorticoid receptor.

This object has been achieved by the subject-matter of the patent claims.

It was surprisingly found that the compounds according to the invention are highly potent modulators of the glucocorticoid receptor.

The invention relates to a compound according to general formula (I),

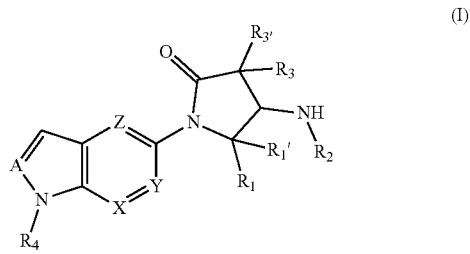

wherein
$R_1$ represents phenyl; —$C_{1-6}$-alkylene-phenyl; 5 or 6-membered heteroaryl; —$C_{1-6}$-alkylene-(5 or 6-membered heteroaryl); or —$C_{1-10}$-alkyl;
$R_{1'}$ represents H; —$C_{1-10}$-alkyl; or —$C_{3-10}$-cycloalkyl;
$R_2$ represents —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-(3 to 7 membered heterocycloalkyl); —C(=O)—$C_{1-6}$-alkylene-(3 to 7 membered heterocycloalkyl); —C(=O)-phenyl; —C(=O)—$C_{1-6}$-alkylene-phenyl; —C(=O)-(5 or 6-membered heteroaryl); —C(=O)—$C_{1-6}$-alkylene-(5 or 6-membered heteroaryl); —S(=O)$_{1-2}$—$C_{1-10}$-alkyl; —S(=O)$_{1-2}$—$C_{3-10}$-cycloalkyl; —S(=O)$_{1-2}$—$C_{1-6}$-alkylene-$C_{3-10}$-cycloalkyl; —S(=O)$_{1-2}$-(3 to 7 membered heterocycloalkyl); —S(=O)$_{1-2}$—$C_{1-6}$-alkylene-(3 to 7 membered heterocycloalkyl); —S(=O)$_{1-2}$-phenyl; —S(=O)$_{1-2}$—$C_{1-6}$-alkylene-phenyl; —S(=O)$_{1-2}$-(5 or 6-membered heteroaryl); or —S(=O)$_{1-2}$—$C_{1-6}$-alkylene-(5 or 6-membered heteroaryl);

$R_3$ and $R_{3'}$ independently from one another represent H; F; Cl; —$C_{1-10}$-alkyl; —$C_{3-6}$-cycloalkyl; —$CH_2$—$C_{3-6}$-cycloalkyl; 3 to 7 membered heterocycloalkyl; —$CH_2$-(3 to 7 membered heterocycloalkyl); —$CH_2$-phenyl; or —$CH_2$-(5 or 6-membered heteroaryl); or $R_3$ and $R_{3'}$ together with the carbon atom to which they are bound form a $C_{3-10}$-cycloalkyl; or 3 to 7 membered heterocycloalkyl;

$R_4$ represents -phenyl; —$C_{1-6}$-alkylene-phenyl; -5 or 6-membered heteroaryl; or —$C_{1-6}$-alkylene-(5 or 6-membered heteroaryl);

A, X, Y and Z independently from one another represent N or CH;

wherein at least one of $R_1$, $R_3$ and $R_{3'}$ is not H;

wherein —$C_{1-10}$-alkyl and —$C_{1-6}$-alkylene- in each case independently from one another is linear or branched, saturated or unsaturated;

wherein —$C_{1-10}$-alkyl, —$C_{1-6}$-alkylene-, —$C_{3-10}$-cycloalkyl and 3 to 7 membered heterocycloalkyl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —C(=O)—$C_{1-6}$-alkyl; —C(=O)—OH; —C(=O)—O$C_{1-6}$-alkyl; —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—C(=O)—$C_{1-6}$-alkyl; —O—C(=O)—O—$C_{1-6}$-alkyl; —O—(CO)—NH($C_{1-6}$-alkyl); —O—C(=O)—N($C_{1-6}$-alkyl)$_2$; —O—S(=O)$_2$—$NH_2$; —O—S(=O)$_2$—NH($C_{1-6}$-alkyl); —O—S(=O)$_2$—N($C_{1-6}$-alkyl)$_2$; —$NH_2$; —NH($C_{1-6}$-alkyl); —N($C_{1-6}$-alkyl)$_2$; —NH—C(=O)—$C_{1-6}$-alkyl; —NH—C(=O)—O—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—$C_{1-6}$-alkyl; —N($C_{1-6}$-alkyl)-C(=O)—O—$C_{1-6}$-alkyl; —N($C_{1-6}$-alkyl)-C(=O)—$NH_2$; —N($C_{1-6}$-alkyl)-C(=O)—NH($C_{1-6}$-alkyl); —N($C_{1-6}$-alkyl)-C(=O)—N($C_{1-6}$-alkyl)$_2$; —NH—S(=O)$_2$OH; —NH—S(=O)$_2$—$C_{1-6}$-alkyl; —NH—S(=O)$_2$—O—$C_{1-6}$-alkyl; —NH—S(=O)$_2$—$NH_2$; —NH—S(=O)$_2$—NH($C_{1-6}$-alkyl); —NH—S(=O)$_2$N($C_{1-6}$-alkyl)$_2$; —N($C_{1-6}$-alkyl)-S(=O)$_2$—OH; —N($C_{1-6}$-alkyl)-S(=O)$_2$—$C_{1-6}$-alkyl; —N($C_{1-6}$-alkyl)-S(=O)$_2$—O—$C_{1-6}$-alkyl; —N($C_{1-6}$-alkyl)-S(=O)$_2$—$NH_2$; —N($C_{1-6}$-alkyl)-S(=O)$_2$—NH($C_{1-6}$-alkyl); —N($C_{1-6}$-alkyl)-S(=O)$_2$—N($C_{1-6}$-alkyl)$_2$; —$SCF_3$; —$SCF_2H$; —$SCFH_2$; —S—$C_{1-6}$-alkyl; —S(=O)—$C_{1-6}$-alkyl; —S(=O)$_2$—$C_{1-6}$-alkyl; —S(=O)$_2$—OH; —S(=O)$_2$—O—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; 3 to 6-membered heterocycloalkyl; phenyl; 5 or 6-membered heteroaryl; —O—$C_{3-6}$-cycloalkyl; —O-(3 to 6-membered heterocycloalkyl); —O-phenyl; —O-(5 or 6-membered heteroaryl); —C(=O)—$C_{3-6}$-cycloalkyl; —C(=O)-(3 to 6-membered heterocycloalkyl); —C(=O)-phenyl; —C(=O)-(5 or 6-membered heteroaryl); —S(=O)$_2$—($C_{3-6}$-cycloalkyl); —S(=O)$_2$-(3 to 6-membered heterocycloalkyl); —S(=O)$_2$-phenyl or —S(=O)$_2$-(5 or 6-membered heteroaryl);

wherein phenyl and 5 or 6-membered heteroaryl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —$C_{1-4}$-alkylene-$CF_3$; —$C_{1-4}$-alkylene-$CF_2H$; —$C_{1-4}$-alkylene-$CFH_2$; —C(=O)—$C_{1-6}$-alkyl; —C(=O)—OH; —C(=O)—O$C_{1-6}$-alkyl; —C(=O)—NH(OH); —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—$C_{3-6}$-cycloalkyl; —O-(3 to 6-membered heterocycloalkyl); —$NH_2$; —NH($C_{1-6}$-alkyl); —N($C_{1-6}$-alkyl)$_2$; —NH—C(=O)—$C_{1-6}$-alkyl; —N($C_{1-6}$-alkyl)-C(=O)—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—NH($C_{1-6}$-alkyl); —N($C_{1-6}$-alkyl)-C(=O)—N($C_{1-6}$-alkyl)$_2$; —NH—S(=O)$_2$—$C_{1-6}$-alkyl; —$SCF_3$; —S—$C_{1-6}$-alkyl; —S(=O)—$C_{1-6}$-alkyl; —S(=O)$_2$—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; —$C_{1-4}$-alkylene-$C_{3-6}$-cycloalkyl; 3 to 6-membered heterocycloalkyl; —$C_{1-4}$-alkylene-(3 to 6-membered heterocycloalkyl); phenyl or 5 or 6-membered heteroaryl;

in the form of the free compound or a physiologically acceptable salt thereof;

with the proviso that the following compounds are excluded:

N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-cyclopropanecarboxylic acid amide;

N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-cyclopropanecarboxylic acid amide;

N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-1-methyl-1H-pyrazole-3-carboxylic acid amide;

N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-[1,2,4]oxadiazole-3-carboxylic acid amide;

N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-4-methyl-thiazole-5-carboxylic acid amide;

N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-thiazole-4-carboxylic acid amide; and N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-thiazole-4-carboxylic acid amide.

In a preferred embodiment, the compound according to the invention is present in form of the free compound. For the purpose of specification, "free compound" preferably means that the compound according to the invention is not present in form of a salt. Methods to determine whether a chemical substance is present as the free compound or as a salt are known to the skilled artisan such as $^{14}$N or $^{15}$N solid state NMR, x-ray diffraction, x-ray powder diffraction, IR, Raman, XPS. $^1$H-NMR recorded in solution may also be used to consider the presence of protonation.

In another preferred embodiment, the compound according to the invention is present in form of a physiologically acceptable salt. For the purposes of this specification, the term "physiologically acceptable salt" preferably refers to a salt obtained from a compound according to the invention and a physiologically acceptable acid or base.

According to the invention, the compound according to the invention may be present in any possible form including solvates, cocrystals and polymorphs. For the purposes of this specification, the term "solvate" preferably refers to an adduct of (i) a compound according to the invention and/or a physiologically acceptable salt thereof with (ii) distinct molecular equivalents of one or more solvents.

Further, the compound according to the invention may be present in form of the racemate, enantiomers, diastereomers, tautomers or any mixtures thereof.

The invention also includes isotopic isomers of a compound of the invention, wherein at least one atom of the compound is replaced by an isotope of the respective atom which is different from the naturally predominantly occurring isotope, as well as any mixtures of isotopic isomers of such a compound. Preferred isotopes are $^2H$ (deuterium), $^3H$ (tritium), $^{13}C$ and $^{14}C$. Isotopic isomers of a compound of the invention can generally be prepared by conventional procedures known to a person skilled in the art.

According to the invention, the terms "—$C_{1-10}$-alkyl", "—$C_{1-8}$-alkyl", "—$C_{1-6}$-alkyl" and "—$C_{1-4}$-alkyl" preferably mean acyclic saturated or unsaturated aliphatic (i.e. non-aromatic) hydrocarbon residues, which can be linear (i.e. unbranched) or branched and which can be unsubstituted or mono- or polysubstituted (e.g. di- or trisubstituted), and which contain 1 to 10 (i.e. 1, 2, 3, 4, 5, 6, 7, 8, 9 or 10), 1 to 8 (i.e. 1, 2, 3, 4, 5, 6, 7 or 8), 1 to 6 (i.e. 1, 2, 3, 4, 5 or 6) and 1 to 4 (i.e. 1, 2, 3 or 4) carbon atoms, respectively. In a preferred embodiment, —$C_{1-10}$-alkyl, —$C_{1-6}$-alkyl and —$C_{1-4}$-alkyl are saturated.

Preferred —$C_{1-10}$-alkyl groups are selected from methyl, ethyl, ethenyl (vinyl), n-propyl, 2-propyl, 1-propynyl, 2-propynyl, propenyl (—$CH_2CH=CH_2$, —$CH=CH—CH_3$, —$C(=CH_2)—CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—$CH_2CH=CH_2$, —$CH=CH—CH_3$, —$C(=CH_2)—CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl, n-octyl, n-nonyl and n-decyl. Particularly preferred —$C_{1-10}$-alkyl groups are selected from $C_{1-4}$-alkyl groups.

Preferred —$C_{1-8}$-alkyl groups are selected from methyl, ethyl, ethenyl (vinyl), n-propyl, 2-propyl, 1-propynyl, 2-propynyl, propenyl (—$CH_2CH=CH_2$, —$CH=CH—CH_3$, —$C(=CH_2)—CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—$CH_2$—$CH=CH_2$, —$CH=CH$—$CH_3$, —$C(=CH_2)$—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl, n-heptyl and n-octyl. Particularly preferred —$C_{1-8}$-alkyl groups are selected from $C_{1-4}$-alkyl groups.

Preferred —$C_{1-6}$-alkyl groups are selected from methyl, ethyl, ethenyl (vinyl), n-propyl, 2-propyl, n-butyl, isobutyl, sec-butyl, tert-butyl, n-pentyl, 2-pentyl, 3-pentyl, 2-methylbutyl, 3-methylbutyl, 3-methylbut-2-yl, 2-methylbut-2-yl, 2,2-dimethylpropyl, n-hexyl, 2-hexyl, 3-hexyl, 2-methylpentyl, 4-methylpentyl, 4-methylpent-2-yl, 2-methylpent-2-yl, 3,3-dimethylbutyl, 3,3-dimethylbut-2-yl, 3-methylpentyl, 3-methylpent-2-yl and 3-methylpent-3-yl; more preferably methyl, ethyl, n-propyl, 2-propyl, 1-propynyl, 2-propynyl, propenyl (—$CH_2$—$CH=CH_2$, —$CH=CH$—$CH_3$, —$C(=CH_2)$—$CH_3$), n-butyl, 1-butynyl, 2-butynyl, 1-butenyl, 2-butenyl, isobutyl, sec-butyl, tert-butyl, n-pentyl, 2-pentyl, 3-pentyl, 1-pentenyl, 2-pentenyl, 1-pentynyl, 2-pentynyl, 2-methylbutyl, 3-methylbutyl, 3-methylbut-2-yl, 2-methylbut-2-yl, 3-methylbut-1-ynyl, 2,2-dimethylpropyl, n-hexyl. Particularly preferred —$C_{1-6}$-alkyl groups are selected from $C_{1-4}$-alkyl groups.

Preferred —$C_{1-4}$-alkyl groups are selected from methyl, ethyl, ethenyl (vinyl), n-propyl, 2-propyl, 1-propynyl, 2-propynyl, propenyl (—$CH_2CH=CH_2$, —$CH=CH—CH_3$, —$C(=CH_2)—CH_3$), n-butyl, 1-butynyl, 2-butynyl, 1-butenyl, 2-butenyl, isobutyl, sec-butyl, tert-butyl and 3-methylbut-1-ynyl. More preferred —$C_{1-4}$-alkyl groups are selected from methyl, ethyl, n-propyl, 2-propyl, n-butyl, isobutyl, sec-butyl, and tert-butyl.

Further according to the invention, the terms "—$C_{1-6}$-alkylene-"; "—$C_{1-4}$-alkylene-" and "—$C_{1-2}$-alkylene" relate to a linear or branched, preferably linear, and preferably saturated aliphatic residues which are preferably selected from the group consisting of methylene (—$CH_2$—), ethylene (—$CH_2CH_2$—), propylene (—$CH_2CH_2CH_2$— or $C(CH_3)_2$—), butylene (—$CH_2CH_2CH_2CH_2$—), pentylene (—$CH_2CH_2CH_2CH_2CH_2$—) and hexylene (—$CH_2CH_2CH_2CH_2CH_2CH_2$—); more preferably methylene (—$CH_2$—) and ethylene (—$CH_2CH_2$—) and most preferably methylene (—$CH_2$—). Preferably, —$C_{1-6}$-alkylene- is selected from —$C_{1-4}$-alkylene-, more preferably from —$C_{1-2}$-alkylene-.

Still further according to the invention, the terms "—$C_{3-10}$-cycloalkyl" and "—$C_{3-6}$-cycloalkyl" preferably mean cyclic aliphatic hydrocarbons containing 3, 4, 5, 6, 7, 8, 9 or 10 carbon atoms and 3, 4, 5 or 6 carbon atoms, respectively, wherein the hydrocarbons in each case can be saturated or unsaturated (but not aromatic), unsubstituted or mono- or polysubstituted.

Preferably, —$C_{3-10}$-cycloalkyl and —$C_{3-6}$-cycloalkyl are saturated. The —$C_{3-10}$-cycloalkyl and —$C_{3-6}$-cycloalkyl can be bound to the respective superordinate general structure via any desired and possible ring member of the cycloalkyl group. The —$C_{3-10}$-cycloalkyl and —$C_{3-6}$-cycloalkyl groups can also be condensed with further saturated, (partially) unsaturated, (hetero)cyclic, aromatic or heteroaromatic ring systems, i.e. with cycloalkyl, heterocyclyl, aryl or heteroaryl residues, which in each case can in turn be unsubstituted or mono- or polysubstituted. Further, —$C_{3-10}$-cycloalkyl and —$C_{3-6}$-cycloalkyl can be singly or multiply bridged such as, for example, in the case of adamantyl, bicyclo[2.2.1]heptyl or bicyclo[2.2.2]octyl. However, preferably, —$C_{3-10}$-cycloalkyl and —$C_{3-6}$-cycloalkyl are neither condensed with further ring systems nor bridged. More preferably, —$C_{3-10}$-cycloalkyl and —$C_{3-6}$-cycloalkyl are neither condensed with further ring systems nor bridged and are saturated. Preferred —$C_{3-10}$-cycloalkyl groups are selected from the group consisting of cyclopropyl, cyclobutyl, cyclopentyl, cyclohexyl, cyclopentenyl, cyclohexenyl, cycloheptyl, cyclooctyl, cyclononyl, cyclodecyl, adamantly, cycloheptenyl, cyclohexenyl, cycloheptenyl, cyclooctenyl, bicyclo[2.2.1]heptyl and bicyclo[2.2.2]octyl. Particularly preferred —$C_{3-10}$-cycloalkyl groups are selected from —$C_{3-6}$-cycloalkyl groups.

Preferred —$C_{3-6}$-cycloalkyl groups are selected from the group consisting of cyclopropyl, cyclobutyl, cyclopentyl, cyclohexyl, cyclopentenyl and cyclohexenyl. Particularly preferred —$C_{3-6}$-cycloalkyl groups are selected from the group consisting of cyclopropyl, cyclobutyl, cyclopentyl and cyclohexyl, most preferably cyclopropyl.

According to the invention, the terms "3 to 7-membered heterocycloalkyl" and "3 to 6-membered heterocycloalkyl" preferably mean heterocycloaliphatic saturated or unsaturated (but not aromatic) residues having 3 to 7, i.e. 3, 4, 5, 6 or 7 ring members and 3 to 6, i.e. 3, 4, 5 or 6 ring members, respectively, wherein in each case at least one, if appropriate also two or three carbon atoms are replaced by a heteroatom or a heteroatom group each selected independently of one another from the group consisting of O, S, S(=O), S(=O)$_2$, N, NH and N($C_{1-4}$-alkyl) such as N($CH_3$), wherein the carbon atoms of the ring can be unsubstituted or mono- or polysubstituted. Preferably, the 3 to 7-membered heterocycloalkyl and the 3 to 6-membered heterocycloalkyl contain only one heteroatom or heteroatom group within the ring.

Preferably, 3 to 7-membered heterocycloalkyl and 3 to 6-membered heterocycloalkyl are saturated. The 3 to 7-membered heterocycloalkyl and the 3 to 6-membered heterocycloalkyl groups can also be condensed with further saturated or (partially) unsaturated cycloalkyl or heterocyclyl, aromatic or heteroaromatic ring systems. However, more preferably, 3 to 7-membered heterocycloalkyl and 3 to 6-membered heterocycloalkyl are not condensed with further ring systems. Still more preferably, 3 to 7-membered heterocycloalkyl and 3 to 6-membered heterocycloalkyl are not condensed with further ring systems and are saturated. The 3 to 7-membered heterocycloalkyl and the 3 to 6-membered heterocycloalkyl group can be bound to the superordinate general structure via any desired and possible ring member of the heterocycloaliphatic residue if not indicated otherwise. In a preferred embodiment, 3 to 7-membered heterocycloalkyl and 3 to 6-membered heterocycloalkyl are bound to the superordinate general structure via a carbon atom.

Preferred 3 to 7-membered heterocycloalkyl groups are selected from the group consisting of tetrahydrofuranyl, azepanyl, dioxepanyl, oxazepanyl, diazepanyl, thiazolidinyl, tetrahydrothiophenyl, tetrahydropyridinyl, thiomorpholinyl, tetrahydropyranyl, oxetanyl, oxiranyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl; tetrahydropyrrolyl, dihydroquinolinyl, dihydroisoquinolinyl, dihydroindolinyl, dihydroisoindolyl, tetrahydroquinolinyl, tetrahydroisoquinolinyl and tetrahydroindolinyl. Particularly preferred 3 to 7-membered heterocycloalkyl groups are selected from 3 to 6-membered heterocycloalkyl groups.

Preferred 3 to 6-membered heterocycloalkyl groups are selected from the group consisting of tetrahydrofuranyl, tetrahydropyranyl, oxetanyl, oxiranyl, thiazolidinyl, tetrahydrothiophenyl, tetra-hydropyridinyl, thiomorpholinyl, morpholinyl, pyrrolidinyl, 4-methylpiperazinyl, morpholinonyl, azetidinyl, aziridinyl, dithiolanyl, dihydropyrrolyl, dioxanyl, dioxolanyl, dihydropyridinyl, dihydrofuranyl, dihydroisoxazolyl, dihydrooxazolyl, imidazolidinyl, isoxazolidinyl, oxazolidinyl, piperazinyl, piperidinyl, pyrazolidinyl, pyranyl, tetrahydropyrrolyl, dihydroindolinyl, dihydroisoindolyl and tetrahydroindolinyl. More preferred 3 to 6-membered heterocycloalkyl groups are selected from the group consisting of tetrahydrofuranyl, tetrahydropyranyl, oxetanyl, and oxiranyl; still more preferably tetrahydrofuranyl.

According to the invention, the term "5- to 6-membered heteroaryl" preferably means a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted, if not indicated otherwise. In the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. Preferably, the 5- to 6-membered heteroaryl is bound to the suprordinate general structure via a carbon atom of the heterocycle. The heteroaryl can also be part of a bi- or polycyclic system having up to 14 ring members, wherein the ring system can be formed with further saturated or (partially) unsaturated cycloalkyl or heterocycloalkyl, aromatic or heteroaromatic ring systems, which can in turn be unsubstituted or mono- or polysubstituted, if not indicated otherwise. In a preferred embodiment, the 5- to 6-membered heteroaryl is part of a bi- or polycyclic, preferably bicyclic, system. In another preferred embodiment, the 5- to 6-membered heteroaryl is not part of a bi- or polycyclic system.

Preferably, the 5- to 6-membered heteroaryl is selected from the group consisting of pyridyl (i.e. 2-pyridyl, 3-pyridyl, 4-pyridyl), thiazolyl, oxazolyl, isoxazolyl, pyrazolyl, oxadiazolyl, pyridone (pyridinone), pyrimidinyl, pyridazinyl, pyrazinyl, pyrrolyl, imidazolyl, isothiazolyl, furanyl, thienyl (thiophenyl), triazolyl, thiadiazolyl, 4,5,6,7-tetrahydro-2H-indazolyl, 2,4,5,6-tetrahydrocyclo-penta[c]pyrazolyl, benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, imidazothiazolyl, indazolyl, indolizinyl, indolyl, isoquinolinyl, naphthyridinyl, oxazolyl, phenazinyl, phenothiazinyl, phthalazinyl, purinyl, phenazinyl, tetrazolyl and triazinyl. Particularly preferred 5- to 6-membered heteroaryl are selected from the group consisting of pyridyl (i.e. 2-pyridyl, 3-pyridyl, 4-pyridyl), thiazolyl, oxazolyl, isoxazolyl, pyrazolyl, and oxadiazolyl. As pyridones can be regarded as pyridines that are substituted with =O, for the purpose of the specification the definition of pyridines that may optionally be substituted with =O covers pyridones.

The compounds according to the invention are defined by substituents, for example by $R_1$, $R_2$ and $R_3$ ($1^{st}$ generation substituents) which may optionally be for their part themselves be substituted ($2^{nd}$ generation substituents). Depending on the definition, these substituents of the substituents can optionally be for their part resubstituted ($3^{rd}$ generation substituents). If, for example, $R_1$=phenyl ($1^{st}$ generation substituent), then the phenyl can for its part be substituted, for example with —$C_{1-6}$-alkyl ($2^{nd}$ generation substituent). This produces the functional group $R_1$=phenyl-$C_{1-6}$-alkyl. The —$C_{1-6}$-alkyl can then for its part be resubstituted, for example with —F ($3^{rd}$ generation substituent). Overall, this produces the functional group $R_1$=phenyl-$C_{1-6}$-alkyl, wherein the —$C_{1-6}$-alkyl is substituted with —F.

However, in a preferred embodiment, the 3$^{rd}$ generation substituents may not be resubstituted, i.e. there are then no 4$^{th}$ generation substituents. More preferably, the 2$^{nd}$ generation substituents may not be resubstituted, i.e. there are no 3$^{rd}$ generation substituents.

If a residue occurs multiply within a molecule, then this residue can have respectively different meanings for various substituents: if, for example, both R$_3$ and R$_3'$ denote —C$_{1-10}$-alkyl, then —C$_{1-10}$-alkyl can e.g. represent ethyl for R$_3$ and can represent methyl for R$_{3'}$.

In connection with the terms "—C$_{1-10}$-alkyl", "—C$_{1-6}$-alkyl", "—C$_{1-4}$-alkyl", "—C$_{3-10}$-cycloalkyl", "—C$_{3-6}$-cycloalkyl", "3 to 7 membered heterocycloalkyl", "3 to 6-membered heterocycloalkyl", "—C$_{1-6}$-alkylene-", "—C$_{1-4}$-alkylene-" and "—C$_{1-2}$-alkylene-", the term "substituted" refers in the sense of the invention, with respect to the corresponding residues or groups, to the single substitution (monosubstitution) or multiple substitution (polysubstitution), e.g. disubstitution or trisubstitution; more preferably to monosubstitution or disubstitution; of one or more hydrogen atoms each independently of one another by at least one substituent. In case of a multiple substitution, i.e. in case of polysubstituted residues, such as di- or trisubstituted residues, these residues may be polysubstituted either on different or on the same atoms, for example trisubstituted on the same carbon atom, as in the case of —CF$_3$, —CH$_2$CF$_3$ or disubstituted as in the case of 1,1-difluorocyclohexyl, or at various points, as in the case of —CH(OH)—CH=CH—CHCl$_2$ or 1-chloro-3-fluorocyclohexyl. The multiple substitution can be carried out using the same or using different substituents.

In relation to the terms "phenyl", "heteroaryl" and "5- to 6-membered heteroaryl", the term "substituted" refers in the sense of this invention to the single substitution (monosubstitution) or multiple substitution (polysubstitution), e.g. disubstitution or trisubstitution, of one or more hydrogen atoms each independently of one another by at least one substituent. The multiple substitution can be carried out using the same or using different substituents.

According to the invention, preferably —C$_{1-10}$-alkyl-, —C$_{1-6}$-alkyl, —C$_{1-4}$-alkyl, —C$_{3-10}$-cycloalkyl, —C$_{3-6}$-cycloalkyl, 3 to 7 membered heterocycloalkyl, 3 to 6-membered heterocycloalkyl, —C$_{1-6}$-alkylene-, —C$_{1-4}$-alkylene- and —C$_{1-2}$-alkylene- in each case independently from one another are unsubstituted or mono- or polysubstituted with one or more substituents selected from —F; —Cl; —Br; —I; —CN; —C$_{1-6}$-alkyl; —CF$_3$; —CF$_2$H; —CFH$_2$; —CF$_2$Cl; —CFCl$_2$; —C(=O)—C$_{1-6}$-alkyl; —C(=O)—OH; —C(=O)—OC$_{1-6}$-alkyl; —C(=O)—NH$_2$; —C(=O)—NH(C$_{1-6}$-alkyl); —C(=O)—N(C$_{1-6}$-alkyl)$_2$; —OH; =O; —OCF$_3$; —OCF$_2$H; —OCFH$_2$; —OCF$_2$Cl; —OCFCl$_2$; —O—C$_{1-6}$-alkyl; —O—C(=O)—C$_{1-6}$-alkyl; —O—C(=O)—O—C$_{1-6}$-alkyl; —O—(CO)—NH(C$_{1-6}$-alkyl); —O—C(=O)—N(C$_{1-6}$-alkyl)$_2$; —O—S(=O)$_2$—NH$_2$; —O—S(=O)$_2$—NH(C$_{1-6}$-alkyl); —O—S(=O)$_2$—N(C$_{1-6}$-alkyl)$_2$; —NH$_2$; —NH(C$_{1-6}$-alkyl); —N(C$_{1-6}$-alkyl)$_2$; —NH—C(=O)—C$_{1-6}$-alkyl; —NH—C(=O)—O—C$_{1-6}$-alkyl; —NH—C(=O)—NH$_2$; —NH—C(=O)—NH(C$_{1-6}$-alkyl); —NH—C(=O)—N(C$_{1-6}$-alkyl)$_2$; —N(C$_{1-6}$-alkyl)-C(=O)—C$_{1-6}$-alkyl; —N(C$_{1-6}$-alkyl)-C(=O)—O—C$_{1-6}$-alkyl; —N(C$_{1-6}$-alkyl)-C(=O)—NH$_2$; —N(C$_{1-6}$-alkyl)-C(=O)—NH(C$_{1-6}$-alkyl); —N(C$_{1-6}$-alkyl)-C(=O)—N(C$_{1-6}$-alkyl)$_2$; —NH—S(=O)$_2$OH; —NH—S(=O)$_2$—C$_{1-6}$-alkyl; —NH—S(=O)$_2$—O—C$_{1-6}$-alkyl; —NH—S(=O)$_2$—NH$_2$; —NH—S(=O)$_2$—NH(C$_{1-6}$-alkyl); —NH—S(=O)$_2$N(C$_{1-6}$-alkyl)$_2$; —N(C$_{1-6}$-alkyl)-S(=O)$_2$—OH; —N(C$_{1-6}$-alkyl)-S(=O)$_2$—C$_{1-6}$-alkyl; —N(C$_{1-6}$-alkyl)-S(=O)$_2$—O—C$_{1-6}$-alkyl; —N(C$_{1-6}$-alkyl)-S(=O)$_2$—NH$_2$; —N(C$_{1-6}$-alkyl)-S(=O)$_2$—NH(C$_{1-6}$-alkyl); —N(C$_{1-6}$-alkyl)-S(=O)$_2$—N(C$_{1-6}$-alkyl)$_2$; —SCF$_3$; —SCF$_2$H; —SCFH$_2$; —S—C$_{1-6}$-alkyl; —S(=O)—C$_{1-6}$-alkyl; —S(=O)$_2$—C$_{1-6}$-alkyl; —S(=O)$_2$—OH; —S(=O)$_2$—O—C$_{1-6}$-alkyl; —S(=O)$_2$—NH$_2$; —S(=O)$_2$—NH(C$_{1-6}$-alkyl); —S(=O)$_2$—N(C$_{1-6}$-alkyl)$_2$; —C$_{3-6}$-cycloalkyl; 3 to 6-membered heterocycloalkyl; phenyl; 5 or 6-membered heteroaryl; —O—C$_{3-6}$-cycloalkyl; —O-(3 to 6-membered heterocycloalkyl); —O-phenyl; —O-(5 or 6-membered heteroaryl); —C(=O)—C$_{3-6}$-cycloalkyl; C(=O)-(3 to 6-membered heterocycloalkyl); —C(=O)-phenyl; —C(=O)-(5 or 6-membered heteroaryl); —S(=O)$_2$—(C$_{3-6}$-cycloalkyl); —S(=O)$_2$-(3 to 6-membered heterocycloalkyl); —S(=O)$_2$-phenyl and —S(=O)$_2$-(5 or 6-membered heteroaryl).

Preferred substituents of —C$_{1-10}$-alkyl, —C$_{1-6}$-alkyl, —C$_{3-10}$-cycloalkyl, —C$_{3-6}$-cycloalkyl, 3 to 7 membered heterocycloalkyl, 3 to 6-membered heterocycloalkyl, —C$_{1-6}$-alkylene- and —C$_{1-4}$-alkylene- are selected from the group consisting of —F; —Cl; —Br; —I; —CN; —C$_{1-6}$-alkyl; —CF$_3$; —CF$_2$H; —CFH$_2$; —C(=O)—NH$_2$; —C(=O)—NH(C$_{1-6}$-alkyl); —C(=O)—N(C$_{1-6}$-alkyl)$_2$; —OH; —OCF$_3$; —OCF$_2$H; —OCFH$_2$; —O—C$_{1-6}$-alkyl; —NH$_2$; —NH(C$_{1-6}$-alkyl); —N(C$_{1-6}$-alkyl)$_2$; —SCF$_3$; —SCF$_2$H; —SCFH$_2$; —S—C$_{1-6}$-alkyl; —S(=O)—C$_{1-6}$-alkyl; —S(=O)$_2$—C$_{1-6}$-alkyl; —C$_{3-6}$-cycloalkyl; 3 to 6-membered heterocycloalkyl; phenyl and 5 or 6-membered heteroaryl; and particularly preferably —F, —CN, —CH$_3$, —CH$_2$CH$_3$, —CF$_3$; —CF$_2$H; —CFH$_2$; —C(=O)—NH$_2$; —C(=O)—NH(CH$_3$); —C(=O)—N(CH$_3$)$_2$; —OH, —NH$_2$, —OCH$_3$, —SCH$_3$, —S(=O)$_2$(CH$_3$), —S(=O)(CH$_3$), —N(CH$_3$)$_2$, cyclopropyl and oxetanyl. According to this embodiment, —C$_{1-10}$-alkyl, —C$_{1-6}$-alkyl, —C$_{1-4}$-alkyl, —C$_{3-10}$-cycloalkyl, —C$_{3-6}$-cycloalkyl, 3 to 7 membered heterocycloalkyl, 3 to 6-membered heterocycloalkyl are preferably each independently from one another unsubstituted, mono- di- or trisubstituted, more preferably unsubstituted or monosubstituted or disubstituted with a substituent selected from the group consisting of —F; —Cl; —Br; —I; —CN; —C$_{1-6}$-alkyl; —CF$_3$; —CF$_2$H; —CFH$_2$; —C(=O)—NH$_2$; —C(=O)—NH(C$_{1-6}$-alkyl); —C(=O)—N(C$_{1-6}$-alkyl)$_2$; —OH; —OCF$_3$; —OCF$_2$H; —OCFH$_2$; —O—C$_{1-6}$-alkyl; —NH$_2$; —NH(C$_{1-6}$-alkyl); —N(C$_{1-6}$-alkyl)$_2$; —SCF$_3$; —SCF$_2$H; —SCFH$_2$; —S—C$_{1-6}$-alkyl; —S(=O)—C$_{1-6}$-alkyl; —S(=O)$_2$—C$_{1-6}$-alkyl; —C$_{3-6}$-cycloalkyl; 3 to 6-membered heterocycloalkyl; phenyl and 5 or 6-membered heteroaryl; more preferably —F; —Cl; —Br; —CN; —C$_{1-6}$-alkyl; —CF$_3$; —CF$_2$H; —CFH$_2$; —OH; —OCF$_3$; —OCF$_2$H; and —OCFH$_2$; and particularly preferably —F; —Cl; —Br. Preferably, —C$_{1-6}$-alkylene- groups and —C$_{1-4}$-alkylene- groups are unsubstituted.

According to the invention, preferably phenyl and 5 or 6-membered heteroaryl in each case independently from one another are unsubstituted or mono- or polysubstituted; preferably unsubstituted, mono- di- or trisubstituted, still more preferably unsubstituted or monosubstituted or disubstituted; with one or more substituents selected from —F; —Cl; —Br; —I; —CN; —CF$_3$; —CF$_2$H; —CFH$_2$; —CF$_2$Cl; —CFCl$_2$; —C$_{1-4}$-alkylene-CF$_3$; C$_{1-4}$-alkylene-CF$_2$H; —C$_{1-4}$-alkylene-CFH$_2$; —C(=O)—C$_{1-6}$-alkyl; —C(=O)—OH; —C(=O)—OC$_{1-6}$-alkyl; —C(=O)—NH(OH); —C(=O)—NH$_2$; —C(=O)—NH(C$_{1-6}$-alkyl); —C(=O)—N(C$_{1-6}$-alkyl)$_2$; =O; —OH; —OCF$_3$; —OCF$_2$H; —OCFH$_2$; —OCF$_2$Cl; —OCFCl$_2$; —O—C$_{1-6}$-alkyl; —O—C$_{3-6}$-cycloalkyl; —O-(3 to 6-membered heterocycloalkyl); —NH$_2$; —NH(C$_{1-6}$-alkyl); —N(C$_{1-6}$-alkyl)$_2$; —NH—C(=O)—C$_{1-6}$-alkyl; —N(C$_{1-6}$-alkyl)-C(=O)—C$_{1-6}$-alkyl; —NH—C(=O)—NH$_2$; —NH—C(=O)—NH(C$_{1-6}$-alkyl); —NH—C(=O)—N(C$_{1-6}$-alkyl)$_2$; —N(C$_{1-6}$-alkyl)-C(=O)—NH(C$_{1-6}$-alkyl); —N(C$_{1-6}$-alkyl)-C(=O)—N(C$_{1-6}$-alkyl)$_2$; —NH—S(=O)$_2$—C$_{1-6}$-alkyl; —SCF$_3$; —S(=O)—C$_{1-6}$-alkyl; —S(=O)$_2$—C$_{1-6}$-alkyl; —S(=O)$_2$—NH$_2$; —S(=O)$_2$—NH(C$_{1-6}$-alkyl); —S(=O)$_2$—N(C$_{1-6}$-alkyl)$_2$; —C$_{3-6}$-cycloalkyl; —C$_{1-4}$-alkylene-C$_{3-6}$-cycloalkyl; 3 to 6-membered heterocycloalkyl; —C$_{1-4}$-alkylene-(3 to 6-membered heterocycloalkyl); phenyl or 5 or 6-membered heteroaryl.

Preferred substituents of phenyl and 5 or 6-membered heteroaryl are selected from the group consisting of —F; —Cl; —Br; —I; —CN; —CF$_3$; —CF$_2$H; —CFH$_2$; —C$_{1-4}$-alkylene-CF$_3$; —C$_{1-4}$-alkylene-—CF$_2$H; —C$_{1-4}$-alkylene-CFH$_2$; —OH; —OCF$_3$; —OCF$_2$H; —OCFH$_2$; —O—C$_{1-6}$-alkyl; —O—C$_{3-6}$-cycloalkyl and —C$_{3-6}$-cycloalkyl; and more preferably of —F; —Cl; —Br; —CN; —CH$_3$; —CH$_2$CH$_3$; —CF$_3$; —CF$_2$H; —CFH$_2$; —CH$_2$—CF$_3$; =O; —OH; —OCF$_3$; —OCF$_2$H; —OCFH$_2$; —O—CH$_3$; —O-cyclopropyl and cyclopropyl; still more preferably —F; —Cl; —Br; —CH$_3$; —CH$_2$CH$_3$; —CF$_3$; —CF$_2$H; —CFH$_2$; =O; —OH; —OCF$_3$; and —O—CH$_3$; and particularly preferably preferably —F; —Cl; —Br; —CH$_3$; =O; and —O—CH$_3$. According to this embodiment, phenyl and 5 or 6-membered heteroaryl are preferably each independently from one another unsubstituted, mono- di- or trisubstituted, more preferably unsubstituted or monosubstituted or disubstituted with a substituent selected from the group consisting of —F; —Cl; —Br; —I; —CN; —CF$_3$; —CF$_2$H; —CFH$_2$; —C$_{1-4}$-alkylene-CF$_3$; —C$_{1-4}$-alkylene-CF$_2$H; —C$_{1-4}$-alkylene-CFH$_2$; =O; —OH; —OCF$_3$; —OCF$_2$H; —OCFH$_2$; —O—C$_{1-6}$-alkyl; —O—C$_{3-6}$-cycloalkyl and —C$_{3-6}$-cycloalkyl. A particularly preferred substituted 5 or 6-membered heteroaryl is N-methyl-2-oxo-pyridyl.

In a preferred embodiment, the compound according to the invention has a stereochemistry according to general formula (II), (III), (IV), (V), (VI), (VII), (VIII), or (IX)

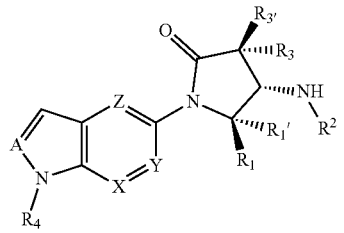

(II)

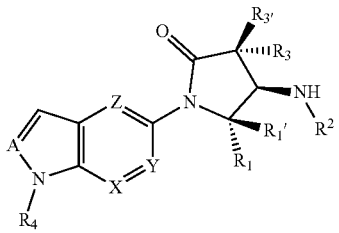

(III)

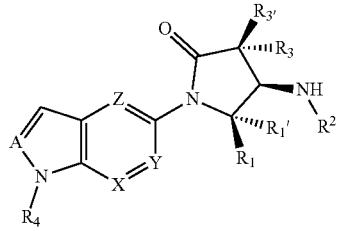

(IV)

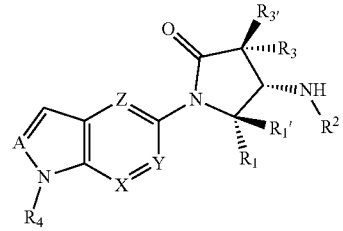

(V)

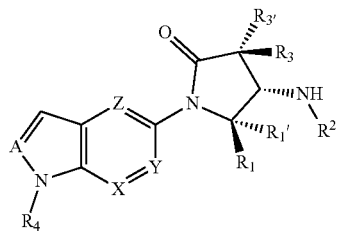

(VI)

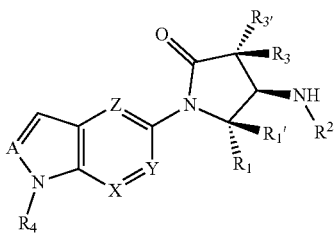

(VII)

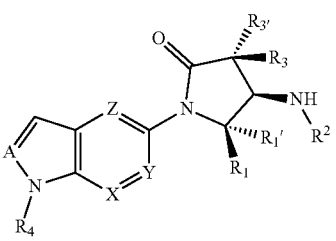

(VIII)

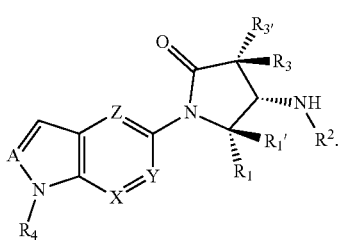

(IX)

In a preferred embodiment, the compound according to the invention has a stereochemistry according to general formula (II), (III), (VI) or (VII), such that the residues —R$_1$ and —NH—R$_2$ on the pyrrolidone ring are oriented trans. Preferably, the compound according to the invention has a stereochemistry according to general formula (II) or (VI). Preferably, the compound according to the invention has a stereochemistry according to general formula (III) or (VII). The stereochemistry according to general formula (II) or (VI) is particularly preferred.

In another preferred embodiment, the compound according to the invention has a stereochemistry according to general formula (IV), (V), (VIII) or (IX), such that the residues —$R_1$ and —NH—$R_2$ on the pyrrolidone ring are oriented cis. Preferably, the compound according to the invention has a stereochemistry according to general formula (IV) or (VIII). Preferably, the compound according to the invention has a stereochemistry according to general formula (V) or (IX).

In a particularly preferred embodiment, the compound according to the invention has a stereochemistry according to general formula (II) or (VI), more preferably (II).

In the compound of the invention according to any of general formulas (I), (II), (III), (IV), (V), (VI), (VII), (VIII), or (IX) $R_1$ represents phenyl; —$C_{1-6}$-alkylene-phenyl; 5 or 6-membered heteroaryl; —$C_{1-6}$-alkylene-(5 or 6-membered heteroaryl); or —$C_{1-10}$-alkyl.

In a preferred embodiment, $R_1$ represents phenyl or ethyl; more preferably phenyl.

In a particularly preferred embodiment, $R_1$ represents phenyl, unsubstituted or mono- or disubstituted with substituents independently of one another selected from the group consisting of —F, —Cl, —Br, —$OCH_3$; —$CH_3$, —$CF_3$, —CN, and cyclopropyl; more preferably —F, —$OCH_3$; and —$CH_3$.

In the compound of the invention according to any of general formulas (I), (II), (III), (IV), (V), (VI), (VII), (VIII), or (IX) $R_{1'}$ represents H; —$C_{1-10}$-alkyl; or —$C_{3-10}$-cycloalkyl.

In a preferred embodiment, $R_{1'}$ represents H; methyl, ethyl, n-propyl, cyclopropyl, cyclobutyl, cyclopentyl or cyclohexyl; more preferably H, methyl, ethyl, cyclopropyl or cyclobutyl; still more preferably H, methyl or cyclopropyl.

In a particularly preferred embodiment, $R_{1'}$ represents H.

In the compound of the invention according to any of general formulas (I), (II), (III), (IV), (V), (VI), (VII), (VIII), or (IX) $R_2$ represents —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-(3 to 7 membered heterocycloalkyl); —C(=O)—$C_{1-6}$-alkylene-(3 to 7 membered heterocycloalkyl); —C(=O)-phenyl; —C(=O)—$C_{1-6}$-alkylene-phenyl; —C(=O)-(5 or 6-membered heteroaryl); —C(=O)—$C_{1-6}$-alkylene-(5 or 6-membered heteroaryl); —S(=O)$_{1-2}$—$C_{1-10}$-alkyl; —S(=O)$_{1-2}$—$C_{3-10}$-cycloalkyl; —S(=O)$_{1-2}$—$C_{1-6}$-alkylene-$C_{3-10}$-cycloalkyl; —S(=O)$_{1-2}$-(3 to 7 membered heterocycloalkyl); —S(=O)$_{1-2}$—$C_{1-6}$-alkylene-(3 to 7 membered heterocycloalkyl); —S(=O)$_{1-2}$-phenyl; —S(=O)$_{1-2}$—$C_{1-6}$-alkylene-phenyl; —S(=O)$_{1-2}$-(5 or 6-membered heteroaryl); or —S(=O)$_{1-2}$—$C_{1-6}$-alkylene-(5 or 6-membered heteroaryl).

In a preferred embodiment, $R_2$ represents —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-(3 to 7 membered heterocycloalkyl); —C(=O)-(5 or 6-membered heteroaryl); —S(=O)$_2$—$C_{1-10}$-alkyl; —S(=O)$_2$—$C_{3-10}$-cycloalkyl; —S(=O)$_2$—$C_{1-6}$-alkylene-$C_{3-10}$-cycloalkyl; —S(=O)$_2$-(3 to 7 membered heterocycloalkyl); or —S(=O)$_2$-(5 or 6-membered heteroaryl).

In particularly preferred embodiments, $R_2$ represents
(i) —C(=O)—$C_{1-10}$-alkyl, unsubstituted or mono- or disubstituted with substituents independently of one another selected from the group consisting of —F, —Cl, and —Br;

(ii) —C(=O)-cyclopropyl, unsubstituted or mono- or disubstituted with substituents independently of one another selected from the group consisting of —F, —Cl, —Br, —$CH_3$, —$CF_3$, —CN, and —$OCH_3$;
(iii) —C(=O)-2-tetrahydrofuranyl, unsubstituted;
(iv) —C(=O)-(5- to 6-membered heteroaryl), wherein said 5- to 6-membered heteroaryl is selected from the group consisting of thiazolyl, pyrazolyl, oxazolyl, isoxazolyl, 1-oxa-2,4-diazolyl, 1,2,5-oxadiazolyl, and isothiazolyl, wherein in each case said 5- to 6-membered heteroaryl is unsubstituted or mono- or disubstituted with substituents independently of one another selected from the group consisting of —F, —Cl, —Br, —$CH_3$, —$CF_3$, —CN, =O, and —$OCH_3$;
(v) —S(=O)$_2$—$C_{1-10}$-alkyl, unsubstituted;
(vi) —S(=O)$_2$-cyclopropyl, unsubstituted;
(vii) —S(=O)$_2$—$CH_2$-cyclopropyl, unsubstituted;
(viii) —S(=O)$_2$-2-tetrahydrofuranyl; or
(ix) —S(=O)$_2$-(5- to 6-membered heteroaryl), wherein said 5- to 6-membered heteroaryl is selected from the group consisting of thiazolyl, pyrazolyl, oxazolyl, isoxazolyl, 1-oxa-2,4-diazolyl, 1,2,5-oxadiazolyl, and isothiazolyl, wherein in each case said 5- to 6-membered heteroaryl is unsubstituted or mono- or disubstituted with substituents independently of one another selected from the group consisting of —F, —Cl, —Br, —$CH_3$, —$CF_3$, —CN, =O, and —$OCH_3$.

In the compound of the invention according to any of general formulas (I), (II), (III), (IV), (V), (VI), (VII), (VIII), or (IX) $R_3$ and $R_{3'}$ independently from one another represent H; F; Cl; —$C_{1-10}$-alkyl; —$C_{3-6}$-cycloalkyl; —$CH_2$—$C_{3-6}$-cycloalkyl; 3 to 7 membered heterocycloalkyl; —$CH_2$-(3 to 7 membered heterocycloalkyl); —$CH_2$-phenyl; or —$CH_2$-(5 or 6-membered heteroaryl); or $R_3$ and $R_{3'}$ together with the carbon atom to which they are bound form a $C_{3-10}$-cycloalkyl, or 3 to 7 membered heterocycloalkyl.

In a preferred embodiment, $R_3$ and $R_{3'}$ both represent —$C_{1-10}$-alkyl. In a particularly preferred embodiment, $R_3$ and $R_{3'}$ both represent —$CH_3$.

In another preferred embodiment, $R_3$ and $R_{3'}$ independently from one another represent H; F; —$CH_3$; cyclopropyl; —$CH_2$-cyclopropyl; or —$CH_2$-phenyl. In still another preferred embodiment, $R_3$ and $R_{3'}$ both represent F.

In another preferred embodiment, at least one of $R_3$ and $R_{3'}$ represents not H. In yet another preferred embodiment, one of $R_3$ and $R_{3'}$ represents H.

In still another preferred embodiment, $R_3$ and $R_{3'}$ together with the carbon atom to which they are bound form cyclopropyl.

In the compound of the invention according to any of general formulas (I), (II), (III), (IV), (V), (VI), (VII), (VIII), or (IX) $R_4$ represents phenyl; —$C_{1-6}$-alkylene-phenyl; 5 or 6-membered heteroaryl; or —$C_{1-6}$-alkylene-(5 or 6-membered heteroaryl).

In a preferred embodiment, $R_4$ represents phenyl or 5 or 6-membered heteroaryl.

In particularly preferred embodiments, $R_4$ represents
phenyl, unsubstituted or mono- or disubstituted with substituents independently of one another selected from the group consisting of —F, —Cl, —Br, —$CH_3$, —$CF_3$, —CN, and —$OCH_3$; or
5 or 6-membered heteroaryl selected from the group consisting of pyridyl, pyrazolyl, and pyrimidinyl, wherein in each case said 5- to 6-membered heteroaryl is unsubstituted or mono- or disubstituted with substituents independently of one another selected from the group consisting of =O, —F, —Cl, —Br, —CH$_3$, —CF$_3$, —CN, and —OCH$_3$.

In a particularly preferred embodiment, R$_4$ does not represent N-methylpyridinone.

In the compound of the invention according to any of general formulas (I), (II), (III), (IV), (V), (VI), (VII), (VIII), or (IX) A, X, Y and Z independently from one another represent N or CH. In a preferred embodiment, A represents N.

In a preferred embodiment, X represents CH.
In a preferred embodiment, Y represents CH.
In a preferred embodiment, Z represents CH.
In a preferred embodiment of the invention,
(i) A represents N, X represents CH, Y represents CH; and Z represents CH; or
(ii) A represents N, X represents N, Y represents CH; and Z represents CH; or
(iii) A represents N, X represents CH, Y represents N; and Z represents CH; or
(iv) A represents N, X represents CH, Y represents CH; and Z represents N; or
(v) A represents N, X represents N, Y represents N; and Z represents CH; or
(vi) A represents N, X represents N, Y represents CH; and Z represents N; or
(vii) A represents N, X represents CH, Y represents N; and Z represents N; or
(viii) A represents N, X represents N, Y represents N; and Z represents N; or
(ix) A represents CH, X represents CH, Y represents CH; and Z represents CH; or
(x) A represents CH, X represents N, Y represents CH; and Z represents CH; or
(xi) A represents CH, X represents CH, Y represents N; and Z represents CH; or
(xii) A represents CH, X represents CH, Y represents CH; and Z represents N; or
(xiii) A represents CH, X represents N, Y represents N; and Z represents CH; or
(xiv) A represents CH, X represents N, Y represents CH; and Z represents N; or
(xv) A represents CH, X represents CH, Y represents N; and Z represents N; or
(xvi) A represents CH, X represents N, Y represents N; and Z represents N.

In a particularly preferred embodiment of the invention according to any of general formulas (I), (II), (III), (IV), (V), (VI), (VII), (VIII), or (IX)

R$_1$ represents phenyl, unsubstituted or mono- or disubstituted with substituents independently of one another selected from the group consisting of —F, —Cl, —Br, —CH$_3$, and —OCH$_3$; and/or R$_1$' represents H, CH$_3$, or cyclopropyl and/or R$_2$ represents —C(=O)—C$_{1-6}$-alkyl; —C(=O)-cyclopropyl; or or —C(=O)-(5- to 6-membered heteroaryl) unsusbtituted or mono- or disubstituted with substituents independently of one another selected from the group consisting of —F, —Cl, —Br; and —CH$_3$; and/or R$_4$ represents fluoro-phenyl or N-methyl-2-oxo-pyridyl.

In a preferred embodiment, the compound according to the invention is selected from the group consisting of 1  N-[(2R,3S)-1-[1-(4-Fluorophenyl)-1H-indazol-5-yl]-4,4-dimethyl-5-oxo-2-phenyl-pyrrolidin-3-yl]-cyclopropanecarboxylic acid amide 2  N-[(2S,3R)-1-[1-(4-Fluorophenyl)-1H-indazol-5-yl]-4,4-dimethyl-5-oxo-2-phenyl-pyrrolidin-3-yl]-cyclopropanecarboxylic acid amide 3  N-[rac-(6R,7S)-5-[1-(4-Fluorophenyl)-1H-indazol-5-yl]-4-oxo-6-phenyl-5-azaspiro[2.4]heptan-7-yl]-cyclopropanecarboxylic acid amide 4  2,2-Difluoro-N-[(2S,3R)-1-[1-(4-fluorophenyl)-1H-indazol-5-yl]-4,4-dimethyl-5-oxo-2-phenyl-pyrrolidin-3-yl]-propionamide 5  N-[rac-(6R,7S)-5-[1-(4-Fluorophenyl)-1H-indol-5-yl]-4-oxo-6-phenyl-5-azaspiro[2.4]heptan-7-yl]-cyclopropanecarboxylic acid amide 6  N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-thiazole-2-carboxylic acid amide 7  N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-isoxazole-3-carboxylic acid amide 8  N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-2,2-difluoro-propionamide 9  N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-2,2-difluoro-propionamide 10  2,2-Difluoro-N-[(2R,3S)-1-[1-(4-fluorophenyl)-1H-indazol-5-yl]-4,4-dimethyl-5-oxo-2-phenyl-pyrrolidin-3-yl]-propionamide 12  N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-1-methyl-1H-pyrazole-3-carboxylic acid amide 13  N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-oxazole-5-carboxylic acid amide 14  N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-[1,2,4]oxadiazole-3-carboxylic acid amide 15  N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-thiazole-5-carboxylic acid amide 16  N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-4-methyl-thiazole-5-carboxylic acid amide 17  N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-thiazole-4-carboxylic acid amide 18  N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-thiazole-4-carboxylic acid amide 21  N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-oxazole-5-carboxylic acid amide 22  N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-isoxazole-3-carboxylic acid amide 24  N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-thiazole-5-carboxylic acid amide 26  N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-thiazole-2-carboxylic acid amide 30  N-[rac-(6R,7S)-5-[1-(1-Methyl-6-oxo-1H-pyridin-3-yl)-1H-indazol-5-yl]-4-oxo-6-phenyl-5-azaspiro[2.4]heptan-7-yl]-cyclopropanecarboxylic acid amide 31  N-[rac-(6R,7S)-5-[1-(4-Fluorophenyl)-1H-pyrazolo[3,4-b]pyridin-5-yl]-4-oxo-6-phenyl-5-azaspiro[2.4]heptan-7-yl]-cyclopropanecarboxylic acid amide 32 N-[rac-(6R,7S)-5-[1-(4-Fluorophenyl)-1H-pyrazolo[3,4-c]pyridin-5-yl]-4-oxo-6-phenyl-5-azaspiro[2.4]heptan-7-yl]-cyclopropanecarboxylic acid amide 33 N-[rac-(6R,7S)-5-[1-(4-Fluorophenyl)-1H-pyrazolo[4,3-b]pyridin-5-yl]-4-oxo-6-phenyl-5-azaspiro[2.4]heptan-7-yl]-cyclopropanecarboxylic acid amide 34a N-((2R,3S)-1-(1-(4-fluorophenyl)-1H-indazol-5-yl)-4,4-dimethyl-5-oxo-2-phenylpyrrolidin-3-yl)methanesulfonamide 34b N-((2S,3R)-1-(1-(4-fluorophenyl)-1H-indazol-5-yl)-4,4-dimethyl-5-oxo-2-phenylpyrrolidin-3-yl)methanesulfonamide 35a N-((2R,3S)-1-(1-(4-fluorophenyl)-1H-indazol-5-yl)-4,4-dimethyl-5-oxo-2-phenylpyrrolidin-3-yl)cyclopropanesulfonamide 35b N-((2S,3R)-1-(1-(4-fluorophenyl)-1H-indazol-5-yl)-4,4-dimethyl-5-oxo-2-phenylpyrrolidin-3-yl)cyclopropanesulfonamide 36a N-((2R,3S)-1-(1-(4-fluorophenyl)-1H-indazol-5-yl)-4,4-dimethyl-5-oxo-2-phenylpyrrolidin-3-yl)oxazole-5-carboxamide 36b N-((2S,3R)-1-(1-(4-fluorophenyl)-1H-indazol-5-yl)-4,4-dimethyl-5-oxo-2-phenylpyrrolidin-3-yl)oxazole-5-carboxamide 37 N-((2R,3S)-1-(1-(4-fluorophenyl)-1H-indazol-5-yl)-4,4-dimethyl-5-oxo-2-phenylpyrrolidin-3-yl)-1-methyl-1H-pyrazole-3-carboxamide 38a N-((2S,3R)-1-(1-(4-fluorophenyl)-1H-indazol-5-yl)-4,4-dimethyl-5-oxo-2-phenylpyrrolidin-3-yl)-4-methylthiazole-5-carboxamide 38b N-((2R,3S)-1-(1-(4-fluorophenyl)-1H-indazol-5-yl)-4,4-dimethyl-5-oxo-2-phenylpyrrolidin-3-yl)-4-methylthiazole-5-carboxamide 39a N-((2R,3S)-1-(1-(4-fluorophenyl)-1H-indazol-5-yl)-4,4-dimethyl-5-oxo-2-phenylpyrrolidin-3-yl)-5-methylthiazole-4-carboxamide 39b N-((2S,3R)-1-(1-(4-fluorophenyl)-1H-indazol-5-yl)-4,4-dimethyl-5-oxo-2-phenylpyrrolidin-3-yl)-5-methylthiazole-4-carboxamide 40a N-((2R,3S)-1-(1-(4-fluorophenyl)-1H-indazol-5-yl)-4,4-dimethyl-5-oxo-2-phenylpyrrolidin-3-yl)-3-methylisoxazole-4-carboxamide 40b N-((2S,3R)-1-(1-(4-fluorophenyl)-1H-indazol-5-yl)-4,4-dimethyl-5-oxo-2-phenylpyrrolidin-3-yl)-3-methylisoxazole-4-carboxamide 41a N-((2R,3S)-1-(1-(4-fluorophenyl)-1H-indazol-5-yl)-4,4-dimethyl-5-oxo-2-phenylpyrrolidin-3-yl)-1-methyl-1H-pyrazole-4-carboxamide 41b N-((2S,3R)-1-(1-(4-fluorophenyl)-1H-indazol-5-yl)-4,4-dimethyl-5-oxo-2-phenylpyrrolidin-3-yl)-1-methyl-1H-pyrazole-4-carboxamide 42a N-((2R,3S)-1-(1-(4-fluorophenyl)-1H-indazol-5-yl)-4,4-dimethyl-5-oxo-2-phenylpyrrolidin-3-yl)nicotinamide 42b N-((2S,3R)-1-(1-(4-fluorophenyl)-1H-indazol-5-yl)-4,4-dimethyl-5-oxo-2-phenylpyrrolidin-3-yl)nicotinamide 43a N-((2R,3S)-1-(1-(4-fluorophenyl)-1H-indazol-5-yl)-4,4-dimethyl-5-oxo-2-phenylpyrrolidin-3-yl)pyrimidine-2-carboxamide 43b N-((2S,3R)-1-(1-(4-fluorophenyl)-1H-indazol-5-yl)-4,4-dimethyl-5-oxo-2-phenylpyrrolidin-3-yl)pyrimidine-2-carboxamide 44a N-((2R,3S)-1-(1-(4-fluorophenyl)-1H-indazol-5-yl)-4,4-dimethyl-5-oxo-2-phenylpyrrolidin-3-yl)-2-methyloxazole-5-carboxamide 44b N-((2S,3R)-1-(1-(4-fluorophenyl)-1H-indazol-5-yl)-4,4-dimethyl-5-oxo-2-phenylpyrrolidin-3-yl)-2-methyloxazole-5-carboxamide 45a N-((2R,3S)-1-(1-(4-fluorophenyl)-1H-indazol-5-yl)-4,4-dimethyl-5-oxo-2-phenylpyrrolidin-3-yl)-4-methyloxazole-5-carboxamide 45b N-((2S,3R)-1-(1-(4-fluorophenyl)-1H-indazol-5-yl)-4,4-dimethyl-5-oxo-2-phenylpyrrolidin-3-yl)-4-methyloxazole-5-carboxamide 46 N-[rac-(2R,3S,4S)-1-[1-(4-Fluorophenyl)-1H-indazol-5-yl]-4-methyl-5-oxo-2-phenyl-pyrrolidin-3-yl]-cyclopropanecarboxylic acid amide 47 N-[rac-(2R,3S,4S)-2-(2-Chlorophenyl)-1-[1-(4-fluorophenyl)-1H-indazol-5-yl]-4-methyl-5-oxo-pyrrolidin-3-yl]-2,2-difluoro-propionamide 48 N-[rac-(2R,3S,4S)-1-[1-(4-Fluorophenyl)-1H-indazol-5-yl]-2-(3-methoxyphenyl)-4-methyl-5-oxo-pyrrolidin-3-yl]-cyclopropanecarboxylic acid amide 49 N-[rac-(2R,3S,4S)-2-(4-Fluorophenyl)-1-[1-(4-fluorophenyl)-1H-indazol-5-yl]-4-methyl-5-oxo-pyrrolidin-3-yl]-cyclopropanecarboxylic acid amide 60 N-[rac(2R,3S,4S)-1-[1-(4-Fluorophenyl)-1H-indazol-5-yl]-4-methyl-5-oxo-2-phenyl-pyrrolidin-3-yl]-4-methyl-thiazole-5-carboxylic acid amide 61 N-[rac-(2R,3S,4S)-1-[1-(4-Fluorophenyl)-1H-indazol-5-yl]-4-methyl-5-oxo-2-phenyl-pyrrolidin-3-yl]-methanesulfonic acid amide 62 N-[rac-(2R,3S,4S)-1-[1-(4-Fluorophenyl)-1H-indazol-5-yl]-4-methyl-2-m-tolyl-5-oxo-pyrrolidin-3-yl]-methanesulfonic acid amide 63 N-[rac-(2R,3S,4S)-1-[1-(4-Fluorophenyl)-1H-indazol-5-yl]-4-methyl-2-m-tolyl-5-oxo-pyrrolidin-3-yl]-cyclopropanecarboxylic acid amide 64 N-[rac-(2R,3S,4S)-1-[1-(4-Fluorophenyl)-1H-indazol-5-yl]-4-methyl-5-oxo-2-phenyl-pyrrolidin-3-yl]-1-methyl-1H-pyrazole-3-carboxylic acid amide 65 N-[rac-(2R,3S,4S)-1-[1-(4-Fluorophenyl)-1H-indazol-5-yl]-4-methyl-5-oxo-2-phenyl-pyrrolidin-3-yl]-pyridine-3-carboxylic acid amide 66 N-[rac-(2R,3S,4S)-1-[1-(4-Fluorophenyl)-1H-indazol-5-yl]-4-methyl-5-oxo-2-phenyl-pyrrolidin-3-yl]-pyrimidine-2-carboxylic acid amide 67 N-[rac-(2R,3S,4S)-1-[1-(4-Fluorophenyl)-1H-indazol-5-yl]-4-methyl-2-m-tolyl-5-oxo-pyrrolidin-3-yl]-4-methyl-thiazole-5-carboxylic acid amide 68 N-[rac-(2R,3S,4S)-1-[1-(4-Fluorophenyl)-1H-indazol-5-yl]-4-methyl-2-m-tolyl-5-oxo-pyrrolidin-3-yl]-pyridine-3-carboxylic acid amide 69 N-[rac-(2R,3S,4S)-1-[1-(4-Fluorophenyl)-1H-indazol-5-yl]-4-methyl-2-m-tolyl-5-oxo-pyrrolidin-3-yl]-pyrimidine-2-carboxylic acid amide 70 N-[rac-(2R,3S,4R)-1-[1-(4-Fluorophenyl)-1H-indazol-5-yl]-4-methyl-2-m-tolyl-5-oxo-pyrrolidin-3-yl]-cyclopropanecarboxylic acid amide 71 N-[rac-(2R,3S,4R)-1-[1-(4-Fluorophenyl)-1H-indazol-5-yl]-4-methyl-2-m-tolyl-5-oxo-pyrrolidin-3-yl]-4-methyl-thiazole-5-carboxylic acid amide 72 N-[rac-(2R,3S,4R)-1-[1-(4-Fluorophenyl)-1H-indazol-5-yl]-4-methyl-2-m-tolyl-5-oxo-pyrrolidin-3-yl]-1-methyl-1H-pyrazole-3-carboxylic acid amide 73 N-[rac-(2R,3S,4R)-1-[1-(4-Fluorophenyl)-1H-indazol-5-yl]-4-methyl-2-m-tolyl-5-oxo-pyrrolidin-3-yl]-pyridine-3-carboxylic acid amide 74 N-[rac-(2R,3S,4R)-1-[1-(4-Fluorophenyl)-1H-indazol-5-yl]-4-methyl-2-m-tolyl-5-oxo-pyrrolidin-3-yl]-pyrimidine-2-carboxylic acid amide 75 N-[rac-(2R,3S,4S)-1-[1-(4-Fluorophenyl)-1H-indazol-5-yl]-4-methyl-2-m-tolyl-5-oxo-pyrrolidin-3-yl]-1-methyl-1H-pyrazole-3-carboxylic acid amide 76 N-[rac-(2R,3S,4R)-1-[1-(4-Fluorophenyl)-1H-indazol-5-yl]-4-methyl-2-m-tolyl-5-oxo-pyrrolidin-3-yl]-methanesulfonic acid amide 77 2,2-Difluoro-N-[rac-(2R,3S,4R)-1-[1-(4-fluorophenyl)-1H-indazol-5-yl]-4-methyl-2-m-tolyl-5-oxo-pyrrolidin-3-yl]-propionamide 78 N-[rac-(2R,3S,4R)-2-(2-Chlorophenyl)-1-[1-(4-fluorophenyl)-1H-indazol-5-yl]-4-methyl-5-oxo-pyrrolidin-3-yl]-cyclopropanecarboxylic acid amide 79 N-[rac-(2R,3S,4R)-2-(2-Chlorophenyl)-1-[1-(4-fluorophenyl)-1H-indazol-5-yl]-4-methyl-5-oxo-pyrrolidin-3-yl]-2,2-difluoro-propionamide 80 2,2-Difluoro-N-[rac-(2R,3S,4S)-1-[1-(4-fluorophenyl)-1H-indazol-5-yl]-4-methyl-5-oxo-2-phenyl-pyrrolidin-3-yl]-propionamide 81 2,2-Difluoro-N-[rac-(2R,3S,4S)-1-[1-(4-fluorophenyl)-1H-indazol-5-yl]-4-methyl-2-m-tolyl-5-oxo-pyrrolidin-3-yl]-propionamide 82 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-4-methyl-thiazole-5-carboxylic acid amide 83 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-1-methyl-1H-pyrazole-3-carboxylic acid amide 84 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-pyridine-3-carboxylic acid amide 85 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-pyrimidine-2-carboxylic acid amide 86 N-[rac-(2R,3S,4R)-2-(2-Chlorophenyl)-1-[1-(4-fluorophenyl)-1H-indazol-5-yl]-4-methyl-5-oxo-pyrrolidin-3-yl]-methanesulfonic acid amide 87 N-[rac-(2R,3S,4R)-2-(2-Chlorophenyl)-1-[1-(4-fluorophenyl)-1H-indazol-5-yl]-4-methyl-5-oxo-pyrrolidin-3-yl]-pyridine-3-carboxylic acid amide 88 N-[rac-(2R,3S,4R)-2-(2-Chlorophenyl)-1-[1-(4-fluorophenyl)-1H-indazol-5-yl]-4-methyl-5-oxo-pyrrolidin-3-yl]-pyrimidine-2-carboxylic acid amide 89 N-[rac-(2R,3S,4S)-4-Benzyl-2-ethyl-1-[1-(4-fluorophenyl)-1H-indazol-5-yl]-5-oxo-pyrrolidin-3-yl]-pyridine-3-carboxylic acid amide 90 N-[rac-(2R,3S,4S)-4-Benzyl-2-ethyl-1-[1-(4-fluorophenyl)-1H-indazol-5-yl]-5-oxo-pyrrolidin-3-yl]-pyrimidine-2-carboxylic acid amide 91 N-[rac-(2R,3S,4S)-4-Benzyl-2-ethyl-1-[1-(4-fluorophenyl)-1H-indazol-5-yl]-5-oxo-pyrrolidin-3-yl]-methanesulfonic acid amide 92 N-[rac-(2R,3S,4S)-2-(2-Chlorophenyl)-1-[1-(4-fluorophenyl)-1H-indazol-5-yl]-4-methyl-5-oxo-pyrrolidin-3-yl]-pyridine-3-carboxylic acid amide 93 N-[rac-(2R,3S,4S)-2-(2-Chlorophenyl)-1-[1-(4-fluorophenyl)-1H-indazol-5-yl]-4-methyl-5-oxo-pyrrolidin-3-yl]-methanesulfonic acid amide 94 N-[rac-(2R,3S,4R)-2-(2-Chlorophenyl)-1-[1-(4-fluorophenyl)-1H-indazol-5-yl]-4-methyl-5-oxo-pyrrolidin-3-yl]-1-methyl-1H-pyrazole-3-carboxylic acid amide 95 N-((2R,3R,4S)-4-fluoro-1-(1-(4-fluorophenyl)-1H-indazol-5-yl)-5-oxo-2-phenylpyrrolidin-3-yl)cyclopropanecarboxamide 96 N-((2R,3R)-4,4-difluoro-1-(1-(4-fluorophenyl)-1H-indazol-5-yl)-5-oxo-2-phenylpyrrolidin-3-yl)cyclopropanecarboxamide 97 2,2-Difluoro-N-[rac-(2R,3S,4R)-1-[1-(4-fluorophenyl)-1H-indazol-5-yl]-2-(4-methoxyphenyl)-4-methyl-5-oxo-pyrrolidin-3-yl]-propionamide 98 2,2-Difluoro-N-[rac-(2R,3S,4S)-1-[1-(4-fluorophenyl)-1H-indazol-5-yl]-2-(4-methoxyphenyl)-4-methyl-5-oxo-pyrrolidin-3-yl]-propionamide 99 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-methanesulfonic acid amide 100 2,2-Difluoro-N-[rac-(2R,3S)-1-[1-(4-fluorophenyl)-1H-indazol-5-yl]-2-methyl-5-oxo-2-phenyl-pyrrolidin-3-yl]-propionamide 101 N-[rac-(2R,3S)-1-[1-(4-Fluorophenyl)-1H-indazol-5-yl]-2-methyl-5-oxo-2-phenyl-pyrrolidin-3-yl]-cyclopropanecarboxylic acid amide 102 2,2-Difluoro-N-[rac-(2R,3S)-2-methyl-1-[1-(1-methyl-6-oxo-1H-pyridin-3-yl)-1H-indazol-5-yl]-5-oxo-2-phenyl-pyrrolidin-3-yl]-propionamide 103 N-[rac-(2R,3S)-2-Methyl-1-[1-(1-methyl-6-oxo-1H-pyridin-3-yl)-1H-indazol-5-yl]-5-oxo-2-phenyl-pyrrolidin-3-yl]-cyclopropanecarboxylic acid amide 104 N-[rac-(2R,3S,4S)-4-Benzyl-2-ethyl-1-[1-(4-fluorophenyl)-1H-indazol-5-yl]-5-oxo-pyrrolidin-3-yl]-1-methyl-1H-pyrazole-3-carboxylic acid amide 105 N-[rac-(2R,3S,4S)-4-Benzyl-2-ethyl-1-[1-(4-fluorophenyl)-1H-indazol-5-yl]-5-oxo-pyrrolidin-3-yl]-4-methyl-thiazole-5-carboxylic acid amide 106 N-[rac-(2R,3S,4S)-4-Benzyl-2-ethyl-1-[1-(4-fluorophenyl)-1H-indazol-5-yl]-5-oxo-pyrrolidin-3-yl]-cyclopropanecarboxylic acid amide 107 N-[rac-(2R,3S,4S)-4-Benzyl-2-ethyl-1-[1-(4-fluorophenyl)-1H-indazol-5-yl]-5-oxo-pyrrolidin-3-yl]-2,2-difluoro-propionamide 108 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-cyclopropanecarboxylic acid amide 109 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-pyrimidine-2-carboxylic acid amide 110 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-1-methyl-1H-pyrazole-3-carboxylic acid amide 111 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-pyridine-3-carboxylic acid amide 112 N-[rac-(2R,3S,4S)-2-(2-Chlorophenyl)-1-[1-(4-fluorophenyl)-1H-indazol-5-yl]-4-methyl-5-oxo-pyrrolidin-3-yl]-cyclopropanecarboxylic acid amide 113 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-4-methyl-thiazole-5-carboxylic acid amide 114 N-[(2S,3S,4S)-2-(5-Chloro-thiophen-2-yl)-1-[1-(4-fluorophenyl)-1H-indazol-5-yl]-4-methyl-5-oxo-pyrrolidin-3-yl]-methanesulfonic acid amide 115 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-cyclopropanecarboxylic acid amide 116 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-4-methyl-thiazole-5-carboxylic acid amide 117 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-1-methyl-1H-pyrazole-3-carboxylic acid amide 118 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-pyridine-3-carboxylic acid amide 119 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-pyrimidine-2-carboxylic acid amide 120 2,2-Difluoro-N-[rac-(2S,3S,4S)-1-[1-(4-fluorophenyl)-1H-indazol-5-yl]-4-methyl-2-(1-methyl-1H-pyrazol-3-yl)-5-oxo-pyrrolidin-3-yl]-propionamide 121 N-[rac-(2R,3S,4S)-4-(Cyclopropyl-methyl)-1-[1-(4-fluorophenyl)-1H-indazol-5-yl]-5-oxo-2-phenyl-pyrrolidin-3-yl]-cyclopropanecarboxylic acid amide
122 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-methanesulfonic acid amide
123 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-2,2-difluoro-propionamide
124 N-[rac-(2S,3S,4R)-2-(5-Chloro-thiophen-2-yl)-1-[1-(4-fluorophenyl)-1H-indazol-5-yl]-4-methyl-5-oxo-pyrrolidin-3-yl]-cyclopropanecarboxylic acid amide
125 N-[rac-(2S,3S,4R)-2-(5-Chloro-thiophen-2-yl)-1-[1-(4-fluorophenyl)-1H-indazol-5-yl]-4-methyl-5-oxo-pyrrolidin-3-yl]-2,2-difluoro-propionamide
126 N-[rac-(2R,3S,4S)-4-Ethyl-1-[1-(4-fluorophenyl)-1H-indazol-5-yl]-5-oxo-2-phenyl-pyrrolidin-3-yl]-cyclopropanecarboxylic acid amide
127 N-((2R,3S)-1-(1-(4-fluorophenyl)-1H-indazol-5-yl)-5-oxo-4-phenethyl-2-phenylpyrrolidin-3-yl)cyclopropanecarboxamide, diastereomer 2
128 N-[rac-(2R,3R,4R)-4-Fluoro-1-[1-(4-fluorophenyl)-1H-indazol-5-yl]-4-methyl-5-oxo-2-phenyl-pyrrolidin-3-yl]-cyclopropanecarboxylic acid amide
129 N-[rac-(2R,3R,4S)-4-Fluoro-1-[1-(4-fluorophenyl)-1H-indazol-5-yl]-4-methyl-5-oxo-2-phenyl-pyrrolidin-3-yl]-cyclopropanecarboxylic acid amide
130 N-((2R,3S)-1-(1-(4-fluorophenyl)-1H-indazol-5-yl)-5-oxo-4-phenethyl-2-phenylpyrrolidin-3-yl)cyclopropanecarboxamide, diastereomer 1
131 N-((2R,3S,4S)-4-(2,2-difluoroethyl)-1-(1-(4-fluorophenyl)-1H-indazol-5-yl)-5-oxo-2-phenylpyrrolidin-3-yl)cyclopropanecarboxamide
132 N-((2R,3S,4R)-4-(2,2-difluoroethyl)-1-(1-(4-fluorophenyl)-1H-indazol-5-yl)-5-oxo-2-phenylpyrrolidin-3-yl)cyclopropanecarboxamide
133 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-cyclopropanecarboxylic acid amide
134 N-(rac-(2R,3S,4R)-4-ethyl-1-(1-(4-fluorophenyl)-1H-indazol-5-yl)-4-methyl-5-oxo-2-phenylpyrrolidin-3-yl)cyclopropanecarboxamide
135 N-((7R,8S)-6-(1-(4-fluorophenyl)-1H-indazol-5-yl)-5-oxo-7-phenyl-6-azaspiro[3.4]octan-8-yl)cyclopropanecarboxamid
136 N-(rac(2R,3S,4S)-4-(2,2-difluoroethyl)-1-(1-(4-fluorophenyl)-1H-indazol-5-yl)-4-methyl-5-oxo-2-phenylpyrrolidin-3-yl)cyclopropanecarboxamide
137 N-(rac-(2R,3R,4S)-4-benzyl-2-ethyl-4-fluoro-1-(1-(4-fluorophenyl)-1H-indazol-5-yl)-5-oxopyrrolidin-3-yl)cyclopropanecarboxamide
138 N-((2R,3S,4S)-1-(1-(4-fluorophenyl)-1H-indazol-5-yl)-4-((3-methyl-1,2,4-oxadiazol-5-yl)methyl)-5-oxo-2-phenylpyrrolidin-3-yl)cyclopropanecarboxamide
139 N-((2R,3S,4S)-1-(1-(4-fluorophenyl)-1H-indazol-5-yl)-4-((1-methyl-1H-pyrazol-4-yl)methyl)-5-oxo-2-phenylpyrrolidin-3-yl)cyclopropanecarboxamide
142 N-(rac-(2R,3S)-2-cyclopropyl-1-(1-(4-fluorophenyl)-1H-indazol-5-yl)-5-oxo-2-phenylpyrrolidin-3-yl)cyclopropanecarboxamide
143 N-(rac-(2R,3R)-2-cyclopropyl-1-(1-(4-fluorophenyl)-1H-indazol-5-yl)-5-oxo-2-phenylpyrrolidin-3-yl)cyclopropanecarboxamide
144 N-(rac-(2R,3S)-2-cyclopropyl-1-(1-(4-fluorophenyl)-1H-indazol-5-yl)-5-oxo-2-phenylpyrrolidin-3-yl)-2,2-difluoropropanamide
145 N-(rac-(2R,3R)-2-cyclopropyl-1-(1-(4-fluorophenyl)-1H-indazol-5-yl)-5-oxo-2-phenylpyrrolidin-3-yl)-2,2-difluoropropanamide
146 N-(rac-(2R,3S)-2-cyclopropyl-1-(1-(4-fluorophenyl)-1H-indazol-5-yl)-5-oxo-2-phenylpyrrolidin-3-yl)oxetane-3-carboxamide
147 N-(rac-(2R,3R)-2-cyclopropyl-1-(1-(4-fluorophenyl)-1H-indazol-5-yl)-5-oxo-2-phenylpyrrolidin-3-yl)oxetane-3-carboxamide
148 N-(rac-(2R,3S,4S)-4-(2,2-difluoroethyl)-1-(1-(4-fluorophenyl)-1H-indazol-5-yl)-4-methyl-5-oxo-2-phenylpyrrolidin-3-yl)cyclopropanecarboxamide
149 N-(rac-(2R,3S,4S)-4-(cyclopropylmethyl)-1-(1-(4-fluorophenyl)-1H-indazol-5-yl)-4-methyl-5-oxo-2-phenylpyrrolidin-3-yl)cyclopropanecarboxamide
150 N-((2R,3S,4R)-1-(1-(4-fluorophenyl)-1H-indazol-5-yl)-5-oxo-2-phenyl-4-(thiazol-2-ylmethyl)pyrrolidin-3-yl)cyclopropanecarboxamide
151 N-((2S,3S)-2-(5-chlorothiophen-2-yl)-1-(1-(4-fluorophenyl)-1H-indazol-5-yl)-2-methyl-5-oxopyrrolidin-3-yl)cyclopropanecarboxamide in each case in the form of the free compound or a physiologically acceptable salt thereof.

The compounds according to the invention can be synthesized by standard reactions in the field of organic chemistry known to the person skilled in the art or in a manner as described herein (cf. Reaction Schemes below) or analogously. The reaction conditions in the synthesis routes described herein are known to the skilled person and are for some cases also exemplified in the Examples described herein.

Reaction Scheme 1

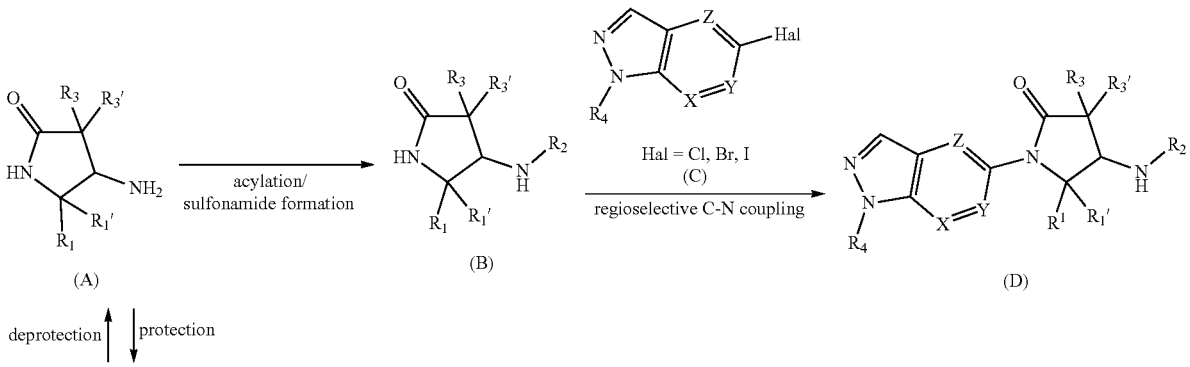

-continued

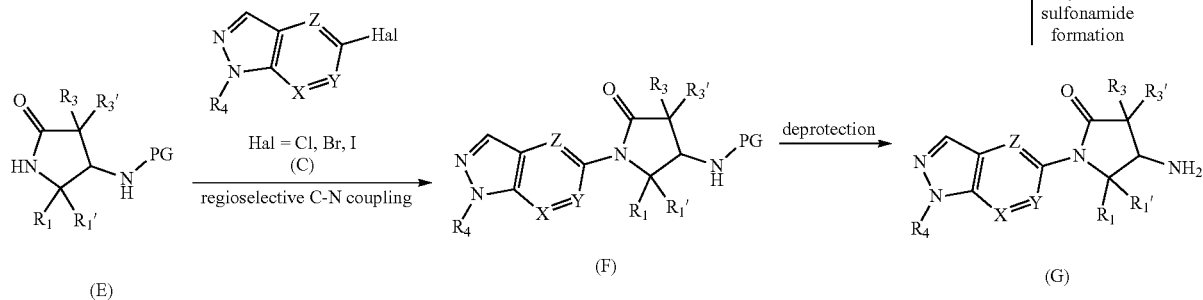

Substituted indazole moieties in compounds of formula (D) and formula (F) are introduced by subjecting lactam (B) or lactam (E) in a regioselective metal catalyzed C—N coupling reaction with corresponding indazole halides (C), preferred with corresponding indazole iodides. Metal catalyzed C—N coupling reactions are generally known in the art (*Current Organic Synthesis*, 2011, 8, 53). Favorable C—N coupling reactions are palladium and copper catalyzed cross-coupling reactions (*Chem. Rev.*, 2016, 116, 12564; *Chem. Soc. Rev.*, 2014, 43, 3525; *Chem. Sci.*, 2010, 1, 13). Regioselective C—N couplings with arylhalides are known in the art (*Chem. Sci.*, 2011, 2, 27; *J. Am. Chem. Soc.*, 2001, 123, 7727).

Primary amines (A) and (G) are converted to corresponding amides and sulfonamides (acylation and sulfonamide formation) (B) and (D) using commercially available acids (activation of acids using e.g. HATU) or acid chlorides under standard amide coupling reaction conditions (*March's Advanced Organic Chemistry*, 2007, 6th Edition, page 1427-1474).

Introduction of different orthogonal protecting groups PG (e.g. Boc, Cbz) to convert (A) to (E) as well as deprotection of compounds of formula (E) to (A) is well described in the literature (T. W. Green, P. G. M. Wuts, *Protective Groups in Organic Synthesis*, Wiley-Interscience, New York, 1999).

Reaction Scheme 1.1

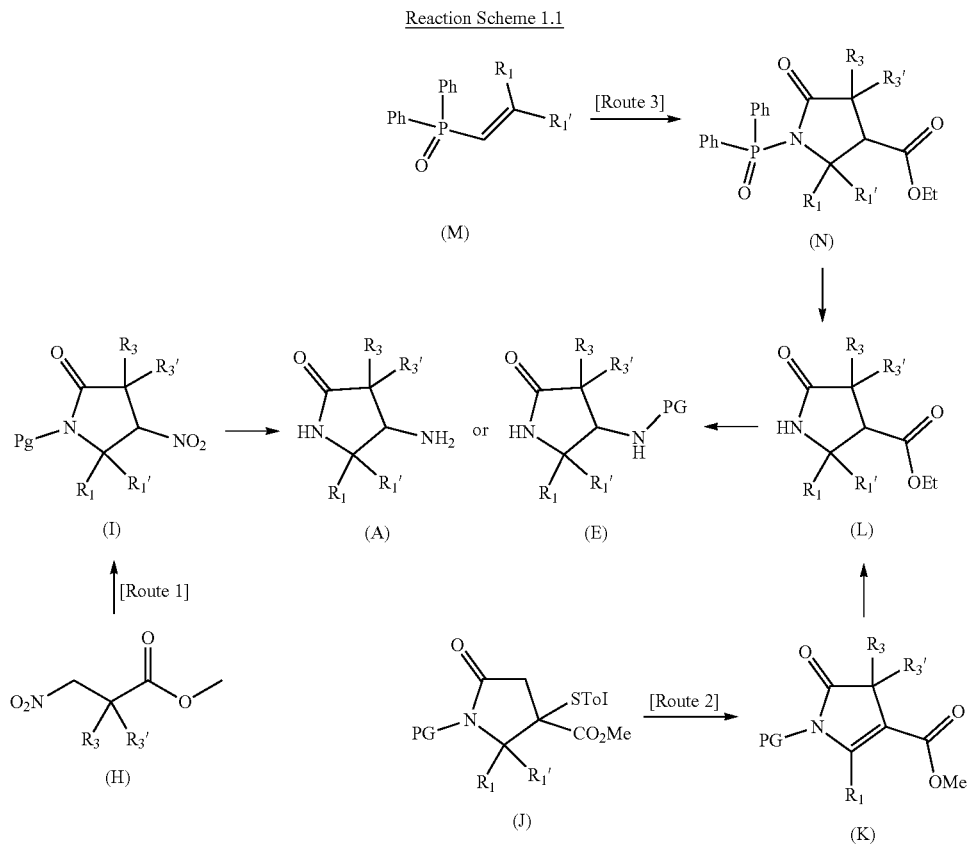

Compounds (A) and (E) can be synthesized according to procedures which are described in the literature.

Route 1: Synthesis of compounds of formula (I) starting from compounds of formula (H) is described in the literature (*Org. Lett.*, 2011, 13, 6406; *Org. Lett*, 2009, 4512; *ACS Sustainable Chem. Eng.* 2015, 1873). For R3 and R3'=Me the synthesis of the corresponding acid of (H) is described (*Journal of Chemical and Engineering Data*, 1966, 11, 617) and the synthesis can be carried out in analogy to the references above. Removal of PG=PMB is well known in the art (*Greene's Protective Groups in Organic Synthesis*, 2007, 4th Edition, page 905ff). Reduction of nitro groups is well known in the art (*March's Advanced Organic Chemistry*, 2007, 6th Edition, page 1815f).

Route 2: Synthesis of compounds of formula (J) is described in the literature (*Org. Lett.*, 2007, 9, 4077). Introduction of substituents R3 and R3' can be achieved via alkylation. C-alkylations of pyrrolidinones (*Tetrahedron*, 1999, 55, 13321) and elimination of sulfonium salts (*Tetrahedron Letters* 1983, 24, 4331) are well known in the art. Compounds of formula (A) and (E) can be synthesized using Curtius rearrangement as key step to convert carboxylic acid (L) to corresponding primary amine (A) or (E). Curtius rearrangement is well known in the art (*Tetrahedron Letters*, 2010, 51, 385).

Route 3: Synthesis of compounds of formula (N) starting from compounds of formula (M) is described in the literature (*J. Am. Chem. Soc.*, 2008, 130, 16146). Amidophosphate cleavage is described in the literature (*J. Am. Chem. Soc.*, 2008, 130, 16146). Compounds of formula (A) and (E) can be synthesized using Curtius rearrangement as key step to convert carboxylic acid (L) to corresponding primary amine (A) or (E). Curtius rearrangement is well known in the art (*Tetrahedron Letters*, 2010, 51, 385).

Compounds of formula (D) can be synthesized via regioselective C—N coupling of compound (O). Suitable C—N coupling reactions for N—H containing heterocycles are known in the art (*Synthesis*, 2011, 829; *Chem. Sci.*, 2011, 2, 27; *Beilstein J. Org. Chem.*, 2011, 7, 59; *J. Org. Chem.*, 2004, 69, 5578). Compound of formula (O) is synthesized via deprotection of compound (N) under acidic conditions.

The compounds according to the invention can be produced in the manner described here or in an analogous manner.

In a preferred embodiment, the compounds according to the invention are modulators of the glucocorticoid receptor. In the sense of the invention, the term "selective modulator of the glucocorticoid receptor (glucocorticoid receptor modulator)" preferably means that the respective compound exhibits in a cellular target engagement assay for agonistic or antagonistic potency on the glucocorticoid receptor an EC50 or IC50 value on the glucocorticoid receptor of at most 15 µM ($10 \cdot 10^{-6}$ mol/L) or at most 10 µM; more preferably at most 1 µM; still more preferably at most 500 nM ($10^{-9}$ mol/L); yet more preferably at most 300 nM; even more preferably at most 100 nM; most preferably at most 10 nM; and in particular at most 1 nM. In a preferred embodiment, the compound according to the invention exhibits in a cellular target engagement assay for agonistic or antagonistic potency on the glucocorticoid receptor an EC50 or IC50 value on the glucocorticoid receptor in the range of from 1 µM to 15 µM, more preferably from 100 nM to 1 µM, most preferably below 100 nM.

The person skilled in the art knows how to test compounds for modulation (agonistic or antagonistic) of the activity of the glucocorticoid receptor. Preferred target engagement assays for testing compounds for their agonistic or antagonistic potency (EC50, IC50) on the glucocorticoid receptor are described herein below:

Glucocorticoid Receptor Cell-Based Assays

Potential selective glucocorticoid receptor modulators of this intervention can be tested for modulation of the activity of the glucocorticoid receptor using cell-based assays. These assays involve a Chinese hamster ovary (CHO) cell line which contains fragments of the glucocorticoid receptor as well as fusion proteins. The glucocorticoid receptor frag- Reaction scheme 2

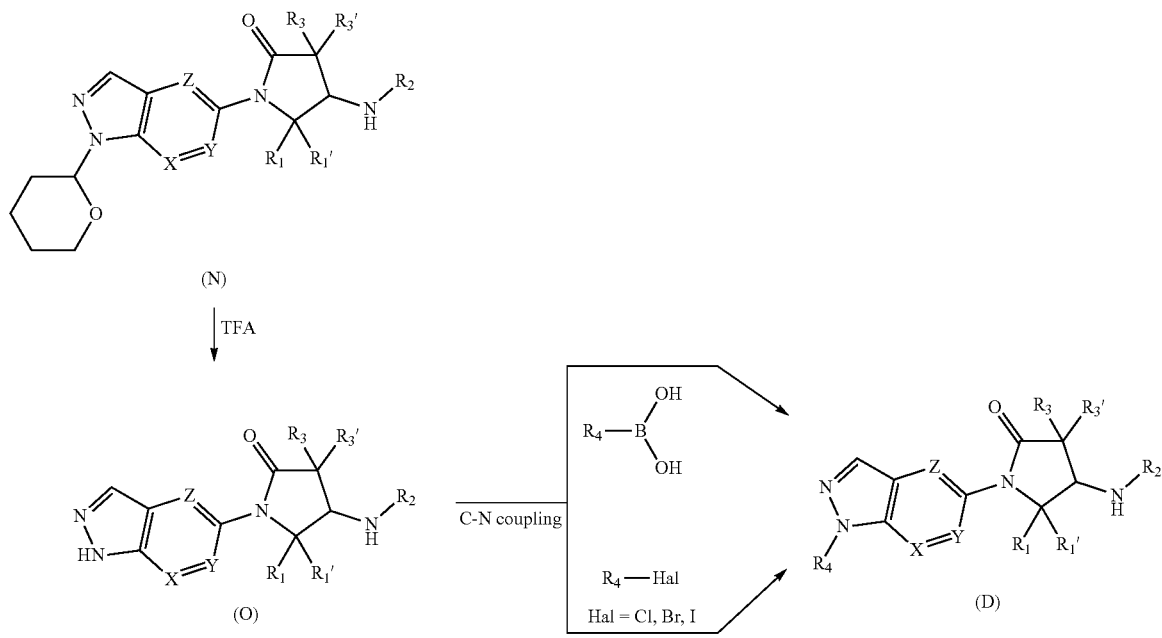

ments used are capable of binding the ligand (e.g. beclomethasone) to identify molecules that compete for binding with glucocorticoid receptor ligands. In more detail, the glucocorticoid receptor ligand binding domain is fused to the DNA binding domain (DBD) of the transcription factor GAL4 (GAL4 DBD-GR) and is stably integrated into a CHO cell line containing a GAL4-UAS-Luciferase reporter construct. To identify selective glucocorticoid receptor modulators, the reporter cell line is incubated with the molecules using an 8-point half-log compound dilution curve for several hours. After cell lysis the luminescence that is produced by luciferase after addition of the substrate is detected and EC50 or IC50 values can be calcuated. Engagement of molecules which induce gene expression via glucocortocoid receptor binding to the DNA leads to expression of the luciferase gene under the control of the fusion protein GAL4 DBD-GR and therefore to a dose-dependent increase of the luminescence signal. Binding of molecules which repress beclomethasone-induced gene expression of the luciferase gene under the control of the fusion protein GAL4 DBD-GR leads to a dose-dependent reduction of the luminescence signal.

In a preferred embodiment, the compound according to the invention exhibits in a cellular target engagement assay for agonistic or antagonistic potency on the glucocorticoid receptor an EC50 or IC50 value on the glucocorticoid receptor of at most 1 µM ($10^{-6}$ mol/L); still more preferably at most 500 nM ($10^{-9}$ mol/L); yet more preferably at most 300 nM; even more preferably at most 100 nM; most preferably at most 50 nM; and in particular at most 10 nM or at most 1 nM.

In a preferred embodiment, the compound according to the invention exhibits in a cellular target engagement assay for agonistic or antagonistic potency on the glucocorticoid receptor an EC50 or IC50 value on the glucocorticoid receptor in the range of from 1 µM to 15 µM, more preferably from 100 nM to 1 µM, most preferably below 100 nM.

In a preferred embodiment, the compound according to the invention exhibits in a cellular target engagement assay for agonistic or antagonistic potency on the glucocorticoid receptor an EC50 or IC50 value on the glucocorticoid receptor in the range of from 0.1 nM ($10^{-9}$ mol/L) to 1000 nM; still more preferably 1 nM to 800 nM; yet more preferably 1 nM to 500 nM; even more preferably 1 nM to 300 nM; most preferably 1 nM to 100 nM; and in particular 1 nM to 80 nM.

Human Glucocorticoid Receptor (hGR) Ligand-Binding Assay

Potential selective glucocorticoid receptor modulators of this intervention can be tested for their binding affinity at the glucocorticoid receptor using the binding assay described below.

Preferably, the glucocortitcoid receptor extracted from cytosol of IM9 cells is used for competitive radioligand binding assays to calculate percentage inhibition of the binding of radiolabeled ligand 3H-dexamethasone at the human glucocorticoid receptor. Preferably, a fixed concentration of the radioligand 3H-dexamethasone and 1 µM of compound according to the present invention (as unlabeled competitors of dexamethasone) are mixed with the extracted glucocorticoid receptor in order to measure the percentage of inhibition of 3H-dexamethasone binding.

In a preferred embodiment, the compound according to the invention exhibits in a hGR ligand-binding assay an inhibition of 3H-dexamethasone binding at 1 µM of at least 40%, more preferably at least 60%, most preferably at least 85%. In a preferred embodiment, the compound according to the invention exhibits in a hGR ligand-binding assay an inhibition of 3H-dexamethasone binding at 1 µM which is in the range from 40% to 60%, more preferably from greater than 60% to 85%, most preferably greater than 85%.

Preferably, the compounds according to the invention are useful as selective modulators of the glucocorticoid receptor.

Therefore, the compounds according to the invention are preferably useful for the in vivo treatment or prevention of diseases in which participation of the glucocorticoid receptor is implicated.

The invention therefore further relates to a compound according to the invention for use in the modulation of glucocorticoid receptor activity.

Therefore, another aspect of the invention relates to a compound according to the invention for use in the treatment and/or prophylaxis of a disorder which is mediated at least in part by the glucocorticoid receptor. Still another aspect of the invention relates to a method of treatment of a disorder which is mediated at least in part by the glucocorticoid receptor comprising the administration of a therapeutically effective amount of a compound according to the invention to a subject in need thereof, preferably a human.

A further aspect of the invention relates to the use of a compound according to the invention as medicament.

Another aspect of the invention relates to a pharmaceutical dosage form comprising a compound according to the invention. Preferably, the pharmaceutical dosage form comprises a compound according to the invention and one or more pharmaceutical excipients such as physiologically acceptable carriers, additives and/or auxiliary substances; and optionally one or more further pharmacologically active ingredient. Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik und angrenzende Gebiete, Editio Cantor Aulendoff).

The pharmaceutical dosage form according to the invention is preferably for systemic, topical or local administration, preferably for oral administration. Therefore, the pharmaceutical dosage form can be in form of a liquid, semisolid or solid, e.g. in the form of injection solutions, drops, juices, syrups, sprays, suspensions, tablets, patches, films, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and can also be administered as such.

The pharmaceutical dosage form according to the invention is preferably prepared with the aid of conventional means, devices, methods and processes known in the art. The amount of the compound according to the invention to be administered to the patient may vary and is e.g. dependent on the patient's weight or age and also on the type of administration, the indication and the severity of the disorder. Preferably 0.001 to 100 mg/kg, more preferably 0.05 to 75 mg/kg, most preferably 0.05 to 50 mg of a compound according to the invention are administered per kg of the patient's body weight.

The glucocorticoid receptor is believed to have potential to modify a variety of diseases or disorders in mammals such as humans. These include in particular inflammatory diseases.

Another aspect of the invention relates to a compound according to the invention for use in the treatment and/or prophylaxis of pain and/or inflammation; more preferably inflammatory pain.

A further aspect of the invention relates to a method of treatment of pain and/or inflammation; more preferably inflammatory pain.

The following examples further illustrate the invention but are not to be construed as limiting its scope.

The following abbreviations are used in the descriptions of the experiments: AcOH=acetic acid; Cbz=carboxybenzyl; DCM=dichloromethane; DEA=diethylamine; DIPEA=N,N-diisopropylethylamine; DMAP=4-(dimethylamino)-pyridine; DMF=N,N-dimethylformamide; DMSO=dimethylsulfoxide; DPPA=diphenyl phosphoryl azide; EtOAc=ethyl acetate; EtOH=ethanol; HATU=1-[bis(dimethylamino)methylene]-1H-1,2,3-triazolo[4,5-b]pyridinium 3-oxide hexafluorophosphate; h=hour; MeOH=methanol; min=minute; sat.=saturated; RT=room temperature; $R_f$=retention time; tert=tertiary; TEA=triethylamine; TFA=trifluoro acetic acid; THF=tetrahydrofuran.

Synthesis of trans-benzyl 4,4-dimethyl-(5-oxo-2-phenylpyrrolidin-3-yl)carbamate (Intermediate A1)

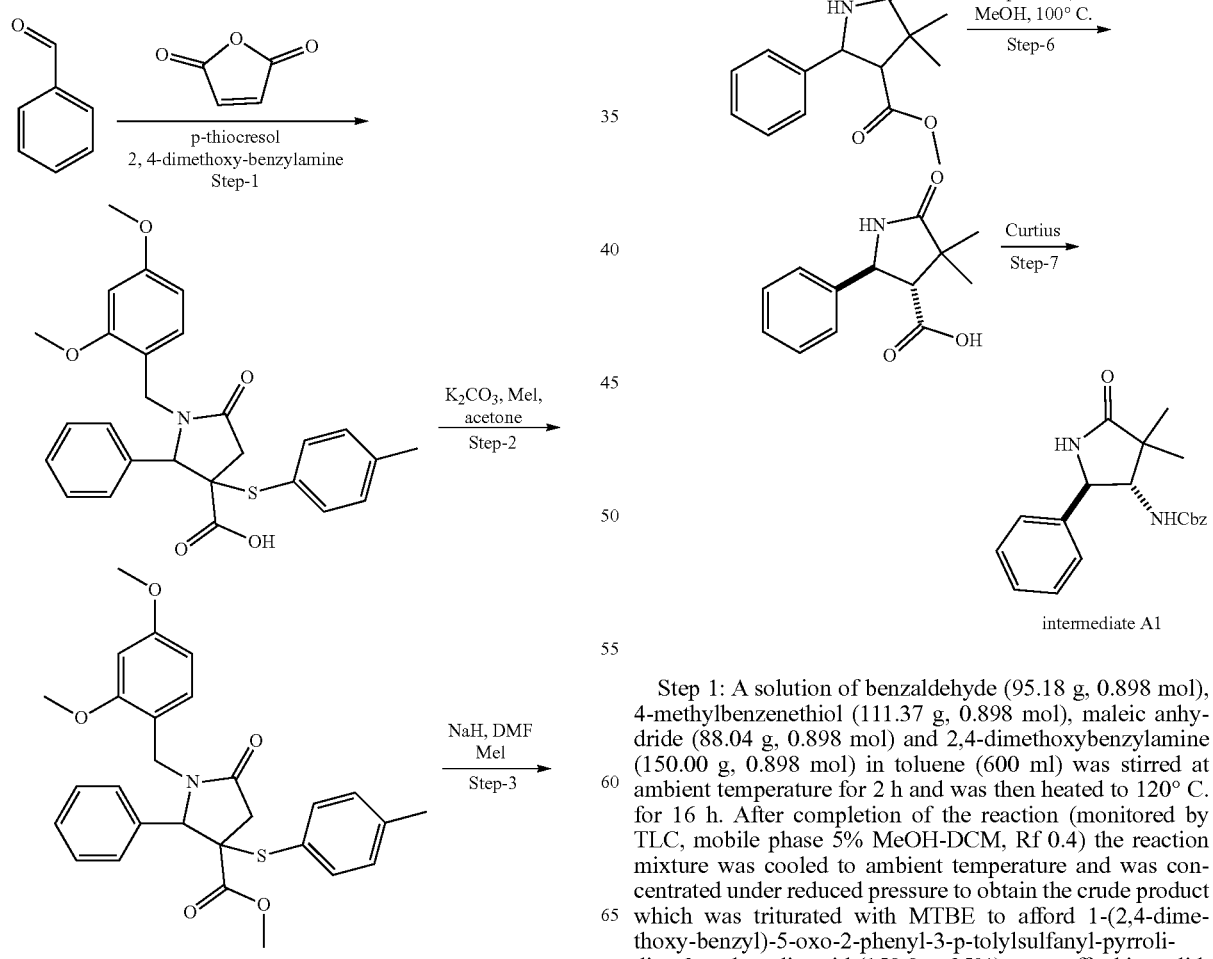

Step 1: A solution of benzaldehyde (95.18 g, 0.898 mol), 4-methylbenzenethiol (111.37 g, 0.898 mol), maleic anhydride (88.04 g, 0.898 mol) and 2,4-dimethoxybenzylamine (150.00 g, 0.898 mol) in toluene (600 ml) was stirred at ambient temperature for 2 h and was then heated to 120° C. for 16 h. After completion of the reaction (monitored by TLC, mobile phase 5% MeOH-DCM, Rf 0.4) the reaction mixture was cooled to ambient temperature and was concentrated under reduced pressure to obtain the crude product which was triturated with MTBE to afford 1-(2,4-dimethoxy-benzyl)-5-oxo-2-phenyl-3-p-tolylsulfanyl-pyrrolidine-3-carboxylic acid (150.0 g, 35%) as an off white solid.

Step 2: To a suspension of 1-(2,4-dimethoxy-benzyl)-5-oxo-2-phenyl-3-p-tolylsulfanyl-pyrrolidine-3-carboxylic acid (500.0 g, 1.05 mol) in acetone (5 L) was added K$_2$CO$_3$ (579.0 g, 4.19 mol) followed by methyl iodide (261.0 ml, 4.19 mol). The resulting suspension was stirred at ambient temperature for 16 h. The reaction mixture was then filtered and the filtrate was concentrated. The residue was taken up in EtOAc (1.5 L) and was washed with water. The organic layer was washed with brine, dried over sodium sulfate and was concentrated under reduced pressure to afford 1-(2,4-dimethoxy-benzyl)-5-oxo-2-phenyl-3-p-tolylsulfanyl-pyrrolidine-3-carboxylic acid methyl ester (480.0 g, 94%) as an off white solid.

Step 3: To a solution of 1-(2,4-dimethoxy-benzyl)-5-oxo-2-phenyl-3-p-tolylsulfanyl-pyrrolidine-3-carboxylic acid methyl ester (50.0 g, 0.101 mol) in DMF (0.5 L) was added sodium hydride (50% in mineral oil, 24.4 g, 0.509 mol) at 0° C. The resulting reaction mixture was stirred at 0° C. for 30 minutes. After 30 minutes, methyl iodide (31.7 ml, 0.509 mol) was added slowly. The resulting reaction mixture was then stirred for 30 min at 0° C. After completion of the reaction (monitored by TLC, mobile phase 30%-ethyl acetate-hexane, Rf 0.3) the reaction was quenched with saturated ammonium chloride solution and extracted with EtOAc (2.0 L). The combined organic layers were dried over sodium sulfate and concentrated under reduced pressure to obtain the crude compound, which was purified by column chromatography (silica gel, 100-200 mesh, 10-20% EtOAc/hexane) to afford 1-(2,4-dimethoxy-benzyl)-4,4-dimethyl-5-oxo-2-phenyl-4,5-dihydro-1H-pyrrole-3-carboxylic acid methyl ester (28.0 g, 70%) as a pale yellow solid.

Step 4: To a solution of 1-(2,4-dimethoxy-benzyl)-4,4-dimethyl-5-oxo-2-phenyl-4,5-dihydro-1H-pyrrole-3-carboxylic acid methyl ester (26.0 g, 0.117 mol) in methanol (300 ml) was added 10% palladium on charcoal (50% moisture, 13.4 g, 0.063 mol) and the resulting mixture was stirred for 16 h at ambient temperature under hydrogen pressure (balloon pressure). After completion of the reaction (monitored by TLC, mobile phase 30%-ethyl acetate-hexane, R$_f$ 0.30) the reaction mixture was filtered through a celite pad. The filtrate was concentrated under reduced pressure to obtain the crude compound which was triturated in diethyl ether to afford 1-(2,4-dimethoxy-benzyl)-4,4-dimethyl-5-oxo-2-phenyl-pyrrolidine-3-carboxylic acid methyl ester (25.0 g, 96%).

Step 5: A stirred suspension of 1-(2,4-dimethoxy-benzyl)-4,4-dimethyl-5-oxo-2-phenyl-pyrrolidine-3-carboxylic acid methyl ester (25.0 g, 0.063 mol) in TFA (250 ml) was heated to 90° C. for 16 h. After completion of the reaction (monitored by TLC, 50% ethyl ether-hexane, R$_f$-0.3) the reaction was cooled to ambient temperature and was concentrated under reduced pressure. The remains were basified with sat. NaHCO$_3$ solution, followed by the addition of EtOAc (1 L) and stirring of the resulting mixture for 30 minutes. The obtained solid was filtered off and dried under high vacuum to afford 4,4-dimethyl-5-oxo-2-phenyl-pyrrolidine-3-carboxylic acid methyl ester (18.0 g, crude) which was used in the next step.

Step 6: To a suspension of 4,4-dimethyl-5-oxo-2-phenyl-pyrrolidine-3-carboxylic acid methyl ester (43.0 g, 0.174 mmol) in MeOH (400 ml) was added 2 M NaOH (174 ml) at 0° C. The resulting suspension was stirred at 100° C. for 4 h. After consumption of the starting material (monitored by TLC, mobile phase 5% MeOH/DCM, Rf 0.2) the reaction mixture was concentrated and the residue was diluted with water and was washed with ethyl acetate (2×75 ml). The aqueous layer was then acidified to pH 3 with 6N HCl and was extracted with 10% MeOH/DCM (2×75 ml). The combined organic layers were dried over anhydrous Na$_2$SO$_4$, filtered and concentrated under reduced pressure to afford trans-4,4-dimethyl-5-oxo-2-phenyl-pyrrolidine-3-carboxylic acid (22.0 g, 55.0%) as a brown solid.

Step 7: To a stirred solution of trans-4,4-dimethyl-5-oxo-2-phenyl-pyrrolidine-3-carboxylic acid (22.0 g, 0.095 mol) in benzene-THF (4:1, 125 ml) was added DPPA (25.0 ml, 0.114 mol) followed by TEA (13.35 ml, 0.095 mol) at ambient temperature and the mixture was stirred for 2 h. Benzyl alcohol (14.8 ml, 0.142 mol) was then added and the reaction mixture was heated to 90° C. for 4 h. After completion of the reaction (monitored by TLC) the reaction mixtire was diluted with water (10 ml) and extracted with ethyl acetate (3×100 ml). The combined organic layers were washed with 10% citric acid solution (100 ml) followed by saturated NaHCO$_3$ solution (2×100 ml) and were then dried over anhydrous Na$_2$SO$_4$ and concentrated under reduced pressure. The residue was triturated with diethyl ether (2×80 ml). The obtained solid was filtered off and was dried under high vacuum to afford intermediate A1 (25.0 g, 78%) as an off white solid.

Synthesis of N-((trans)-4,4-dimethyl-5-oxo-2-phenylpyrrolidin-3-yl)cyclopropanecarboxamide (Intermediate A2)

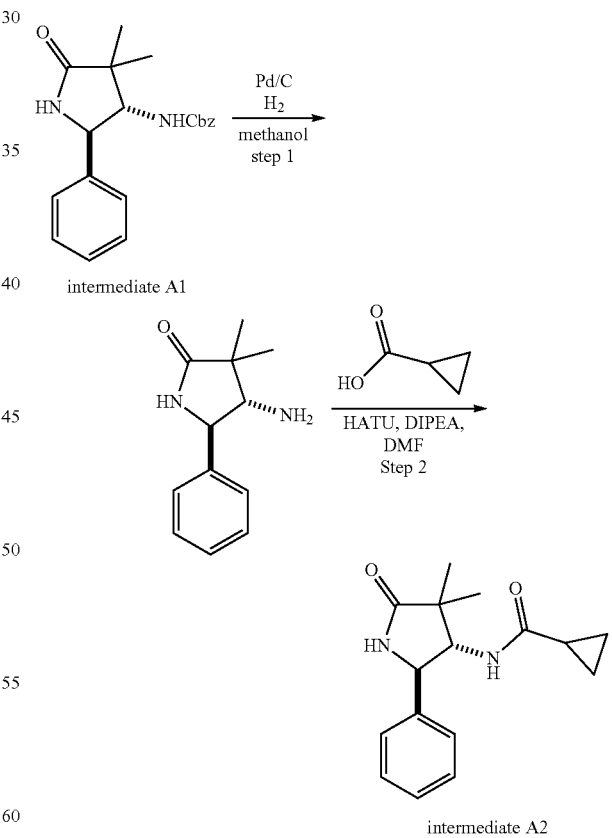

intermediate A1 intermediate A2

Step 1: To a stirred solution of intermediate A1 (5.0 g, 14.775 mmol, 1.0 eq.) in methanol:THF (80 mL, 2:1), Pd/C (10.0 g, 10%, moist) was added and the reaction was stirred under a hydrogen balloon for 2 h at ambient temperature. After completion, (monitored by TLC, TLC system 5% methanol in DCM, Rf-0.2) the reaction mixture was filtered through a celite pad which was then washed 2-3 times with THF. The filtrate was concentrated to obtain (trans)-4-amino-3,3-dimethyl-5-phenylpyrrolidin-2-one as a brown gum (3.0 g, 99%).

Step 2: To a stirred solution of cyclopropanecarboxylic acid (0.253 g, 2.941 mmol, 1.2 eq) in DMF (10 mL), HATU (1.86 g, 4.90 mmol, 2.0 eq), DIPEA (2.0 ml 12.25 mmol, 5.0 eq) and (trans)-4-amino-3,3-dimethyl-5-phenylpyrrolidin-2-one (0.50 g, 2.45 mmol, 1.0 eq) were added at 0° C. and the reaction was stirred at ambient temperature for 16 h. After completion of the reaction (monitored by TLC, TLC system 5% methanol in DCM, Rf-0.3) the reaction mixture was diluted with EtOAc (50 mL), washed with ice cold water (3×25 mL), dried over Na₂SO₄ and concentrated to obtain a residue which was purified via column chromatography (230-400 mesh silica gel; 0 to 2% MeOH-DCM) to afford intermediate A2 (0.46 g, 70%).

Synthesis of N-((trans)-4,4-dimethyl-5-oxo-2-phenylpyrrolidin-3-yl)-2,2-difluoropropanamide (Intermediate A3)

Synthesis of 5-(5-((4S,5R)-4-amino-3,3-dimethyl-2-oxo-5-phenylpyrrolidin-1-yl)-1H-indazol-1-yl)-1-methylpyridin-2(1H)-one (Intermediate A4-ent1) and 5-(5-((4R,5S)-4-amino-3,3-dimethyl-2-oxo-5-phenylpyrrolidin-1-yl)-1H-indazol-1-yl)-1-methylpyridin-2(1H)-one (Intermediate A4-ent 2)

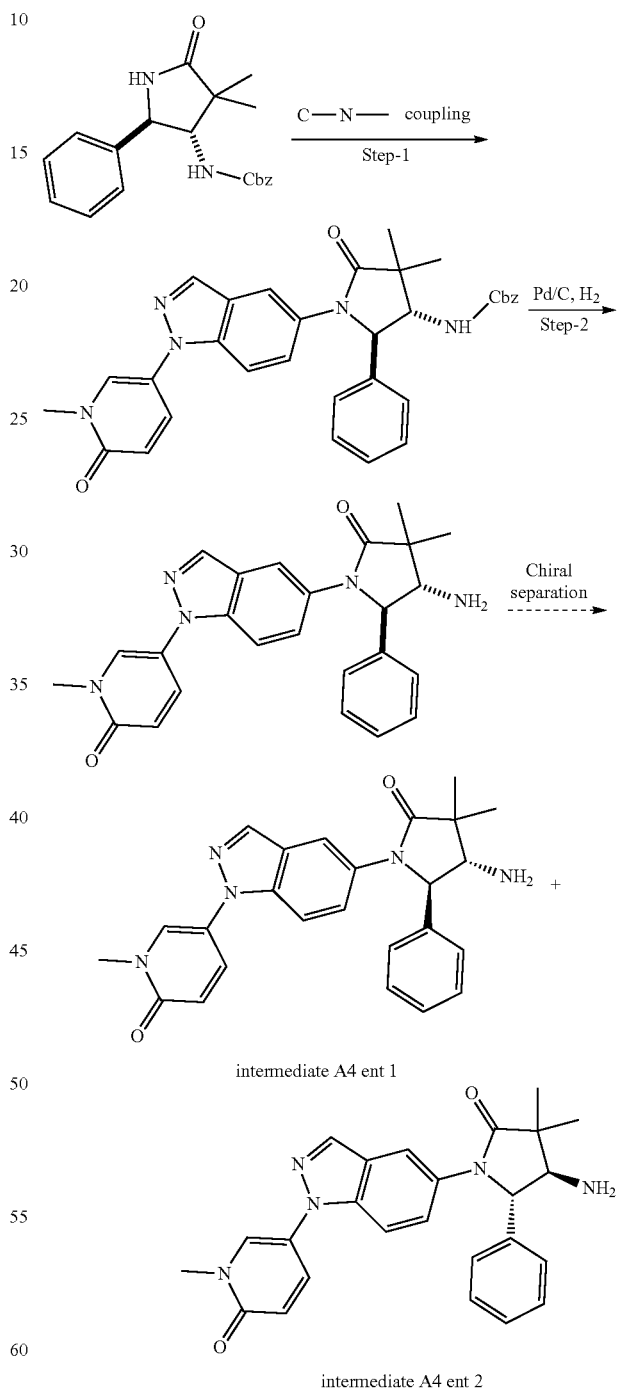

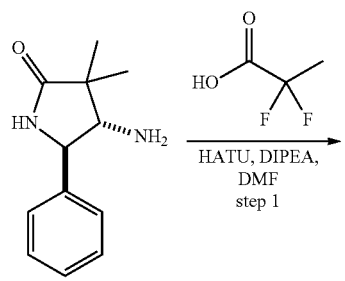

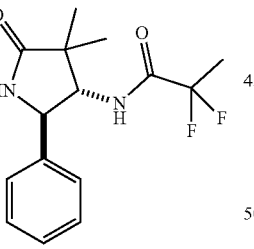

intermediate A3

Step 1: To a stirred solution of 2,2-difluoropropanoic acid (0.647 g, 5.88 mmol, 1.2 eq) in DMF (15 mL), HATU (3.72 g, 9.80 mmol, 2.0 eq), DIPEA (4.0 ml 24.50 mmol, 5.0 eq), and (trans)-4-amino-3,3-dimethyl-5-phenylpyrrolidin-2-one (1.0 g, 4.90 mmol, 1.0 eq) were added at 0° C. and the reaction was stirred at ambient temperature for 16 h. After completion of the reaction (monitored by TLC, TLC system 5% methanol in DCM, Rf-0.3) the reaction mixture was diluted with ethyl acetate (50 mL), washed with ice cold water (3×25 mL), dried over Na₂SO₄ and concentrated to obtain a residue which was purified by column chromatography (230-400 mesh silica gel; 0 to 2% MeOH-DCM) to afford intermediate A3 (0.93 g, 64%).

Step 1: To a stirred solution of trans-benzyl 4,4-dimethyl-(5-oxo-2-phenylpyrrolidin-3-yl)carbamate (2.0 g, 5.91 mmol) in 1,4-dioxane (80 ml) in a sealed tube was added 5-(5-iodo-indazol-1-yl)-1-methyl-1H-pyridin-2-one (2.28 g, 6.5 mmol) followed by potassium phosphate (2.51 g, 11.83 mmol). The mixture was degassed under argon atmosphere for 30 minutes. Trans-N,N'-dimethyl cyclohexane-1,2-diamine (0.37 ml, 2.36 mmol) and CuI (225 mg, 1.18 mmol) were added and the mixture was heated to 90° C. for 16 h. After completion of the reaction (monitored by LCMS) the reaction mixture was filtered through a celite bed and the celite bed was washed with 1,4-dioxane (100 ml). The filtrate was then concentrated under reduced pressure. The reaction was carried out in parallel in four batches (2.0 g each) and the remains of all batches were purified together by column chromatography (silica gel, 100-200 mesh, 1-2% MeOH/DCM) to afford benzyl ((trans)-4,4-dimethyl-1-(1-(1-methyl-6-oxo-1,6-dihydropyridin-3-yl)-1H-indazol-5-yl)-5-oxo-2-phenylpyrrolidin-3-yl)-carbamate (12.8 g, 48%) as a pale yellow solid.

Step 2: A stirred suspension of benzyl ((trans)-4,4-dimethyl-1-(1-(1-methyl-6-oxo-1,6-dihydropyridin-3-yl)-1H-indazol-5-yl)-5-oxo-2-phenylpyrrolidin-3-yl)-carbamate (3.0 g, 5.35 mmol) in TFA (30 ml) was heated to 90° C. for 3 h. After completion of the reaction (monitored by LCMS, 5% MeOH in DCM), the reaction mixture was cooled to ambient temperature and was concentrated under reduced pressure. The remains were then azeotroped with toluene (2×50 ml). The resulting residue was basified with saturated NaHCO$_3$ solution and the mixture was extracted with 5% MeOH/DCM (2×150 ml). The combined organic layers were dried over anhydrous Na$_2$SO$_4$, filtered and concentrated under reduced pressure to obtain the crude compound. This reaction was conducted in parallel in four batches (3.0 g each) and the combined crude compound was purified by column chromatography (100-200 Silica gel, 1.5-2% MeOH/DCM as eluent) to afford 5-(5-((trans)-4-amino-3,3-dimethyl-2-oxo-5-phenylpyrrolidin-1-yl)-1H-indazol-1-yl)-1-methylpyridin-2(1H)-one (7.0 g, 76%) as a grey solid.

Chiral separation (Chiralpak IC (21.0×250 mm), 5 µm, mobile phase DCM:EtOH 50:50, flow rate 18.0 mL/min) of the racemic compound (7.0 g) in normal phase afforded (intermediate A4-ent1, retention time 5.56 minutes) and (intermediate A4-ent2, retention time 6.41 minutes).

Synthesis of N-[rac-((6R,7S)-4-oxo-6-phenyl-5-azaspiro[2.4]heptan-7-yl)]cyclopropanecarboxamide (Intermediate A5)

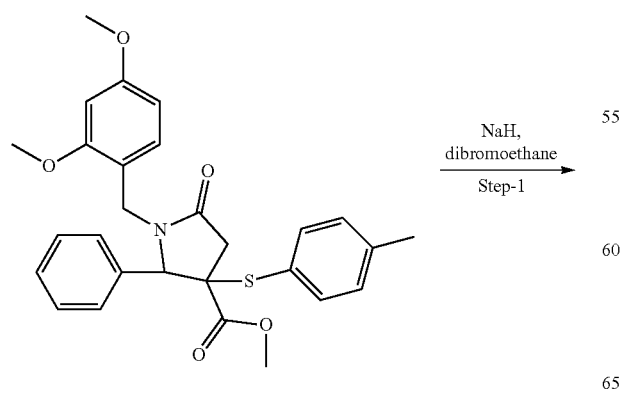

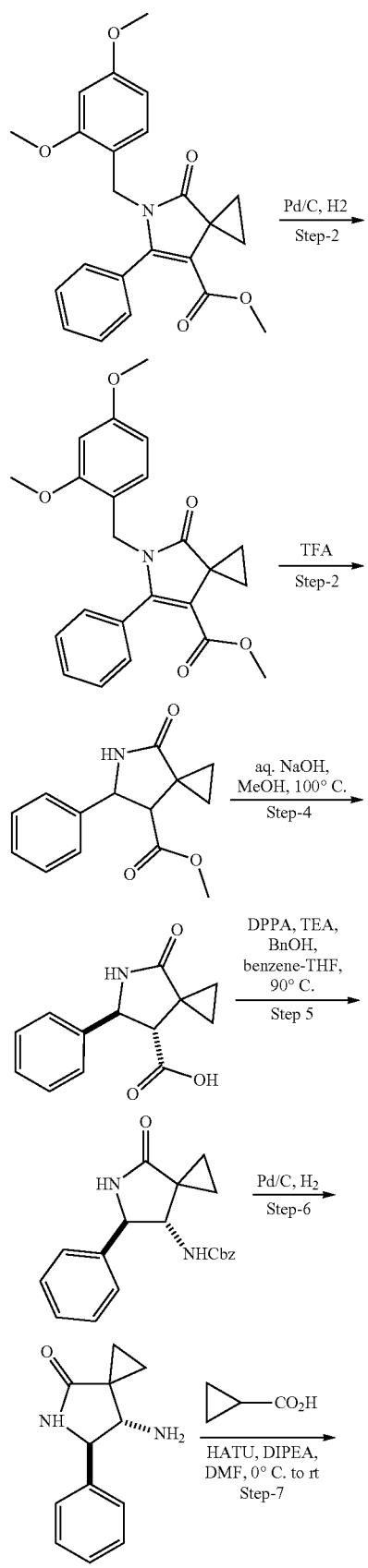

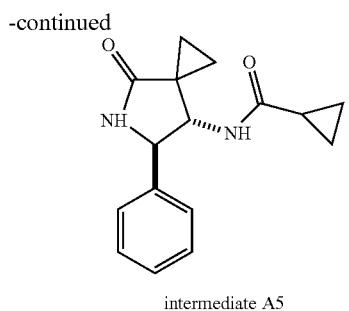

intermediate A5

Step 1: To a stirred solution of (2,4-dimethoxy-benzyl)-5-oxo-2-phenyl-3-p-tolylsulfanyl-pyrrolidine-3-carboxylicacid methyl ester (56.0 g 152.42 mmol) in DMF (560 ml) was slowly added NaH (18.3 g, 60% dispersion in mineral oil, 457.24 mmol) followed by 1,2-dibromoethane (17.13 ml, 198.14 mmol) at 0° C. The resulting reaction mixture was stirred at 0° C. for 3 h. After completion of the reaction (monitored by TLC, mobile phase 20%-ethyl acetate-hexane, $R_f$ 0.4) the reaction mixture was poured into a cold saturated solution of $NH_4Cl$. The mixture was then extracted with EtOAc (2×1 L). The combined organic layers were washed with brine, dried over sodium sulfate and concentrated under reduced pressure to obtain the crude compound which was purified by column chromatography (100-200 mesh silica gel, 10% ethyl acetate-hexane as eluent) to afford methyl 5-(2,4-dimethoxybenzyl)-4-oxo-6-phenyl-5-azaspiro[2.4]hept-6-ene-7-carboxylate (34.0 g, 57%) as an off-white solid.

Step 2: To a stirred solution of methyl 5-(2,4-dimethoxybenzyl)-4-oxo-6-phenyl-5-azaspiro[2.4]hept-6-ene-7-carboxylate (7.5 g, 19.08 mmol) in MeOH (125 ml) was added 10% Pd/C (3.0 g, 50% moist) and a catalytic amount of AcOH. The reaction mixture was stirred under hydrogen pressure (using a balloon) until consumption of starting material (monitored by LCMS) was achieved. The reaction was carried out in parallel in two batches, which were united for workup. The combined reaction mixture was filtered through a celite bed, which was washed with MeOH (75 ml). The filtrate was then concentrated to afford crude 5-(2,4-dimethoxybenzyl)-4-oxo-6-phenyl-5-aza-spiro[2.4]heptane-7-carboxylic acid methyl ester (12.0 g), which was used in next step without further purification.

Step 3: A stirred suspension of 5-(2,4-dimethoxybenzyl)-4-oxo-6-phenyl-5-aza-spiro[2.4]heptane-7-carboxylic acid methyl ester (16.0 g, 40.5 mmol) in TFA (80 ml) was heated to 50° C. for 14 h. After completion of the reaction (monitored by LCMS) the reaction mixture was cooled to ambient temperature and was concentrated under reduced pressure. The remains were azeotroped with toluene, were then basified with $NaHCO_3$ solution followed by extraction with ethyl acetate (2×125 ml). The combined organic layers were dried over anhydrous $Na_2SO_4$, filtered and concentrated under reduced pressure to afford 4-oxo-6-phenyl-5-aza-spiro[2.4]heptane-7-carboxylic acid methyl ester (9.0 g crude) as a brown solid.

Step 4: To a suspension of 4-oxo-6-phenyl-5-aza-spiro[2.4]heptane-7-carboxylic acid methyl ester (9.0 g crude) in MeOH (90 ml) was added 2 M NaOH (60 ml, 3.0 eq.) at 10° C. The resulting suspension was then stirred at 100° C. for 4 h. After completion of the reaction (monitored by TLC, mobile phase 50% EtOAc-hexane, Rf 0.1) the reaction mixture was concentrated. The residue was diluted with water and washed with EtOAc. The basic aqueous layer was acidified to pH 2-3 with 6N HCl and was then extracted with 10% MeOH/DCM (3×60 ml). The combined organic layers were dried over anhydrous $Na_2SO_4$, filtered and concentrated under reduced pressure to afford trans-4-oxo-6-phenyl-5-azaspiro[2.4]heptane-7-carboxylic acid (40 g, 32% over 3 steps) as a brown solid.

Step 5: To a stirred solution of trans-4-oxo-6-phenyl-5-azaspiro[2.4]heptane-7-carboxylic acid (5.0 g, 21.6 mmol) in benzene-THF (4:1, 80 ml) and DPPA (5.6 ml, 25.9 mmol) was added TEA (3 ml, 21.6 mmol) at ambient temperature. The resulting reaction mixture was stirred at ambient temperature for 2 h followed by the addition of benzyl alcohol (3.4 ml, 32.4 mmol) and heating to 90° C. for 4 h. After completion of the reaction (monitored by TLC, mobile phase 5% MeOH in DCM, $R_f$ 0.4) the reaction mixture was diluted with water and extracted with ethyl acetate (3×20 ml). The combined organic layers were washed with a 10% citric acid solution, then sat. $NaHCO_3$, dried over anhydrous $Na_2SO_4$ and concentrated under reduced pressure. The obtained residue was triturated with 10% DCM-Hexane followed by MTBE (25 ml). The obtained solid was filtered off and dried to afford 6.5 g of the crude compound, which was purified by prep HPLC to afford N-(trans-4-oxo-6-phenyl-5-azaspiro[2.4]hept-7-yl)carbamic acid benzyl ester (1.16 g, 16%) as an off white solid Step 6: To a stirred solution of N-(trans-4-oxo-6-phenyl-5-aza-spiro[2.4]hept-7-yl)carbamic acid benzyl ester (3.2 g, 9.52 mmol) in MeOH (300 ml) was added 10% Pd/C (1.7 g, 50% moist) and the reaction mixture was stirred at ambient temperature under a hydrogen atmosphere using a balloon. After completion of the reaction (monitored by TLC, mobile phase 10% MeOH/DCM, $R_f$ 0.2) the reaction mixture was filtered through a celite bed, which was then washed with MeOH (50 ml×2). The filtrate was concentrated under reduced pressure. The resulting residue was triturated with diethyl ether (5 ml) to afford crude trans-7-amino-6-phenyl-5-azaspiro[2.4]heptan-4-one (1.6 g), which was used without further purification in the next step.

Step 7: To a stirred suspension of trans-7-amino-6-phenyl-5-azaspiro[2.4]heptan-4-one (1.1 g, 5.44 mmol) in DCM (25 ml) was added TEA (1.3 ml, 1.7 eq.) followed by the addition of cyclopropanecarbonyl chloride (0.65 ml, 1.3 eq.) at 0° C. The resulting reaction mixture was then stirred for 1 h at the same temperature. After completion of the reaction (monitored by TLC, mobile phase 5% MeOH/DCM) the reaction mixture was concentrated and diluted with water. The resulting mixture was stirred for 30 min at ambient temperature, causing precipitation of a white solid. The solid was filtered off and was washed with diethyl ether (10 ml×2) and was dried to afford crude N-(trans-4-oxo-6-phenyl-5-azaspiro[2.4]heptan-7-yl)cyclopropanecarboxamide (1.2 g). The reaction was conducted in parallel in two batches. The obtained solid from both batches batches were mixed together and were purified by reverse phase prep HPLC to afford intermediate A5 (436.9 mg, 13%) as an off white solid.

Synthesis of benzyl(trans-2-methyl-5-oxo-2-phenylpyrrolidin-3-yl)carbamate (Intermediate A6)

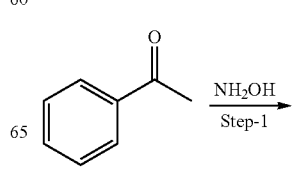

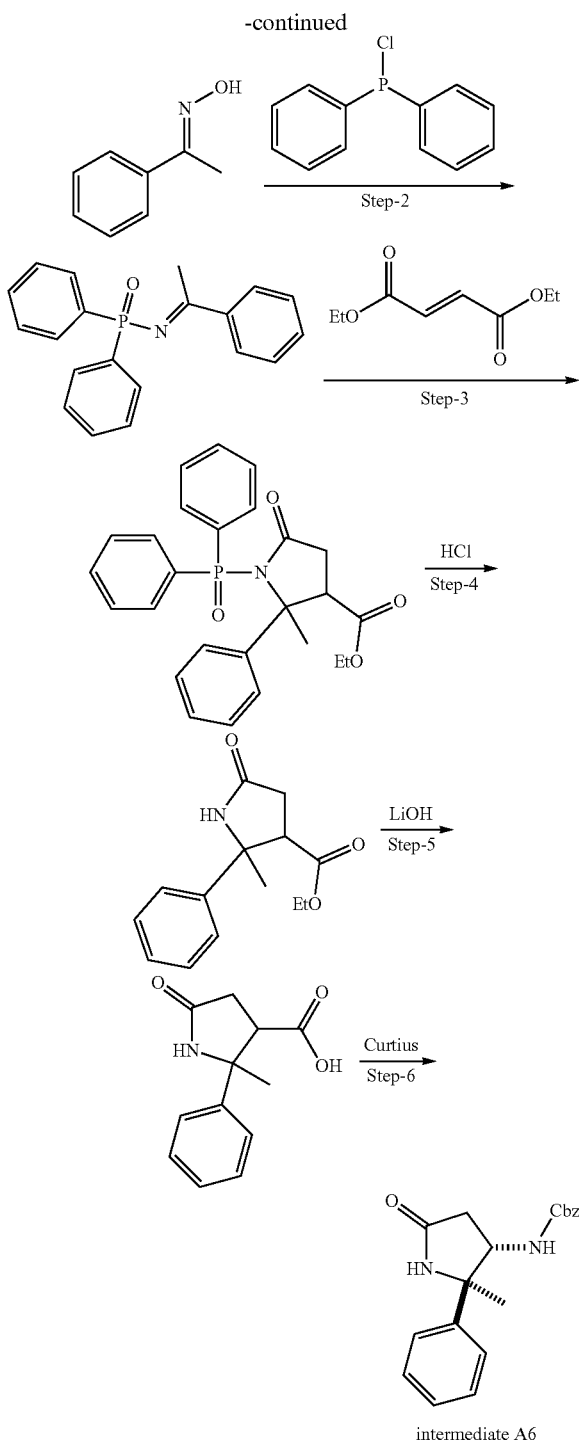

intermediate A6

Step 1: To a stirred solution of acetophenone (5 g, 41.614 mmol, 1.0 eq) in EtOH (50 mL) and Hydroxylamine hydrochloride (8.68 g, 124.844 mmol, 3.0 eq), sodium acetate (17.07 g, 208.07 mmol, 5 eq) was added and the mixture was heated to reflux for 12 h. After completion (monitored by TLC) the reaction mixture was evaporated to remove EtOH and diluted with EtOAc (2×300 mL) and water (300 mL). The extracted organic layer was washed with brine (300 mL), dried over anhydrous $Na_2SO_4$ and concentrated under reduced pressure to get crude product. The crude product was purified by column chromatography (230-400 mesh silica gel, TLC system: EtOAc/hexane (2:8); $R_f$=0.3) to give (E)-1-phenylethan-1-one oxime (4.73 g, 84%).

Step 2: To a stirred solution of (E)-1-phenylethan-1-one oxime (5 g, 36.993 mmol, 1 eq) in DCM (50 mL), TEA (5.7 mL, 40.692 mmol, 1.2 eq) followed by chlorodiphenylphosphane (7.3 mL, 40.692 mmol, 1.1 eq) was added at −40° C. The reaction mixture was then stirred at RT for 16 h. After completion of reaction (monitored by TLC, 50% EtOAc in hexane, $R_f$=0.3), reaction mixture was quenched with ice and extracted with EtOAc. The organic layer was washed with water (200 mL), brine (200 mL), dried over $Na_2SO_4$, filtered and evaporated under reduced pressure to get the crude product which was purified by column chromatography using 230-400 silica gel and 30 to 50% EtOAc in hexane to afford (E)-P,P-diphenyl-N-(1-phenylethylidene)phosphinic amide (10.1 g, 86%) as brown gum.

Step 3: To a stirred solution of (E)-P,P-diphenyl-N-(1-phenylethylidene)phosphinic amide (5 g, 15.657 mmol, 1 eq) in THF (75 mL), 1,4-diethyl (2E)-but-2-enedioate (6.75 g, 39.143 mmol, 2.5 eq), Cu(OAc) (285 mg, 1.5657 mmol, 0.1 eq), $PPh_3$ (410 mg, 1.5657 mmol, 0.1 eq) were added at RT and the mixture was stirred at RT for 20 min. Then pinacolborane (5.62 g, 43.839 mmol, 2.8 eq) was added at RT and the reaction mixture was stirred at RT for 48 h. After completion of reaction (monitored by TLC, 50% EtOAc in hexane, $R_f$=0.4), reaction mixture was diluted with EtOAc, washed with water (100 mL) and brine (100 mL), dried over $Na_2SO_4$ and concentrated to get the crude product which was purified by column chromatography using 230-400 silica gel and 20-40% EtOAc in hexane to afford pure desired ethyl 1-(diphenylphosphoryl)-2-methyl-5-oxo-2-phenylpyrrolidine-3-carboxylate (4 g, 57%).

Step 4: To a solution of ethyl 1-(diphenylphosphoryl)-2-methyl-5-oxo-2-phenylpyrrolidine-3-carboxylate (5 g, 11.174 mmol, 1 eq) in EtOH (50 mL), concentrated HCl (6 ml) was added at RT. The mixture was stirred at 90° C. for 16 h. After completion of reaction (monitored by TLC, 50% EtOAc in Hexane, $R_f$=0.6), reaction mixture was evaporated under reduced pressure, neutralized with saturated sodium bicarbonate solution, extracted with EtOAc, dried over $Na_2SO_4$ and concentrated to afford ethyl 2-methyl-5-oxo-2-phenylpyrrolidine-3-carboxylate (1.1 g, 40%) as off white solid.

Step 5: To a solution of ethyl 2-methyl-5-oxo-2-phenylpyrrolidine-3-carboxylate (4 g, 16.1753 mmol, 1 eq) in THF:$H_2O$ (3:1) (80 mL), LiOH·$H_2O$ (1.36 g, 32.351 mmol, 2 eq) was added at RT. The reaction mixture was stirred at RT for 16 h. After completion of reaction (monitored by TLC, 5% MeOH in DCM, $R_f$=0.1), organic solvent was evaporated under reduced pressure, dissolved in water and washed with ether and acidified with HCl. A solid precipitate was formed, filtered, washed with water and hexane, dried over rotary evaporator to afford 2-methyl-5-oxo-2-phenylpyrrolidine-3-carboxylic acid (3 g, 85%) as white solid.

Step 6: To a stirred solution of 2-methyl-5-oxo-2-phenylpyrrolidine-3-carboxylic acid (3 g, 13.684 mmol, 1.0 eq) in toluene (60 mL) was added TEA (2 mL, 14.368 mmol, 1.05 eq) and DPPA (4.5 g, 16.4203 mmol, 1.2 eq) and the reaction mixture was stirred at 90° C. for 30 min. Then benzyl alcohol (2.8 g, 27.3672 mmol, 2.0 eq) was added to the reaction mixture and the mixture was heated to reflux for 16 h. After completion (monitored by TLC, TLC system 5% MeOH in DCM, $R_f$=0.3), reaction mixture was concentrated under reduced pressure and diluted with EtOAc (100 mL), washed with water (2×100 mL), dried over anh. $Na_2SO_4$ and concentrated under reduced pressure to get the crude product which was purified by column chromatography (230-400 mesh silica gel; 0-3% MeOH in DCM) to afford benzyl (trans-2-methyl-5-oxo-2-phenylpyrrolidin-3-yl)carbamate (1.8 g, 41%).

Synthesis of (4S,5R)-4-amino-1-(1-(4-fluorophenyl)-1H-indazol-5-yl)-3,3-dimethyl-5-phenylpyrrolidin-2-one (Intermediate A7-ent1) and (4R,5S)-4-amino-1-(1-(4-fluorophenyl)-1H-indazol-5-yl)-3,3-dimethyl-5-phenylpyrrolidin-2-one (Intermediate A7-ent 2)

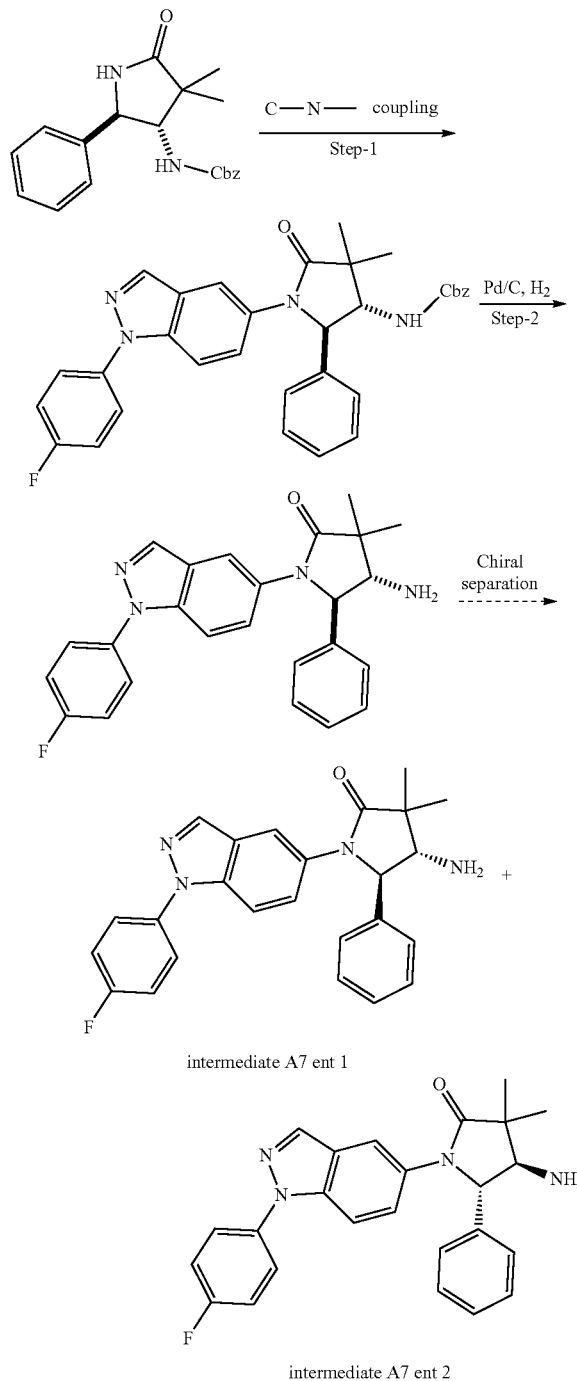

intermediate A7 ent 1 intermediate A7 ent 2

Step 1: To a stirred solution of benzyl (trans-4,4-dimethyl-5-oxo-2-phenylpyrrolidin-3-yl)carbamate (2.0 g, 5.91 mmol) in 1,4-dioxane (100 mL) in a sealed tube was added 1-(4-Fluoro-phenyl)-5-iodo-1H-indazole (2.4 g, 7.10 mmol) followed by potassium phosphate (2.51 g, 11.83 mmol) and the mixture was degassed using argon for 30 minutes. Then, trans-N,N'-dimethyl cyclohexane-1,2-diamine (0.4 ml, 2.37 mmol) and copper(I)iodide (225 mg, 1.18 mmol) were added and the mixture was heated to 100-110° C. for 16 h. After completion of the reaction (monitored by LCMS, 5% MeOH in DCM), the reaction mixture was filtered through a celite bed and the celite bed was washed with 1,4-dioxane (100 mL), the filtrate was then concentrated under reduced pressure. The reaction was carried out in 10 batches in parallel (2 g each). The combined crude material was purified by column chromatography (silica gel, 100-200 mesh, 2-2.5% MeOH/DCM) to afford benzyl (trans-1-(1-(4-fluorophenyl)-1H-indazol-5-yl)-4,4-dimethyl-5-oxo-2-phenylpyrrolidin-3-yl)carbamate (14.5 g, 45%) as a pale yellow solid.

Step 2: To a stirred solution of benzyl (trans-1-(1-(4-fluorophenyl)-1H-indazol-5-yl)-4,4-dimethyl-5-oxo-2-phenylpyrrolidin-3-yl)carbamate (4.0 g, 7.68 mmol) in THF/MeOH (500 mL, 1:1) was added 10% Pd/C (50% moist, 2.0 g) and the resulting mixture was stirred at ambient temperature under $H_2$ balloon pressure until completion of the reaction (monitored by TLC, 5% MeOH in DCM). The reaction mixture was then filtered through celite and the celite bed was washed with THF. The filtrate was then concentrated under reduced pressure. The reaction was carried out in four batches in parallel (4 g each) and the combined crude material was purified by column chromatography (silica gel, 100-200 mesh, 1.5-2.% MeOH/DCM as eluent) to afford trans-4-amino-1-(1-(4-fluorophenyl)-1H-indazol-5-yl)-3,3-dimethyl-5-phenylpyrrolidin-2-one (7.1 g, 56%) as an off-white solid.

Chiral separation (Chiralpak IC (21.0×250 mm), 5 μm, mobile phase n-hexane/EtOAc/EtOH/isopropylamine 70/15/15/0.1, flow rate 21.0 mL/min) of the racemic compound (7.1 g) in normal phase afforded (intermediate A7-ent1, retention time 6.10 minutes) and (intermediate A7-ent2, retention time 7.30 minutes).

Synthesis of methyl 2-methyl-3-nitropropanoate

Step 1: Preparation of 3-Nitro-propionic acid methyl ester: To a stirred solution of 3-Bromo-propionic acid methyl ester (200 g, 1.19 mol) in DMSO (3 l) was added $NaNO_2$ (120.6 g, 1.74 mol) portion wise at 0° C. The resulting solution was stirred at room temperature for 24 h. After the reaction was judged to be complete, the mixture was was diluted with cold brine (1.5 L) and extracted with MTBE (3×1500 ml). The combined organics were washed with cold water (500 ml×2), followed by brine (500 ml), dried over Na₂SO₄ and concentrated under reduced pressure (bath temp at 30 C) to afford crude 3-Nitro-propionic acid methyl ester. The crude material was purified by column chromatography (using silica gel 100-200 mesh, 10% EA-Hexane as eluent). An oil was obtained, which was further distilled under reduced pressure (120° C., 0.1-0.5 mm Hg) to afford 3-Nitro-propionic acid methyl ester (45 g, 28%) as light yellow oil.

Step 2: methyl 2-methyl-3-nitropropanoate: To a stirred solution of 3-nitro-propionic acid methyl ester (25 g, 187.97 mmol) in THF (400 ml) was added LDA (2M in THF, 188 ml, 376 mmol 2.0 eq) at −78° C. and stirred for 30 min at the same temperature. MeI (23.4 ml, 375.93 mmol, 2.0 eq.) was added at −78° C. The reaction mixture was gradually warmed up to 25° C. and stirring was continued for 16 h. The reaction mixture was quenched with aqueous NH₄Cl at 0° C. The layers were separated and the aqueous part was extracted with ethyl acetate (600 ml×3). The combined organic layers were washed with brine (300 ml), dried over Na₂SO₄ and concentrated. Crude was purified by column chromatography (using 100-200 silica gel, 5-10% Ethyl acetate-Hexane as eluent) to afford methyl 2-methyl-3-nitropropanoate (10 g, 36%).

Synthesis of Intermediate A8 (benzyl(rac-(2R,3S, 4S)-4-methyl-5-oxo-2-phenylpyrrolidin-3-yl)carbamate)

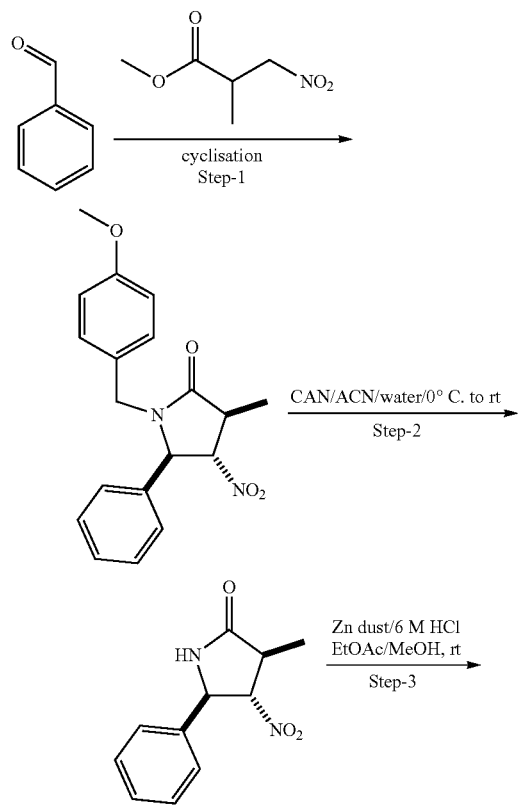

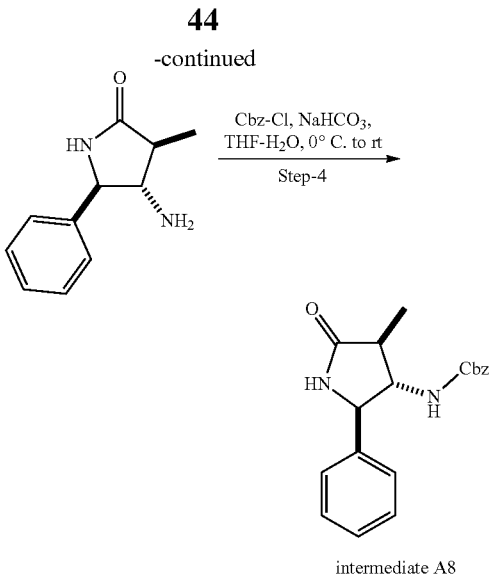

intermediate A8

Step 1: Synthesis of rac-(3S,4S,5R)-1-(4-methoxybenzyl)-3-methyl-4-nitro-5-phenylpyrrolidin-2-one: To a stirred solution of benzaldehyde (10.82 g, 102.04 mmol) in toluene (100 ml) was added 4-methoxy benzylamine (13.99 g, 102.04 mmol) at rt and stirred for 2 h at rt. To this reaction mixture was added methyl 2-methyl-3-nitropropanoate (10 g, 68.03 mmol) followed by benzoic acid (12.46 g, 102.04 mmol) and stirring was continued for 16 h at 70° C. After completion of reaction (monitored by LCMS), the reaction mixture was diluted with ethyl acetate (400 ml) and washed with water (100 ml×2), followed by sat.NaHCO₃ (100 ml×2). The organic layer was dried over anhydrous Na₂SO₄ and concentrated. The crude product was purified through column chromatography (using silica gel 100-200 mesh; 25-30% ethyl acetate in hexane as eluent) to afford rac-(3S, 4S,5R)-1-(4-methoxybenzyl)-3-methyl-4-nitro-5-phenylpyrrolidin-2-one (10 g, 43%) as brownish solid.

Step 2: Synthesis of rac-(3S,4S,5R)-3-methyl-4-nitro-5-phenylpyrrolidin-2-one. To a stirred solution of rac-(3S,4S, 5R)-1-(4-methoxybenzyl)-3-methyl-4-nitro-5-phenylpyrrolidin-2-one (10 g, 29.41 mmol) in acetonitrile (100 ml) was added a solution of CAN (48.37 g, 88.24 mmol) in water (100 ml) dropwise at 0° C. The reaction mixture was slowly warmed to 15° C. and stirring was continued for 3-4 h. After completion (monitored by TLC, 50% ethyl acetate/hexane, R_f 0.2), the reaction mixture was diluted with ethyl acetate (500 ml) and washed with water (100 ml×2) followed by brine (250 ml). The organic layer was dried over Na₂SO₄ and concentrated. The crude material was purified by column chromatography (using silica gel 100-200 mesh; 40-50% ethyl acetate in hexane as eluent) to afford of rac-(3S,4S,5R)-3-methyl-4-nitro-5-phenylpyrrolidin-2-one (4.00 g, 62%) as light yellow solid.

Step 3: Synthesis of rac-(3S,4S,5R)-4-amino-3-methyl-5-phenylpyrrolidin-2-one: To a stirred solution of of rac-(3S, 4S,5R)-3-methyl-4-nitro-5-phenylpyrrolidin-2-one (4.5 g, 20.45 mmol) in EtOAc-MeOH (2:1, 450 ml) was added 6 M aq. HCl (102.2 ml) at 0° C. To this reaction mixture was added Zn dust (80.25 g, 1.227 mol) portionwise at the same temperature. The resulting suspension was stirred at room temperature for 16 h. After completion of reaction (monitorrd by LCMS), the reaction mixture was quenched with saturated NaHCO₃ solution at 0° C., stirred for 1 h, filtered over celite and washed with EtOAc-MeOH (500 ml, 2:1). The filtrate was concentrated to afford rac-(3S,4S,5R)-4- amino-3-methyl-5-phenylpyrrolidin-2-one (3.9 g crude, considered as 100% yield) which was used without further purification.

Step 4: To a stirred suspension of rac-(3S,4S,5R)-4-amino-3-methyl-5-phenylpyrrolidin-2-one (3.9 g crude, 20.45 mmol) in THF:Water (1:1, 225 ml) was added sodium bicarbonate (9.95 g, 118.42 mmol) at 0° C. and stirred for 30 minutes. Benzyl chloroformate (11.8 ml, 35.53 mmol, 50% in toluene) was added to the reaction mixture at 0° C. and stirring was continued for 16 h at rt. After completion (monitored by LCMS), the reaction mixture was diluted with water (300 ml) and extracted with ethyl acetate (3×500 ml). The combined organics were washed with water (200 ml×2) followed by brine (200 ml) and dried over $Na_2SO_4$. After removal of the solvent, the crude material was purified by column chromatography (using silica gel 100-200 mesh; 2-2.5% MeOH in DCM as eluent) to afford intermediate A8 benzyl(rac-(2R,3S,4S)-4-methyl-5-oxo-2-phenylpyrrolidin-3-yl)carbamate (3.5 g, 53% in two steps).

Synthesis of Intermediate A10-trans(benzyl(rac(2R,3S,4S)-4-methyl-5-oxo-2-(m-tolyl)pyrrolidin-3-yl)carbamate) and Intermediate A10-cis(benzyl(rac(2S,3S,4S)-4-methyl-5-oxo-2-(m-tolyl)pyrrolidin-3-yl)carbamate)

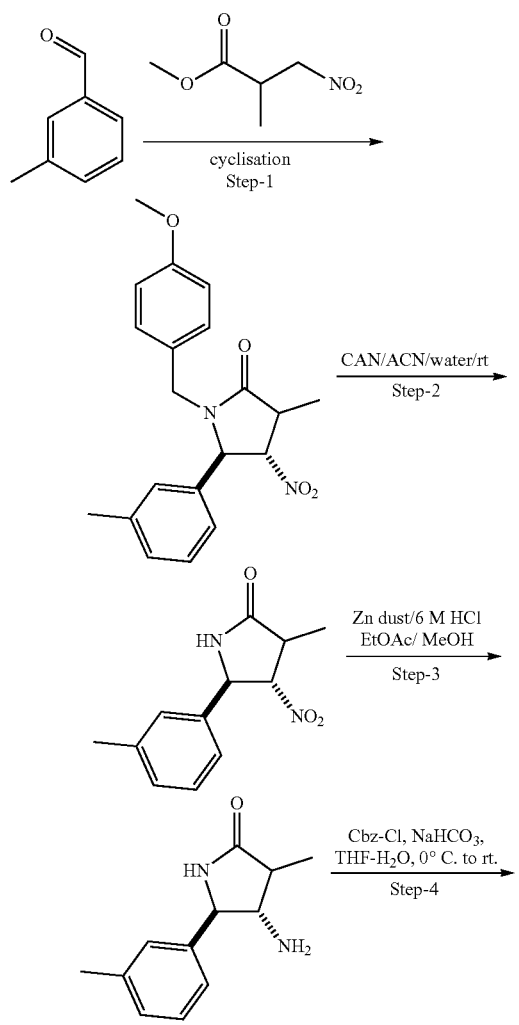

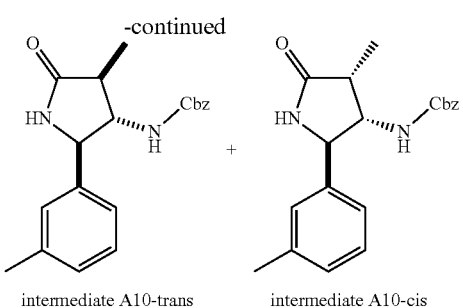

intermediate A10-trans     intermediate A10-cis

Step 1: Synthesis of rac-(4S,5R)-1-(4-methoxybenzyl)-3-methyl-4-nitro-5-(m-tolyl)pyrrolidin-2-one: To a stirred solution of 3-methyl-benzaldehyde (11.02 g, 91.75 mmol) in toluene (90 ml) was added 4-methoxy benzylamine (12.58 g, 91.75 mmol) at rt and stirred for 2 h. To this reaction mixture was added methyl 2-methyl-3-nitropropanoate (9.00 g, 61.27 mmol) followed by benzoic acid (11.2 g, 91.75 mmol) and stirred for 16 h at 70° C. After completion of reaction (monitored by LCMS), the reaction mixture was diluted with ethyl acetate (500 ml) and washed with water (200 ml×2), followed by sat.$NaHCO_3$ (150 ml×2). The organic layer was dried over anhydrous $Na_2SO_4$ and concentrated to give rac-(4S,5R)-1-(4-methoxybenzyl)-3-methyl-4-nitro-5-(m-tolyl)pyrrolidin-2-one (7.1 g, 32.7%) as brown resin.

Step 2: Synthesis of rac-(4S,5R)-3-methyl-4-nitro-5-(m-tolyl)pyrrolidin-2-one: To a stirred solution of rac-(4S,5R)-1-(4-methoxybenzyl)-3-methyl-4-nitro-5-(m-tolyl)pyrrolidin-2-one (4 g, 11.28 mmol) in acetonitrile (42 ml) was added a solution of CAN (18.56 g, 33.86 mmol) in water (42 ml) dropwise at 0° C. Reaction mixture was slowly warmed to 15° C. and continued stirring was continued for 3-4 h. After completion (monitored by LCMS), the reaction mixture was diluted with ethyl acetate (300 ml) and washed with water (100 ml×2) followed by brine (200 ml). The organic layer was dried over $Na_2SO_4$ and concentrated. The crude material was purified by column chromatography (using silica gel 100-200 mesh; 1-1.5% MeOH in DCM)) to afford rac-(4S,5R)-3-methyl-4-nitro-5-(m-tolyl)pyrrolidin-2-one (1.5 g, 56.8%) as off white solid.

Step 3: Synthesis of rac-(4S,5R)-4-amino-3-methyl-5-(m-tolyl)pyrrolidin-2-one: To a stirred solution of rac-(4S,5R)-3-methyl-4-nitro-5-(m-tolyl)pyrrolidin-2-one (1.5 g, 6.37 mmol) in EtOAc-MeOH (2:1, 136 ml) was added 6N aq. HCl (34 ml) at 0° C. To this reaction mixture was added Zn dust (25.01 g, 382.55 mmol) in small portions the same temperature. The resulting suspension was stirred at room temperature for 16 h. After completion of the reaction (monitored by LCMS), the reaction mixture was quenched with saturated $NaHCO_3$ solution (until basic reaction) at 0° C., stirred for 1 h, filtered over celite and washed with EtOAc:MeOH (250 ml, 2:1). The filtrate was concentrated to afford rac-(4S,5R)-4-amino-3-methyl-5-(m-tolyl)pyrrolidin-2-one (1.3 g crude, considered as 100% yield).

Step 4: Synthesis of intermediate A10-trans and A10-cis
a. To a stirred suspension of rac-(4S,5R)-4-amino-3-methyl-5-(m-tolyl)pyrrolidin-2-one (1.3 g crude, 6.37 mmol) in THF-Water (1:1, 160 ml) was added sodium bicarbonate (2.67 g, 31.89 mmol) at 0° C. and stirred for 30 minutes. To this reaction mixture was added Benzyl chloroformate (50% in toluene, 3.7 ml) at 0° C. and stirred at rt for 16 h. After completion (monitored by LCMS), the reaction mixture was diluted with water (75 ml) and extracted with ethyl acetate (3×75 ml). Combined organics were washed with water (50 ml×2) followed by brine (50 ml×2), dried over Na₂SO₄ and concentrated. The crude material was mixed with another batch of the same size and was purified by column chromatography (using silica gel 100-200 mesh; 1-2% MeOH in DCM as eluent) to afford intermediate A10-trans (benzyl (rac-(2R,3S,4S)-4-methyl-5-oxo-2-(m-tolyl)pyrrolidin-3-yl)carbamate, 1.39 g, 20.8% in two steps) and an impure fraction contain which was further purified by prep HPLC to afford intermediate A10-cis (benzyl(rac-(2R,3S,4S)-4-methyl-5-oxo-2-(m-tolyl)pyrrolidin-3-yl)carbamate_690 mg, 10.3% in two steps).

Synthesis of Intermediate A12-trans benzyl(rac-(2R, 3S,4S)-2-(2-chlorophenyl)-4-methyl-5-oxopyrrolidin-3-yl)carbamate and Intermediate A12-cis benzyl (rac-(2S,3S,4S)-2-(2-chlorophenyl)-4-methyl-5-oxopyrrolidin-3-yl)carbamate

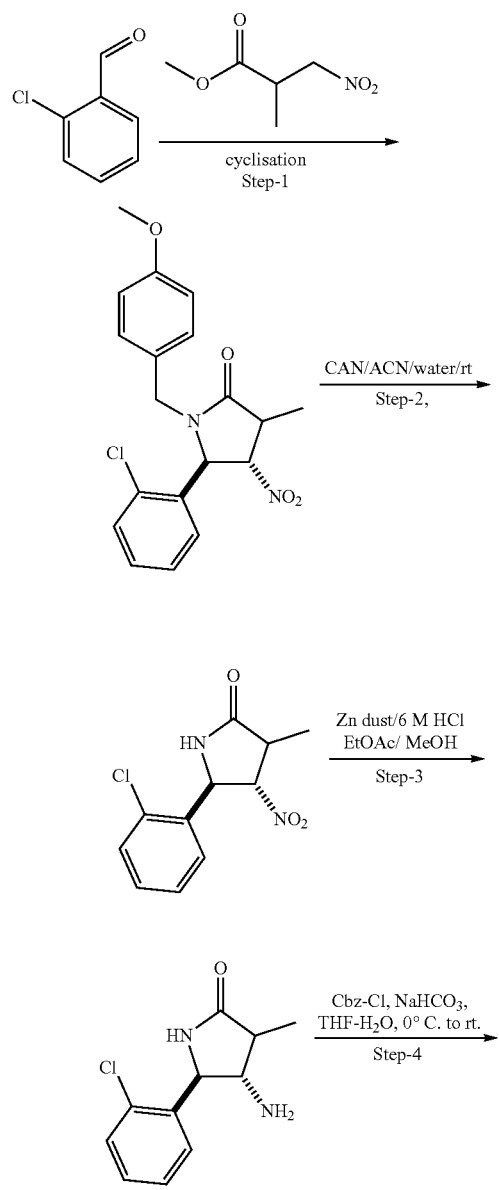

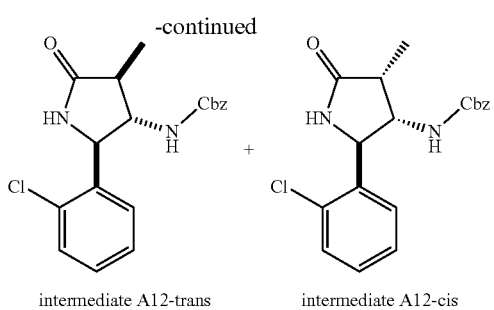

intermediate A12-trans        intermediate A12-cis

Step 1: Synthesis of rac-(4S,5R)-5-(2-chlorophenyl)-1-(4-methoxybenzyl)-3-methyl-4-nitropyrrolidin-2-one. To a stirred solution of 2-Chloro-benzaldehyde (11.46 g, 81.56 mmol) in Toluene (80 ml) was added 4-methoxy benzylamine (11.2 g, 81.56 mmol) at rt and stirred for 2 h. To this reaction mixture was added methyl 2-methyl-3-nitropropanoate (8 g, 54.37 mmol) followed by benzoic acid (9.96 g, 81.56 mmol) and stirred for 16 h at 70° C. After completion of reaction (monitored by LCMS), the reaction mixture was diluted with ethyl acetate (500 ml) and washed with water (150 ml×2), followed by sat. aq. NaHCO₃ (150 ml×2). The organic layer was dried over anhydrous Na₂SO₄ and concentrated to afford rac-(4S,5R)-5-(2-chlorophenyl)-1-(4-methoxybenzyl)-3-methyl-4-nitropyrrolidin-2-one (8.2 g, 40.3%) as brown solid.

Step 2: Synthesis of rac-(4S,5R)-5-(2-chlorophenyl)-3-methyl-4-nitropyrrolidin-2-one To a stirred solution of rac-(4S,5R)-5-(2-chlorophenyl)-1-(4-methoxybenzyl)-3-methyl-4-nitropyrrolidin-2-one (8 g, 21.33 mmol) in acetonitrile (80 ml) was added an aqueous solution of CAN (35 g, 64 mmol) in water (80 ml) dropwise at 0° C. The reaction mixture was slowly warmed to 15° C. and stirring was continued for 3-4 h. After completion (monitored by LCMS), the reaction mixture was diluted with ethyl acetate (500 ml) and washed with water (100 ml×2) followed by brine (200 ml). The organic layer was dried over Na₂SO₄ and concentrated. The crude material was purified by column chromatography (using silica gel 100-200 mesh; 25-30% ethyl acetate in hexane eluent) to afford rac-(4S, 5R)-5-(2-chlorophenyl)-3-methyl-4-nitropyrrolidin-2-one (2.5 g, 46%) as off white solid.

Step 3: rac-(4S,5R)-4-amino-5-(2-chlorophenyl)-3-methylpyrrolidin-2-one. To a stirred solution of rac-(4S,5R)-5-(2-chlorophenyl)-3-methyl-4-nitropyrrolidin-2-one (2.5 g, 10.684 mol) in EtOAc/MeOH (2:1, 250 ml) was added 6 N aq. HCl (53 ml) at 0° C. To this reaction mixture was added Zn dust (41.92 g, 641 mmol) portionwise at the same temperature. The resulting suspension was stirred at room temperature for 16 h. After completion of the reaction (monitored by LCMS), the mixture was quenched with saturated NaHCO₃ solution (until basic reaction) at 0° C., stirred for 1 h, filtered over celite and washed with EtOAc/MeOH (250 ml, 2:1). The filtrate was concentrated to afford rac-(4S,5R)-4-amino-5-(2-chlorophenyl)-3-methylpyrrolidin-2-one (2.2 g crude, considered as 100% yield). The crude product was used without further purification in the next step.

Step 4: Synthesis of intermediate A12-trans and intermediate A12-cis. To a stirred suspension of rac-(4S,5R)-4-amino-5-(2-chlorophenyl)-3-methylpyrrolidin-2-one (1.9 g crude, 8.48 mmol) in THF-Water (1:1, 100 ml) was added sodium bicarbonate (3.56 g, 86.36 mmol) at 0° C. and the mixture was stirred for 30 minutes. To this reaction mixture was added benzyl chloroformate (50% in toluene, 4.3 ml) at 0° C. and stirred at rt for 16 h. After the reaction was judged to be complete (monitored by LCMS), the reaction mixture was diluted with water (100 ml) and extracted with ethyl acetate (3×100 ml). The combined organic layers were washed with water (100 ml×2) followed by brine (100 ml), dried over Na₂SO₄ and concentrated. The crude product was mixed with another 1.5 g batch and the combined material was purified by column chromatography (using silica gel 100-200 mesh; 1-2% MeOH in DCM as eluent) to afford an mixture of isomers of intermediate A12-trans and intermediate A12-cis (3.3 g). Prep HPLC purification afforded intermediate A12-trans benzyl(rac-(2R,3S,4S)-2-(2-chlorophenyl)-4-methyl-5-oxopyrrolidin-3-yl)carbamate (815 mg, 14.9%, in two steps, after prep-purification) and another fraction (1.7 g) which was further purified further by prep HPLC to afford intermediate A12-cis benzyl(rac-(2R,3S,4S)-2-(2-chlorophenyl)-4-methyl-5-oxopyrrolidin-3-yl)carbamate (810 mg, 14.8%).

Synthesis of Intermediate A14 benzyl(rac-(2R,3S,4S)-2-(4-methoxyphenyl)-4-methyl-5-oxopyrrolidin-3-yl)carbamate

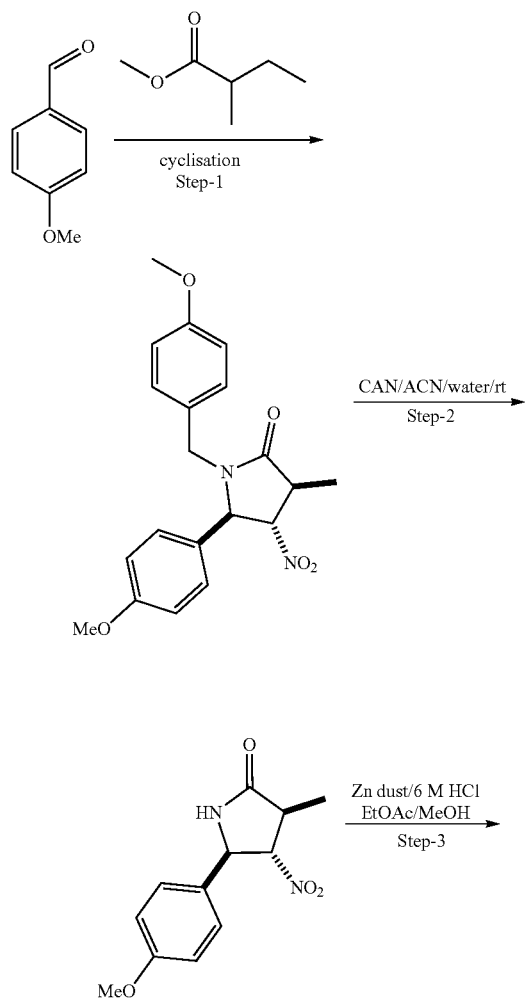

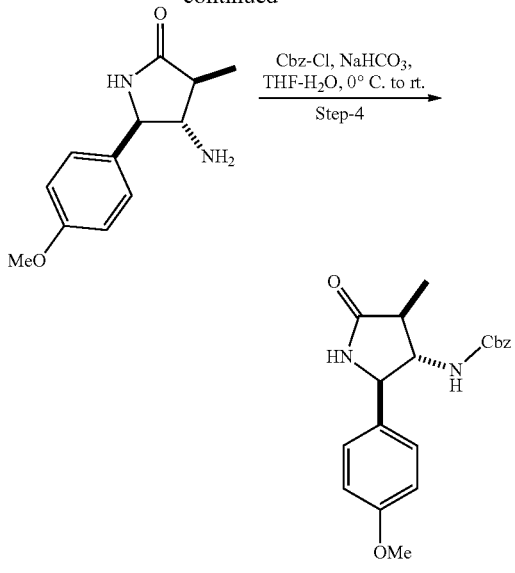

intermediate A14

Step 1: Synthesis of rac-(3S,4S,5R)-1-(4-methoxybenzyl)-5-(4-methoxyphenyl)-3-methyl-4-nitropyrrolidin-2-one. To a stirred solution of 4-methoxy-benzaldehyde (13.88 g, 101.95 mmol) in toluene (100 ml) was added 4-methoxy-benzyl amine (13.98 g, 101.95 mmol) at rt and the mixture was stirred for 2 h. To this reaction mixture was added 2-methyl-3-nitropropanoate (10.0 g, 67.96 mmol) followed by benzoic acid (12.45 g, 101.95 mmol) and stirred for 16 h at 70° C. After completion of the reaction (monitored by LCMS), the mixture was diluted with ethyl acetate (250 ml) and washed with water (100 ml), followed by sat. aq. NaHCO₃ (100 ml×2). The organic layer was dried over anhydrous Na₂SO₄ and concentrated. The crude material was purified by column chromatography (using silica gel 100-200 mesh; 20-25% ethyl acetate/hexanes eluent) rac-(3S,4S,5R)-1-(4-methoxybenzyl)-5-(4-methoxyphenyl)-3-methyl-4-nitropyrrolidin-2-one (11.5 g, 45.7%) as brown solid.

Step 2: Synthesis of rac-(3S,4S,5R)-5-(4-methoxyphenyl)-3-methyl-4-nitropyrrolidin-2-one. To a stirred solution of rac-(3S,4S,5R)-1-(4-methoxybenzyl)-5-(4-methoxyphenyl)-3-methyl-4-nitropyrrolidin-2-one (14.5 g, 39.04 mmol) in acetonitrile (150 ml) was added a solution of CAN (64.2 g, 117.12 mmol) in water (150 ml) dropwise at 0° C. The reaction mixture was slowly warmed up to 15° C. and stirring was continued for 3-4 h. After the starting material was consumed (monitored by TLC, 50% ethyl acetate/hexane, Rf 0.2), the reaction mixture was diluted with ethyl acetate (300 ml) and washed with water (100 ml×2) followed by brine (150 ml). The organic layer was dried over Na₂SO₄ and concentrated. The crude material was purified by column chromatography (using silica gel 100-200 mesh; 20-30% ethyl acetate/hexane eluent) to afford rac-(3S,4S,5R)-5-(4-methoxyphenyl)-3-methyl-4-nitropyrrolidin-2-one (3.82 g, 39%) as light yellow solid.

Step 3: Synthesis of rac-(3S,4S,5R)-4-amino-5-(4-methoxyphenyl)-3-methylpyrrolidin-2-one. To a stirred solution of rac-(3S,4S,5R)-5-(4-methoxyphenyl)-3-methyl-4-nitropyrrolidin-2-one (3.8 g, 15.2 mmol) in EtOAc/MeOH (2:1, 380 ml) was added 6N aq. HCl (76 ml) at 0° C. To this reaction mixture was added Zn dust (59.64 g, 912 mmol) portionwise at the same temperature. The resulting suspension was stirred at room temperature for 16 h. After completion of the reaction (monitored by LCMS), the reaction mixture was quenched with saturated NaHCO₃ solution at 0° C., stirred for 1 h, filtered over celite and washed with EtOAc/MeOH (300 ml, 2:1). The filtrate was concentrated to afford rac-(3S,4S,5R)-4-amino-5-(4-methoxyphenyl)-3-methylpyrrolidin-2-one (3.52 g crude, considered as 100% yield). The crude product was used in the next step without further purification.

Step 4: To a stirred suspension of rac-(3S,4S,5R)-4-amino-5-(4-methoxyphenyl)-3-methylpyrrolidin-2-one (3.52 g crude, 15.2 mmol) in THF-Water (1:1, 200 ml) was added sodium bicarbonate (7.25 g, 86.36 mmol) at 0° C. and stirred for 30 minutes. To this reaction mixture was added benzyl chloroformate (50% in toluene, 8.66 ml) at 0° C. and stirring was continued at rt for 16 h. After completion (monitored by LCMS), the reaction mixture was diluted with water (100 ml) and extracted with ethyl acetate (3×150 ml). The combined organics were washed with water (150 ml×2) followed by brine (200 ml), dried over Na₂SO₄ and concentrated. The crude material was purified by column chromatography (using silica gel 100-200 mesh; 1-2% MeOH in DCM as eluent) to intermediate A14 as an off-white solid. (2.5 g, 39% in two steps)

Synthesis of Intermediate A16 benzyl(rac-(2S,3S,4S)-2-(5-chlorothiophen-2-yl)-4-methyl-5-oxopyrrolidin-3-yl)carbamate

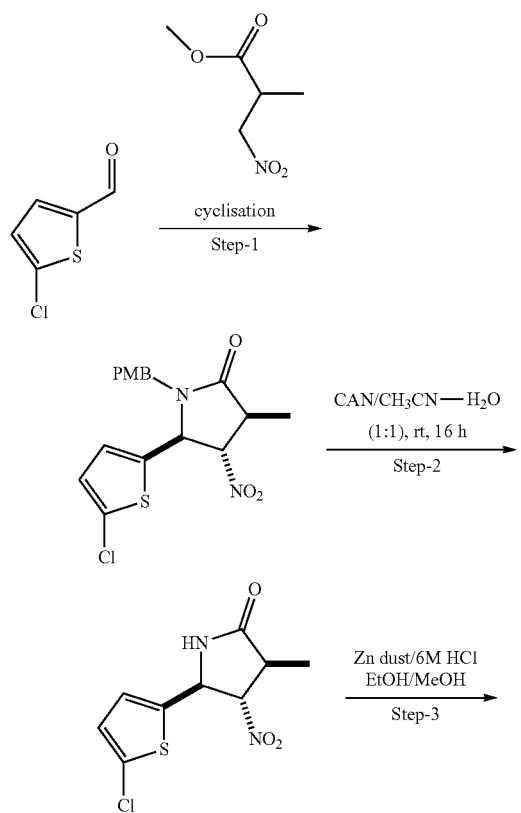

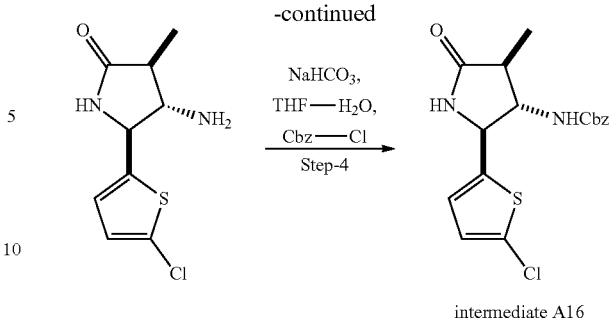

intermediate A16

Step-1: Synthesis of rac-(3S,4S,5S)-5-(5-chlorothiophen-2-yl)-1-(4-methoxybenzyl)-3-methyl-4-nitropyrrolidin-2-one. To a stirred solution of 5-chloro-thiophene-2-carbaldehyde (10 g, 0.068 mol) in toluene (250 ml) was added 4-methoxy benzylamine (10.26 g, 0.0748 mol) at rt and stirred for 2 h. To this reaction mixture was added 2-methyl-3-nitropropanoate (11 g, 0.0748 mol) followed by benzoic acid (12.46 g, 0.102 mol) and stirred at 80° C. for 16 h. After completion of the reaction (monitored by TLC, 30% EA/Hexane), the reaction mixture was diluted with ethyl acetate (200 ml) and washed with water (500 ml), followed by sat. aq. NaHCO3 (300 ml×3). The organic layer was dried over anhydrous Na₂SO₄ and concentrated. The obtained crude material was purified through column chromatography (using silica gel 100-200 mesh; 25-30% ethyl acetate/hexane eluent) to afford rac-(3S,4S,5S)-5-(5-chlorothiophen-2-yl)-1-(4-methoxybenzyl)-3-methyl-4-nitropyrrolidin-2-one (8 g, 28%) as a brown resin.

Step-2: Synthesis of rac-(3S,4S,5S)-5-(5-chlorothiophen-2-yl)-3-methyl-4-nitropyrrolidin-2-one. To a stirred solution of rac-(3S,4S,5S)-5-(5-chlorothiophen-2-yl)-1-(4-methoxybenzyl)-3-methyl-4-nitropyrrolidin-2-one (5 g, 0.013 mol) in CH₃CN (50 ml) was added a solution of CAN (21.38 g, 0.039 mol) in water (50 ml) dropwise at 0° C. the reaction mixture was stirred at same temperature for 2 h. After completion (monitored by TLC in 50% EA-Hexane, Rf 0.3), the reaction mixture was diluted with ethyl acetate and washed with water followed by brine. The organic layer was dried over Na₂SO₄ and concentrated. The obtained crude material was purified by column chromatography (using silica gel 100-200 mesh, 70% EA-hexane as eluent) to obtain rac-(3S,4S,5S)-5-(5-chlorothiophen-2-yl)-3-methyl-4-nitropyrrolidin-2-one (2.3 g, 82%) as off white solid.

Step-3: Synthesis of rac-(3S,4S,5S)-4-amino-5-(5-chlorothiophen-2-yl)-3-methylpyrrolidin-2-one. To a stirred solution of rac-(3S,4S,5S)-5-(5-chlorothiophen-2-yl)-3-methyl-4-nitropyrrolidin-2-one (1.8 g, 6.9 mmol) in EtOAc/MeOH (360 ml, 2:1) was added 6 N aq. HCl (35 ml) at 0° C. To the mixturewas added Zn dust (27.07 g, 414 mmol) portionwise at the same temperature. The resulting suspension was stirred at room temperature for 16 h. After completion (monitored by LCMS), the reaction mixture was quenched with saturated NaHCO₃ solution at 0° C., stirred for 1 h, filtered over celite and washed with EtOAc/MeOH (500 ml, 2:1). The filtrate was concentrated to afford rac-(3S,4S,5S)-4-amino-5-(5-chlorothiophen-2-yl)-3-methylpyrrolidin-2-one (1.6 g, crude) as off white solid. The crude product was used in the next step without further purification.

Step-4: Synthesis of intermediate A16. To a stirred suspension rac-(3S,4S,5S)-4-amino-5-(5-chlorothiophen-2-yl)-3-methylpyrrolidin-2-one (3 g, 0.013 mol) in THF/Water (60 ml, 1:1) was added sodium bicarbonate (5.46 g, 0.065 mol) at 0° C. and stirred for 30 minutes. To this was added benzyl chloroformate (50% solution in toluene, 6.65 g, 0.0195 mol) at the same temperature and stirring was continued at rt for 16 h. After completion (monitored by LCMS), the reaction mixture was diluted with water (100 ml) and extracted with ethyl acetate (3×90 ml). The combined organics were washed with water (90 ml) followed by brine (90 ml). The organic layer was dried over Na$_2$SO$_4$ and concentrated. Crude material was purified by column chromatography (using silica gel 100-200 mesh; 2-2.5% MeOH/DCM eluent) to afford intermediate A16 benzyl(rac-(2S,3S,4S)-2-(5-chlorothiophen-2-yl)-4-methyl-5-oxopyrrolidin-3-yl)carbamate (3 g, 79% in 2 steps) as off-white solid.

Synthesis of Intermediate A18 benzyl(rac-(2S,3S, 4S)-4-methyl-2-(1-methyl-1H-pyrazol-3-yl)-5-oxopyrrolidin-3-yl)carbamate

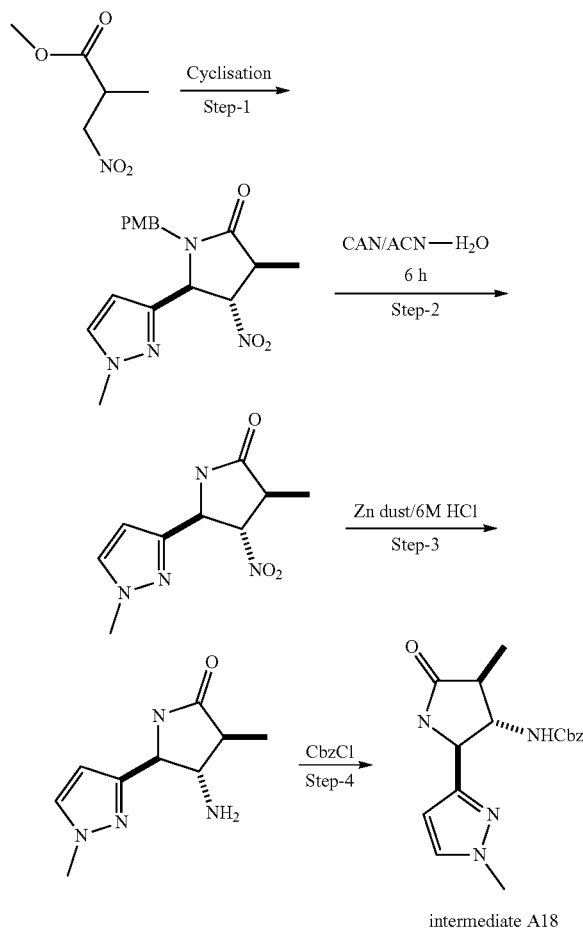

intermediate A18

Step-1: Preparation of rac-(3S,4S,5S)-1-(4-methoxybenzyl)-3-methyl-5-(1-methyl-1H-pyrazol-3-yl)-4-nitropyrrolidin-2-one. To a stirred solution of 1-methyl-1H-pyrazole-3-carbaldehyde (5 g, 45.46 mmol) in Toluene (75 ml) was added 4-methoxy benzylamine (6.86 g, 50.01 mmol) at rt and stirred for 2 h. To this reaction mixture was added 2-methyl-3-nitropropanoate (8.68 g, 59.09 mmol) followed by benzoic acid (8.33 g, 687.18 mmol) and stirring was continued for 16 h at 70° C. After completion of the reaction (monitored by LCMS), the reaction mixture was diluted with ethyl acetate (200 ml) and washed with water (200 ml), followed by sat. aq. NaHCO$_3$ (75 ml×2). The organic layer was dried over anhydrous Na$_2$SO$^4$ and concentrated. Crude was purified by column chromatography (using silica gel 100-200 mesh; 25-30% ethyl acetate/hexane eluent) to afford rac-(3S,4S,5S)-1-(4-methoxybenzyl)-3-methyl-5-(1-methyl-1H-pyrazol-3-yl)-4-nitropyrrolidin-2-one (4 g, 26%) off white solid.

Step-2: Preparation of rac-(3S,4S,5S)-3-methyl-5-(1-methyl-1H-pyrazol-3-yl)-4-nitropyrrolidin-2-one. To a stirred solution of rac-(3S,4S,5S)-1-(4-methoxybenzyl)-3-methyl-5-(1-methyl-1H-pyrazol-3-yl)-4-nitropyrrolidin-2-one (2 g, 5.814 mmol) in CH$_3$CN (40 ml) was added a solution of CAN (6.37 g, 11.63 mmol) in water (40 ml) dropwise at 0° C. The reaction mixture was stirred at same temperature for 2 h. After completion (monitored by TLC in 50% EA-Hexane, Rf 0.3), the reaction mixture was diluted with ethyl acetate and washed with water followed by brine. The organic layer was dried over Na$_2$SO$_4$ and concentrated. Two more identical batches were conducted using the procedure described above. The crude material of the composite batch was purified by column chromatography (using silica gel 100-200 mesh, 70% EA-hexane as eluent) to afford rac-(3S,4S,5S)-3-methyl-5-(1-methyl-1H-pyrazol-3-yl)-4-nitropyrrolidin-2-one (2.4 g, 61.4%) as off white solid.

Step-3: Preparation of rac-(3S,4S,5S)-4-amino-3-methyl-5-(1-methyl-1H-pyrazol-3-yl)pyrrolidin-2-one. To a stirred solution of rac-(3S,4S,5S)-3-methyl-5-(1-methyl-1H-pyrazol-3-yl)-4-nitropyrrolidin-2-one (2.5 g, 11.16 mmol) in EtOAc/MeOH (2; 1, 200 ml) was added aq. 6 N HCl (56 ml) at 0° C. To this reaction mixture was added Zn dust (43.8 g, 669.64 mmol) portionwise at the same temperature. The resulting suspension was stirred at room temperature for 16 h. After completion (monitored by TLC in 10% MeOH-DCM, Rf 0.4), the reaction mixture was quenched with saturated aq. NaHCO$_3$ solution at 0° C. and filtered over celite, washed with EtOAc/MeOH (500 ml, 2:1) and concentrated to afford rac-(3S,4S,5S)-4-amino-3-methyl-5-(1-methyl-1H-pyrazol-3-yl)pyrrolidin-2-one (2.5 g, crude). The crude product was used in the next step without further purification.

Step-4: Preparation of intermediate A18. To a stirred suspension of rac-(3S,4S,5S)-4-amino-3-methyl-5-(1-methyl-1H-pyrazol-3-yl)pyrrolidin-2-one (2.5 g crude, 12.87 mmol) in THF/Water (1; 1, 250 ml) was added sodium bicarbonate (5.41 g, 64.43 mmol) at 0° C. and stirred for 30 minutes. To this reaction mixture was added benzyl chloroformate (6.4 ml, 19.32 mmol, 50% in toluene) at 0° C. and stirred at rt for 16 h. After completion of the reaction (monitored by LCMS), the mixture was diluted with water (500 ml) and extracted with ethyl acetate (3×500 ml). The combined organic layers were washed with water (250 ml×2) followed by brine (500 ml). Organic part was dried over Na$_2$SO$_4$ and concentrated. Crude material was purified by column chromatography (using silica gel 100-200 mesh; 2-2.5% MeOH/DCM as eluent) to afford intermediate A18 benzyl(rac-(2S,3S,4S)-4-methyl-2-(1-methyl-1H-pyrazol-3-yl)-5-oxopyrrolidin-3-yl)carbamate (1.99 g, 54.3% in two steps) as off white solid.

Synthesis of Intermediate A20 benzyl(rac-(2R,3S,4S)-4-benzyl-2-ethyl-5-oxopyrrolidin-3-yl)carbamate

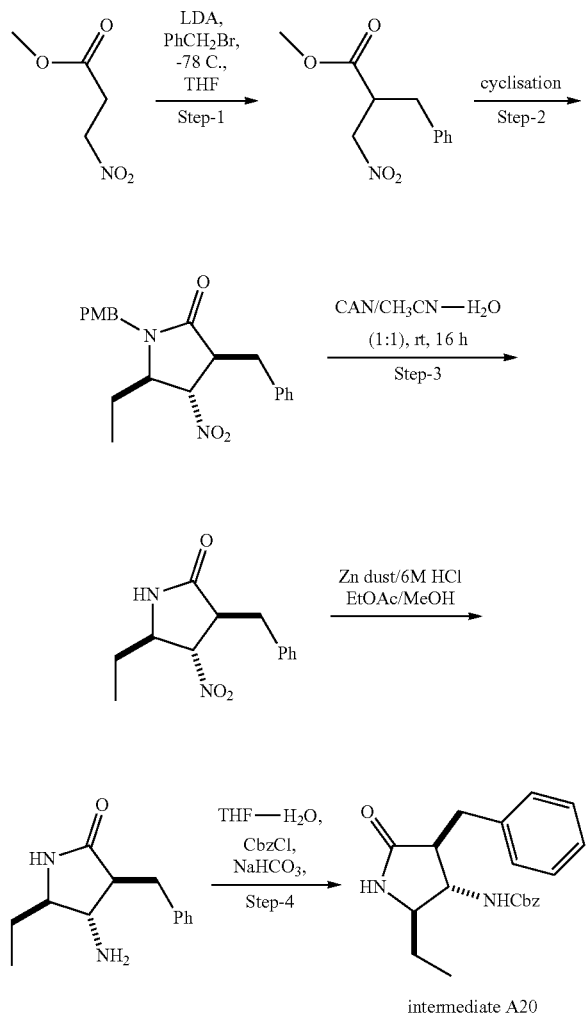

intermediate A20

Step-1: Synthesis of methyl 2-benzyl-3-nitropropanoate. To a stirred solution of LDA (2 M in THF, 22.5 ml, 45.09 mmol) in THF (30 ml) was added a solution of methyl 3-nitropropanoate (3 g, 22.54 mmol) and DMPU (27.3 ml, 222.49 mmol) in THF (20 ml) at −78° C. and stirring was continued for 30 minutes at the same temperature. A solution of (bromomethyl)benzene (2.69 ml, 22.54 mmol) in THF (15 ml) was added at −78° C. and stirred for 2 h at the same temperature. The mixture was gradually allowed to reach 25° C. and stirred for 16 h. The reaction mixture was quenched with 1 N HCl (100 ml) at 0° C. and extracted with ethyl acetate (100 ml×2). The combined organic layers were washed with water (100 ml), saturated aqueous NaHCO$_3$ solution (100 ml) followed by brine (100 ml), dried over Na2SO4 and concentrated. The crude product was purified by column chromatography (using 100-200 silica gel, 10-12% Ethyl acetate-Hexane as eluent) to afford methyl 2-benzyl-3-nitropropanoate (3.3 g, 65.65%) as light yellow oil.

Step-2: Synthesis of rac-(3S,4S,5R)-3-benzyl-5-ethyl-1-(4-methoxybenzyl)-4-nitropyrrolidin-2-one. To a stirred solution of propionaldehyde (3.61 ml, 50.39 mmol) in toluene (75 ml) was added 4-methoxy benzylamine (6.91 g, 50.39 mmol) at 25° C. and stirring was continued for 2 h. To this reaction mixture was added methyl 2-benzyl-3-nitropropanoate (7.5 g, 33.59 mmol) followed by benzoic acid (6.15 g, 50.39 mmol) and stirred for 7-8 h at 70° C. After completion of the reaction (monitored by TLC, 30% EA/Hexane, Rf=0.4), the reaction mixture was diluted with ethyl acetate (300 ml) and washed with water (300 ml), followed by sat. aq. NaHCO$_3$ (200 ml×2). The organic layer was dried over anhydrous Na$_2$SO$_4$ and concentrated. The crude product was purified by column chromatography (using silica gel 100-200 mesh; 25-30% ethyl acetate/hexane eluent) to afford rac-(3S,4S,5R)-3-benzyl-5-ethyl-1-(4-methoxybenzyl)-4-nitropyrrolidin-2-one (3.5 g, 28.3%) as brown oil.

Step-3: Synthesis of rac-(3S,4S,5R)-3-benzyl-5-ethyl-4-nitropyrrolidin-2-one. To a stirred solution of rac-(3S,4S,5R)-3-benzyl-5-ethyl-1-(4-methoxybenzyl)-4-nitropyrrolidin-2-one (3.6 g, 9.77 mmol) in acetonitrile (36 ml) was added a solution of CAN (16.1 g, 29.31 mmol) in water (36 ml) dropwise at 0° C. The reaction mixture was slowly warmed up to 10-15° C. and stirring was continued for 3-4 h. After completion of the reaction (monitored by TLC, 40% acetone in hexanes, Rf 0.3), the mixture was diluted with ethyl acetate (200 ml) and washed with water (200 ml) followed by brine (200 ml). The organic layer was dried over Na$_2$SO$_4$ and concentrated. The crude material was purified by column chromatography (using silica gel 100-200 mesh; 35-40% ethyl acetate/hexanes as eluent) to afford rac-(3S,4S,5R)-3-benzyl-5-ethyl-4-nitropyrrolidin-2-one (1.53 g, 63%) as light yellow solid.

Step-4: Synthesis of rac-(3S,4S,5R)-4-amino-3-benzyl-5-ethylpyrrolidin-2-one. To a stirred solution of rac-(3S,4S,5R)-3-benzyl-5-ethyl-4-nitropyrrolidin-2-one (2.8 g, 11.27 mmol) in EtOAc/MeOH (252 ml, 2:1) was added 6M aq. HCl solution (80 ml) at 0° C. To this was added Zn dust (44.24 g, 676.68 mmol) portionwise at the same temperature. The resulting suspension was stirred at room temperature for 16 h. After completion of the reaction (monitored by LCMS), the reaction mixture was quenched with saturated NaHCO$_3$ solution at 0° C., stirred for 1 h, filtered over celite and washed with EtOAc/MeOH (300 ml, 2:1). Filtrate was concentrated to afford rac-(3S,4S,5R)-4-amino-3-benzyl-5-ethylpyrrolidin-2-one (2.43 g crude, considered as 100% yield) as off white solid which was used in next step as such.

Step-5: Synthesis of intermediate A20. To a stirred suspension of rac-(3S,4S,5R)-4-amino-3-benzyl-5-ethylpyrrolidin-2-one (2.43 g crude 11.18 mmol) in THF/Water (300 ml, 1:1) was added sodium bicarbonate (4.69 g, 55.91 mmol) at 0° C. and stirred for 30 minutes. To this was added benzyl chloroformate (5.58 ml, 16.77 mmol, 50% in toluene) at 0° C. and stirred at rt for 16 h. After completion of the reaction (monitored by LCMS), the reaction mixture was diluted with water (300 ml) and extracted with ethyl acetate (3×300 ml). The combined organic layers were washed with water (300 ml) followed by brine (300 ml), dried over Na$_2$SO$_4$ and concentrated. The crude product was purified by column chromatography (using silica gel 100-200 mesh; 1.5-2% MeOH/DCM eluent) to afford intermediate A20 benzyl(rac-(2R,3S,4S)-4-benzyl-2-ethyl-5-oxopyrrolidin-3-yl)carbamate (2.95 g, 74.9%) as off white solid.

Synthesis of Intermediate A9 rac-(3S,4S,5R)-4-amino-1-(1-(4-fluorophenyl)-1H-indazol-5-yl)-3-methyl-5-phenylpyrrolidin-2-one

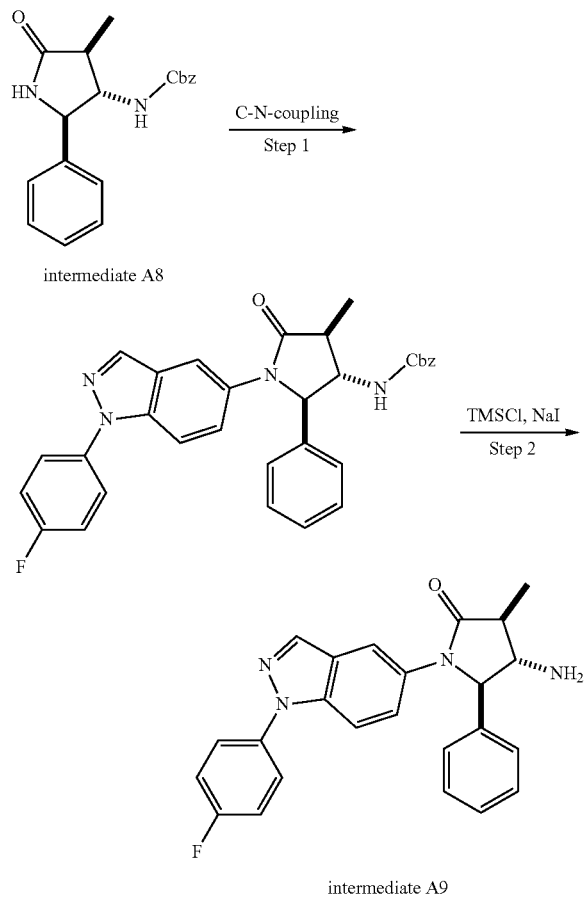

intermediate A8 intermediate A9

Step 1: Synthesis of benzyl N-[rac-(2R,3S,4S)-1-[1-(4-fluorophenyl)indazol-5-yl]-4-methyl-5-oxo-2-phenyl-pyrrolidin-3-yl]carbamate. In a microwave vial, benzyl N-[rac (2R,3S,4S)-4-methyl-5-oxo-2-phenyl-pyrrolidin-3-yl] carbamate (500 mg, 1.54 mmol) was added to 1-(4-fluorophenyl)-5-iodo-indazole (537 mg, 1.70 mmol), $K_3PO_4$ (654 mg, 3.08 mmol) and CuI (58.7 mg, 0.308 mmol). The vial was sealed and purged with nitrogen. To the mixture, 1,4-dioxane (15.4 mL), followed by (1R,2R)—N,N'-Dimethyl-1,2-cyclohexandiamine (87.7 mg, 0.617 mmol) were added subsequently. The mixture was heated to 100° C. overnight and to 110° C. for 5 h afterwards. After reaction control (UPLC) showed full conversion of the starting material, the slurry was allowed to cool down to room temperature and ethyl acetate followed by sat. $NaHCO_3$-solution were added. The mixture was stirred for 5 minutes, the layers were separated and the aqueous layer was extracted with ethyl acetate once. The combined organic layers were washed with brine and dried over $MgSO_4$. Flash chromatography (40 g silica-cartridge, cyclohexane/ethyl acetate gradient as eluent) of the crude material gave N-[rac-(2R,3S,4S)-1-[1-(4-fluorophenyl)indazol-5-yl]-4-methyl-5-oxo-2-phenyl-pyrrolidin-3-yl]carbamate (465 mg, 0.870 mmol, 56%) as a white solid.

Step 2: A solution of N-[rac-(2R,3S,4S)-1-[1-(4-fluorophenyl)indazol-5-yl]-4-methyl-5-oxo-2-phenyl-pyrrolidin-3-yl]carbamate (465 mg, 0.870 mmol) in acetonitrile (23 ml) was added to NaI (783 mg, 5.22 mmol) in a sealed tube. To this mixture, trimethylsilyl chloride (0.442 mL, 3.48 mmol) was added dropwise. The reaction mixture was stirred at room temperature overnight and was slowly added to ethanol (28 ml) after reaction control showed completion (UPLC). The resulting solution was charged on a 5 g SCX cartridge, washed two times with ethanol (15 ml each) and eluated with 2M ammonia in methanol. The methanolic fractions were combined. Evaporation of the solvent gave (rac-3S,4S,5R)-4-amino-1-[1-(4-fluorophenyl)indazol-5-yl]-3-methyl-5-phenyl-pyrrolidin-2-one intermediate A9 (316 mg, 0.789 mmol, 91%) as a white solid.

The intermediates in the following table were synthesized in analogy to intermediate 9 described above, using different building blocks

| Intermediate # | Structure | Made of |
|---|---|---|
| A11-trans | (structure shown) | Intermediate A-10-trans |
| A11-cis | (structure shown) | Intermediate A-10-cis |

| Intermediate # | Structure | Made of |
|---|---|---|
| A13-trans | 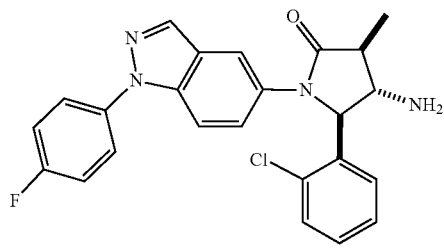 [SMILES: C[C@@H]1C(=O)N(c2ccc3c(cnn3-c3ccc(F)cc3)c2)[C@H](c2ccccc2Cl)[C@H]1N] | Intermediate A12-trans |
| A13-cis | 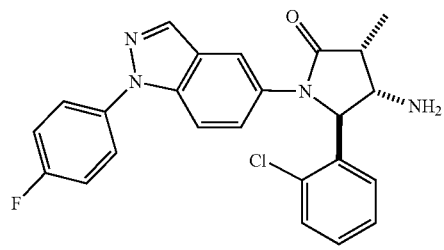 [SMILES: C[C@H]1C(=O)N(c2ccc3c(cnn3-c3ccc(F)cc3)c2)[C@H](c2ccccc2Cl)[C@H]1N] | Intermediate A12-cis |
| A19 | 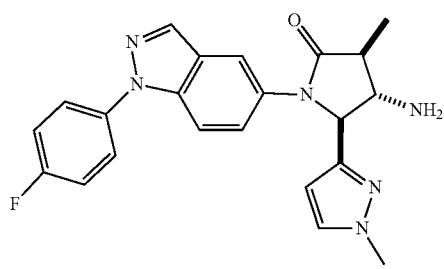 [SMILES: C[C@@H]1C(=O)N(c2ccc3c(cnn3-c3ccc(F)cc3)c2)[C@H](c2ccn(C)n2)[C@H]1N] | Intermediate A18 |
| A21 | 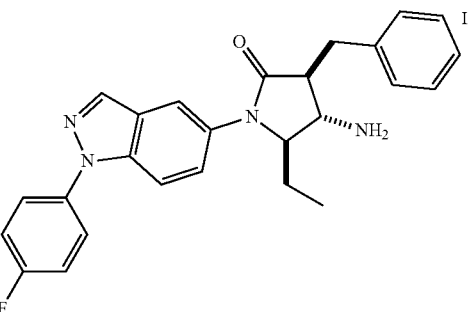 | Intermediate A20 |

Synthesis of Intermediates A15-cis benzyl(rac-(2R,3S,4R)-1-(1-(4-fluorophenyl)-1H-indazol-5-yl)-2-(4-methoxyphenyl)-4-methyl-5-oxopyrrolidin-3-yl)carbamate and Intermediate A15-trans benzyl(rac-(2R,3S,4S)-1-(1-(4-fluorophenyl)-1H-indazol-5-yl)-2-(4-methoxyphenyl)-4-methyl-5-oxopyrrolidin-3-yl)carbamate

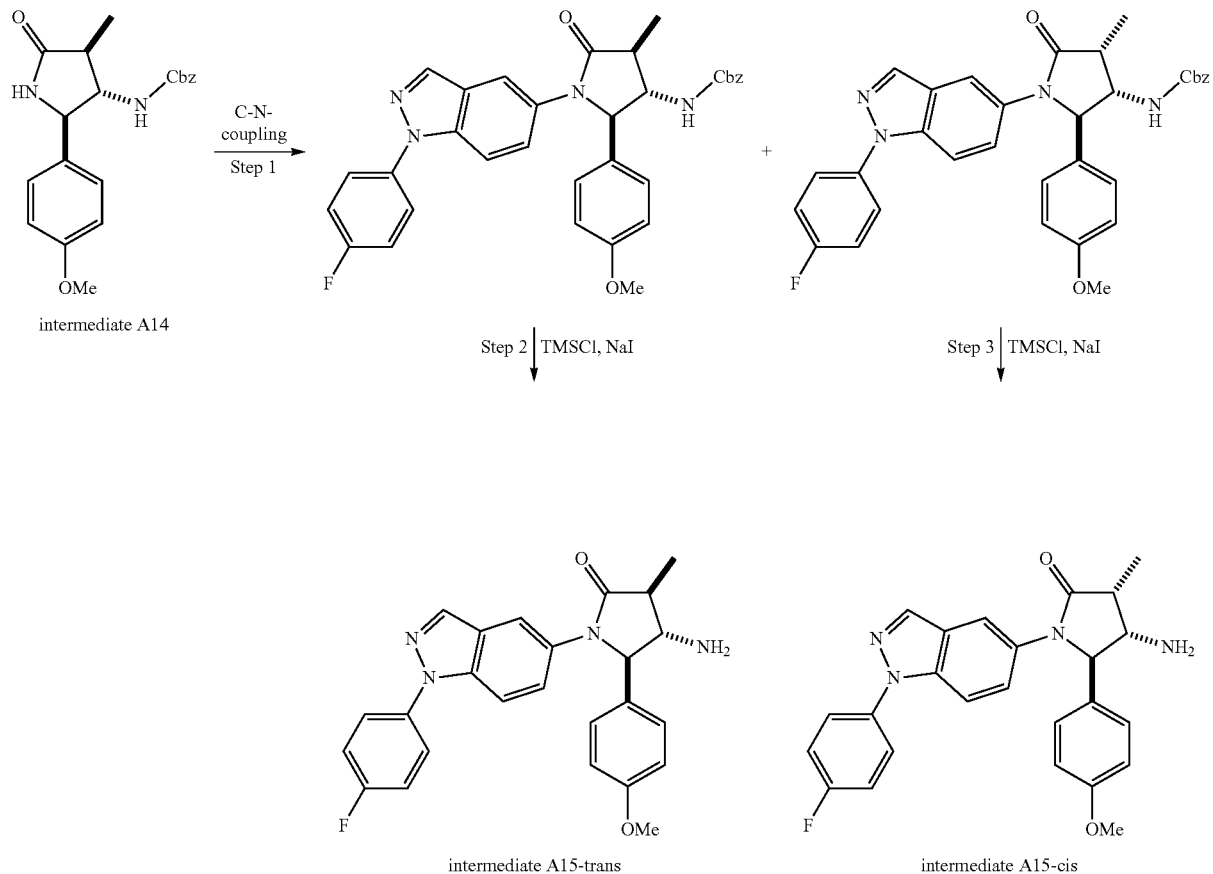

Step 1: Synthesis of benzyl(rac-(2R,3S,4S)-1-(1-(4-fluorophenyl)-1H-indazol-5-yl)-2-(4-methoxyphenyl)-4-methyl-5-oxopyrrolidin-3-yl)carbamate and benzyl(rac-(2R,3S,4R)-1-(1-(4-fluorophenyl)-1H-indazol-5-yl)-2-(4-methoxyphenyl)-4-methyl-5-oxopyrrolidin-3-yl)carbamate. In a microwave vial, intermediate A14 (500 mg, 1.54 mmol) was added to 1-(4-fluorophenyl)-5-iodo-indazole (524 mg, 1.55 mmol, 1.1 eq.), $K_3PO_4$ (599 mg, 2.82 mmol, 2.0 eq.) and CuI (53.7 mg, 0.282 mmol, 0.2 eq.). The vial was sealed and purged with nitrogen. To the mixture 1,4-dioxane (14.1 mL), followed by (1R,2R)—N,N'-Dimethyl-1,2-cyclohexandiamine (80.3 mg, 0.564 mmol, 0.4 eq.) were added subsequently. The mixture was heated to 100° C. overnight and to 110° C. for 5 h. After reaction control (UPLC) showed full conversion of the starting material, the slurry was allowed to cool down to room temperature and ethyl acetate followed by sat. $NaHCO_3$-solution were added. The mixture was stirred for 5 minutes, the layers were separated and the aqueous layer was extracted with ethyl acetate once. The combined organic layers were washed with brine and dried over $MgSO_4$. Flash chromatography (40 g silica-cartridge, cyclohexane/ethyl acetate gradient as eluent) of the crude material gave benzyl(rac-(2R,3S,4S)-1-(1-(4-fluorophenyl)-1H-indazol-5-yl)-2-(4-methoxyphenyl)-4-methyl-5-oxopyrrolidin-3-yl)carbamate (545 mg, 0.965 mmol, 68%) and the epimer benzyl(rac-(2R,3S,4R)-1-(1-(4-fluorophenyl)-1H-indazol-5-yl)-2-(4-methoxyphenyl)-4-methyl-5-oxopyrrolidin-3-yl)carbamate (116 mg, 0.206 mmol, 15%).

Step 2: According to the procedure described for intermediate A9, step 2, (rac-(2R,3S,4S)-1-(1-(4-fluorophenyl)-1H-indazol-5-yl)-2-(4-methoxyphenyl)-4-methyl-5-oxopyrrolidin-3-yl)carbamate was used to obtain intermediate A15-trans benzyl(rac-(2R,3S,4S)-1-(1-(4-fluorophenyl)-1H-indazol-5-yl)-2-(4-methoxyphenyl)-4-methyl-5-oxopyrrolidin-3-yl)carbamate.

Step 3: According to the procedure described for intermediate A9, step 2, (rac-(2R,3S,4R)-1-(1-(4-fluorophenyl)-1H-indazol-5-yl)-2-(4-methoxyphenyl)-4-methyl-5-oxopyrrolidin-3-yl)carbamate was used to obtain intermediate A15-cis benzyl((2R,3S,4S)-1-(1-(4-fluorophenyl)-1H-indazol-5-yl)-2-(4-methoxyphenyl)-4-methyl-5-oxopyrrolidin-3-yl)carbamate.

Synthesis of Intermediate A17-cis (3R,4S,5S)-4-amino-5-(5-chlorothiophen-2-yl)-1-(1-(4-fluorophenyl)-1H-indazol-5-yl)-3-methylpyrrolidin-2-one and Intermediate A17-trans (3S,4S,5S)-4-amino-5-(5-chlorothiophen-2-yl)-1-(1-(4-fluorophenyl)-1H-indazol-5-yl)-3-methylpyrrolidin-2-one

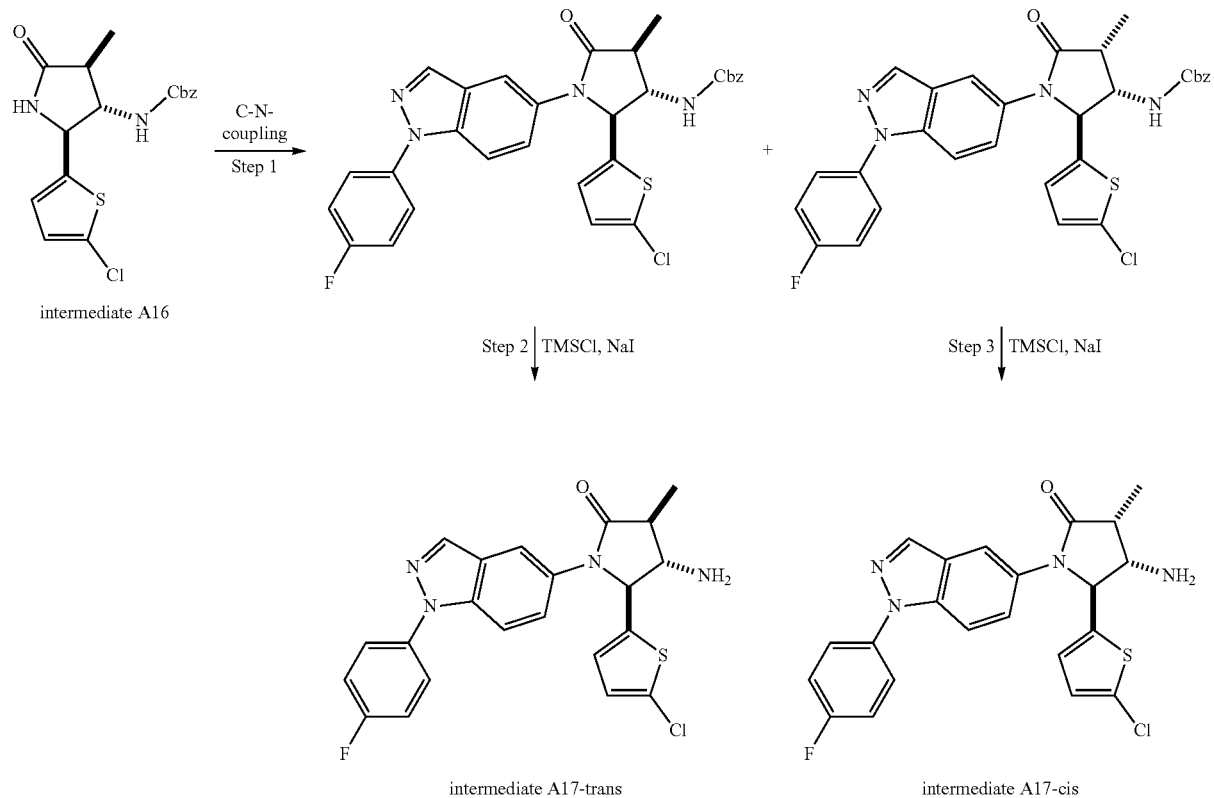

Step 1: Synthesis of benzyl(rac-(2S,3S,4S)-2-(5-chlorothiophen-2-yl)-1-(1-(4-fluorophenyl)-1H-indazol-5-yl)-4-methyl-5-oxopyrrolidin-3-yl)carbamate and benzyl(rac-(2S,3S,4R)-2-(5-chlorothiophen-2-yl)-1-(1-(4-fluorophenyl)-1H-indazol-5-yl)-4-methyl-5-oxopyrrolidin-3-yl)carbamate: In analogy to the procedure described for intermediates A15-trans and A15-cis step 1, intermediate A16 (500 mg, 1.37 mmol) was coupled with 1-(4-fluorophenyl)-5-iodo-indazole (510 mg, 1.51 mmol, 1.1 eq) to obtain benzyl(rac-(2S,3S,4S)-2-(5-chlorothiophen-2-yl)-1-(1-(4-fluorophenyl)-1H-indazol-5-yl)-4-methyl-5-oxopyrrolidin-3-yl)carbamate (644 mg, 1.12 mmol, 82%) and the epimer benzyl(rac-(2S,3S,4R)-2-(5-chlorothiophen-2-yl)-1-(1-(4-fluorophenyl)-1H-indazol-5-yl)-4-methyl-5-oxopyrrolidin-3-yl)carbamate (118 mg, 0.205 mmol, 15%).

Step 2: According to the procedure described for intermediate A9, step 2, ((2S,3S,4S)-2-(5-chlorothiophen-2-yl)-1-(1-(4-fluorophenyl)-1H-indazol-5-yl)-4-methyl-5-oxopyrrolidin-3-yl)carbamate was deprotected to obtain intermediate A17-trans (3S,4S,5S)-4-amino-5-(5-chlorothiophen-2-yl)-1-(1-(4-fluorophenyl)-1H-indazol-5-yl)-3-methylpyrrolidin-2-one.

Step 3: According to the procedure described for intermediate A9, step 2, ((2S,3S,4R)-2-(5-chlorothiophen-2-yl)-1-(1-(4-fluorophenyl)-1H-indazol-5-yl)-4-methyl-5-oxopyrrolidin-3-yl)carbamate was deprotected to obtain intermediate A17-cis (3R,4S,5S)-4-amino-5-(5-chlorothiophen-2-yl)-1-(1-(4-fluorophenyl)-1H-indazol-5-yl)-3-methylpyrrolidin-2-one.

Synthesis of 1-(4-fluorophenyl)-5-iodo-1H-indole (Intermediate B1)

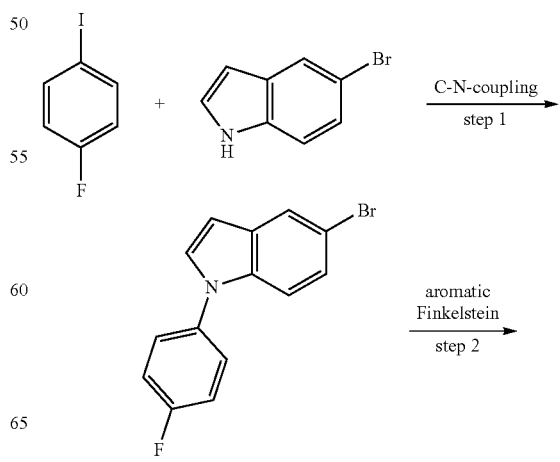

-continued

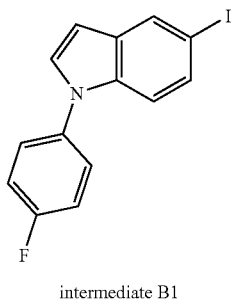

intermediate B1

Step 1: 5-Bromo-1H-indole (750.0 mg, 3.826 mmol, 1.0 eq.), 1-fluoro-4-iodo-benzene (891.7 mg, 4.017 mmol, 1.05 eq.), $K_3PO_4$ (1624.1 mg, 6.513 mmol, 2.0 eq.) and copper iodide (582.9 mg, 3.061 mmol, 0.8 eq.) were weighed out into a vial, a stir bar was added, the vial was sealed and was purged with nitrogen. Then, 1,4-dioxane (19.1 mL) and trans-N,N-dimethyl cyclohexane-1,2-diamine (54.4 mg, 0.3826 mmol, 0.1 eq.) were added, and the reaction mixture was heated to 100° C. for 16 h. The reaction mixture was then cooled to ambient temperature, was diluted with DCM and sat. $NaHCO_3$ solution and was filtered through a hydrophobic frit. The organic solvent was removed, and the remains were purified via silica gel chromatography to yield 5-bromo-1-(4-fluorophenyl)-1H-indole in 35% yield.

Step 2: 5-Bromo-1-(4-fluorophenyl)indole (2300 mg, 7.927 mmol, 1.0 eq.), NaI (5941 mg, 39.6 mmol, 5.0 eq.) $K_3PO_4$ (3365 mg, 15.8 mmol, 2.0 eq.) and copper iodide (1207 mg, 6.3419 mmol, 0.8 eq.) were weighed out into a flask, a stir bar was added, the vial was sealed and was purged with nitrogen. Then, 1,4-dioxane (58.4 mL) and trans-N,N-dimethyl cyclohexane-1,2-diamine (112.8 mg, 0.793 mmol, 0.1 eq.) were added, and the reaction mixture was heated to 100° C. for one week. The reaction mixture was then cooled to ambient temperature, was diluted with DCM and sat. $NaHCO_3$ solution and was filtered through a hydrophobic frit. The organic solvent was removed, and the remains were purified via silica gel chromatography to yield 1580 mg of intermediate B1 (53%).

Synthesis of 5-bromo-1-(4-fluorophenyl)-1H-pyrazolo[3,4-b]pyridine (Intermediate B2)

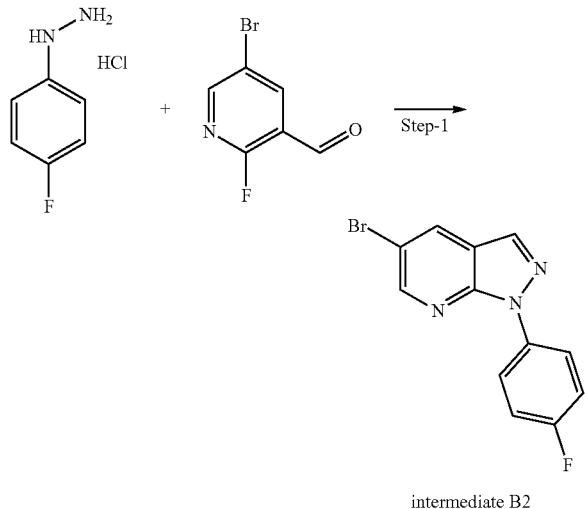

intermediate B2

Step 1: Intermediate B2 was prepared in analogy to the synthesis of intermediate B4, using 5-bromo-2-fluoro-pyridine-3-carbaldehyde instead of 6-bromo-3-fluoro-pyridine-2-carbaldehyde. Yield: 66%

Synthesis of 5-bromo-1-(4-fluorophenyl)-1H-pyrazolo[3,4-c]pyridine (Intermediate B3)

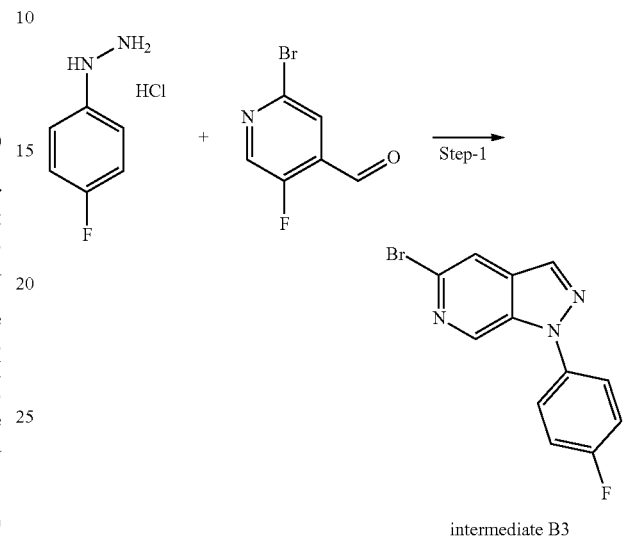

intermediate B3

Step 1: Intermediate B3 was prepared in analogy to the synthesis of intermediate B4, using 2-bromo-5-fluoro-pyridine-4-carbaldehyde instead of 6-bromo-3-fluoro-pyridine-2-carbaldehyde. Yield: 79%

Synthesis of 5-bromo-1-(4-fluorophenyl)-1H-pyrazolo[4,3-b]pyridine (Intermediate B4)

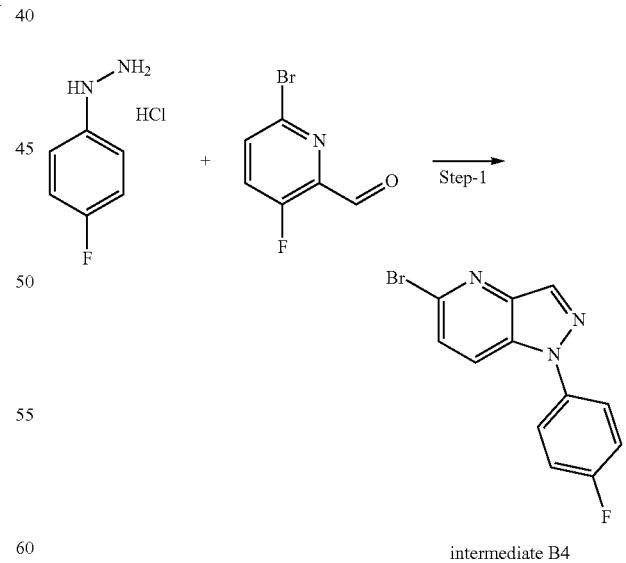

intermediate B4

Step 1: 6-Bromo-3-fluoro-pyridine-2-carbaldehyde (300.0 mg, 1.471 mmol, 1.0 eq.) and (4-fluorophenyl) hydrazine hydrochloride (239.1 mg, 1.471 mmol, 1.0 eq.) were dissolved in NMP (3.0 mL) and the resaction mixture was stirred for 90 minutes. Then, $Cs_2CO_3$ (1437.8 mg, 4.412 mmol, 3.0 eq.) was added and the reaction mixture was heated to 115° C. for 90 minutes. The reaction mixture was then allowed to warm to ambient temperature, and was diluted with EtOAc and water. The layers were separated, and the aquous phase was extracted two time with EtOAc. The combined organic layers were washed with water and brine, dried over MgSO₄ and the solvent was removed under reduced pressure. The obtained residue was then purified by LC to yield 297.0 mg (69%) of 5-bromo-1-(4-fluorophenyl)-1H-pyrazolo[4,3-b]pyridine.

Synthesis of Intermediate C1 N-((2R,3S)-1-(1-(4-fluorophenyl)-1H-indazol-5-yl)-5-oxo-2-phenylpyrrolidin-3-yl)cyclopropanecarboxamide

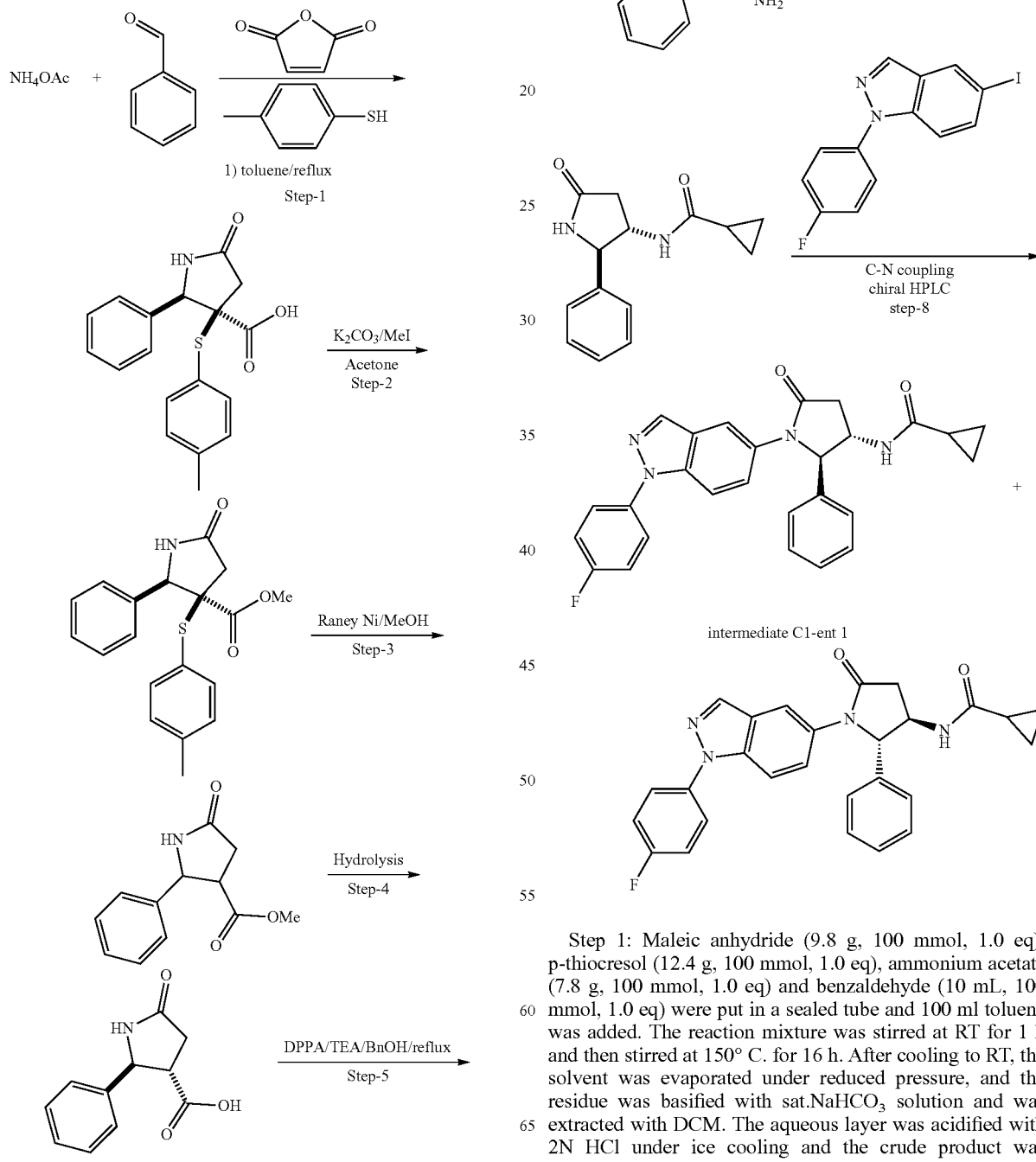

Step 1: Maleic anhydride (9.8 g, 100 mmol, 1.0 eq), p-thiocresol (12.4 g, 100 mmol, 1.0 eq), ammonium acetate (7.8 g, 100 mmol, 1.0 eq) and benzaldehyde (10 mL, 100 mmol, 1.0 eq) were put in a sealed tube and 100 ml toluene was added. The reaction mixture was stirred at RT for 1 h and then stirred at 150° C. for 16 h. After cooling to RT, the solvent was evaporated under reduced pressure, and the residue was basified with sat.NaHCO₃ solution and was extracted with DCM. The aqueous layer was acidified with 2N HCl under ice cooling and the crude product was extracted twice with EtOAc. The combined organic layers were washed with brine, dried over Na₂SO₄, filtered and concentrated to get the crude 5-oxo-2-phenyl-3-(p-tolylthio)pyrrolidine-3-carboxylic acid (10.0 g, crude).

Step 2: To a stirred solution of crude 5-oxo-2-phenyl-3-(p-tolylthio)pyrrolidine-3-carboxylic acid (10.0 g, 30.58 mmol, 1.0 eq) in acetone (100 mL), potassium carbonate (16.8 g, 122.32 mmol, 4.0 eq) and methyl iodide (7.6 ml, 122.32 mmol, 4.0 eq) were added at 0° C., and the reaction was stirred for 16 h at RT. The solvent was removed under reduced pressure, and the residue was partitioned between DCM and water. The aqueous layer was extracted twice with DCM. The combined organic layers were washed with brine, dried over Na₂SO4, filtered, and concentrated. The crude product was purified by column chromatography (100-200 silica gel, 50% EtOAc:hexanes) to give methyl 5-oxo-2-phenyl-3-(p-tolylthio)pyrrolidine-3-carboxylate (4.0 g, 38%) as an off-white solid.

Step 3: To a stirred solution of methyl 5-oxo-2-phenyl-3-(p-tolylthio)pyrrolidine-3-carboxylate (4.0 g, 11.73 mmol, 1.0 eq) in EtOH:THF (100 mL, 2:1), Raney Nickel (1 g) was added and the reaction mixture was stirred for 2 h at RT After completion, the reaction mixture was filtered through a celite bed and the celite bed was washed 2-3 times with EtOAc. The combined organic layers were concentrated and the crude was purified by column chromatography (100-200 silica gel, 50% EtOAc:hexanes) to afford methyl 5-oxo-2-phenylpyrrolidine-3-carboxylate (2.2 g, 88%, syn:anti, 1:1 mixture) as an off-white solid.

Step 4: To a stirred solution of methyl 5-oxo-2-phenylpyrrolidine-3-carboxylate (1.0 g, 4.56 mmol, 1.0 eq) in MeOH (25 mL) was added 2 N NaOH solution (5 mL) and the reaction mixture was stirred at 80° C. for 2 h. After completion of the reaction (monitored by LCMS), the reaction mixture was concentrated and acidified with 2N HCl solution and was extracted with 30% isopropanol-DCM. The combined organic layers were dried over Na₂SO₄ and were concentrated under reduced pressure to get the desired trans-5-oxo-2-phenylpyrrolidine-3-carboxylic acid (0.8 g, 85%).

Step 5: To a stirred solution of trans-5-oxo-2-phenylpyrrolidine-3-carboxylic acid (0.5 g, 2.43 mmol, 1.0 eq) in benzene:THF (25 mL, 4:1) was added TEA (0.68 ml, 4.87 mmol, 2.0 eq) and DPPA (0.68 ml, 3.17 mmol, 1.3 eq) and the reaction mixture was stirred at RT for 2 h. Then benzyl alcohol (0.33 mL, 3.17 mmol, 1.3 eq) was added and the reaction mixture was heated to reflux for 16 h. After completion, the reaction mixture was concentrated under reduced pressure to get the crude compound which was extracted with water and EtOAc. The combined organic layers were dried over Na₂SO₄ and concentrated under reduced pressure to get the crude product which was purified by column chromatography (100-200 mesh silica gel; 2% MeOH-DCM; R$_f$-value-0.5) to afford trans-benzyl (5-oxo-2-phenylpyrrolidin-3-yl)carbamate (0.38 g, 50%).

Step 6: To a stirred solution of trans-benzyl (5-oxo-2-phenylpyrrolidin-3-yl)carbamate (1.7 g, 5.48 mmol, 1.0 eq) in MeOH (20 mL, 2:1), Pd/C (0.058 g, 0.548 mmol, 0.1 eq) was added, and the reaction was stirred with a hydrogen balloon for 2 h at RT. After completion, the reaction mixture was filtered through a celite bed and the celite bed was washed 2-3 times with EtOAc. The combined organic layers were concentrated to get the desired trans-4-amino-5-phenylpyrrolidin-2-one as brown gum (0.9 g, 93%).

Step 7: To a stirred solution of cyclopropanecarboxylic acid (0.59 g, 6.818 mmol, 1.2 eq) in DMF (15 mL) was added HATU (4.32 g, 11.363 mmol, 2.0 eq), DIPEA (5.0 mL, 28.409 mmol, 5.0 eq) and intermediate A2 (1.00 g, 5.681 mmol, 1.0 eq) at 0° C. and the reaction mixture was then stirred at ambient temperature for 16 h. After completion of the reaction (monitored by TLC, TLC system 5% MeOH in DCM, Rf-0.3), the reaction mixture was diluted with EtOAc (35 mL) and was washed with ice cold water (3×25 mL), dried over Na₂SO₄ and concentrated under reduced pressure to get the crude product which was purified by column chromatography (230-400 mesh silica gel; 0 to 4% MeOH-DCM) to afford N-(trans-5-oxo-2-phenylpyrrolidin-3-yl)cyclopropanecarboxamide (0.45 g, 32%).

Step 8: A stirred solution of N-(trans-5-oxo-2-phenylpyrrolidin-3-yl)cyclopropanecarboxamide (0.450 g, 1.844 mmol, 1.0 eq), 1-(4-fluorophenyl)-5-iodo-1H-indazole (0.748 g, 2.213 mmol, 1.2 eq) and K₃PO₄ (0.781 g, 3.688 mmol, 2.0 eq) in 1,4-dioxane (30 mL) was degassed with argon for 30 min. Then, trans-N,N'-dimethylcyclohexane-1,2-diamine (0.104 g, 0.737 mmol, 0.4 eq) and CuI (0.070 g, 0.368 mmol, 0.2 eq) were added and the reaction mixture was stirred for 16 h at 90° C. in a sealed tube. After completion of the reaction (monitored by TLC, TLC system 5% MeOH in DCM, Rf-0.4), the reaction mixture was filtered through a celite bed and the celite bed was washed 2-3 times with 1,4-dioxane. The combined organic layers were concentrated to get the crude product which was purified by column chromatography (230-400 mesh silica gel; 0 to 2% MeOH in DCM) to afford the racemic product. Further enantiomer separation was done by preparative chiral HPLC to afford pure N-((2S,3R)-1-(1-(4-fluorophenyl)-1H-indazol-5-yl)-5-oxo-2-phenylpyrrolidin-3-yl)cyclopropanecarboxamide (0.267 g, 32%; RT=5.56 min; Column Name: Chiralpak IA (250×4.6 mm) 5 μm, Mobile Phase: Hexane/Isopropanol/DCM/DEA: 70/15/15/0.1, Flow Rate: 1.0 ml/min) and intermediate C1-ent1 N-((2R,3S)-1-(1-(4-fluorophenyl)-1H-indazol-5-yl)-5-oxo-2-phenylpyrrolidin-3-yl)cyclopropanecarboxamide (0.254 g, 30%; RT=7.13 min; Column Name: Chiralpak IA (250×4.6 mm) 5 μm, Mobile Phase: Hexane/Isopropanol/DCM/DEA: 70/15/15/0.1, Flow Rate: 1.0 ml/min).

Examples 1 and 2: N-((2R,3S)-1-(1-(4-fluorophenyl)-1H-indazol-5-yl)-4,4-dimethyl-5-oxo-2-phenylpyrrolidin-3-yl)cyclopropanecarboxamide (Example 1) and N-((2 S,3R)-1-(1-(4-fluorophenyl)-1H-indazol-5-yl)-4,4-dimethyl-5-oxo-2-phenylpyrrolidin-3-yl)cyclopropanecarboxamide (Example 2)

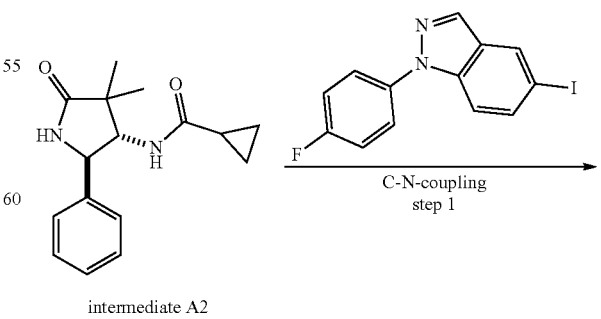

intermediate A2

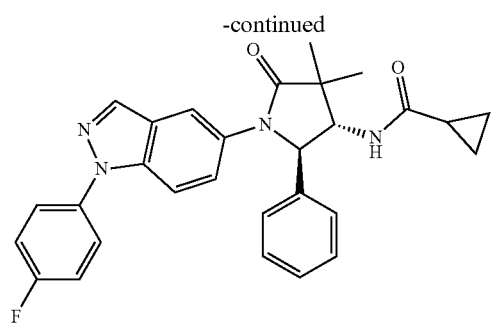

example 1

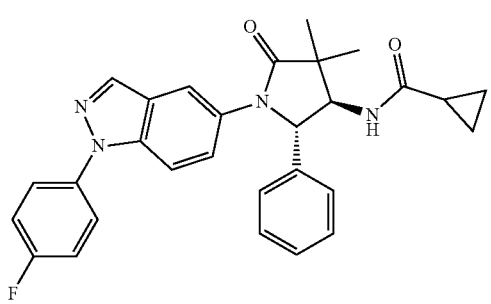

example 2

Step 1: A stirred solution of intermediate A2 (0.35 g, 1.286 mmol, 1.0 eq), 1-(4-fluorophenyl)-5-iodo-1H-indazole (0.520 g, 1.54 mmol, 1.2 eq), K$_3$PO$_4$ (0.545 g, 2.572 mmol, 2.0 eq) in 1,4 dioxane (20 mL) was degassed with argon for 30 min. Then, trans-N,N'-dimethyl cyclohexane-1,2-diamine (0.073 g, 0.514 mmol, 0.4 eq) and CuI (0.049 g, 0.257 mmol, 0.2 eq) were added and the reaction was stirred for 16 h at 90° C. in a sealed tube. After completion of the reaction (monitored by TLC, TLC system 5% MeOH in DCM, Rf-0.4) the reaction mixture was filtered through a celite pad, which was then washed 2-3 times with 1,4-dioxane. The combined organic layers were concentrated to obtain the crude product which was purified by column chromatography (230-400 mesh silica gel; 0 to 2% MeOH in DCM) to afford the racemic compound and further enantiomer separation was carried out via prep. chiral HPLC (column: Chiralpak IC (4.6×250 mm), 5 μm, mobile phase: hexane:ethyl acetate:EtOH:isopropylamine 70:15:15:0.1, flow rate: 1.0 mL/min) to afford example 1 (0.055 g, 9%, retention time: 4.62 minutes) and example 2 (0.057 g, 9%, retention time 6.48 minutes).

$^1$H NMR (400 MHz, DMSO-d$_6$): δ=8.46 (d, 1H), 8.29 (s, 1H), 7.74-7.71 (m, 3H), 7.67 (d, 1H), 7.46 (m, 1H), 7.39 (d, 2H), 7.34-7.32 (m, 2H), 7.22 (t, 2H), 7.14 (t, 2H), 5.11 (d, 1H), 4.29 (t, 1H), 1.69-1.63 (m, 1H), 1.21 (s, 3H), 1.12 (s, 3H), 0.7-0.52 (m, 4H).

Example 5: N-trans-(5-(1-(4-fluorophenyl)-1H-indol-5-yl)-4-oxo-6-phenyl-5-azaspiro[2.4]heptan-7-yl)cyclopropanecarboxamide

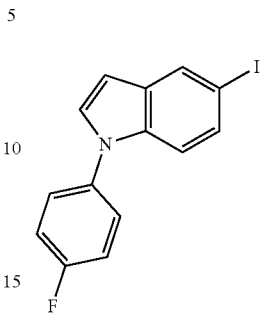

intermediate B1

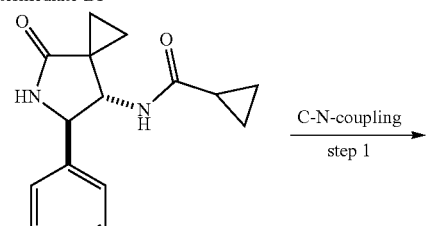

intermediate A5

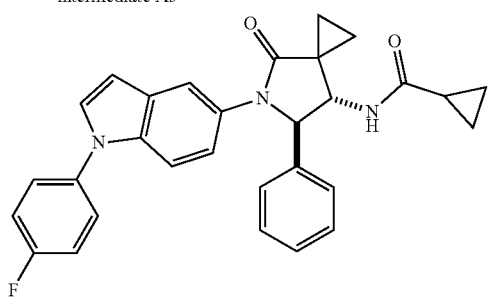

example 5

Step 1: Intermediate A5 (50.0 mg, 0.185 mmol, 1.0 eq.), intermediate B1 (65.5 mg, 0.194 mmol, 1.05 eq.), K$_3$PO$_4$ (78.5 mg, 0.370 mmol, 2.0 eq.) and copper iodide (28.2 mg, 0.148 mmol, 0.8 eq.) were weighed out into a vial, a stir bar was added, the vial was sealed and was purged with nitrogen. Then, 1,4-dioxane (0.9 mL) and trans-N,N'-dimethyl cyclohexane-1,2-diamine (2.5 mg, 0.019 mmol, 0.1 eq.) were added, and the reaction mixture was heated to 100° C. for six days. The reaction mixture was then cooled to ambient temperature, was diluted with DCM and sat. NaHCO$_3$ solution and was filtered through a hydrophobic frit. The organic solvent was removed, and the remains were purified via silica gel chromatography to yield 4.0 mg (4%) of example 5.

$^1$H NMR (DMSO-d$_6$) δ: 8.88 (d, 1H), 7.74-7.70 (m, 1H), 7.62-7.54 (m, 3H), 7.45-7.35 (m, 6H), 7.33 (dd, 2H), 7.27-7.19 (m, 1H), 6.63 (d, 1H), 5.22 (d, 1H), 4.01 (dd, 1H), 1.72-1.64 (m, 1H), 1.28-1.05 (m, 2H), 0.97-0.89 (m, 2H), 0.79-0.73 (m, 1H), 0.73-0.68 (m, 3H).

Example 7: N-((2R,3S)-4,4-dimethyl-1-(1-(1-methyl-6-oxo-1,6-dihydropyridin-3-yl)-1H-indazol-5-yl)-5-oxo-2-phenylpyrrolidin-3-yl)-5-methylisoxazole-3-carboxamide Example 31: N-[rac-((6R,7S)-5-(1-(4-fluorophenyl)-1H-pyrazolo[3,4-b]pyridin-5-yl)-4-oxo-6-phenyl-5-azaspiro[2.4]heptan-7-yl)]cyclopropanecarboxamide

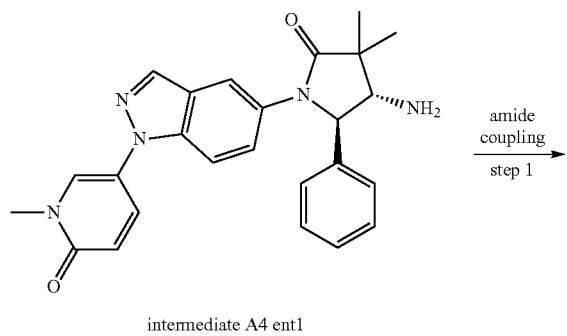

intermediate A4 ent1

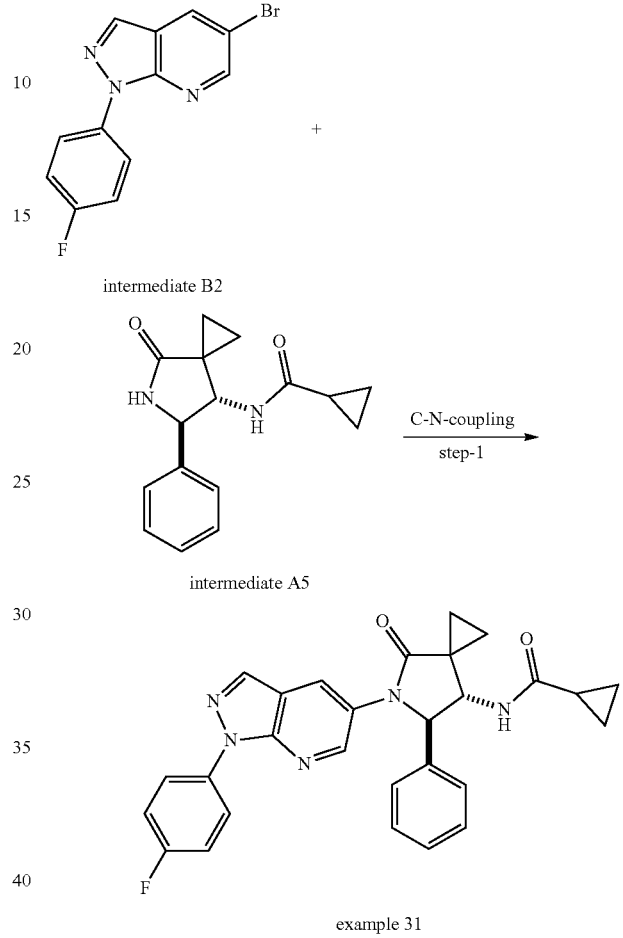

intermediate B2 intermediate A5 example 31

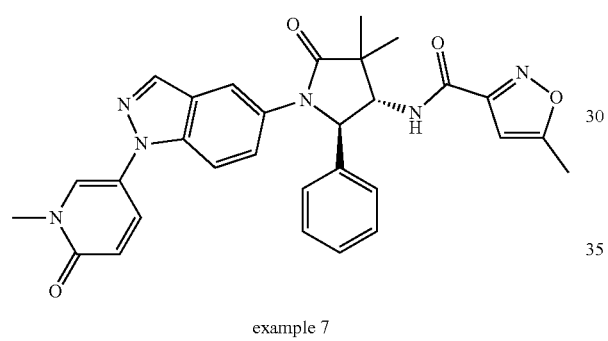

example 7

Step 1: 5-Methylisoxazole-3-carboxylic acid (22.3 mg, 0.175 mmol, 1.5 eq.) was disolved in DCM (1.2 mL), followed by the addition of triethylamine (0.05 mL, 0.351 mmol, 3.0 eq.). Then propylphosphonic anhydride solution (≥50 wt. % in ethyl acetate, 0.14 mL, 2.0 eq.) was added, and the mixture was stirred at ambient temperature for 20 minutes. Then, intermediate A4 ent1 (50.0 mg, 0.117 mmol, 1.0 eq.), was added, and the mixture was stirred for 48 hours at ambient temperature. Then, saturated NaHCO₃ solution and more DCM were added, and the mixture was stirred for 10 minutes. The mixture was then filtered through a hydrophobic frit, and the organic solvent was then removed. The crude remains were purified via silica gel chromatography to yield 36.0 mg (57%) of example 7.

$^1$H NMR (DMSO-d$_6$) δ: 9.09 (d, 1H), 8.26 (d, 1H), 8.17 (d, 1H), 7.72-7.67 (m, 2H), 7.59 (d, 1H), 7.39 (dd, 1H), 7.38-7.36 (m, 2H), 7.26-7.20 (m, 2H), 7.18-7.12 (m, 1H), 6.54 (d, 1H), 6.51 (d, 1H), 5.50 (d, 1H), 4.47 (t, 1H), 3.50 (s, 3H), 2.47 (d, 3H), 1.32 (s, 3H), 1.17 (s, 3H).

Step 1: 5-Bromo-1-(4-fluorophenyl)pyrazolo[3,4-b]pyridine (64.8 mg, 0.222 mmol, 1.2 eq.), intermediate A5 (50.0 mg, 0.185 mmol, 1.0 eq.), K₃PO₄ (78.5 mg, 0.370 mmol, 2.0 eq.), CuI (7.0 mg, 0.037 mmol, 0.2 eq.) and NaI (55.4 mg, 0.370 mmol, 2.0 eq.) were weighed out into a microwave vial. A stir bar was added, the vial was sealed and purged with nitrogen. Then, 1,4-dioxane (1.0 mL) and trans-N,N'-dimethyl cyclohexane-1,2-diamine (0.012 mL, 0.074 mmol, 0.4 eq.) were added and the mixture was stirred at 110° C. for 16 hours. The mixture was then allowed to cool to ambient temperature and was diluted with sat. NaHCO₃ solution and DCM. The mixture was then filtered through a hydrophobic frit. The organic layer was evaporated under reduced pressure and the residue was purified via LC to yield 42.0 mg (47%) of N-[rac-((6R,7S)-5-(1-(4-fluorophenyl)-1H-pyrazolo[3,4-b]pyridin-5-yl)-4-oxo-6-phenyl-5-azaspiro[2.4]heptan-7-yl)]cyclopropanecarboxamide $^1$H NMR (DMSO-d$_6$): δ=8.92-8.86 (m, 2H), 8.44 (d, 1H), 8.40 (s, 1H), 8.25-8.16 (m, 2H), 7.44-7.37 (m, 4H), 7.35 (t, 2H), 7.29-7.23 (m, 1H), 5.37 (d, 1H), 4.13 (dd, 1H), 1.71-1.63 (m, 1H), 1.25 (dd, 1H), 1.18-1.11 (m, 1H), 1.05-0.96 (m, 2H), 0.78-0.68 (m, 4H)

Example 32: N-[rac-((6R,7S)-5-(1-(4-fluorophenyl)-1H-pyrazolo[3,4-c]pyridin-5-yl)-4-oxo-6-phenyl-5-azaspiro[2.4]heptan-7-yl)]cyclopropanecarboxamide

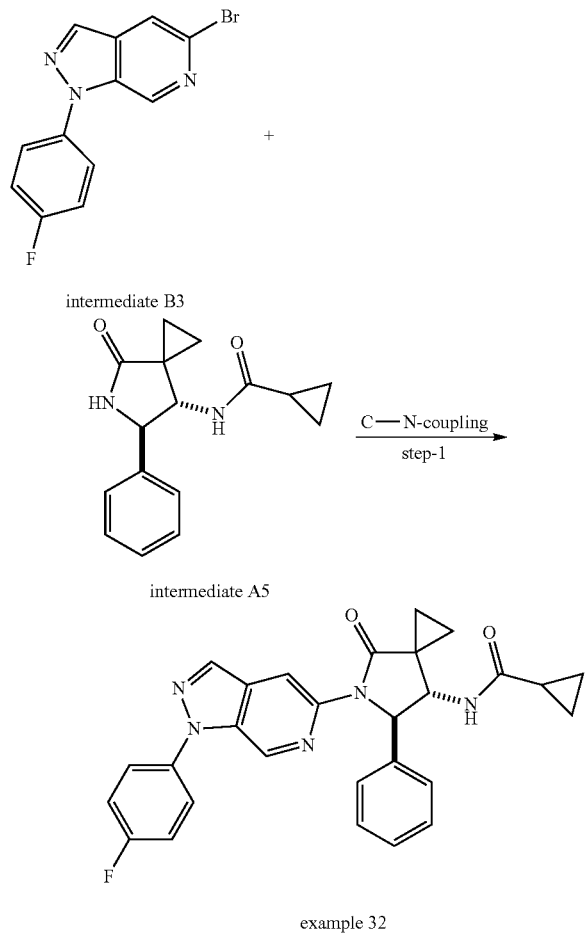

intermediate B3 intermediate A5 example 32

Example 32 was prepared in analogy to the synthesis described for example 31, using intermediate B3 instead of intermediate B2 and requiring an additional HPLC purification. Yield: 35%

¹H NMR (DMSO-d₆): δ=8.99 (p, 1H), 8.90 (d, 1H), 8.76 (q, 1H), 8.54 (q, 1H), 7.88-7.81 (m, 2H), 7.43-7.36 (m, 2H), 7.36-7.26 (m, 4H), 7.23-7.17 (m, 1H), 5.79 (s, 1H), 3.95 (dd, 1H), 1.72-1.64 (m, 1H), 1.25-1.12 (m, 2H), 1.04-0.91 (m, 2H), 0.81-0.66 (m, 4H)

Example 33: N-[rac-((6R,7S)-5-(1-(4-fluorophenyl)-1H-pyrazolo[4,3-b]pyridin-5-yl)-4-oxo-6-phenyl-5-azaspiro[2.4]heptan-7-yl)]cyclopropanecarboxamide

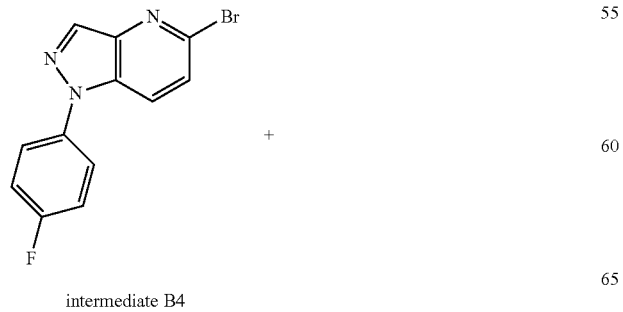

intermediate B4

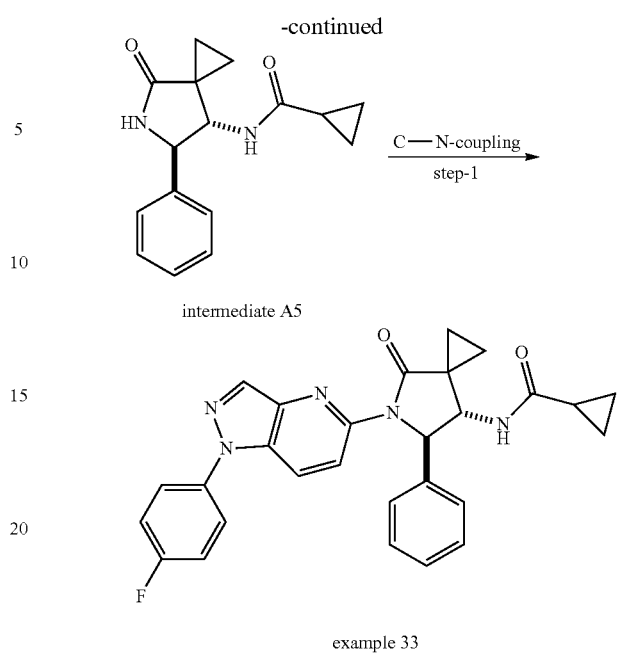

intermediate A5 example 33

Example 33 was prepared in analogy to the synthesis described for example 31, using intermediate B4 instead of intermediate B2. Yield: 32%

¹H NMR (DMSO-d₆): δ=8.91 (d, 1H), 8.62 (d, 1H), 8.39-8.34 (m, 2H), 7.84-7.77 (m, 2H), 7.47-7.40 (m, 2H), 7.40-7.34 (m, 2H), 7.32 (t, 2H), 7.22 (t, 1H), 5.80 (d, 1H), 3.98-3.94 (m, 1H), 1.72-1.62 (m, 1H), 1.26-1.14 (m, 2H), 1.05-0.96 (m, 2H), 0.83-0.75 (m, 1H), 0.75-0.65 (m, 3H)

Example 34a: N-((2R,3S)-1-(1-(4-fluorophenyl)-1H-indazol-5-yl)-4,4-dimethyl-5-oxo-2-phenylpyrrolidin-3-yl)methanesulfonamide

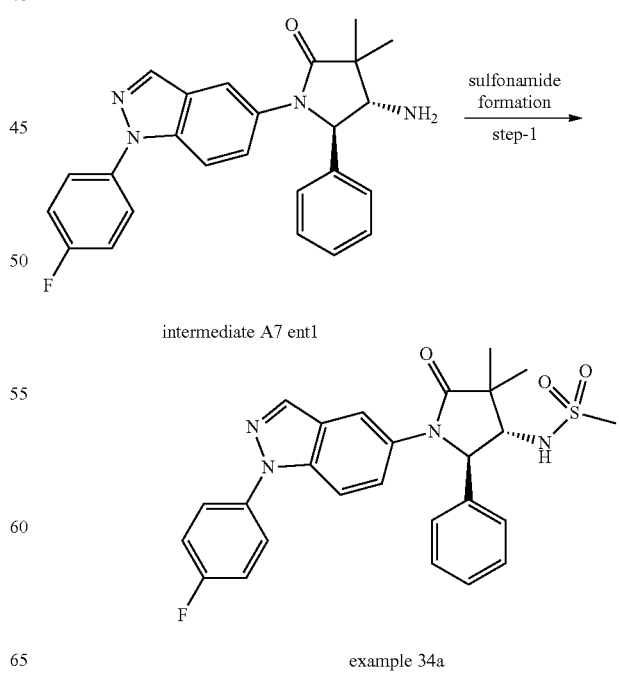

intermediate A7 ent1 example 34a

Step 1: (4S,5R)-4-Amino-1-(1-(4-fluorophenyl)-1H-indazol-5-yl)-3,3-dimethyl-5-phenylpyrrolidin-2-one (50.0 mg, 0.121 mmol, 1.0 eq.) was weighed out into a vial under a nitrogen atmosphere, followed by the addition of DCM (1.2 mL) and triethylamine (0.067 mL, 0.483 mmol, 4.0 eq.). The mixture was then cooled to 0° C., then methanesulfonyl chloride (0.019 mL, 0.241 mmol, 2.0 eq.) was added and the mixture was allowed to stir for 10 minutes at that temperature. The reaction mixture was then diluted with sat. NaHCO$_3$ solution and DCM. The mixture was then filtered through a hydrophobic frit and the organic layer was evaporated to dryness under reduced pressure. The obtained residue was purified via LC to yield 59.4 mg (76%) of N-((2R,3S)-1-(1-(4-fluorophenyl)-1H-indazol-5-yl)-4,4-dimethyl-5-oxo-2-phenylpyrrolidin-3-yl)methane sulfonamide $^1$H NMR (DMSO-d$_6$): δ=8.28 (d, 1H), 8.02 (d, 1H), 7.76-7.69 (m, 3H), 7.69-7.63 (m, 1H), 7.52-7.47 (m, 2H), 7.44-7.35 (m, 3H), 7.29 (dd, 2H), 7.23-7.18 (m, 1H), 5.07 (d, 1H), 3.70 (t, 1H), 2.03 (s, 3H), 1.26 (s, 3H), 1.14 (s, 3H)

The examples in the following table were synthesized in analogy to Example 34a described above, using different intermediates. The individual reaction times vary.

| Ex. # | Intermediate (INT) | Structure | Yield (%) | $^1$H NMR |
|---|---|---|---|---|
| 34a | Int A7 ent 2 | 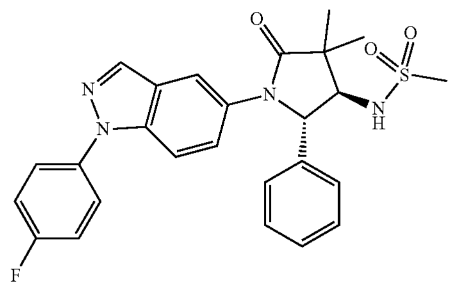 [SMILES: CC1(C)C(=O)N(c2ccc3c(cnn3-c3ccc(F)cc3)c2)[C@@H](c2ccccc2)[C@@H]1NS(C)(=O)=O] | 52 | $^1$H NMR (DMSO-d$_6$): δ = 8.28 (d, 1H), 8.02 (d, 1H), 7.76-7.69 (m, 3H), 7.69-7.63 (m, 1H), 7.52-7.47 (m, 2H), 7.44-7.35 (m, 3H), 7.29 (dd, 2H), 7.23-7.18 (m, 1H), 5.07 (d, 1H), 3.70 (t, 1H), 2.03 (s, 3H), 1.26 (s, 3H), 1.14 (s, 3H) |
| 35a | Int A7 ent 1 | 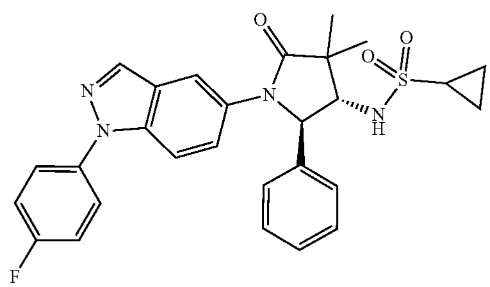 [SMILES: CC1(C)C(=O)N(c2ccc3c(cnn3-c3ccc(F)cc3)c2)[C@H](c2ccccc2)[C@H]1NS(=O)(=O)C1CC1] | 13 | $^1$H NMR (DMSO-d$_6$): δ = 8.28 (d, 1H), 7.95 (d, 1H), 7.76-7.68 (m, 3H), 7.65 (dd, 1H), 7.49-7.44 (m, 2H), 7.43-7.35 (m, 3H), 7.26 (t, 2H), 7.20-7.14 (m, 1H), 5.09 (d, 1H), 3.74 (t, 1H), 1.46 (tt, 1H), 1.28 (s, 3H), 1.15 (s, 3H), 0.70-0.49 (m, 2H), 0.49-0.25 (m, 2H) |
| 35b | Int A7 ent 2 | 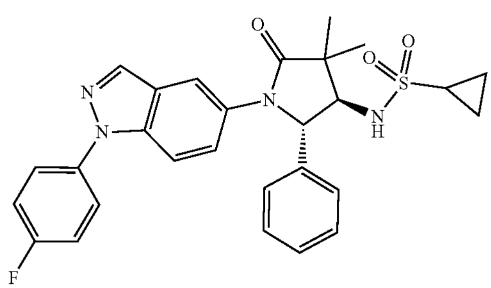 [SMILES: CC1(C)C(=O)N(c2ccc3c(cnn3-c3ccc(F)cc3)c2)[C@@H](c2ccccc2)[C@@H]1NS(=O)(=O)C1CC1] | 8 | $^1$H NMR (DMSO-d$_6$): δ = 8.28 (d, 1H), 7.95 (d, 1H), 7.76-7.68 (m, 3H), 7.65 (dd, 1H), 7.49-7.44 (m, 2H), 7.43-7.35 (m, 3H), 7.26 (t, 2H), 7.20-7.14 (m, 1H), 5.09 (d, 1H), 3.74 (t, 1H), 1.46 (tt, 1H), 1.28 (s, 3H), 1.15 (s, 3H), 0.70-0.49 (m, 2H), 0.49-0.25 (m, 2H) |
| 61 | A9 | 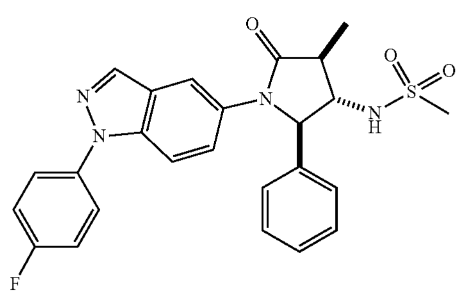 [SMILES: C[C@@H]1C(=O)N(c2ccc3c(cnn3-c3ccc(F)cc3)c2)[C@H](c2ccccc2)[C@H]1NS(C)(=O)=O] | 74 | $^1$H NMR (DMSO-d$_6$) δ: 8.28 (d, 1H), 7.99 (d, 1H), 7.76-7.69 (m, 3H), 7.65 (dt, 1H), 7.48-7.42 (m, 3H), 7.42-7.35 (m, 2H), 7.30-7.25 (m, 2H), 7.22-7.17 (m, 1H), 5.10 (d, 1H), 3.61 (dt, 1H), 2.68 (dq, 1H), 2.26 (s, 3H), 1.31 (d, 3H) |

| Ex. # | Intermediate (INT) | Structure | Yield (%) | ¹H NMR |
|---|---|---|---|---|
| 62 | A11-trans | 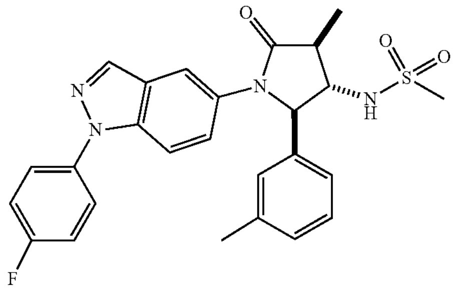 [SMILES: Cc1cccc([C@@H]2[C@@H](NS(C)(=O)=O)[C@H](C)C(=O)N2c2ccc3c(cnn3-c3ccc(F)cc3)c2)c1] | 50 | ¹H NMR (DMSO-d$_6$) δ: 8.29 (s, 1H), 7.96 (d, 1H), 7.77-7.71 (m, 3H), 7.69-7.64 (m, 1H), 7.44 (dd, 1H), 7.44-7.36 (m, 2H), 7.27 (d, 1H), 7.25-7.21 (m, 1H), 7.16 (t, 1H), 7.01 (d, 1H), 5.05 (d, 1H), 3.58 (dt, 1H), 2.67 (dq, 1H), 2.26 (s, 3H), 2.22 (s, 3H), 1.31 (d, 3H) |
| 76 | A11-cis | 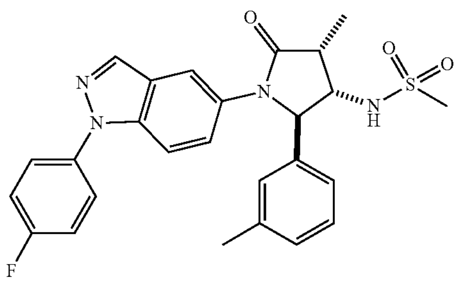 [SMILES: Cc1cccc([C@@H]2[C@@H](NS(C)(=O)=O)[C@@H](C)C(=O)N2c2ccc3c(cnn3-c3ccc(F)cc3)c2)c1] | 40 | ¹H NMR (DMSO-d$_6$) δ: 7.89 (dd, 1H), 7.79-7.68 (m, 5H), 7.44-7.37 (m, 2H), 7.24 (t, 1H), 7.19 (d, 1H), 7.17-7.13 (m, 1H), 7.08 (ddd, 1H), 5.24 (d, 1H), 3.97 (d, 1H), 3.01 (p, 1H), 2.87 (s, 3H), 2.27 (s, 3H), 1.18 (d, 3H) |
| 86 | A13-cis | 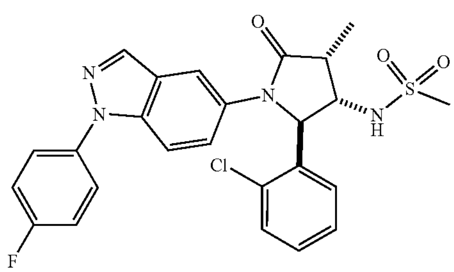 [SMILES: C[C@H]1C(=O)N(c2ccc3c(cnn3-c3ccc(F)cc3)c2)[C@H](c2ccccc2Cl)[C@H]1NS(C)(=O)=O] | 35 | ¹H NMR (DMSO-d$_6$) δ: 8.35 (d, 1H), 8.19 (d, 0H), 7.87 (dd, 1H), 7.80-7.73 (m, 3H), 7.65 (dd, 1H), 7.54-7.48 (m, 1H), 7.44-7.37 (m, 2H), 7.37-7.28 (m, 3H), 5.58 (d, 1H), 4.09 (s, 1H), 3.04 (p, 1H), 2.95 (s, 3H), 1.20 (d, 3H) |
| 91 | A21 | 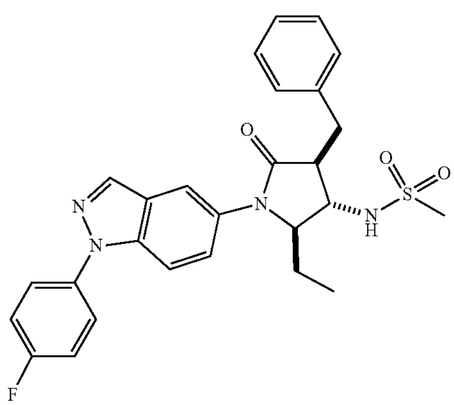 [SMILES: CC[C@@H]1[C@@H](NS(C)(=O)=O)[C@H](Cc2ccccc2)C(=O)N1c1ccc2c(cnn2-c2ccc(F)cc2)c1] | 42 | ¹H NMR (DMSO-d$_6$) δ: 8.40 (d, 1H), 7.87-7.76 (m, 4H), 7.72 (d, 1H), 7.45 (ddd, 3H), 7.40-7.33 (m, 4H), 7.26 (ft, 1H), 4.07 (td, 1H), 3.62 (ddd, 1H), 3.15 (dd, 1H), 3.09 (dd, 1H), 2.96 (q, 1H), 2.79 (s, 3H), 1.51 (ddd, 1H), 1.22 (dp, 1H), 0.40 (t, 3H) |
| 93 | A13-trans | 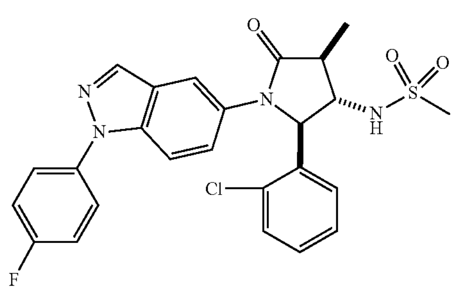 | 19 | ¹H NMR (Chloroform-d$_3$) δ: 8.10 (d, 1H), 7.68 (dd, 1H), 7.64-7.58 (m, 2H), 7.55 (dd, 1H), 7.38 (dd, 2H), 7.31 (d, 1H), 7.26-7.18 (m, 4H), 5.68 (s, 1H), 4.79 (d, 1H), 2.72 (dq, 1H), 2.51 (s, 3H), 1.55 (d, 3H), 0.97-0.77 (m, 1H) |

| Ex. # | Intermediate (INT) | Structure | Yield (%) | ¹H NMR |
|---|---|---|---|---|
| 99 | A15-trans | 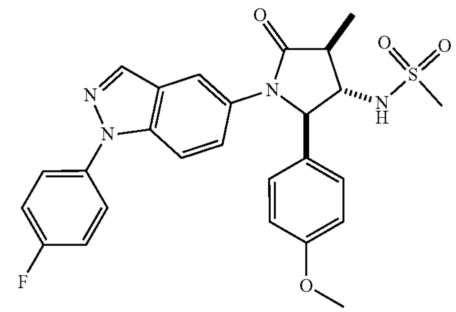 [SMILES: COc1ccc([C@@H]2[C@@H](NS(C)(=O)=O)[C@H](C)C(=O)N2c2ccc3c(cnn3-c3ccc(F)cc3)c2)cc1] | 13 | ¹H NMR (DMSO-$d_6$) δ: 8.28 (d, 1H), 7.93 (d, 1H), 7.75-7.72 (m, 2H), 7.71 (dd, 1H), 7.65 (dt, 1H), 7.43-7.34 (m, 5H), 6.85-6.79 (m, 2H), 5.03 (d, 1H), 3.65 (s, 3H), 3.59 (dt, 1H), 2.65 (dt, 1H), 2.29 (s, 3H), 1.31 (d, 3H) |
| 114 | A17-trans | 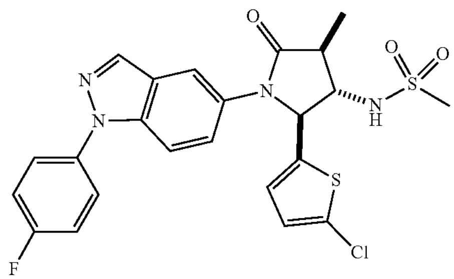 [SMILES: C[C@@H]1C(=O)N(c2ccc3c(cnn3-c3ccc(F)cc3)c2)[C@H](c2ccc(Cl)s2)[C@H]1NS(C)(=O)=O] | 25 | ¹H NMR (DMSO-$d_6$) δ: 8.34 (d, 1H), 7.98 (d, 1H), 7.81-7.74 (m, 3H), 7.72 (dt, 1H), 7.47-7.38 (m, 3H), 7.14 (d, 1H), 6.89 (d, 1H), 5.34 (d, 1H), 3.68 (dt, 1H), 2.70 (dq, 1H), 2.64 (s, 3H), 1.31 (d, 3H) |
| 122 | A19 | 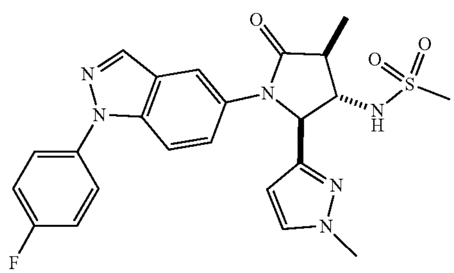 [SMILES: C[C@@H]1C(=O)N(c2ccc3c(cnn3-c3ccc(F)cc3)c2)[C@H](c2ccn(C)n2)[C@H]1NS(C)(=O)=O] | 47 | ¹H NMR (DMSO-$d_6$) δ: 8.31 (t, 1H), 7.92 (d, 1H), 7.79-7.73 (m, 2H), 7.72 (dd, 1H), 7.69 (dd, 1H), 7.52 (d, 1H), 7.45-7.37 (m, 3H), 6.27 (dd, 1H), 5.11 (d, 1H), 3.79 (q, 1H), 3.70 (s, 3H), 2.67 2.59 (m, 1H), 2.46 (s, 3H), 1.30 (d, 3H) |

Examples 95 and 96 (2-(((2R,3R,4S)-4-fluoro-1-(1-(4-fluorophenyl)-1H-indazol-5-yl)-5-oxo-2-phenylpyrrolidin-3-yl)carbamoyl)cyclopropan-1-ylium (Example 95) and N-((2R,3R)-4,4-difluoro-1-(1-(4-fluorophenyl)-1H-indazol-5-yl)-5-oxo-2-phenylpyrrolidin-3-yl)cyclopropanecarboxamide (Example 96)

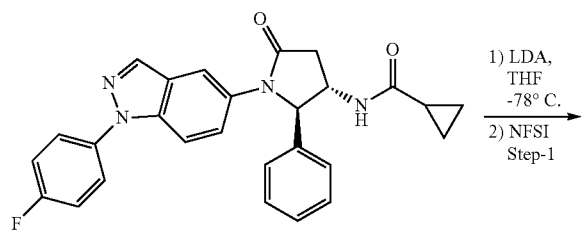

intermediate C1 - ent 1

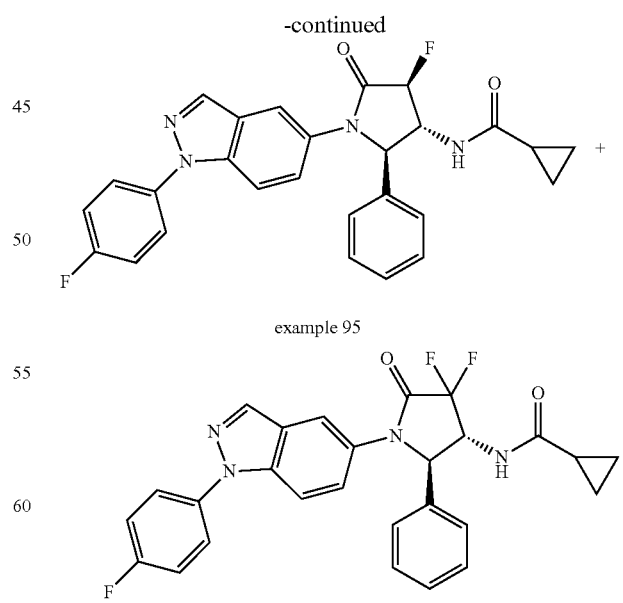

example 95 example 96

Step-1: In a dried vessel, intermediate C1-ent 1 (150 mg, 0.33 mmol) was dissolved in dry THF (3.3 ml) under inert atmosphere. The solution was cooled down to −78° C. and a solution of LDA (1 M in THF/heptanes/ethyl benzene, 1.32 ml, 4.0 eq.) was added dropwise. After stirring for 15 min at −78° C., N-fluoro-N-(phenylsulfonyl)benzenesulfonamide (NFSI, 229 mg, 0.726 mmol, 2.2 eq.) dissolved in dry THF (1.7 mL) was added dropwise. The mixture was stirred for two hours at −78° C. before additional amounts of LDA (330 µl, 1 eq.) and NFSI (100 mg, 1 eq.) were added subsequently. After stirring for another 30 min at −78° C., the reaction was quenched with sat. NH₄Cl-solution and ethyl acetate was added after stirring for 5 minutes. The layers were separated, the organic layer was dried over sodium sulfate and the solvent was removed in vacuo. The crude material was purified via flash chromatography (silica, cyclohexane/ethyl acetate gradient as eluent) and subsequent prep.-HPLC (water/acetonitrile gradient) to obtain example 95 (25.5 mg, 0.054 mmol, 16%) and example 96 (3.0 mg, 0.006 mmol, 2%) as white solids.

Example 95: $^1$H NMR (Chloroform-$d_3$) δ: 8.07 (d, 1H), 7.76 (dd, 0.7 Hz, 1H), 7.67-7.50 (m, 2H), 7.58-7.45 (m, 1H), 7.39 (dd, 1H), 7.41-7.06 (m, 6H), 6.31 (d, 1H), 5.86 (dd, 1H), 5.54 (dd, 1H), 3.98 (dq, 1H), 1.44 (tt, 1H), 0.86 (dtd, 2H).

Example 96: $^1$H NMR (Chloroform-$d_3$) δ: 8.10 (s, 1H), 7.52 (d, 1H), 7.41 (dd, 1H), 7.43-7.19 (m, 5H), 7.28-7.11 (m, 2H), 6.42 (s, 1H), 5.14 (d, 1H), 4.88 (dddd, 1H), 1.51 (tq, 1H), 1.05 (tq, 1H), 0.96-0.74 (m, 2H).

Example 100: 2,2-difluoro-N-(trans-1-(1-(4-fluorophenyl)-1H-indazol-5-yl)-2-methyl-5-oxo-2-phenylpyrrolidin-3-yl)propanamide

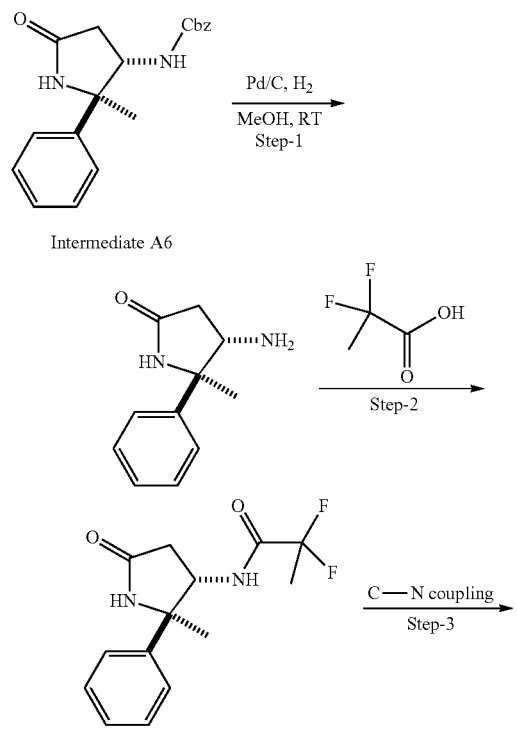

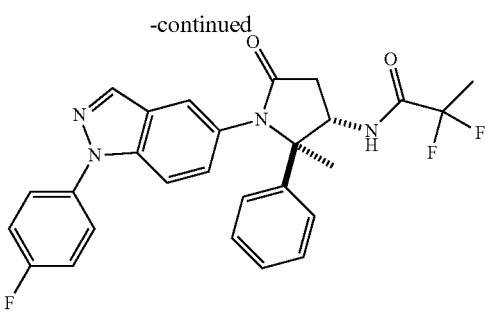

example 100

Step 1: To a stirred solution of intermediate A6 (1 g, 3.08 mmol, 1.0 eq) in methanol (30 mL), Pd—C (820 g, 10%, moist) was added and the reaction was stirred with hydrogen balloon for 2 h at RT. After completion, (monitored by TLC, TLC system 5% MeOH in DCM, $R_f$-0.2), the reaction mixture was filtered through celite bed and washed 2-3 times with MeOH. The filtrate was concentrated to get the desired trans-4-amino-5-methyl-5-phenylpyrrolidin-2-one as off-white solid (0.693 g, 94%).

Step 2: To a stirred solution of 2,2-difluoropropanoic acid (0.304 g, 2.759 mmol, 1.5 eq) in DMF (10 mL), DIPEA (1.6 mL 9.14 mmol, 5.0 eq), HATU (1.4 g, 3.678 mmol, 2.0 eq), and trans-4-amino-5-methyl-5-phenylpyrrolidin-2-one (350 mg, 1.839 mmol, 1 eq) was added at ice cold condition and the reaction was stirred at RT for 16 h. After completion of the reaction, (monitored by TLC, TLC system 5% MeOH in DCM, $R_f$-0.3), the reaction mixture was diluted with EtOAc (20 mL) and washed with ice cold water (3×25 mL), dried over Na₂SO₄ and concentrated to get the crude product which was purified by column chromatography (230-400 mesh silica gel; 0 to 2% MeOH-DCM) to afford 2,2-difluoro-N-(trans-2-methyl-5-oxo-2-phenylpyrrolidin-3-yl)propanamide (0.350 g, 67%).

Step 3: A stirred solution of 2,2-difluoro-N-(trans-2-methyl-5-oxo-2-phenylpyrrolidin-3-yl)propanamide (0.250 g, 0.885 mmol, 1 eq), 1-(4-fluorophenyl)-5-iodo-1H-indazole (0.359 g, 1.0627 mmol, 1.2 eq), K₃PO₄ (0.376 g, 1.770 mmol, 2 eq) in 1,4 dioxane (10 mL) was degassed with argon for 30 min N,N'-dimethylethylenediamine (0.032 g, 0.354 mmol, 0.4 eq) and CuI (0.033 g, 0.177 mmol, 0.2 eq) was added and the reaction mixture was stirred for 72 h at 90° C. in a sealed tube. After completion of the reaction, (monitored by TLC, TLC system 5% MeOH in DCM, $R_f$-0.4), the reaction mixture was filtered through celite bed and washed 2-3 times with dioxane. The combined organic layer was concentrated to get the crude product which was purified by column chromatography (230-400 mesh silica gel; 0 to 2% MeOH in DCM) to afford 2,2-difluoro-N-(trans-1-(1-(4-fluorophenyl)-1H-indazol-5-yl)-2-methyl-5-oxo-2-phenylpyrrolidin-3-yl)propanamide (0.046 g, 11%) as off-white solid.

$^1$H NMR (400 MHz, DMSO-$d_6$) δ 9.49 (d, J=8.84 Hz, 1H), 8.32 (s, 1H), 7.78-7.73 (m, 3H), 7.49-7.30 (m, 9H), 4.53-4.49 (m, 1H), 3.00-2.93 (m, 1H), 2.47-2.42 (m, 1H), 1.78 (t, J=19.52 Hz, 3H), 1.44 (s, 3H).

Example 101: N-(trans-1-(1-(4-fluorophenyl)-1H-indazol-5-yl)-2-methyl-5-oxo-2-phenylpyrrolidin-3-yl)cyclopropanecarboxamide

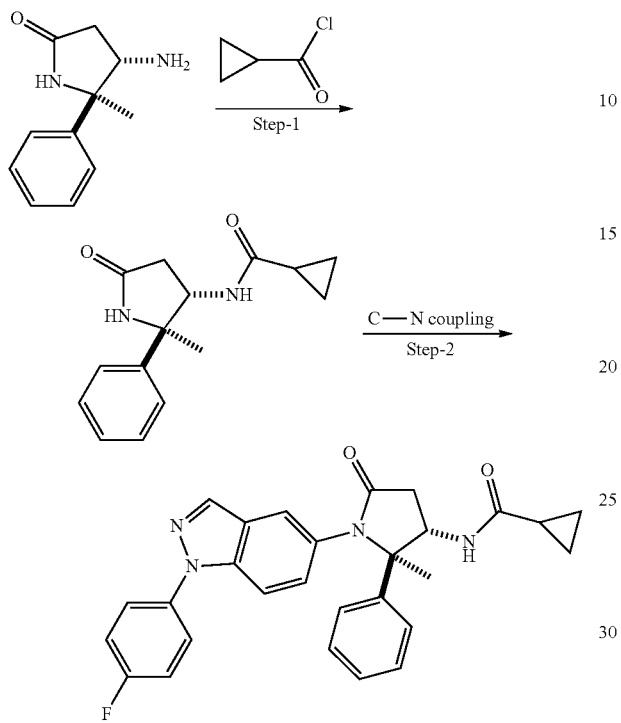

Step 1: To a stirred solution of trans-4-amino-5-methyl-5-phenylpyrrolidin-2-one (350 mg, 1.84 mmol, 1 eq) in DMF (10 mL) TEA (1.2 mL, 9.14 mmol, 5.0 eq), cyclopropanecarbonyl chloride (288 mg, 2.76 mmol, 1.5 eq) was added at ice cold condition and the reaction mixture was stirred at RT for 2 h. After completion of the reaction, (monitored by TLC, TLC system 5% MeOH in DCM, $R_f$-0.3), the reaction mixture was diluted with EtOAc (50 mL) and washed with ice cold water (3×25 mL), dried over $Na_2SO_4$ and concentrated to get the crude product which was purified by column chromatography (230-400 mesh silica gel; 0 to 2% MeOH-DCM) to afford N-(trans-2-methyl-5-oxo-2-phenylpyrrolidin-3-yl)cyclopropanecarboxamide (350 mg, 74%).

Step 2: A stirred solution of N-(trans-2-methyl-5-oxo-2-phenylpyrrolidin-3-yl)cyclopropanecarboxamide (0.250 g, 0.967 mmol, 1 eq), 1-(4-fluorophenyl)-5-iodo-1H-indazole (0.393 g, 1.16 mmol, 1.2 eq), $K_3PO_4$ (0.410 g, 1.93 mmol, 2 eq) in 1,4 dioxane (10 mL) was degassed with argon for 30 min N,N'-dimethylethylenediamine (0.034 g, 0.387 mmol, 0.4 eq) and CuI (0.037 g, 0.193 mmol, 0.2 eq) was added and the reaction mixture was stirred for 72 h at 90° C. in a sealed tube. After completion of the reaction, (monitored by TLC, TLC system 5% MeOH in DCM, $R_f$-0.4), the reaction mixture was filtered through celite bed and washed 2-3 times with dioxane. The combined organic layer was concentrated to get the crude product which was purified by column chromatography (230-400 mesh silica gel; 0 to 2% MeOH in DCM) to afford N-(trans-1-(1-(4-fluorophenyl)-1H-indazol-5-yl)-2-methyl-5-oxo-2-phenylpyrrolidin-3-yl)cyclopropanecarboxamide (0.046 g, 10%) as off-white solid.

$^1$H NMR (400 MHz, DMSO-$d_6$) δ 8.81 (d, J=8.88 Hz, 1H), 8.35 (s, 1H), 7.79-7.74 (m, 3H), 7.52 (s, 1H), 7.48-7.32 (m, 8H), 4.50-4.45 (m, 1H), 2.91-2.85 (m, 1H), 2.30-2.26 (m, 1H), 1.66-1.63 (m, 1H), 1.44 (s, 3H), 0.69 (d, J=6.2 Hz, 4H).

Example 121 N-(rac-(2R,3S,4S)-4-(cyclopropylmethyl)-1-(1-(4-fluorophenyl)-1H-indazol-5-yl)-5-oxo-2-phenylpyrrolidin-3-yl)cyclopropanecarboxamide

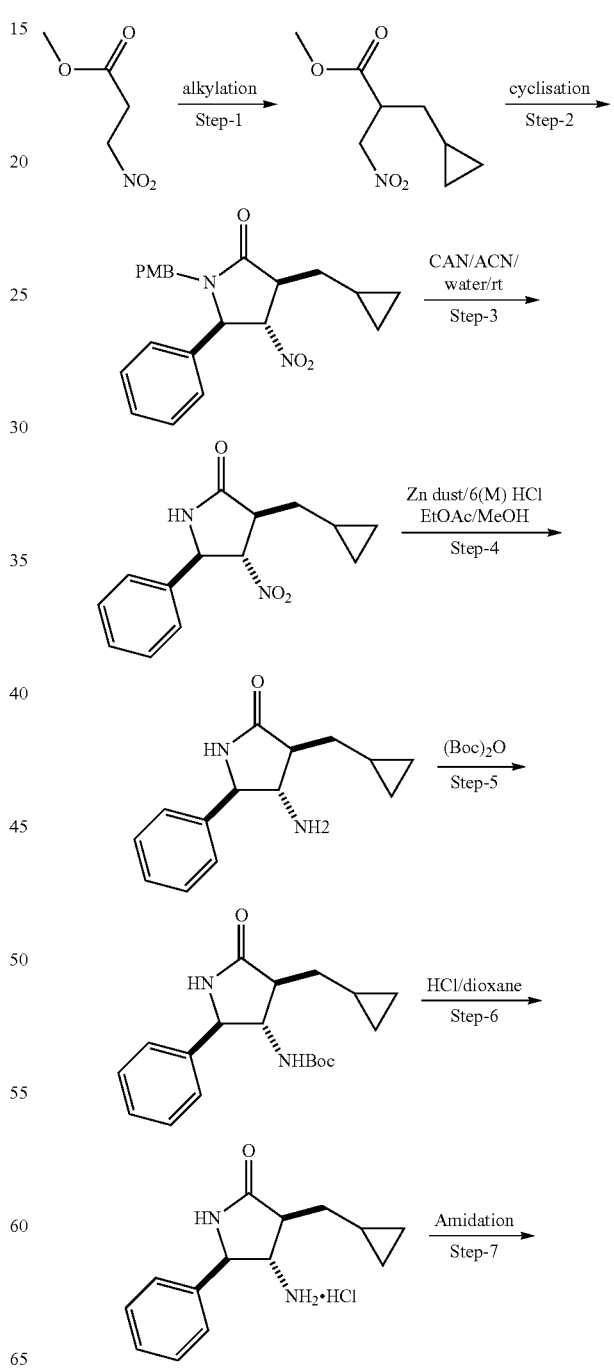

-continued

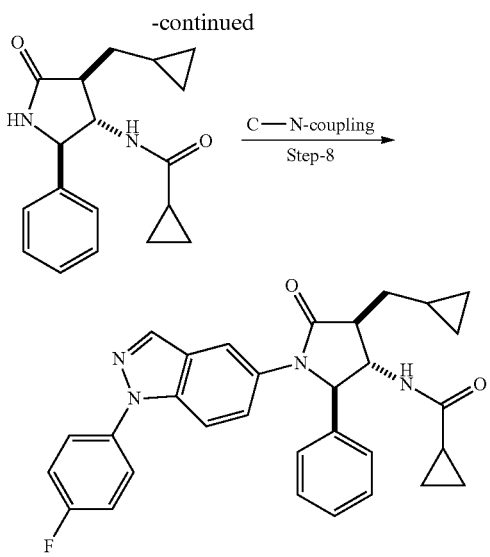

example 121

Step-1: Synthesis of methyl 3-cyclopropyl-2-(nitromethyl)propanoate. To a stirred solution of methyl 3-nitropropanoate (15 g, 112.74 mmol) in THF (105 ml) was added LDA (2M in THF, 112.7 ml, 225.5 mmol) at −78° C. and the resulting solution was stirred for 1 h at the same temperature. (Bromomethyl)cyclopropane (21.28 ml, 225.5 mmol) was added at −78 C. The reaction mixture was gradually allowed to reach rt and stirring was continued for 16 h. The reaction mixture was quenched with aqueous $NH_4Cl$ at 0° C. The layers were separated and the queous part was extracted with ethyl acetate (600 ml×3). The combined organic layers were washed with brine (300 ml), dried over $Na_2SO_4$ and concentrated. The crude product was purified by column chromatography (using 100-200 mesh silica gel, 6-8% ethyl acetate-hexanes as eluent) to afford 3-cyclopropyl-2-(nitromethyl)propanoate as brown oil.

Step-2: Synthesis of rac-(3S,4S,5R)-3-(cyclopropylmethyl)-1-(4-methoxybenzyl)-4-nitro-5-phenylpyrrolidin-2-one. To a stirred solution of benzaldehyde (6.07 ml, 60.09 mmol) in toluene (112.5 ml) was added 4-methoxy benzylamine (8.24 g, 60.09 mmol) at rt and stirred for 2 h. methyl 3-cyclopropyl-2-(nitromethyl)propanoate (7.5 g, 40.06 mmol) was added to the reaction mixture followed by benzoic acid (7.34 g, 60.09 mmol) and the resulting mixture was stirred for 7-8 h at 70° C. After completion of the reaction (monitored by LCMS), the mixture was diluted with ethyl acetate (300 ml) and washed with water (200 ml), followed by sat.$NaHCO_3$ (100 ml×2). The organic layer was dried over anhydrous $Na_2SO_4$ and concentrated. The crude product was purified by column chromatography (using silica gel 100-200 mesh; 12-15% ethyl acetate in hexanes as eluent) to afford 4 rac-(3S,4S,5R)-3-(cyclopropylmethyl)-1-(4-methoxybenzyl)-4-nitro-5-phenylpyrrolidin-2-one (7.5 g, 49.1%) as brown oil.

Step-3: rac-(3S,4S,5R)-3-(cyclopropylmethyl)-4-nitro-5-phenylpyrrolidin-2-one. To a stirred solution of rac-(3S,4S,5R)-3-(cyclopropylmethyl)-1-(4-methoxybenzyl)-4-nitro-5-phenylpyrrolidin-2-one (6 g, 15.77 mmol) in acetonitrile (120 ml) was dropwise added a solution of CAN (25.93 g, 47.31 mmol) in water (120 ml) at 0° C. The reaction mixture was slowly warmed to 10-15° C. and stirring was continued for 3-4 h. After completion of the reaction (monitored by TLC, 30% ethyl acetate/hexane, Rf 0.3), the mixture was diluted with ethyl acetate (400 ml) and washed with water (200 ml) followed by brine (200 ml). The organic layer was dried over $Na_2SO_4$ and concentrated. The crude material was purified by column chromatography (using silica gel 100-200 mesh; 25-30% ethyl acetate in hexane as eluent) to afford rac-(3S,4S,5R)-3-(cyclopropylmethyl)-4-nitro-5-phenylpyrrolidin-2-one (3.51 g, 85.6%) as a colorless oil.

Step-4: rac-(3S,4S,5R)-4-amino-3-(cyclopropylmethyl)-5-phenylpyrrolidin-2-one. To a stirred solution of rac-(3S,4S,5R)-3-(cyclopropylmethyl)-4-nitro-5-phenylpyrrolidin-2-one (4 g, 15.36 mmol) in ethyl acetate-methanol (360 ml, 2:1) was added 6 N aq. HCl (118 ml) at 0° C. Zinc dust (60.29 g, 922.04 mmol) was added portionwise at the same temperature. The resulting suspension was stirred at room temperature for 16 h. After completion of the reaction (monitored by LCMS), it was quenched with saturated $NaHCO_3$ solution at 0° C., stirred for 1 h, filtered over celite and washed with ethyl acetate-methanol (500 ml, 2:1). The filtrate was concentrated to afford rac-(3S,4S,5R)-4-amino-3-(cyclopropylmethyl)-5-phenylpyrrolidin-2-one (3.53 g crude, considered as 100% yield) as off white solid which was used in next step without further purification.

Step-5: Synthesisis of tert-butyl (rac-(2R,3S,4S)-4-(cyclopropylmethyl)-5-oxo-2-phenylpyrrolidin-3-yl)carbamate. To a stirred suspension of rac-(3S,4S,5R)-4-amino-3-(cyclopropylmethyl)-5-phenylpyrrolidin-2-one (3.53 g crude, 15.34 mmol) in THF-Water (1:1, 400 ml) was added sodium bicarbonate (3.86 g, 46.04 mmol) at 0° C. and the resulting mixture was stirred for 30 minutes at the same temperature. Di-tert-butyl dicarbonate (10.6 ml, 46.04 mmol) was added to the reaction mixture at 0° C. and stirring was continued for 16 h at rt. After completion of the reaction (monitored by LCMS), the mixture was diluted with water (200 ml) and extracted with ethyl acetate (3×300 ml). The combined organic layers were washed with water (300 ml) followed by brine (300 ml). After drying over $Na_2SO_4$ and concentrating, the crude material was purified by column chromatography (using silica gel 100-200 mesh; 1.5-2% MeOH in DCM as eluent) to afford (rac-(2R,3S,4S)-4-(cyclopropylmethyl)-5-oxo-2-phenylpyrrolidin-3-yl)carbamate (3.52 g, 69.5%) as off white solid.

Step-6: Synthesisis of rac-(3S,4S,5R)-4-amino-3-(cyclopropylmethyl)-5-phenylpyrrolidin-2-one hydrochloride. To a stirred suspension of (rac-(2R,3S,4S)-4-(cyclopropylmethyl)-5-oxo-2-phenylpyrrolidin-3-yl)carbamate (2 g, 6.05 mmol) in 1,4-dioxane (10 ml) was added 4 N HCl in 1,4-dioxane at 0° C. and stirring was continued at rt for 16 h. After completion of the reaction (monitored by LCMS), the mixture was concentrated and tritauted with ether to afford rac-(3S,4S,5R)-4-amino-3-(cyclopropylmethyl)-5-phenylpyrrolidin-2-one hydrochloride (1.62 g, crude) as off white solid.

Step-7: Synthesis of N-(rac-(2R,3S,4S)-4-(cyclopropylmethyl)-5-oxo-2-phenylpyrrolidin-3-yl)cyclopropanecarboxamide. To a stirred solution of 4-amino-3-(cyclopropylmethyl)-5-phenylpyrrolidin-2-one hydrochloride (7) (1.62 g, 6.06 mmol) in DCM (30 ml) was added $Et_3N$ (2.54 ml, 18.21 mmol) at 0° C. and the resulting mixture was stirred at the same temperature for 20 minutes. A solution of cyclopropanecarbonyl chloride (0.56 ml, 6.06 mmol) in DCM (5 ml) was added and stirring was continued at 0° C.-10° C. for 3 h. After complete consumption of the starting material (monitored by LCMS), the reaction was diluted with $H_2O$, the formed precipitate was filtered and washed with cold water followed by pentane-ether to afford N-(rac-(2R,3S, 4S)-4-(cyclopropylmethyl)-5-oxo-2-phenylpyrrolidin-3-yl)cyclopropanecarboxamide (1.41 g, 78%) as off white solid.

Step-8: C—N-coupling was performed in analogy to the procedure described for example 7 Step using N-(rac-(2R,3S,4S)-4-(cyclopropylmethyl)-5-oxo-2-phenylpyrrolidin-3-yl)cyclopropanecarboxamide. Yield 53%.

$^1$H NMR (DMSO-$d_6$) δ: 8.59 (d, 1H), 8.29 (s, 1H), 7.79 (d, 1H), 7.77-7.70 (m, 2H), 7.68 (d, 1H), 7.51 (dd, 1H), 7.43-7.36 (m, 2H), 7.32 (d, 2H), 7.25 (t, 2H), 7.19-7.13 (m, 1H), 5.21 (d, 1H), 4.33 (q, 1H), 2.83 (dt, 1H), 1.67-1.59 (m, 2H), 1.57 (ddd, 1H), 0.90 (ddt, 1H), 0.73-0.60 (m, 4H), 0.50-0.32 (m, 2H), 0.18-0.01 (m, 2H)

Example 127: N-((2R,3S)-1-(1-(4-fluorophenyl)-1H-indazol-5-yl)-5-oxo-4-phenethyl-2-phenylpyrrolidin-3-yl)cyclopropanecarboxamide, diastereomer 2; and Example 130: N-((2R,3S)-1-(1-(4-fluorophenyl)-1H-indazol-5-yl)-5-oxo-4-phenethyl-2-phenylpyrrolidin-3-yl)cyclopropanecarboxamide, diastereomer 1 ethyl)benzene (99.6 mg, 0.429 mmol, 1.3 eq.) and LDA (1 M in THF, 0.682 ml, 2.0 eq.) were added. After stirring for 90 minutes at −60° C., a third amount of (2-Iodoethyl)benzene (99.6 mg, 0.429 mmol, 1.3 eq.) followed by LDA (1 M in THF, 0.34 ml, 1.0 eq.). The mixture was stirred again overnight at −20° C. and quenched with saturated NH$_4$Cl solution at that temperature before the mixture was diluted with ethyl acetate. The crude material was purified via flash chromatography (silica, cyclohexane/ethyl acetate gradient as eluent) and subsequent prep.-HPLC (water/acetonitrile gradient) to obtain example 127 (N-((2R,3S)-1-(1-(4-fluorophenyl)-1H-indazol-5-yl)-5-oxo-4-phenethyl-2-phenylpyrrolidin-3-yl)cyclopropanecarboxamide second eluting diastereomer, 6 mg, 0.011 mmol, 3%) and example 130 (N-((2R,3S)-1-(1-(4-fluorophenyl)-1H-indazol-5-yl)-5-oxo-4-phenethyl-2-phenylpyrrolidin-3-yl)cyclopropanecarboxamide first eluting diastereomer, 12.0 mg, 0.021 mmol, 6%) as white solids.

Example 127: $^1$H NMR (DMSO-$d_6$) δ: 8.94 (d, 1H), 8.35-8.28 (m, 1H), 8.01 (d, 1H), 7.83 (dd, 1H), 7.80-7.63 (m, 3H), 7.44-7.23 (m, 9H), 7.26-7.16 (m, 1H), 7.19-7.13 (m,

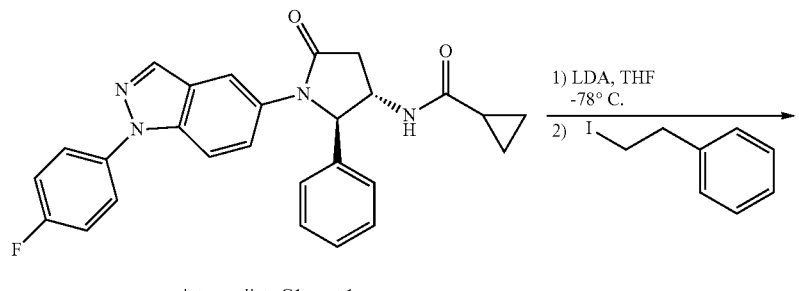

intermediate C1 - ent 1

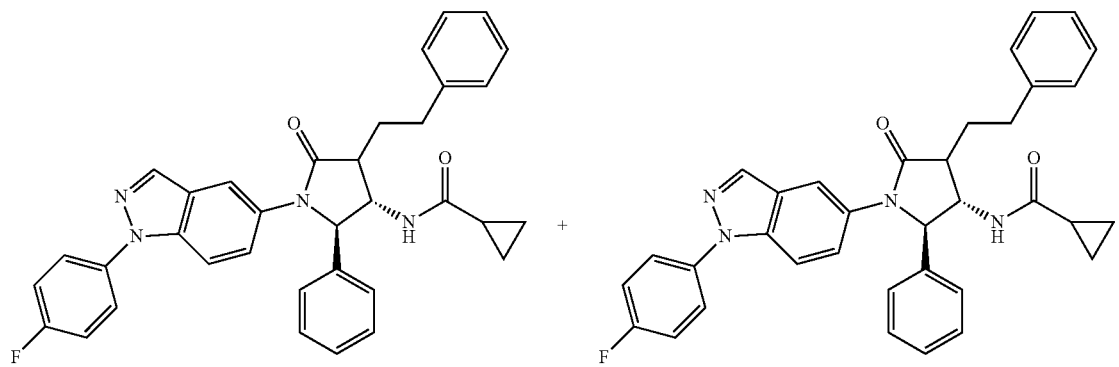

diastereomer 2 example 127      diastereomer 1 example 130

In a dried vessel, intermediate C1-ent 1 (150 mg, 0.33 mmol) was dissolved in dry THF (3.3 ml) under inert atmosphere. The solution was cooled down to −78° C. and a solution of freshly prepared LDA (1 M in THF, 0.825 ml, 2.5 eq.) was added dropwise. After stirring for 15 min at −78° C., (2-Iodoethyl)benzene (99.6 mg, 0.429 mmol, 1.3 eq.) dissolved in dry THF (1.7 mL) was added dropwise. The mixture was allowed to warm up to −20° overnight and cooled down again to −60° C. before additional (2-Iodo- 2H), 7.15-7.03 (m, 1H), 5.26 (d, 1H), 4.52 (ddd, 1H), 2.93 (tdd, 1H), 2.65-2.52 (m, 2H), 1.85-1.68 (m, 2H), 1.24 (s, 1H), 1.18 (s, 1H), 0.90-0.69 (m, 3H).

Example 128: $^1$H NMR (DMSO-$d_6$) δ: 8.66 (d, J=8.4 Hz, 1H), 8.29 (d, J=1.3 Hz, 1H), 7.79 (d, J=1.9 Hz, 1H), 7.74 (ddd, 1H), 7.68 (d, 1H), 7.54 7.48 (m, 1H), 7.43 7.36 (m, 2H), 7.36 7.28 (m, 4H), 7.26 (t, 2H), 7.23 7.14 (m, 4H), 5.21 (d, 1H), 4.22 (td, 1H), 2.76 (t, 2H), 2.70 (td, 1H), 2.18 2.06 (m, 2H), 1.88 (dq, 1H), 1.58 (tt, 1H), 0.77 0.62 (m, 4H).

Examples 128 N-(rac-(2R,3R,4R)-4-fluoro-1-(1-(4-fluorophenyl)-1H-indazol-5-yl)-4-methyl-5-oxo-2-phenylpyrrolidin-3-yl)cyclopropanecarboxamide and Example 129 N-((2R,3R,4S)-4-fluoro-1-(1-(4-fluorophenyl)-1H-indazol-5-yl)-4-methyl-5-oxo-2-phenylpyrrolidin-3-yl)cyclopropanecarboxamide

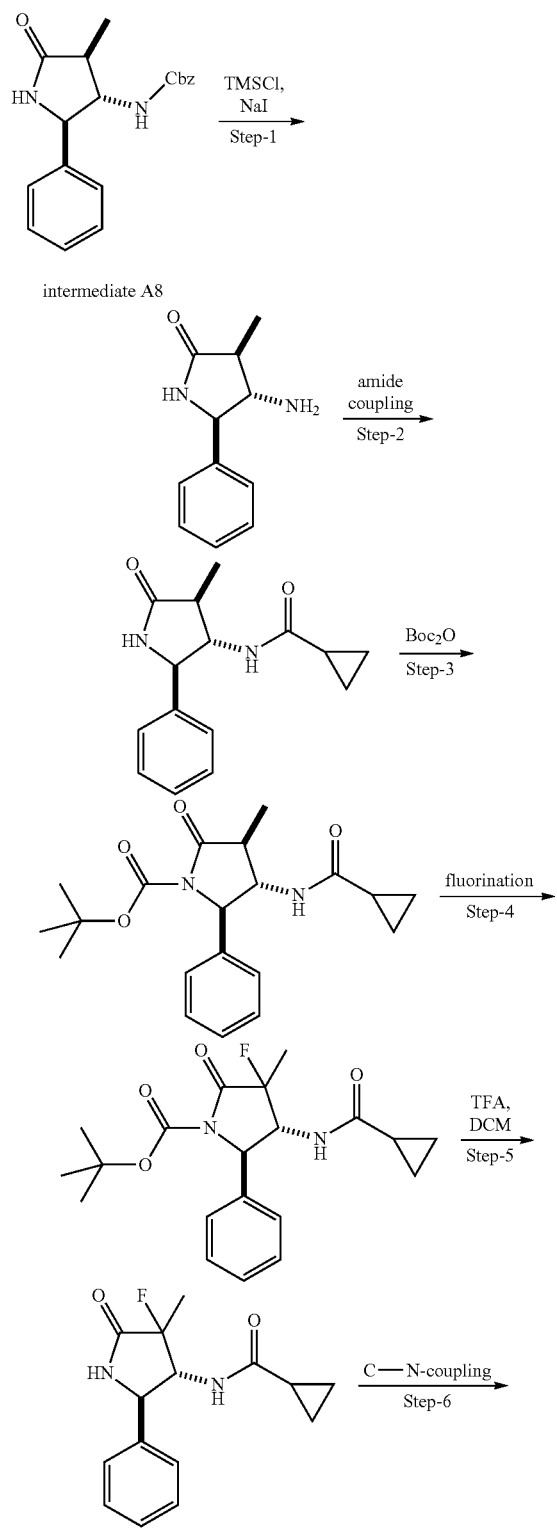

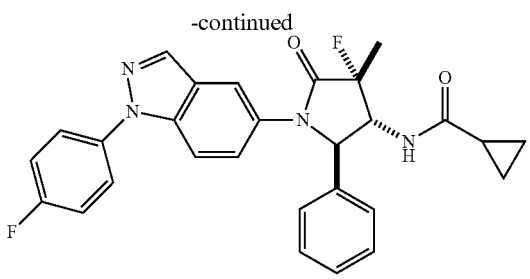

example 128

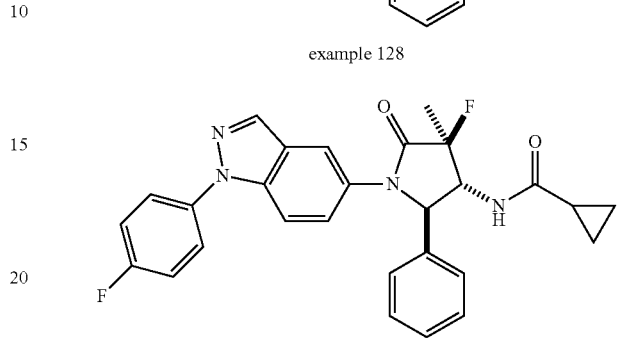

example 129

Step-1: In a 250 ml round-bottom-flask, a solution of intermediate A8 (2370 mg, 7.31 mmol) in acetonitrile (120 ml) was added to sodium iodide (6570 mg, 43.8 mmol, 6 eq.) under nitrogen atmosphere. To the resulting mixture, trimethylsilyl chloride (3.71 ml, 29.2 mmol 4.0 eq.) was added dropwise. After stirring overnight at room temperature, the reaction mixture was added dropwise to ethanol (142 ml) and filtered over celite. The filtrate was loaded on a strong cation exchange-cartridge (SCX, 5 g), flushed two times with ethanol (15 ml each) and eluted with 2 M $NH_3$ in methanol (2×10 mL). This procedure was repeated using the product-containing fractions two times. The clean fractions were combined, and the solvent was removed in vacuo to obtain rac-(3S,4S,5R)-4-amino-3-methyl-5-phenylpyrrolidin-2-one (296 mg, 1.56 mmol, 21%) as a colorless resin.

Step-2: rac-(3S,4S,5R)-4-amino-3-methyl-5-phenylpyrrolidin-2-one (328 mg, 1.72 mmol) and cyclopropanecarboxylic acid (297 mg, 3.45 mmol, 2.0 eq.) were dissolved in dichloromethane (17.2 ml) at room temperature. Triethylamine (689 mg, 6.90 mmol, 4.0 eq.) was added dropwise to the mixture which was stirred until all starting materials had dissolved. Propylphosphonic anhydride solution (≥50 wt. % in ethyl acetate, 2.57 ml, 4.31 mmol, 2.5 eq.) was added to the reaction and stirring was continued at rt. After 3 h, reaction control (UPLC) showed full consumption of the starting materials and the reaction was quenched with 1 M $Na_2CO_3$-solution. After stirring for one hour, the product precipitated and was filtered off yielding N-(rac-(2R,3S,4S)-4-methyl-5-oxo-2-phenylpyrrolidin-3-yl)cyclopropanecarboxamide (264 mg, 1.02 mmol, 59%) as a white solid. The obtained material was used in the next step without further purification.

Step-3: To a suspension of N-(rac-(2R,3S,4S)-4-methyl-5-oxo-2-phenylpyrrolidin-3-yl)cyclopropanecarboxamide (263 mg, 1.02 mmol), triethyl amine (206 mg, 2.04 mmol, 2.0 eq.) and 4-dimethylamino pyridine (12.4 mg, 0.102 mmol, 0.1 eq.) in acetonitrile (10 ml), a solution of di-tert-butyl-dicarbonate (244 mg, 1.12 mmol, 1.1 eq.) in acetonitrile (2 ml) was added in a sealed tube. The reaction mixture was heated to 80° C. for 30 minutes and stirred overnight at room temperature. Additional di-tert-butyl-dicarbonate (133 mg, 0.611 mmol, 0.6 eq.) in acetonitrile (2 ml) was added and stirring was continued at room temperature until reaction control (UPLC) proved the reaction to be complete (2 h). Dichloromethane and saturated NaHCO$_3$-solution were added to the reaction, the layers were separated and the aqueous layer was extracted once with dichloromethane. The combined organic layers were dried over magnesium sulfate and the solvent was removed in vacuo. The crude material was purified via flash chromatography (12 g silica, cyclohexane/ethyl acetate gradient as eluent) and tert-butyl rac-(3S,4S,5R)-4-(cyclopropanecarbonylamino)-3-methyl-2-oxo-5-phenyl-pyrrolidine-1-carboxylate (234 mg, 0.653 mmol, 64%) was obtained as a white solid.

Step-4: In a dried vessel, tert-butyl rac-(3S,4S,5R)-4-(cyclopropanecarbonylamino)-3-methyl-2-oxo-5-phenyl-pyrrolidine-1-carboxylate (80 mg, 0.223 mmol) was dissolved in dry THF (2.2 ml) under inert atmosphere. The solution was cooled down to −78° C. and a solution of lithium bis(trimethylsilyl)amide (1 M in THF, 0.446 ml, 0,446 mmol, 2.0 eq) was added carefully. After stirring for 15 minutes at −78, a solution of N-fluoro-N-(phenylsulfonyl) benzenesulfonamide (70.4 mg, 0.223 mmol, 1.0 eq) in THF (1 mL) was added dropwise. After stirring for 45 min at that temperature, another amount of N-fluoro-N-(phenylsulfonyl)benzenesulfonamide (35.0 mg, 0.111 mmol, 0.5 eq.) in THF (0.5 mL) were added and stirring was continued for 30 min. The reaction was quenched at −78° using sat. NH$_4$Cl solution, diluted with DCM and quickly poured over a hydrophobic frit, before the mixture could warm up. The organic layer was washed with water and separated again. The crude product was purified via flash chromatography (12 g silica, cyclohexane/ethyl acetate gradient as eluent) to yield tert-butyl (4R,5R)-4-(cyclopropanecarboxamido)-3-fluoro-3-methyl-2-oxo-5-phenylpyrrolidine-1-carboxylate (47 mg, 0.125 mmol, 56%) as a mixture of epimers (3:1).

Step-5: To a solution of tert-butyl (4R,5R)-4-(cyclopropanecarboxamido)-3-fluoro-3-methyl-2-oxo-5-phenylpyrrolidine-1-carboxylate (46.0 mg, 0.122 mmol) in dichloromethane (1.22 ml) was added trifluoroacetic acid (0.094 ml, 1.22 mmol, 10.0 eq.) at room temperature. After stirring for 30 minutes, reaction control (UPLC) proved the reaction to be complete and the mixture was quenched using sat. NaHCO$_3$-solution. DCM was added to the mixture and layers were separated by the means of a hydrophobic frit. Evaporation of the organic layer gave N-((2R,3R)-4-fluoro-4-methyl-5-oxo-2-phenylpyrrolidin-3-yl)cyclopropanecarboxamide (27 mg, 0.098 mmol, 80%) as a brown oil which was used without further purification Step-6: In a sealed tube, N-((2R,3R)-4-fluoro-4-methyl-5-oxo-2-phenylpyrrolidin-3-yl)cyclopropanecarboxamide (27.0 mg, 0.098 mmol), 1-(4-fluorophenyl)-5-iodo-indazole (36.3 mg, 0.107 mmol, 1.1 eq.), K$_3$PO$_4$ (41.5 mg, 0.195 mmol, 2.0 eq) and CuI (3.7 mg, 0.020 mmol, 0.2 eq.) were dissolved in degassed 1,4-dioxane (1 ml). To the mixture, (1R,2R)—N,N'-dimethyl-1,2-cyclohexandiamine (5.6 mg, 0.039 mmol, 0.4 eq.) was added and the reaction was heated to 100° C. overnight and to 120° C. for 5 h. The reaction was quenched using sat. NaHCO$_3$-solution and diluted with dichloromethane. The layers were separated by the means of a hydrophobic frit and the aqueous layer was washed multiple times with DCM. The organic layers were combined and the solvent was evaporated. The crude material was purified via flash chromatography (silica, cyclohexane/ethyl acetate gradient as eluent) and subsequent prep.-HPLC (water/acetonitrile gradient) to obtain example 128 N-((2R,3R,4R)-4-fluoro-1-(1-(4-fluorophenyl)-1H-indazol-5-yl)-4-methyl-5-oxo-2-phenylpyrrolidin-3-yl)cyclopropanecarboxamide (1.8 mg, 0.003 mmol, 4%) and example 129 N-((2R,3R,4S)-4-fluoro-1-(1-(4-fluorophenyl)-1H-indazol-5-yl)-4-methyl-5-oxo-2-phenylpyrrolidin-3-yl)cyclopropanecarboxamide (5.8 mg, 0.012 mmol, 12%).

Example 128: $^1$H NMR (DMSO-d$_6$) δ: 8.11 (d, 1H), 7.78 (dd, 1H), 7.67-7.59 (m, 2H), 7.56 (dt, 1H), 7.48 (dd, 1H), 7.39-7.19 (m, 6H), 7.26-7.16 (m, 1H), 6.29-6.20 (m, 1H), 5.15 (d, 1H), 4.66 (ddd, 1H), 1.69 (d, 3H), 1.47 (tt, 1H), 1.01 (dddd, 1H), 0.95-0.90 (m, 1H), 0.82 (m, 2H).

Example 129: $^1$H NMR (DMSO-d$_6$) δ: 8.69 (dd, 1H), 8.33 (d, 1H), 7.87 (d, 1H), 7.82-7.67 (m, 3H), 7.51 (dd, 1H), 7.45-7.30 (m, 4H), 7.26 (t, 2H), 7.22-7.13 (m, 1H), 5.12 (dd, 1H), 4.68 (ddd, 1H), 1.66 (tt, 1H), 1.54 (d, 3H), 0.77-0.65 (m, 3H), 0.58 (dtd, 1H)

Example 131 N-((2R,3S,4S)-4-(2,2-difluoroethyl)-1-(1-(4-fluorophenyl)-1H-indazol-5-yl)-5-oxo-2-phenylpyrrolidin-3-yl)cyclopropanecarboxamide and
Example 132 N-((2R,3S,4R)-4-(2,2-difluoroethyl)-1-(1-(4-fluorophenyl)-1H-indazol-5-yl)-5-oxo-2-phenylpyrrolidin-3-yl)cyclopropanecarboxamide

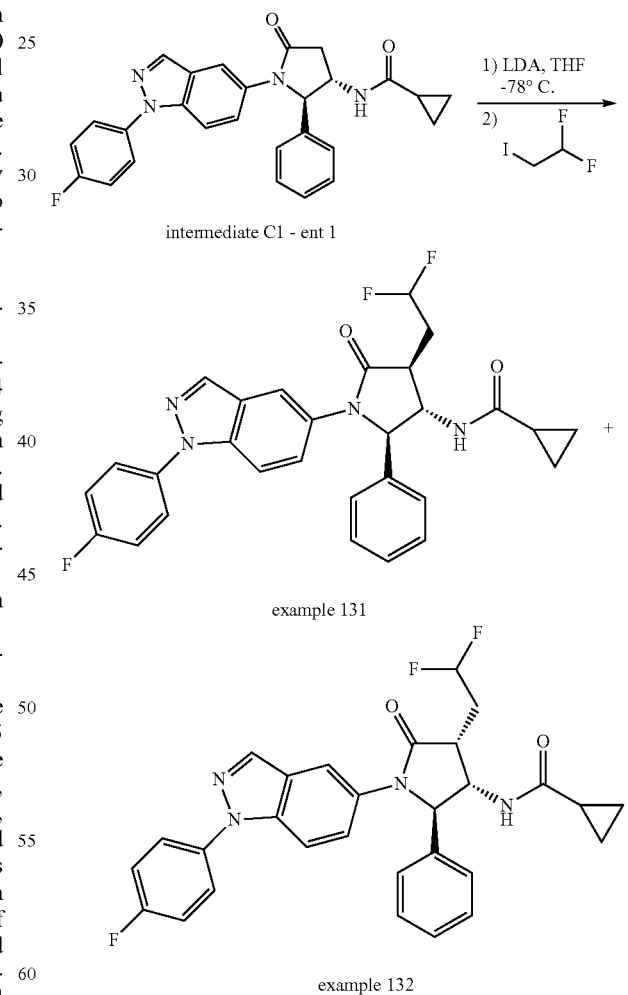

In a dried vessel, intermediate C1-ent 1 (150 mg, 0.33 mmol) was dissolved in dry THF (3.3 ml) under inert atmosphere. The solution was cooled down to −78° C. and a solution of freshly prepared LDA (1 M in THF, 0.825 ml, 2.5 eq.) was added dropwise. After stirring for 15 min at −78° C., 1,1-difluoro-2-iodo-ethane (82.4 mg, 0.429 mmol, 1.3 eq.) dissolved in dry THF (1.7 mL) was added dropwise. The mixture was warmed up to −40° C. and stirred overnight at that temperature. Another amount of, 1,1-difluoro-2-iodo-ethane (82.4 mg, 0.429 mmol, 1.3 eq.) was added and the mixture was warmed up to −20° C. At this temperature, sat. NH$_4$Cl-solution was added and stirring was continued before the mixture was diluted with ethyl acetate. After the layers were separated, the organics were dried over sodium sulfate and the solvent was removed in vacuo. The crude material was purified via flash chromatography (12 g silica, cyclohexane/ethyl acetate gradient as eluent) to obtain example 131 N-((2R,3S,4S)-4-(2,2-difluoroethyl)-1-(1-(4-fluorophenyl)-1H-indazol-5-yl)-5-oxo-2-phenylpyrrolidin-3-yl)cyclopropanecarboxamide (9.0 mg, 0.017 mmol, 5%) and example 132 N-((2R,3S,4R)-4-(2,2-difluoroethyl)-1-(1-(4-fluorophenyl)-1H-indazol-5-yl)-5-oxo-2-phenylpyrrolidin-3-yl)cyclopropanecarboxamide (7.0 mg, 0.014 mmol, 4%) as white solids.

Example 131: $^1$H NMR (DMSO-d$_6$) δ: 8.30 (d, J=1.0 Hz, 1H), 7.85-7.64 (m, 3H), 7.68 (d, 1H), 7.56-7.21 (m, 6H), 7.36-7.07 (m, 3H), 5.24 (d, 1H), 4.25 (q, 1H), 2.97 (q, 1H), 2.54-2.34 (m, 1H), 1.25 (s, 2H), 0.81-0.52 (m, 3H).

Example 132: $^1$H NMR (DMSO-d$_6$) δ: 8.95 (d, 1H), 8.33 (s, 1H), 8.02 (d, 1H), 7.85 (dd, J=9.2, 2.1 Hz, 1H), 7.87-7.67 (m, 3H), 7.51-7.19 (m, 7H), 5.28 (s, 1H), 4.42 (t, 1H), 3.22-3.02 (m, 1H), 2.25-2.02 (m, 1H), 1.24 (s, 2H), 0.96-0.63 (m, 4H).

Example 134 N-(rac-(2R,3S,4R)-4-ethyl-1-(1-(4-fluorophenyl)-1H-indazol-5-yl)-4-methyl-5-oxo-2-phenylpyrrolidin-3-yl)cyclopropanecarboxamide

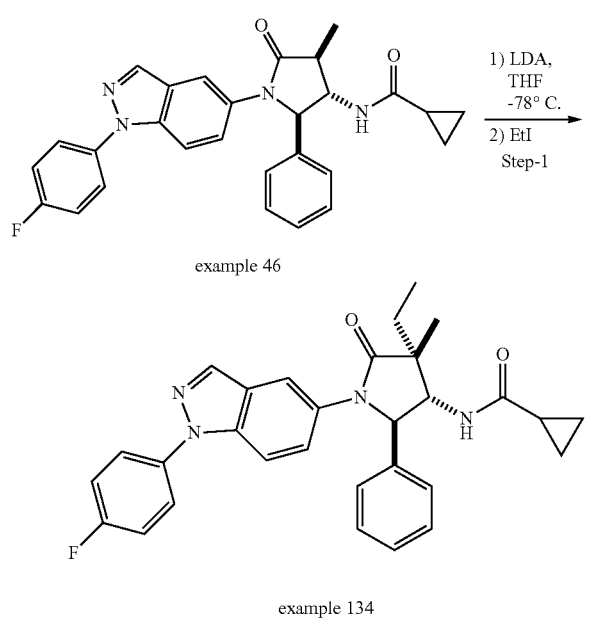

Step-1: In a dried vessel, example 46 (50 mg, 0.107 mmol) was dissolved in dry THF (1.1 ml) under inert atmosphere. The solution was cooled down to −78° C. and a solution of freshly prepared LDA (1 M in THF, 0.267 ml, 2.5 eq.) was added dropwise. After stirring for 15 min at −78° C., iodoethane (25.0 mg, 0.160 mmol, 1.5 eq.) dissolved in dry THF (0.5 mL) was added dropwise. The mixture was warmed up to −60° C. and stirred for 90 minutes at that temperature. Then, the reaction was cooled down again to −78° C. before another amount of Iodoethane (12.5 mg, 0.080 mmol, 0.75 eq.) dissolved in dry THF (0.5 ml) was added. After stirring for 1 h at −78° C. the reaction was quenched with saturated NH$_4$Cl-solution and diluted with dichloromethane after stirring for 5 min. The layers were separated by the means of a hydrophobic frit. The organic layer was washed with water, separated again and dried over sodium sulfate. After removal of the solvent, the crude material was purified via flash chromatography (silica, cyclohexane/ethyl acetate gradient as eluent) and subsequent prep.-HPLC (water/acetonitrile gradient) to obtain example 134 N-(rac-(2R,3S,4R)-4-ethyl-1-(1-(4-fluorophenyl)-1H-indazol-5-yl)-4-methyl-5-oxo-2-phenylpyrrolidin-3-yl)cyclopropanecarboxamide (6 mg, 0.012 mmol, 11%) as a colorless resign.

$^1$H NMR (DMSO-d$_6$) δ 8.47 (d, 1H), 8.30 (d, 1H), 7.77-7.71 (m, 3H), 7.68 (d, 1H), 7.46 (dd, 1H), 7.39 (dd, 2H), 7.36-7.33 (m, 2H), 7.24 (t, 2H), 7.15 (td, 1H), 5.15 (d, 1H), 4.33 (t, 1H), 1.72-1.63 (m, 2H), 1.54 (dq, 1H), 1.24 (s, 3H), 0.95 (d, 2H), 0.73-0.67 (m, 1H), 0.63 (qt, 2H), 0.59-0.50 (m, 1H).

Example 135 N-((7R,8S)-6-(1-(4-fluorophenyl)-1H-indazol-5-yl)-5-oxo-7-phenyl-6-azaspiro[3.4]octan-8-yl)cyclopropanecarboxamid

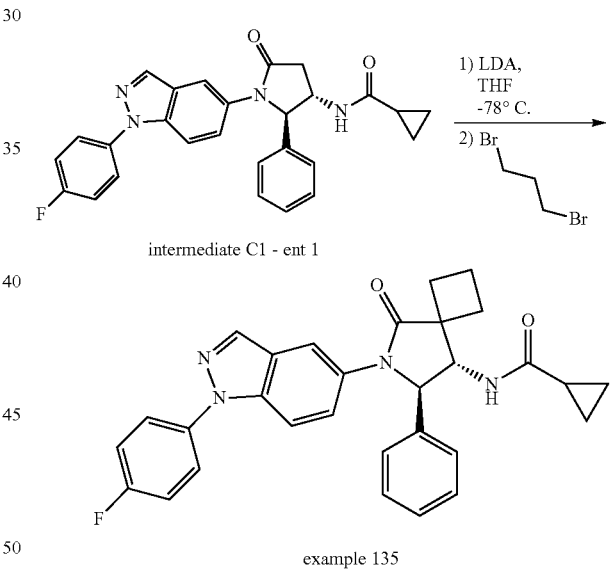

In a dried vessel, intermediate C1-ent 1 (150 mg, 0.33 mmol) was dissolved in dry THF (3.3 ml) under inert atmosphere. The solution was cooled down to −78° C. and a solution of freshly prepared LDA (1 M in THF, 0.825 ml, 2.5 eq.) was added dropwise. After stirring for 15 min at −78° C., 1,3-dibromopropane (93.3 mg, 0.462 mmol, 1.3 eq.) dissolved in dry THF (1.7 mL) was added dropwise. The mixture was warmed up to room temperature overnight. The mixture was cooled down again to −20° C. before additional amounts of LDA (1 M in THF, 0.330 ml, 1.0 eq.) and 1,3-dibromopropane (71.8 mg, 0.355 mmol, 1.0 eq.) were added. After stirring for 15 minutes, another amount of LDA (1 M in THF, 0.495 ml, 1.5 eq.) was added. The mixture was allowed to warm up to room temperature again overnight and quenched with sat. NH$_4$Cl-solution. Stirring was continued for 5 minutes before the mixture was diluted with ethyl acetate. After the layers were separated, the organics were dried over sodium sulfate and the solvent was removed in vacuo. The crude material was purified via flash chromatography (12 g silica, cyclohexane/ethyl acetate gradient as eluent) to obtain example 135 N-((7R,8S)-6-(1-(4-fluorophenyl)-1H-indazol-5-yl)-5-oxo-7-phenyl-6-azaspiro[3.4]octan-8-yl)cyclopropanecarboxamid (11 mg, 0.022 mmol, 7%) colorless resin.

$^1$H NMR (DMSO-d$_6$) δ: 8.09 (d, 1H), 7.99 (dd, 1H), 7.81 (dd, 1H), 7.63 (ddd, 2H), 7.56 (dt, 1H), 7.43-7.39 (m, 2H), 7.35-7.30 (m, 3H), 7.28-7.24 (m, 1H), 7.24-7.20 (m, 2H), 6.03 (d, 1H).

Example 137 N-(rac-(2R,3R,4S)-4-benzyl-2-ethyl-4-fluoro-1-(1-(4-fluorophenyl)-1H-indazol-5-yl)-5-oxopyrrolidin-3-yl)cyclopropanecarboxamide 15 min at −78° C. and quenched with saturated NH$_4$Cl-solution. After stiring for 5 min, the mixture was diluted with ethyl acetate and the layers were separated. After removal of the solvent, the crude material was purified via via flash chromatography (silica, cyclohexane/ethyl acetate gradient as eluent) to give example 137 N-(rac-(2R,3R,4S)-4-benzyl-2-ethyl-4-fluoro-1-(1-(4-fluorophenyl)-1H-indazol-5-yl)-5-oxopyrrolidin-3-yl)cyclopropanecarboxamide (4 mg, 0.008 mmol, 6%) as a colorless oil.

$^1$H NMR (Chloroform-d$_3$) δ: 8.19 (d, 1H), 7.67 (dd, 3H), 7.57 (d 1H), 7.39-7.34 (m, 3H), 7.32 (dd, 2H), 7.28-7.25 (m, 2H), 7.22 (dd, 1H), 6.01 (t, 1H), 4.97-4.86 (m, 1H), 3.51-3.42 (m, 1H), 3.34 (dd, 1H), 3.17-3.08 (m, 1H), 1.54 (qd, 2H), 1.42 (tt, 1H), 1.15-1.09 (m, 1H), 1.10-1.05 (m, 1H), 0.94-0.88 (m, 1H), 0.85 (dddd, 1H), 0.75 (t, 3H).

Example 138 N-((2R,3S,4S)-1-(1-(4-fluorophenyl)-1H-indazol-5-yl)-4-((3-methyl-1,2,4-oxadiazol-5-yl)methyl)-5-oxo-2-phenylpyrrolidin-3-yl)cyclopropanecarboxamide

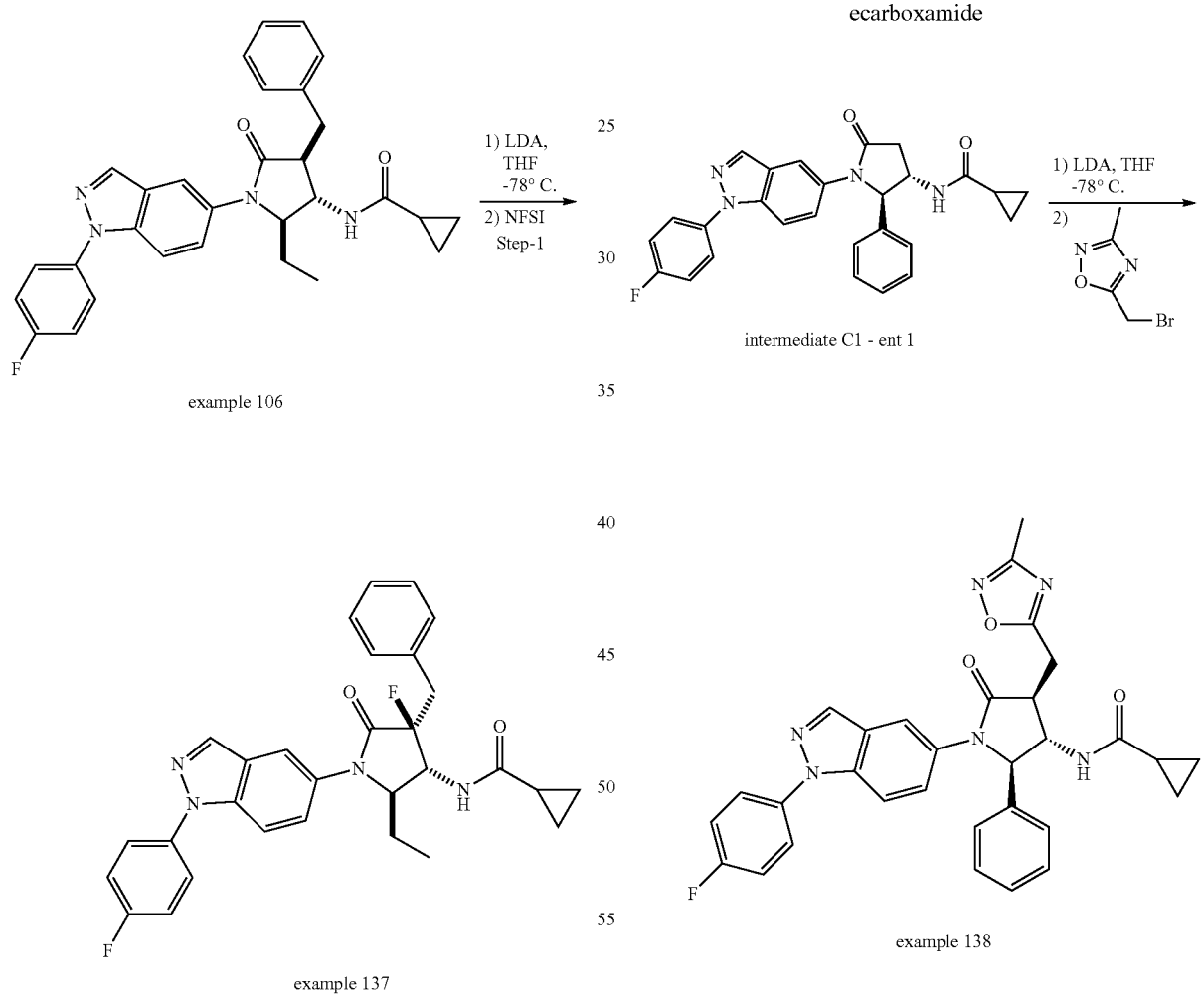

Step-1: In a dried vessel, example 106 (70 mg, 0.141 mmol) was dissolved in dry THF (1.4 ml) under inert atmosphere. The solution was cooled down to −78° C. and a solution of freshly prepared LDA (1 M in THF, 0.352 ml, 2.5 eq.) was added dropwise. After stirring for 15 min at −78° C., N-fluoro-N-(phenylsulfonyl)benzenesulfonamide (NFSI, 66.7 mg, 0.211 mmol, 1.5 eq.) dissolved in dry THF (0.7 mL) was added dropwise. The mixture was stirred for Example 138 was prepared in analogy to the synthesis described for example 131 using 5-(bromomethyl)-3-methyl-1,2,4-oxadiazole instead of 1,1-difluoro-2-iodo-ethane. Yield: 9%

$^1$H NMR (DMSO-d$_6$) δ: 8.55 (d, 1H), 8.29 (d, 1H), 7.77-7.70 (m, 3H), 7.70-7.64 (m, 1H), 7.47-7.36 (m, 5H), 7.24 (t, 2H), 7.17-7.10 (m, 1H), 5.27 (d, 1H), 4.41 (q, 1H), 3.46-3.36 (m, 1H), 2.35 (s, 3H), 1.50 (tt, 1H), 0.71-0.50 (m, 4H).

Example 139a N-((2R,3S,4S)-1-(1-(4-fluorophenyl)-1H-indazol-5-yl)-4-((1-methyl-1H-pyrazol-4-yl)methyl)-5-oxo-2-phenylpyrrolidin-3-yl)cyclopropanecarboxamide and Example 139b N-((2R,3S,4R)-1-(1-(4-fluorophenyl)-1H-indazol-5-yl)-4-((1-methyl-1H-pyrazol-4-yl)methyl)-5-oxo-2-phenylpyrrolidin-3-yl)cyclopropanecarboxamide

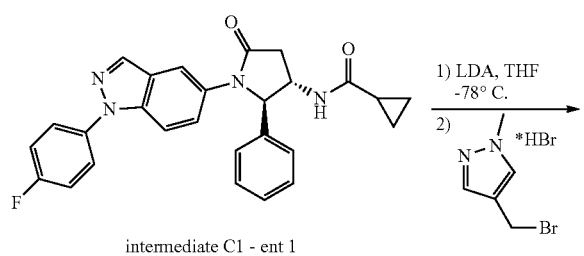

intermediate C1 - ent 1

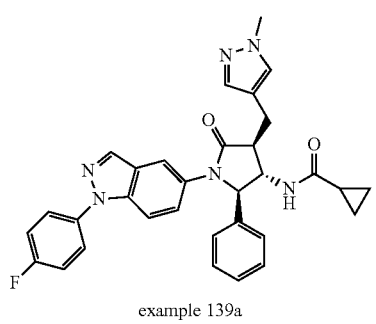

example 139a

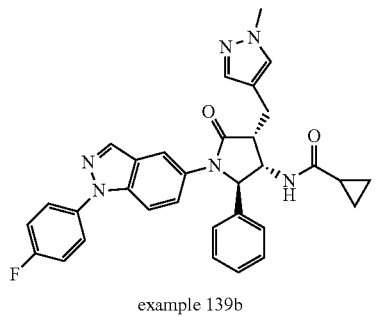

example 139b

Examples 139a and 139b were prepared in analogy to the synthesis described for examples 131 and 132 using and 5.0 eq. of LDA and 4-(bromomethyl)-1-methyl-1H-pyrazole hydrobromide instead of 1,1-difluoro-2-iodo-ethane. Yields: 7% (139a) and 6% (139b).

Example 139a $^1$H NMR (Chloroform-d$_3$) δ: 8.06 (d, 1H), 7.68 (d, 1H), 7.61-7.54 (m, 2H), 7.51-7.43 (m, 2H), 7.37 (dd, 1H), 7.29 (d, 1H), 7.25-7.13 (m, 5H), 7.07-7.00 (m, 2H), 6.13 (d, 1H), 5.13 (d, 1H), 4.23 (dt, 1H), 3.87 (s, 3H), 3.08-2.98 (m, 3H), 1.38 (tt, 1H), 1.05-0.93 (m, 2H), 0.79 (ddddd, 2H).

Example 139b $^1$H NMR (Chloroform-d$_3$) δ: 8.07 (d, 1H), 7.95 (d, 1H), 7.69 (dd, 1H), 7.64-7.58 (m, 2H), 7.51 (d, 1H), 7.42-7.33 (m, 5H), 7.32-7.27 (m, 1H), 7.26 (s, 1H), 7.25-7.19 (m, 2H), 6.58 (d, 1H), 5.17 (s, 1H), 4.58 (t, 1H), 3.84 (s, 3H), 3.21-3.11 (m, 2H), 2.92-2.83 (m, 1H), 1.50 (tt, 1H), 1.16-1.07 (m, 2H), 0.94-0.81 (m, 2H).

Example 148 N-(rac-(2R,3S,4S)-4-(2,2-difluoroethyl)-1-(1-(4-fluorophenyl)-1H-indazol-5-yl)-4-methyl-5-oxo-2-phenylpyrrolidin-3-yl)cyclopropanecarboxamide

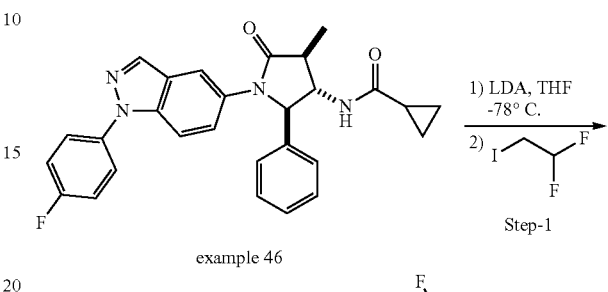

example 46

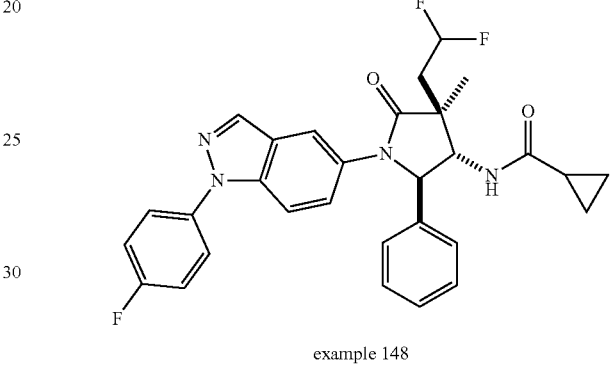

example 148

Step-1: In a dried vessel, example 46 (71 mg, 0.152 mmol) was dissolved in dry THF (1.5 ml) under inert atmosphere. The solution was cooled down to −78° C. and a solution of freshly prepared LDA (1 M in THF, 0.379 ml, 2.5 eq.) was added dropwise. After stirring for 15 min at −78° C., 1,1-difluoro-2-iodo-ethane (43.6 mg, 0.160 mmol, 1.5 eq.) dissolved in dry THF (0.75 mL) was added dropwise. The mixture was warmed up to −50° C. and stirred for 45 minutes at that temperature. Then, another amount of 1,1-difluoro-2-iodo-ethane (11.4 mg, 0.110 mmol, 0.75 eq.) dissolved in dry THF (0.5 ml) was added. After stirring for 1 h at −78° C. the reaction was quenched with saturated NH$_4$Cl-solution and diluted with dichloromethane after stirring for 5 min. The layers were separated by the means of a hydrophobic frit. The organic layer was washed with water, separated again and dried over sodium sulfate. After removal of the solvent, the crude material was purified via prep.-HPLC (water/acetonitrile gradient) to obtain example 148 N-(rac-(2R,3S,4S)-4-(2,2-difluoroethyl)-1-(1-(4-fluorophenyl)-1H-indazol-5-yl)-4-methyl-5-oxo-2-phenylpyrrolidin-3-yl)cyclopropanecarboxamide 3.0 mg 0.0056 mmol, 3.7%) as a colorless resin.

$^1$H NMR (Chloroform-d$_3$) δ: 8.07 (d, 1H), 7.63 (d, 1H), 7.60-7.56 (m, 2H), 7.50 (dt, 1H), 7.32 (dd, 1H), 7.29-7.25 (m, 4H), 7.23-7.18 (m, 3H), 6.43 (tdd, 1H), 5.91 (dd, 1H), 4.92 (d, 1H), 4.78 (t, 1H), 2.50-2.39 (m, 1H), 2.39-2.27 (m, 1H), 1.43 1.37 (m, 1H), 1.36 (s, 3H), 0.97 (dddd, 1H), 0.86 (dddd, 1H), 0.83-0.77 (m, 1H), 0.74 (dddd, 1H).

Example 149 N-(rac-(2R,3S,4S)-4-(cyclopropylmethyl)-1-(1-(4-fluorophenyl)-1H-indazol-5-yl)-4-methyl-5-oxo-2-phenylpyrrolidin-3-yl)cyclopropanecarboxamide

Example 150 N-((2R,3S,4R)-1-(1-(4-fluorophenyl)-1H-indazol-5-yl)-5-oxo-2-phenyl-4-(thiazol-2-ylmethyl)pyrrolidin-3-yl)cyclopropanecarboxamide

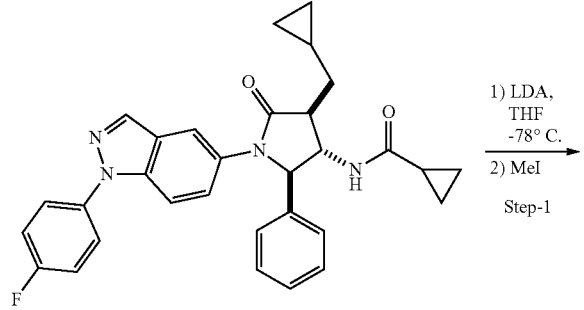

example 121

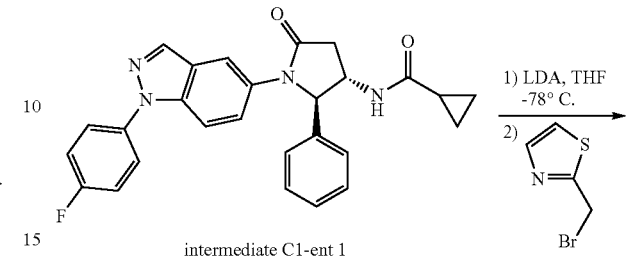

intermediate C1-ent 1

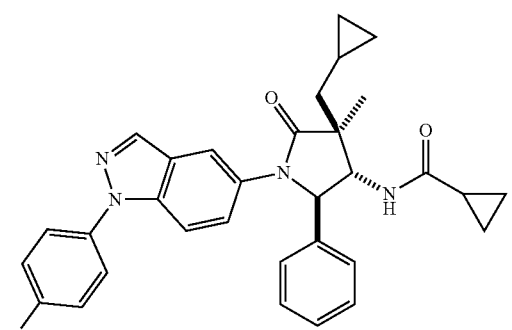

example 149

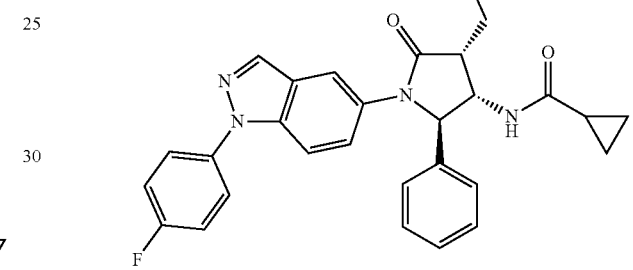

example 150

Step-1: In a dried vessel, example 121 (150 mg, 0.295 mmol) was dissolved in dry THF (3 ml) under inert atmosphere. The solution was cooled down to −78° C. and a solution of freshly prepared LDA (1 M in THF, 0.737 ml, 2.5 eq.) was added dropwise. After stirring for 15 min at −78° C., iodomethane (62.8 mg, 0.442 mmol, 1.5 eq.) was added dropwise. The mixture was stirred for 45 minutes at that temperature. Then, another amount of iodomethane (42 mg, 0.110 mmol, 1 eq.) was added. After stirring for 1 h at −78° C. the reaction was quenched with saturated NH$_4$Cl-solution and diluted with dichloromethane after stirring for 5 min. The layers were separated by the means of a hydrophobic frit. The organic layer was washed with water, separated again and dried over sodium sulfate. After removal of the solvent, the crude material was purified via prep.-HPLC (water/acetonitrile gradient) to obtain Example 149 N-(rac-(2R,3S,4S)-4-(cyclopropylmethyl)-1-(1-(4-fluorophenyl)-1H-indazol-5-yl)-4-methyl-5-oxo-2-phenylpyrrolidin-3-yl)cyclopropanecarboxamide (14.0 mg, 0.0268 mmol, 9%) as a colorless resin.

$^1$H NMR (DMSO-d$_6$) δ: 8.44 (d, 1H), 8.30 (d, 1H), 7.79-7.70 (m, 3H), 7.68 (d, 1H), 7.47 (dd, 1H), 7.43-7.33 (m, 4H), 7.23 (t, 2H), 7.15 (td, 1H), 5.23 (d, 1H), 4.34 (t, 1H), 1.85 (dd, 1H), 1.69 (ddd, 1H), 1.30 (s, 3H), 1.13 (dd, 1H), 1.05 (tt, 1H), 0.71 (tdd, 1H), 0.68-0.58 (m, 2H), 0.55 (tdt, 1H), 0.45-0.36 (m, 2H), 0.08-0.05 (m, 2H).

Step-1: In a dried vessel, intermediate C1-ent 1 (150 mg, 0.295 mmol) was dissolved in dry THF (4.7 ml) under inert atmosphere. The solution was cooled down to −78° C. and a solution of freshly prepared LDA (1 M in THF, 1.32 ml, 4 eq.) was added dropwise. After stirring for 15 min at −78° C., 2-(chloromethyl)-1,3-thiazole hydrochloride (67 mg, 0.396 mmol, 1.2 eq.) was added as a solid. The mixture was for one hour at −40° C. Then, another amount of LDA (1 M in THF, 0.165 ml, 1 eq.) followed by 2-(chloromethyl)-1,3-thiazole hydrochloride (28.1 mg, 0.165 mmol, 0.5 eq.) was added. After stirring overnight at −40° C., the reaction was quenched with saturated NH$_4$Cl-solution and diluted with dichloromethane after stirring for 5 min. The layers were separated by the means of a hydrophobic frit. The organic layer was washed with water, separated again and dried over sodium sulfate. After removal of the solvent, the crude material was purified via prep.-HPLC (water/acetonitrile gradient) to obtain example 150. N-((2R,3S,4R)-1-(1-(4-fluorophenyl)-1H-indazol-5-yl)-5-oxo-2-phenyl-4-(thiazol-2-ylmethyl)pyrrolidin-3-yl)cyclopropanecarboxamide (26.3 mg 0.0477 mmol 14%) as a off-white solid.

$^1$H NMR (600 MHz, Chloroform-d$_3$) δ: 9.22 (d, 1H), 8.06 (d, 1H), 7.77 (d, 1H), 7.72 (d, 1H), 7.65-7.58 (m, 2H), 7.53-7.46 (m, 2H), 7.45-7.40 (m, 2H), 7.37-7.31 (m, 3H), 7.31-7.26 (m, 1H), 7.24-7.18 (m, 2H), 5.09 (d, 1H), 4.72 (td, 1H), 3.71 (dd, 1H), 3.58 (td, 1H), 3.44 (dd, 1H), 1.56 (tt, 1H), 1.09-1.02 (m, 2H), 0.85-0.78 (m, 2H).

Example 151 N-((2S,3S)-2-(5-chlorothiophen-2-yl)-1-(1-(4-fluorophenyl)-1H-indazol-5-yl)-2-methyl-5-oxopyrrolidin-3-yl)cyclopropanecarboxamide

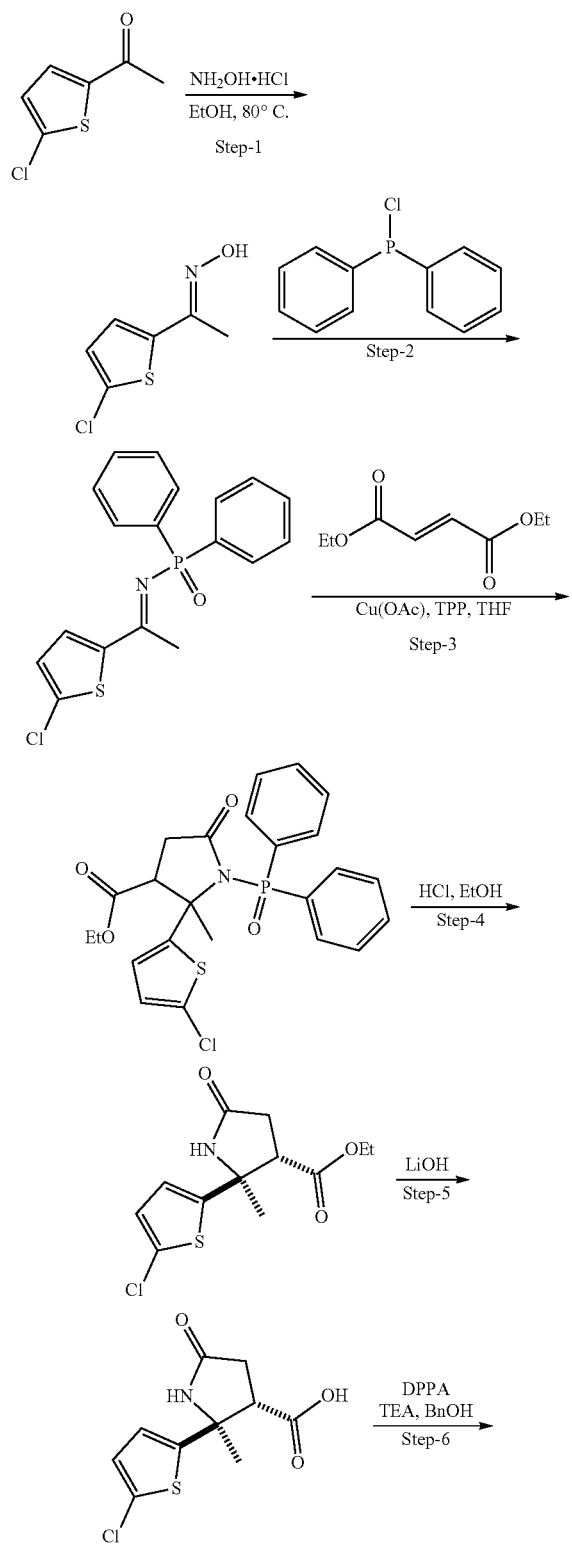

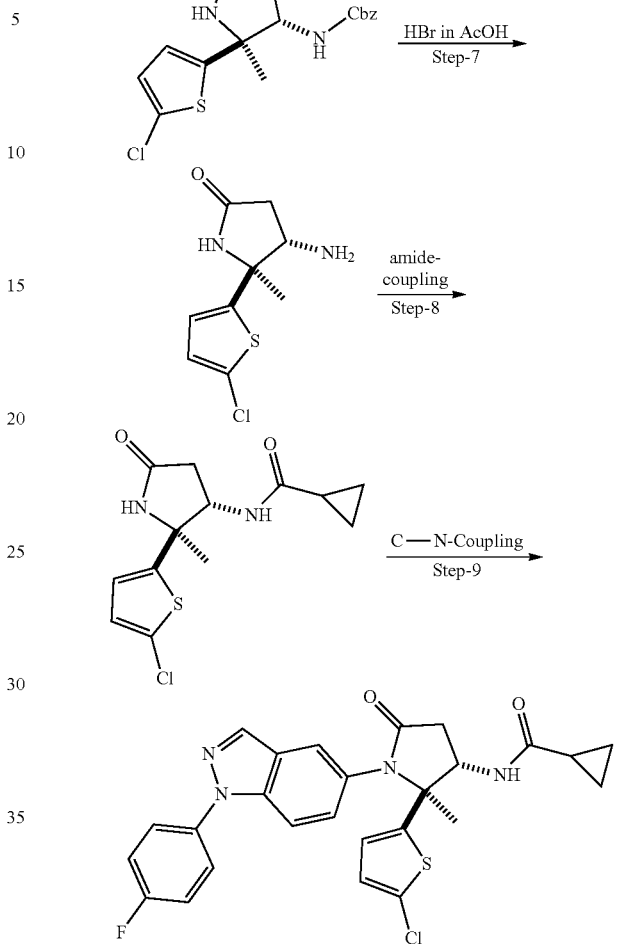

Step-1: To a stirred solution of 1-(5-chlorothiophen-2-yl)ethan-1-one (20 g, 125 mmol, 1.0 eq) in EtOH (250 mL) at RT were added NaOAc (50.6 g, 625 mmol, 5.0 eq) and NH$_2$OH·HCl (25.7 g, 375 mmol, 3.0 eq) and stirred for 16 h at 80° C. The reaction progress was monitored by TLC. The reaction mixture was evaporated, diluted with H$_2$O and the formed precipitate was washed with H$_2$O (100 mL) and dried under vacuum to get (E)-1-(5-chlorothiophen-2-yl)ethan-1-one oxime (20 g, 94%) as a brown liquid.

Step-2: To a stirred solution of compound (E)-1-(5-chlorothiophen-2-yl)ethan-1-one oxime (10 g, 57.14 mmol, 1.0 eq) in DCM (100 mL) at −40° C. were added TEA (9.2 mL, 68.57 mmol, 1.2 eq) and the mixture was stirred for 15 min prior to the addition of chlorodiphenylphosphine (13.8 g, 62.85 mmol, 1.1 eq). The reaction was slowly allowed to warm up to rt and stirred for 2 h. The reaction progress was monitored by TLC. The reaction mixture was diluted with H$_2$O (100 mL), and extracted with DCM (2×200 mL). The combined organic layer was washed with brine (100 mL), dried over Na$_2$SO$_4$ and evaporated. The crude product was purified by flash chromatography (silica 40-60% EtOAc in petroleum ether as an eluent) to get compound (E)-N-(1-(5-chlorothiophen-2-yl)ethylidene)-P,P-diphenylphosphinic amide (15 g, 73%) as a brown solid.

Step-3: To a stirred solution of compound (E)-N-(1-(5-chlorothiophen-2-yl)ethylidene)-P,P-diphenylphosphinic amide (15 g, 41.71 mmol, 1.0 eq) in THF (200 mL) at RT were under nitrogen atmosphere added Cu(OAc)$_2$ (0.377 g, 2.85 mmol, 0.05 eq), TPP (1.0 g, 4.16 mmol, 0.1 eq). The mixture was stirred for 15 min prior to the addition of diethyl fumarate (18 mL, 104 mmol, 2.5 eq), and pinacolborane (14.8 mL, 116 mmol, 2.8 eq). Stirring was continued for 16 h at RT. The reaction progress was monitored by TLC. The reaction mixture was diluted with water (100 mL) and extracted with EtOAc (2×100 mL). The combined organic layers were washed with brine (100 mL), dried (Na$_2$SO$_4$) and evaporated. The crude compound was purified by flash chromatography (silica 40-60% EtOAc in petroleum ether as an eluent) to get compound ethyl 2-(5-chlorothiophen-2-yl)-1-(diphenylphosphoryl)-2-methyl-5-oxopyrrolidine-3-carboxylate (15 g, ~75%) as a white solid.

Step-4: To a stirred solution of compound ethyl 2-(5-chlorothiophen-2-yl)-1-(diphenylphosphoryl)-2-methyl-5-oxopyrrolidine-3-carboxylate (15 g, 30.80 mmol, 1.0 eq) in EtOH (150 mL) at RT was added conc. HCl (15 mL) and stirred for 16 h at 90° C. The reaction progress was monitored by TLC. The reaction mixture was evaporated, diluted with water (50 mL), basified with sat NaHCO$_3$ (pH=8), and extracted with EtOAc (2×200 mL). The combined organic layers were washed with brine (100 mL), dried (Na$_2$SO$_4$) and evaporated. The crude compound was purified by flash chromatography (silica 60-70% EtOAc in petroleum ether as an eluent) to get compound ethyl rac-(2S,3S)-2-(5-chlorothiophen-2-yl)-2-methyl-5-oxopyrrolidine-3-carboxylate (7.0 g, ~81%) as white solid.

Step-5: To a stirred solution of compound ethyl (2S,3S)-2-(5-chlorothiophen-2-yl)-2-methyl-5-oxopyrrolidine-3-carboxylate (7 g, 24.39 mmol, 1.0 eq) in THF/MeOH/H$_2$O (1:1:1, 75 mL) at RT was added LiOH·H$_2$O (1.7 g, 48.78 mmol, 2.0 eq) at Rt and stirring was continued at the same temperature. The reaction progress was monitored by TLC. The reaction mixture was evaporated, diluted with water (30 mL), and extracted with Et$_2$O (2×50 mL). The aqueous layer was acidified with 1N HCl (pH=4-5), and precipitate formed was filtered and dried to get compound (2S,3S)-2-(5-chlorothiophen-2-yl)-2-methyl-5-oxopyrrolidine-3-carboxylic acid (3.5 g, ~97%) as white solid.

Step-6: To a stirred solution of compound rac-(2S,3S)-2-(5-chlorothiophen-2-yl)-2-methyl-5-oxopyrrolidine-3-carboxylic acid (3.4 g, 13.12 mmol, 1.0 eq) in toluene (70 mL) at RT were added TEA (2.0 mL, 13.78 mmol, 1.05 eq), DPPA (3.4 mL, 15.74 mmol, 1.2 eq). Stirring was continued for 2 h at 90° C., the mixture was then cooled to RT, prior to the addition of BnOH (3 mL, 26.25 mmol, 2.0 eq). The resulting mixture was heated for 16 h to 120° C. The reaction progress was monitored by TLC. The reaction mixture was evaporated, diluted with water (50 mL) and extracted with EtOAc (2×100 mL). The combined organic layers were washed with brine (50 mL), dried (Na$_2$SO$_4$) and evaporated. The crude compound was purified by flash chromatography (silica 70-90% EtOAc in petroleum ether as an eluent) to get compound benzyl(rac-(2S,3S)-2-(5-chlorothiophen-2-yl)-2-methyl-5-oxopyrrolidin-3-yl)carbamate (2.0 g, ~41%) as an off-white solid.

Step-7: A stirred solution of compound benzyl(rac-(2S,3S)-2-(5-chlorothiophen-2-yl)-2-methyl-5-oxopyrrolidin-3-yl)carbamate (2.0 g, 5.49 mmol, 1.0 eq) in HBr in AcOH (20 mL) at RT was stirred for 2 h at RT. The reaction progress was monitored by TLC. The reaction mixture was quenched with NaHCO$_3$ solution and extracted with EtOAc (4×100 mL). The combined organic layers were washed with brine (50 mL), dried (Na$_2$SO$_4$) and evaporated. The crude compound was purified by by flash chromatography (silica 70-80% EtOAc in petroleum ether as an eluent) to get compound rac-(4S,5S)-4-amino-5-(5-chlorothiophen-2-yl)-5-methylpyrrolidin-2-one (1.0 g, 41%) as an off-white solid.

Step-8: To a stirred solution of compound rac-(4S,5S)-4-amino-5-(5-chlorothiophen-2-yl)-5-methylpyrrolidin-2-one (400 mg, 1.739 mmol, 1.0 eq) and cyclopropane carboxylic acid (224 mg, 2.608 mmol, 1.5 eq) in DMF (10 mL) at 0° C. under nitrogen atmosphere were added HATU (0.90 g, 2.608 mmol, 1.5 eq), DIPEA (0.9 mL, 5.217 mmol, 3.0 eq) and stirred for 16 h at RT. The reaction progress was monitored by TLC. The reaction mixture was diluted with water (20 mL) and extracted with EtOAc (2×20 mL). The combined organic layers were washed with brine (20 mL), dried (Na$_2$SO$_4$) and evaporated. The crude compound was purified by by flash chromatography (silica 70-90% EtOAc in petroleum ether as an eluent) to get compound N-(rac(2S,3S)-2-(5-chlorothiophen-2-yl)-2-methyl-5-oxopyrrolidin-3-yl)cyclopropanecarboxamide (210 mg, 40%).

Step-9: To a stirred solution of compound N-(rac(2S,3S)-2-(5-chlorothiophen-2-yl)-2-methyl-5-oxopyrrolidin-3-yl)cyclopropanecarboxamide (200 mg, 0.671 mmol, 1.0 eq) and compound 1-(4-fluorophenyl)-5-iodo-1H-indazole (249 mg, 0.738 mmol, 1.5 eq) in dioxane (10 mL) under nitrogen atmosphere were added CuI (127 mg, 0.671 mmol, 1.5 eq), DMEDA (59 mg 0.671 mmol, 1 eq), and K$_2$CO$_3$ (277 mg, 2.013 mmol, 3.0 eq) and stirred at 130° C. for 16 h. The reaction progress was monitored by TLC. The reaction mixture was diluted with water (20 mL) and extracted with EtOAc (2×20 mL). The combined organic layers were washed with brine (20 mL), dried (Na$_2$SO$_4$) and evaporated. The crude compound was purified by by flash chromatography (silica 70-90% EtOAc in petroleum ether as an eluent) followed by prep HPLC to get Example 151 N-((2S,3S)-2-(5-chlorothiophen-2-yl)-1-(1-(4-fluorophenyl)-1H-indazol-5-yl)-2-methyl-5-oxopyrrolidin-3-yl)cyclopropanecarboxamide (50 mg, 53%).

$^1$H NMR (500 MHz, DMSO-d$_6$): δ 8.77 (d, 1H), 8.39 (s, 1H), 7.80-7.76 (m, 3H), 7.58 (d, 1H), 7.63 (s, 1H), 7.44-7.40 (m, 2H), 7.22 (dd, 1H), 7.01 (d, 1H), 6.93 (d, 1H), 4.71-4.67 (m, 1H), 3.10 (dd, 1H), 2.43-2.36 (m, 1H), 1.64-1.61 (m, 1H), 1.48 (s, 3H), 0.72-0.6 (m, 4H).

The examples in the following table were synthesized in analogy to Example 1 described above, using different intermediates.

| Ex. # | Intermediate (INT) | Structure | Yield (%) | ¹H NMR |
|---|---|---|---|---|
| 4 | Int A3 | 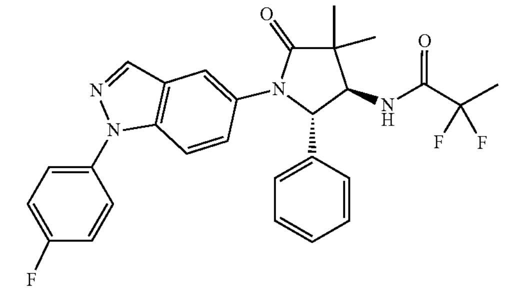 | 12 | ¹H NMR (DMSO-d₆): δ = 9.08 (d, 1H), 8.31 (s, 1H), 7.72-7.69 (m, 4H), 7.41-7.34 (m, 5H), 7.24(s, 2H), 7.17 (m, 1H), 5.41 (d, 1H), 4.26 (t, 1H), 1.71 (t, 3H), 1.27 (s, 3H), 1.13 (s, 3H). |
| 9 | Int A3 | 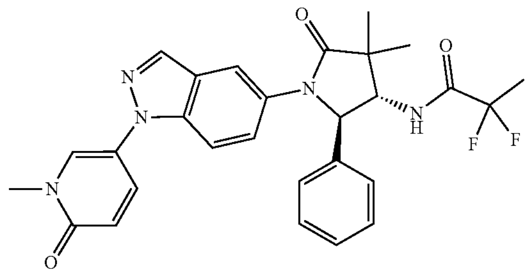 [SMILES: Cn1cc(-n2ncc3cc(N4C(=O)C(C)(C)[C@H](NC(=O)C(C)(F)F)[C@H]4c4ccccc4)ccc32)ccc1=O] | 10 | ¹H NMR (DMSO-d₆): δ = 9.07 (s, 1H), 8.25 (s, 1H), 8.18 (s, 1H), 7.68-7.58 (m, 3H), 7.34-7.17 (m, 6H), 6.51 (s, 1H), 5.39 (s, 1H), 4.25 (s, 1H), 3.48 (s, 3H), 1.71 (t, 3H), 1.27 (s, 3H), 1.13 (s, 3H) |
| 10 | Int A3 | 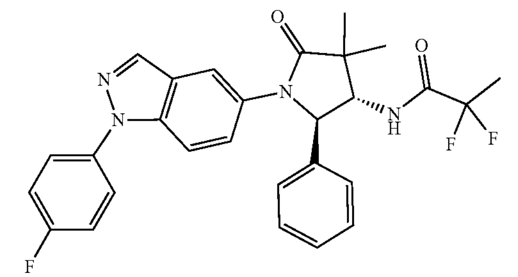 [SMILES: CC(F)(F)C(=O)N[C@@H]1[C@@H](c2ccccc2)N(c2ccc3c(cnn3-c3ccc(F)cc3)c2)C(=O)C1(C)C] | 13 | ¹H NMR (DMSO-d₆): δ = 9.08 (d, 1H), 8.31 (s, 1H), 7.72-7.69 (m, 4H), 7.41-7.34 (m, 5H), 7.24 (s, 2H), 7.17 (m, 1H), 5.41 (d, 1H), 4.26 (t, 1H), 1.71 (t, 3H), 1.27 (s, 3H), 1.13 (s, 3H). |

The examples in the following table were synthesized in analogy to Example 5 described above, using different intermediates.

| Ex. # | Intermediate (INT) | Structure | Yield (%) | ¹H NMR |
|---|---|---|---|---|
| 3 | Int A5 | 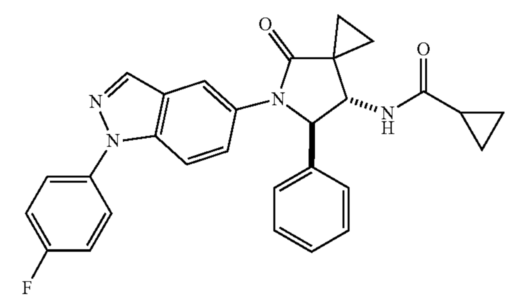 [SMILES: O=C(N[C@@H]1[C@@H](c2ccccc2)N(c2ccc3c(cnn3-c3ccc(F)cc3)c2)C(=O)C12CC2)C1CC1] | 10 | ¹H NMR (DMSO-d₆) δ: 8.90 (d, 1H), 8.30 (t, 1H), 7.93 (dd, 1H), 7.79-7.69 (m, 4H), 7.43-7.37 (m, 4H), 7.34 (t, 2H), 7.28-7.21 (m, 1H), 5.29 (d, 1H), 4.03 (dd, 1H), 1.68 (tt, 1H), 1.31-0.91 (m, 4H), 0.80-0.62 (m, 4H) |

| Ex. # | Intermediate (INT) | Structure | Yield (%) | ¹H NMR |
|---|---|---|---|---|
| 30 | Int A5 | 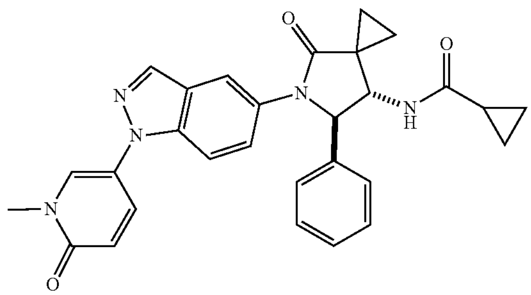 | 4 | ¹H NMR (DMSO-d$_6$) δ: 8.89 (d, 1H), 8.25 (d, 1H), 8.18 (d, 1H), 7.92 (dd, 1H), 7.71 (ddd, 2H), 7.61 (dt, 1H), 7.41-7.36 (m, 2H), 7.33 (t, 2H), 7.27-7.21 (m, 1H), 6.54 (dd, 1H), 5.28 (d, 1H), 4.03 (dd, 1H), 3.50 (s, 3H), 1.72-1.64 (m, 1H), 1.26-1.15 (m, 1H), 1.16-1.08 (m, 1H), 0.95 (q, 2H), 0.74 (ddd, 1H), 0.73-0.68 (m, 3H) |

The examples in the following table were synthesized in analogy to Example 7 described above, using different intermediates.

| Ex. # | Intermediate (INT) | Structure | Yield (%) | ¹H NMR |
|---|---|---|---|---|
| 6 | Int A 4 ent 1 | 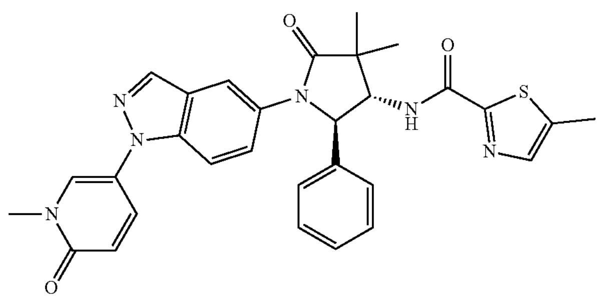 | 31 | ¹H NMR (DMSO-d$_6$) δ: 9.11 (d, 1H), 8.26 (d, 1H), 8.17 (d, 1H), 7.78 (t, 1H), 7.72-7.67 (m, 2H), 7.59 (d, 1H), 7.40 (d, 1H), 7.39-7.35 (m, 2H), 7.22 (t, 2H), 7.17-7.11 (m, 1H), 6.54 (d, 1H), 5.63 (d, 1H), 4.46 (t, 1H), 3.50 (s, 3H), 2.52 (s, 3H), 1.32 (s, 3H), 1.18 (s, 3H) |
| 12 | Int A 4 ent 1 | 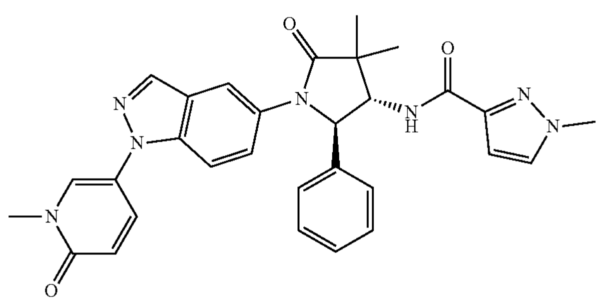 | 80 | ¹H NMR (DMSO-d$_6$) δ: 8.39 (d, 1H), 8.25 (d, 1H), 8.17 (d, 1H), 7.78 (d, 1H), 7.72-7.68 (m, 2H), 7.59 (d, 1H), 7.40 (dd, 1H), 7.38-7.35 (m, 2H), 7.21 (t, 2H), 7.15-7.10 (m, 1H), 6.57 (d, 1H), 6.54 (d, 1H), 5.59 (d, 1H), 4.50 (t, 1H), 3.96 (s, 3H), 3.50 (s, 3H), 1.30 (s, 3H), 1.17 (s, 3H) |
| 13 | Int A 4 ent 1 | 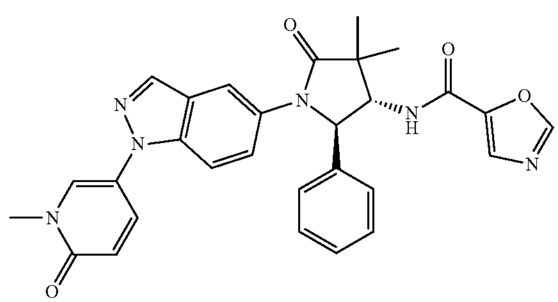 | 85 | ¹H NMR (DMSO-d$_6$) δ: 8.96 (dd, 1H), 8.60 (s, 1H), 8.26 (d, 1H), 8.18 (d, 1H), 7.83 (s, 1H), 7.73 (d, 1H), 7.70 (dd, 1H), 7.62-7.57 (m, 1H), 7.41 (dd, 1H), 7.39-7.36 (m, 2H), 7.23 (t, 2H), 7.18-7.12 (m, 1H), 6.54 (d, 1H), 5.41 (d, 1H), 4.48 (t, 1H), 3.50 (s, 3H), 1.31 (s, 3H), 1.18 (s, 3H) |

-continued

| Ex. # | Intermediate (INT) | Structure | Yield (%) | ¹H NMR |
|---|---|---|---|---|
| 14 | Int A 4 ent 1 | 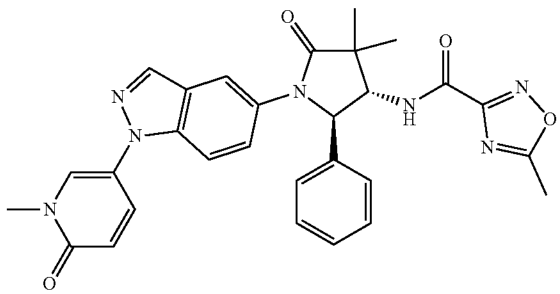 [SMILES: Cc1nc(C(=O)N[C@@H]2[C@@H](c3ccccc3)N(c3ccc4c(cnn4-c4ccc(=O)n(C)c4)c3)C(=O)C2(C)C)no1] | 64 | ¹H NMR (DMSO-d$_6$) δ: 9.38 (d, 1H), 8.26 (d, 1H), 8.18 (d, 1H), 7.72-7.67 (m, 2H), 7.62-7.57 (m, 1H), 7.41-7.37 (m, 3H), 7.24 (t, 2H), 7.18-7.13 (m, 1H), 6.54 (d, 1H), 5.55 (d, 1H), 4.50 (t, 1H), 3.50 (s, 3H), 2.69 (s, 3H), 1.33 (s, 3H), 1.18 (s, 3H) |
| 15 | Int A 4 ent 1 | 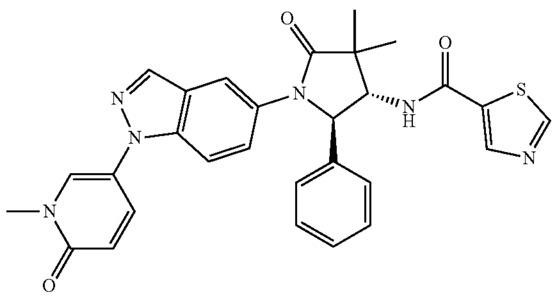 [SMILES: Cn1cc(-n2ncc3cc(N4C(=O)C(C)(C)[C@H](NC(=O)c5cncs5)[C@H]4c4ccccc4)ccc32)ccc1=O] | 70 | ¹H NMR (DMSO-d$_6$) δ: 9.25 (d, 1H), 8.95 (dd, 1H), 8.60 (s, 1H), 8.26 (d, 1H), 8.18 (d, 1H), 7.75 (dd, 1H), 7.74-7.67 (m, 1H), 7.60 (dd, 1H), 7.46-7.41 (m, 1H), 7.39 (dd, 2H), 7.24 (t, 2H), 7.18-7.12 (m, 1H), 6.54 (d, 1H), 5.36 (d, 1H), 4.51-4.45 (m, 1H), 3.50 (d, 3H), 1.32 (s, 3H), 1.20 (s, 3H) |
| 16 | Int A 4 ent 1 | 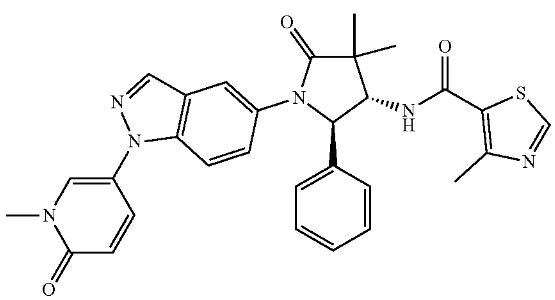 [SMILES: Cc1ncsc1C(=O)N[C@@H]1[C@@H](c2ccccc2)N(c2ccc3c(cnn3-c3ccc(=O)n(C)c3)c2)C(=O)C1(C)C] | 60 | ¹H NMR (DMSO-d$_6$) δ: 9.08 (s, 1H), 8.61 (dd, 1H), 8.25 (d, 1H), 8.18 (d, 1H), 7.73 (d, 1H), 7.70 (dd, 1H), 7.59 (d, 1H), 7.42 (dd, 1H), 7.40-7.37 (m, 2H), 7.25 (t, 2H), 7.20-7.14 (m, 1H), 6.54 (d, 1H), 5.37 (d, 1H), 4.47 (t, 1H), 3.50 (s, 3H), 2.51 (s, 3H), 1.34 (s, 3H), 1.18 (s, 3H) |
| 17 | Int A 4 ent 1 | 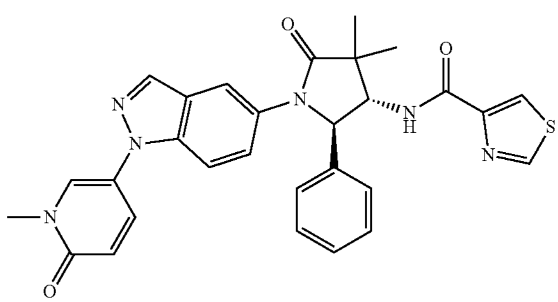 [SMILES: Cn1cc(-n2ncc3cc(N4C(=O)C(C)(C)[C@H](NC(=O)c5cscn5)[C@H]4c4ccccc4)ccc32)ccc1=O] | 87 | ¹H NMR (DMSO-d$_6$) δ: 9.25 (d, 1H), 8.79 (d, 1H), 8.30 (d, 1H), 8.26 (d, 1H), 8.17 (d, 1H), 7.72-7.68 (m, 2H), 7.61-7.57 (m, 1H), 7.41 (dd, 1H), 7.39-7.36 (m, 2H), 7.21 (t, 2H), 7.15-7.10 (m, 1H), 6.54 (d, 1H), 5.64 (d, 1H), 4.53 (t, 1H), 3.50 (s, 3H), 1.33 (s, 3H), 1.19 (s, 3H) |
| 18 | Int A 4 ent 1 | 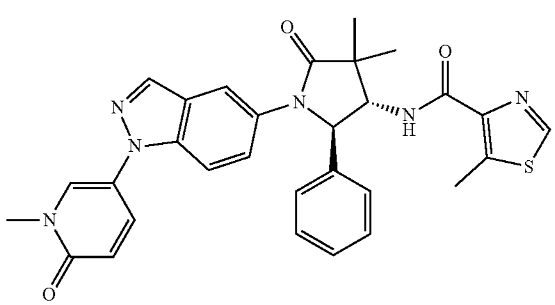 [SMILES: Cc1scnc1C(=O)N[C@@H]1[C@@H](c2ccccc2)N(c2ccc3c(cnn3-c3ccc(=O)n(C)c3)c2)C(=O)C1(C)C] | 73 | ¹H NMR (DMSO-d$_6$) δ: 9.08 (s, 1H), 8.61 (dd, 1H), 8.25 (d, 1H), 8.18 (d, 1H), 7.73 (d, 1H), 7.70 (dd, 1H), 7.61-7.57 (m, 1H), 7.42 (dd, 1H), 7.40-7.36 (m, 2H), 7.25 (t, 2H), 7.20-7.14 (m, 1H), 6.54 (d, 1H), 5.37 (d, 1H), 4.47 (t, 1H), 3.50 (s, 3H), 2.51 (s, 3H), 1.34 (s, 3H), 1.18 (s, 3H) |

| Ex. # | Intermediate (INT) | Structure | Yield (%) | ¹H NMR |
|---|---|---|---|---|
| 21 | Int A 4 ent 2 | 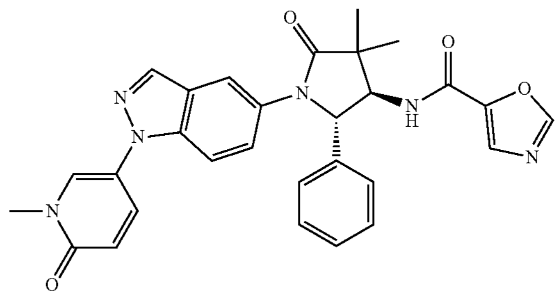 | 77 | ¹H NMR (DMSO-d$_6$) δ: 8.95 (dd, 1H), 8.60 (s, 1H), 8.26 (d, 1H), 8.17 (d, 1H), 7.83 (s, 1H), 7.74-7.72 (m, 1H), 7.70 (dd, 1H), 7.62-7.57 (m, 1H), 7.41 (dd, 1H), 7.39-7.36 (m, 2H), 7.23 (t, 2H), 7.17-7.12 (m, 1H), 6.54 (d, 1H), 5.41 (d, 1H), 4.48 (t, 1H), 3.50 (s, 3H), 1.31 (s, 3H), 1.18 (s, 3H) |
| 22 | Int A 4 ent 2 | 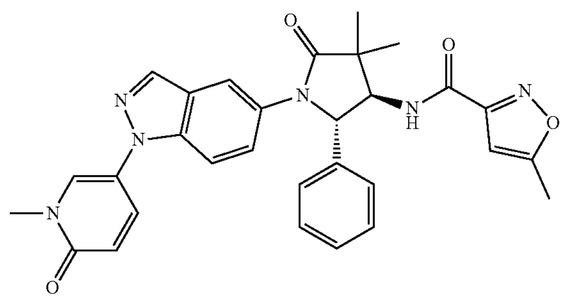 [SMILES: Cc1cc(C(=O)N[C@H]2[C@H](c3ccccc3)N(c3ccc4c(cnn4-c4ccc(=O)n(C)c4)c3)C(=O)C2(C)C)no1] | 80 | ¹H NMR (DMSO-d$_6$) δ: 9.08 (d, 1H), 8.25 (d, 1H), 8.17 (d, 1H), 7.72-7.67 (m, 2H), 7.59 (d, 1H), 7.42-7.35 (m, 3H), 7.23 (t, 2H), 7.18-7.12 (m, 1H), 6.53 (d, 1H), 6.50 (t, 1H), 5.50 (d, 1H), 4.47 (t, 1H), 3.50 (s, 3H), 2.47 (d, 3H), 1.32 (s, 3H), 1.17 (s, 3H) |
| 24 | Int A 4 ent 2 | 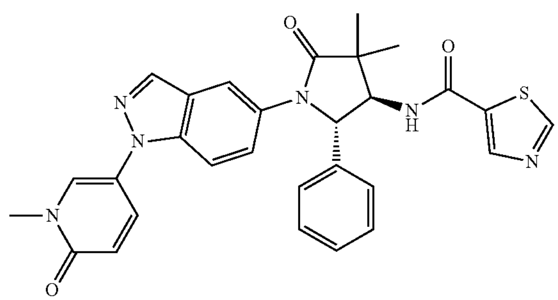 [SMILES: Cn1cc(-n2ncc3cc(N4C(=O)C(C)(C)[C@@H](NC(=O)c5cncs5)[C@@H]4c4ccccc4)ccc32)ccc1=O] | 78 | ¹H NMR (DMSO-d$_6$) δ: 9.25 (d, 1H), 8.95 (dd, 1H), 8.60 (s, 1H), 8.26 (d, 1H), 8.18 (d, 1H), 7.76-7.73 (m, 1H), 7.70 (dd, 1H), 7.62-7.57 (m, 1H), 7.43 (dd, 1H), 7.41-7.37 (m, 2H), 7.24 (t, 2H), 7.18-7.12 (m, 1H), 6.54 (d, 1H), 5.36 (d, 1H), 4.48 (t, 1H), 3.50 (s, 3H), 1.32 (s, 3H), 1.20 (s, 3H) |
| 26 | Int A 4 ent 2 | 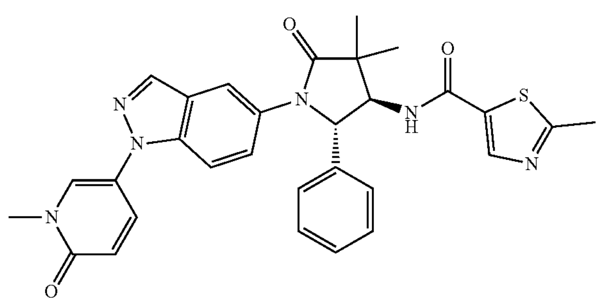 | 63 | ¹H NMR (DMSO-d$_6$) δ: 9.10 (d, 1H), 8.26 (d, 1H), 8.17 (d, 1H), 7.80-7.75 (m, 1H), 7.72-7.67 (m, 2H), 7.61-7.56 (m, 1H), 7.41-7.35 (m, 3H), 7.22 (t, 2H), 7.17-7.11 (m, 1H), 6.53 (d, 1H), 5.62 (d, 1H), 4.45 (t, 1H), 3.50 (s, 3H), 2.53-2.51 (m, 3H), 1.32 (s, 3H), 1.18 (s, 3H) |
| 36a | Int A7 ent 1 | 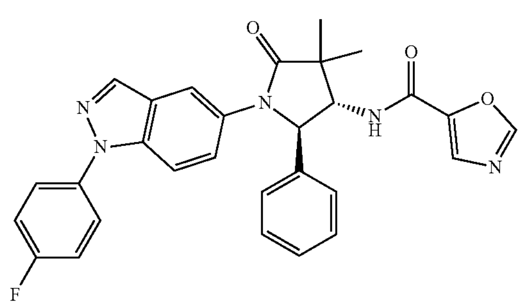 [SMILES: CC1(C)C(=O)N(c2ccc3c(cnn3-c3ccc(F)cc3)c2)[C@H](c2ccccc2)[C@H]1NC(=O)c1cnco1] | 86 | ¹H NMR (DMSO-d$_6$) δ: 8.97 (d, 1H), 8.60 (s, 1H), 8.31 (d, 1H), 7.83 (s, 1H), 7.76-7.72 (m, 3H), 7.70 (dd, 1H), 7.46 (dd, 1H), 7.43-7.35 (m, 4H), 7.23 (dd, 2H), 7.17-7.12 (m, 1H), 5.42 (d, 1H), 4.49 (t, 1H), 1.31 (s, 3H), 1.18 (d, 3H) |

-continued

| Ex. # | Intermediate (INT) | Structure | Yield (%) | ¹H NMR |
|---|---|---|---|---|
| 36b | Int A7 ent 2 | 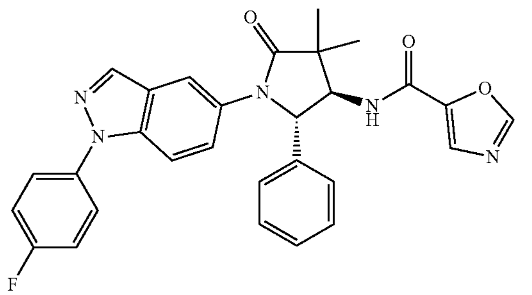 [SMILES: CC1(C)C(=O)N(c2ccc3c(cnn3-c3ccc(F)cc3)c2)[C@@H](c2ccccc2)[C@@H]1NC(=O)c1cnco1] | 40 | ¹H NMR (DMSO-d$_6$) δ: 8.97 (d, 1H), 8.60 (s, 1H), 8.31 (d, 1H), 7.83 (s, 1H), 7.76-7.72 (m, 3H), 7.70 (dd, 1H), 7.46 (dd, 1H), 7.43-7.35 (m, 4H), 7.23 (dd, 2H), 7.17-7.12 (m, 1H), 5.42 (d, 1H), 4.49 (t, 1H), 1.31 (s, 3H), 1.18 (d, 3H) |
| 37 | Int A7 ent 1 | 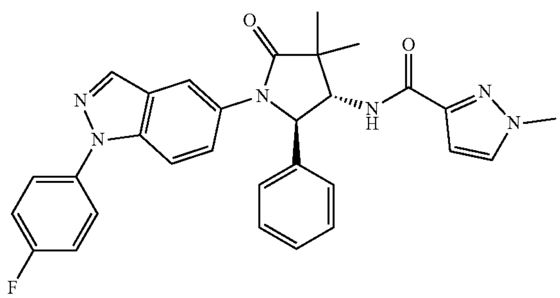 [SMILES: Cn1ccc(C(=O)N[C@@H]2[C@@H](c3ccccc3)N(c3ccc4c(cnn4-c4ccc(F)cc4)c3)C(=O)C2(C)C)n1] | 71 | ¹H NMR (DMSO-d$_6$) δ: 8.40 (d, 1H), 8.31 (d, 1H), 7.78 (d, 1H), 7.76-7.71 (m, 3H), 7.69 (dd, 1H), 7.44 (dd, 1H), 7.41-7.35 (m, 4H), 7.24-7.18 (m, 2H), 7.16-7.10 (m, 1H), 6.58 (dd, 1H), 5.59 (dd, 1H), 4.51 (t, 1H), 3.96 (d, 3H), 1.31 (d, 3H), 1.17 (s, 3H) |
| 38a | Int A7 ent 2 | 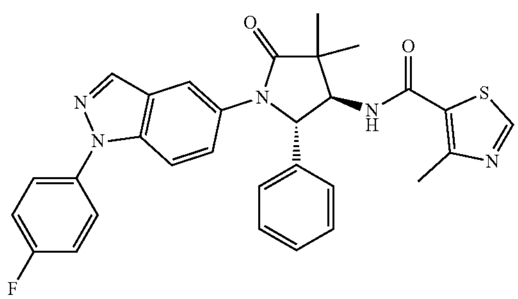 [SMILES: Cc1ncsc1C(=O)N[C@H]1[C@H](c2ccccc2)N(c2ccc3c(cnn3-c3ccc(F)cc3)c2)C(=O)C1(C)C] | 44 | ¹H NMR (DMSO-d$_6$) δ: 9.08 (s, 1H), 8.67-8.57 (m, 1H), 8.31 (d, 1H), 7.80-7.64 (m, 4H), 7.46 (dd, 1H), 7.42-7.35 (m, 4H), 7.25 (dd, 2H), 7.19-7.13 (m, 1H), 5.38 (d, 1H), 4.47 (t, 1H), 2.51 (s, 3H), 1.34 (s, 3H), 1.18 (s, 3H) |
| 38b | Int A7 ent 1 | 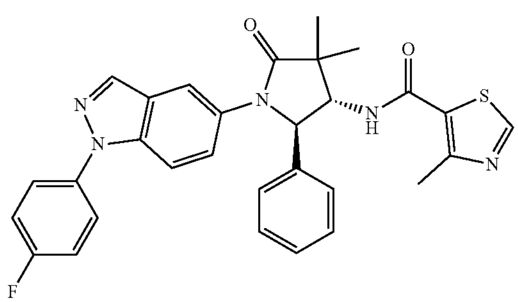 | 92 | ¹H NMR (DMSO-d$_6$) δ: 9.08 (s, 1H), 8.67-8.57 (m, 1H), 8.31 (d, 1H), 7.80-7.64 (m, 4H), 7.46 (dd, 1H), 7.42-7.35 (m, 4H), 7.25 (dd, 2H), 7.19-7.13 (m, 1H), 5.38 (d, 1H), 4.47 (t, 1H), 2.51 (s, 3H), 1.34 (s, 3H), 1.18 (s, 3H) |
| 39a | Int A7 ent 1 | 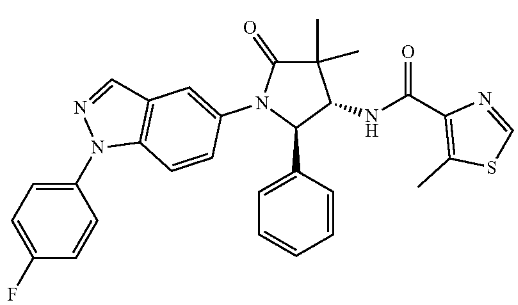 | 88 | ¹H NMR (DMSO-d$_6$) δ: 9.08 (s, 1H), 8.63-8.58 (m, 1H), 8.31 (d, 1H), 7.78-7.72 (m, 3H), 7.70 (dd, 1H), 7.46 (dd, 1H), 7.43-7.36 (m, 4H), 7.25 (t, 2H), 7.17 (t, 1H), 5.38 (d, 1H), 4.47 (t, 1H), 2.52 (s, 3H), 1.34 (s, 3H), 1.18 (s, 3H) |

-continued

| Ex. # | Intermediate (INT) | Structure | Yield (%) | ¹H NMR |
|---|---|---|---|---|
| 39b | Int A7 ent 2 | 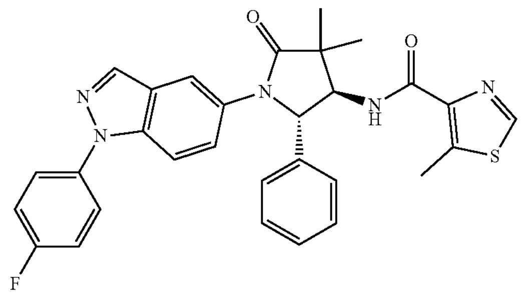 [SMILES: Cc1scnc1C(=O)N[C@H]1[C@H](c2ccccc2)N(c2ccc3c(cnn3-c3ccc(F)cc3)c2)C(=O)C1(C)C] | 51 | ¹H NMR (DMSO-d$_6$) δ: 9.08 (s, 1H), 8.63-8.58 (m, 1H), 8.31 (d, 1H), 7.78-7.72 (m, 3H), 7.70 (dd, 1H), 7.46 (dd, 1H), 7.43-7.36 (m, 4H), 7.25 (t, 2H), 7.17 (t, 1H), 5.38 (d, 1H), 4.47 (t, 1H), 2.52 (s, 3H), 1.34 (s, 3H), 1.18 (s, 3H) |
| 40a | Int A7 ent 1 | 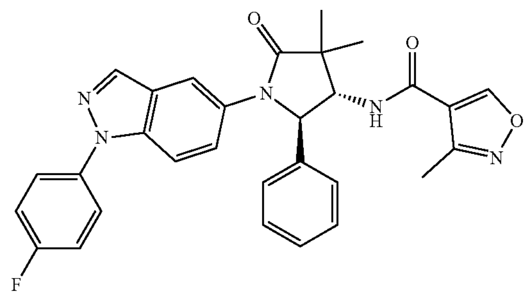 [SMILES: Cc1nocc1C(=O)N[C@@H]1[C@@H](c2ccccc2)N(c2ccc3c(cnn3-c3ccc(F)cc3)c2)C(=O)C1(C)C] | 98 | ¹H NMR (DMSO-d$_6$) δ: 9.37 (d, 1H), 8.64 (d, 1H), 8.31 (d, 1H), 7.78 (dd, 1H), 7.77-7.71 (m, 2H), 7.70 (dd, 1H), 7.47 (dd, 1H), 7.43-7.35 (m, 4H), 7.24 (dd, 2H), 7.19-7.13 (m, 1H), 5.25 (d, 1H), 4.46 (t, 1H), 2.30 (s, 3H), 1.31 (s, 3H), 1.18 (s, 3H) |
| 40b | Int A7 ent 2 | 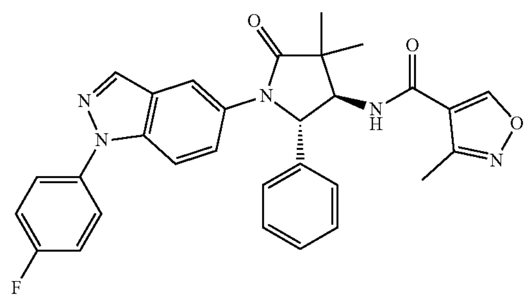 [SMILES: Cc1nocc1C(=O)N[C@H]1[C@H](c2ccccc2)N(c2ccc3c(cnn3-c3ccc(F)cc3)c2)C(=O)C1(C)C] | 62 | ¹H NMR (DMSO-d$_6$) δ: 9.37 (d, 1H), 8.64 (d, 1H), 8.31 (d, 1H), 7.78 (dd, 1H), 7.77-7.71 (m, 2H), 7.70 (dd, 1H), 7.47 (dd, 1H), 7.43-7.35 (m, 4H), 7.24 (dd, 2H), 7.19-7.13 (m, 1H), 5.25 (d, 1H), 4.46 (t, 1H), 2.30 (s, 3H), 1.31 (s, 3H), 1.18 (s, 3H) |
| 41a | Int A7 ent 1 | 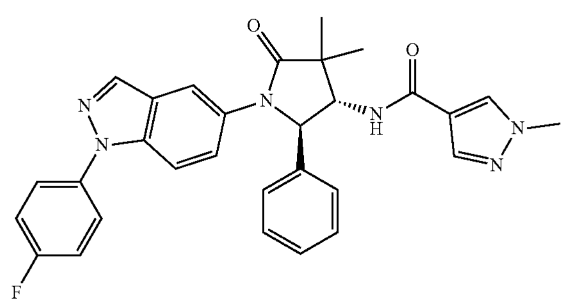 [SMILES: Cn1cc(C(=O)N[C@@H]2[C@@H](c3ccccc3)N(c3ccc4c(cnn4-c4ccc(F)cc4)c3)C(=O)C2(C)C)cn1] | 79 | ¹H NMR (DMSO-d$_6$) δ: 8.31 (d, 1H), 8.26 (d, 1H), 8.16 (s, 1H), 7.88 (d, 1H), 7.78-7.71 (m, 3H), 7.73-7.68 (m, 1H), 7.46 (dd, 1H), 7.43-7.33 (m, 4H), 7.22 (dd, 2H), 7.17-7.11 (m, 1H), 5.30 (d, 1H), 4.47 (t, 1H), 3.87 (s, 3H), 1.29 (s, 3H), 1.15 (s, 3H) |
| 41b | Int A7 ent 2 | 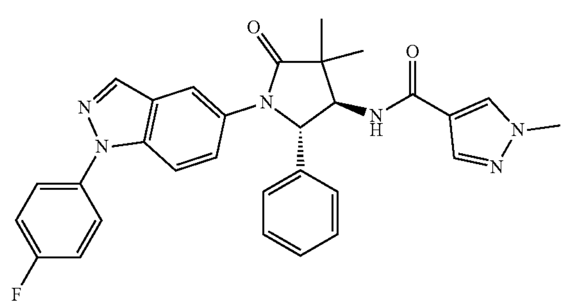 [SMILES: Cn1cc(C(=O)N[C@H]2[C@H](c3ccccc3)N(c3ccc4c(cnn4-c4ccc(F)cc4)c3)C(=O)C2(C)C)cn1] | 35 | ¹H NMR (DMSO-d$_6$) δ: 8.31 (d, 1H), 8.26 (d, 1H), 8.16 (s, 1H), 7.88 (d, 1H), 7.78-7.71 (m, 3H), 7.73-7.68 (m, 1H), 7.46 (dd, 1H), 7.43-7.33 (m, 4H), 7.22 (dd, 2H), 7.17-7.11 (m, 1H), 5.30 (d, 1H), 4.47 (t, 1H), 3.87 (s, 3H), 1.29 (s, 3H), 1.15 (s, 3H) |

-continued

| Ex. # | Intermediate (INT) | Structure | Yield (%) | ¹H NMR |
|---|---|---|---|---|
| 42a | Int A7 ent 1 | 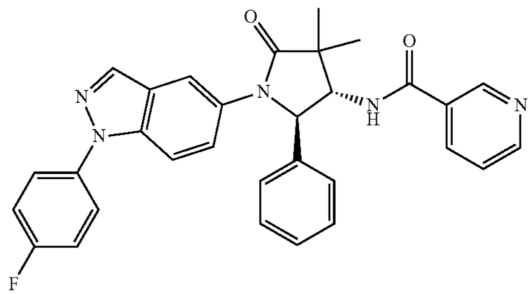 [SMILES: CC1(C)C(=O)N(c2ccc3c(cnn3-c3ccc(F)cc3)c2)[C@H](c2ccccc2)[C@H]1NC(=O)c1cccnc1] | 89 | ¹H NMR (DMSO-d₆) δ: 9.02 (d, 1H), 8.96-8.91 (m, 1H), 8.77-8.72 (m, 1H), 8.32 (d, 1H), 8.21-8.16 (m, 1H), 7.78 (d, 1H), 7.76-7.73 (m, 2H), 7.71 (d, 1H), 7.55 (dd, 1H), 7.48 (dd, 1H), 7.43-7.36 (m, 4H), 7.27-7.21 (m, 2H), 7.18-7.12 (m, 1H), 5.41 (d, 1H), 4.55 (t, 1H), 1.34 (s, 3H), 1.21 (s, 3H). |
| 42b | Int A7 ent 2 | 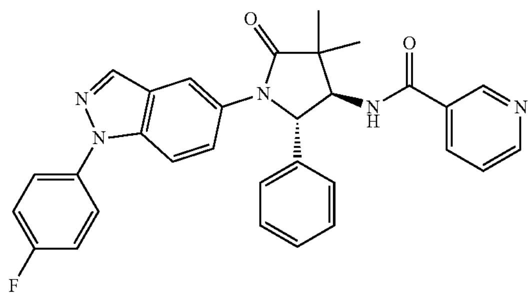 [SMILES: CC1(C)C(=O)N(c2ccc3c(cnn3-c3ccc(F)cc3)c2)[C@@H](c2ccccc2)[C@@H]1NC(=O)c1cccnc1] | 27 | ¹H NMR (DMSO-d₆) δ: 9.02 (d, 1H), 8.96-8.91 (m, 1H), 8.77-8.72 (m, 1H), 8.32 (d, 1H), 8.21-8.16 (m, 1H), 7.78 (d, 1H), 7.76-7.73 (m, 2H), 7.71 (d, 1H), 7.55 (dd, 1H), 7.48 (dd, 1H), 7.43-7.36 (m, 4H), 7.27-7.21 (m, 2H), 7.18-7.12 (m, 1H), 5.41 (d, 1H), 4.55 (t, 1H), 1.34 (s, 3H), 1.21 (s, 3H). |
| 43a | Int A7 ent 1 | 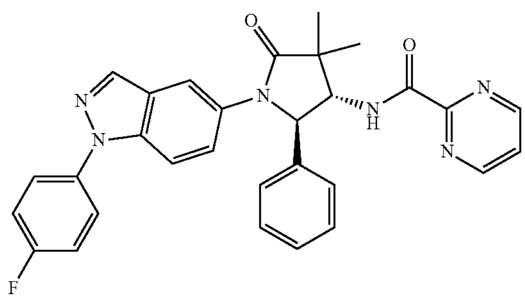 [SMILES: CC1(C)C(=O)N(c2ccc3c(cnn3-c3ccc(F)cc3)c2)[C@H](c2ccccc2)[C@H]1NC(=O)c1ncccn1] | 96 | ¹H NMR (DMSO-d₆) δ: 9.23 (d, 1H), 9.00 (d, 2H), 8.31 (d, 1H), 7.76 (dd, 1H), 7.73 (ddd, 3H), 7.70 (dd, 1H), 7.46 (dd, 1H), 7.43-7.36 (m, 4H), 7.22 (t, 2H), 7.16-7.11 (m, 1H), 5.64 (d, 1H), 4.56 (dd, 1H), 1.35 (s, 3H), 1.22 (s, 3H) |
| 43b | Int A7 ent 2 | 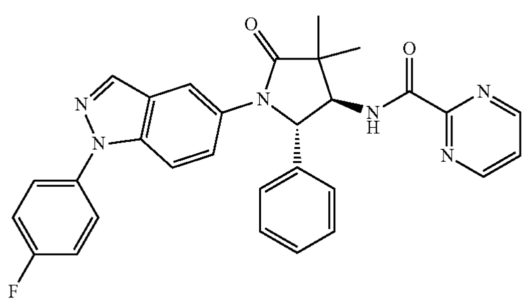 [SMILES: CC1(C)C(=O)N(c2ccc3c(cnn3-c3ccc(F)cc3)c2)[C@@H](c2ccccc2)[C@@H]1NC(=O)c1ncccn1] | 35 | ¹H NMR (DMSO-d₆) δ: 9.23 (d, 1H), 9.00 (d, 2H), 8.31 (d, 1H), 7.76 (dd, 1H), 7.73 (ddd, 3H), 7.70 (dd, 1H), 7.46 (dd, 1H), 7.43-7.36 (m, 4H), 7.22 (t, 2H), 7.16-7.11 (m, 1H), 5.64 (d, 1H), 4.56 (dd, 1H), 1.35 (s, 3H), 1.22 (s, 3H) |
| 44a | Int A7 ent 1 | 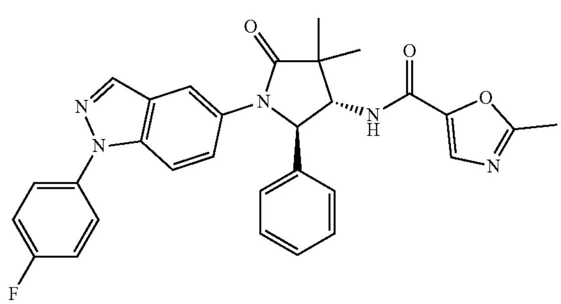 [SMILES: Cc1ncc(C(=O)N[C@@H]2[C@@H](c3ccccc3)N(c3ccc4c(cnn4-c4ccc(F)cc4)c3)C(=O)C2(C)C)o1] | 90 | ¹H NMR (DMSO-d₆) δ: 8.81 (dd, 1H), 8.31 (s, 1H), 7.77-7.65 (m, 5H), 7.45 (dd, 1H), 7.43-7.35 (m, 4H), 7.23 (t, 2H), 7.18-7.12 (m, 1H), 5.41 (d, 1H), 4.48 (t, 1H), 2.51 (s, 3H), 1.30 (s, 3H), 1.17 (s, 3H) |

-continued

| Ex. # | Intermediate (INT) | Structure | Yield (%) | ¹H NMR |
|---|---|---|---|---|
| 44b | Int A7 ent 2 | 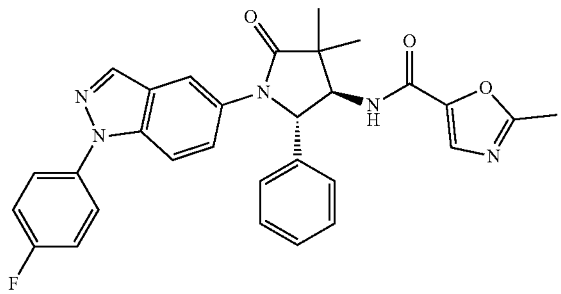 [SMILES: Cc1ncc(C(=O)N[C@H]2[C@H](c3ccccc3)N(c3ccc4c(cnn4-c4ccc(F)cc4)c3)C(=O)C2(C)C)o1] | 37 | ¹H NMR (DMSO-$d_6$) δ: 8.81 (dd, 1H), 8.31 (s, 1H), 7.77-7.65 (m, 5H), 7.45 (dd, 1H), 7.43-7.35 (m, 4H), 7.23 (t, 2H), 7.18-7.12 (m, 1H), 5.41 (d, 1H), 4.48 (t, 1H), 2.51 (s, 3H), 1.30 (s, 3H), 1.17 (s, 3H) |
| 45a | Int A7 ent 1 | 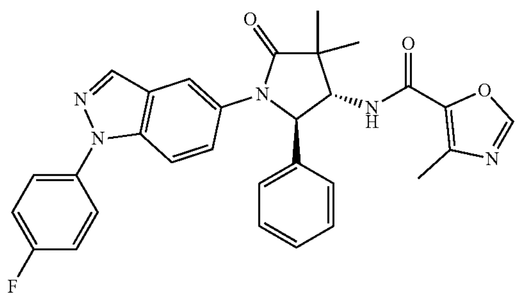 [SMILES: Cc1ncoc1C(=O)N[C@@H]1[C@@H](c2ccccc2)N(c2ccc3c(cnn3-c3ccc(F)cc3)c2)C(=O)C1(C)C] | 89 | ¹H NMR (DMSO-$d_6$) δ: 8.77 (d, 1H), 8.50 (s, 1H), 8.31 (t, 1H), 7.77-7.72 (m, 3H), 7.70 (dd, 1H), 7.44 (dd, 1H), 7.42-7.35 (m, 4H), 7.23 (t, 2H), 7.18-7.12 (m, 1H), 5.51 (d, 1H), 4.49 (t, 1H), 2.32 (s, 3H), 1.32 (s, 3H), 1.17 (s, 3H) |
| 45b | Int A7 ent 2 | 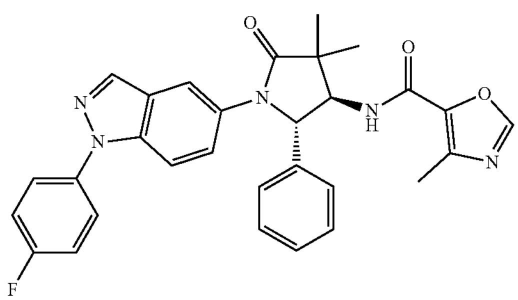 | 62 | ¹H NMR (DMSO-$d_6$) δ: 8.77 (d, 1H), 8.50 (s, 1H), 8.31 (t, 1H), 7.77-7.72 (m, 3H), 7.70 (dd, 1H), 7.44 (dd, 1H), 7.42-7.35 (m, 4H), 7.23 (t, 2H), 7.18-7.12 (m, 1H), 5.51 (d, 1H), 4.49 (t, 1H), 2.32 (s, 3H), 1.32 (s, 3H), 1.17 (s, 3H) |
| 46 | A9 | 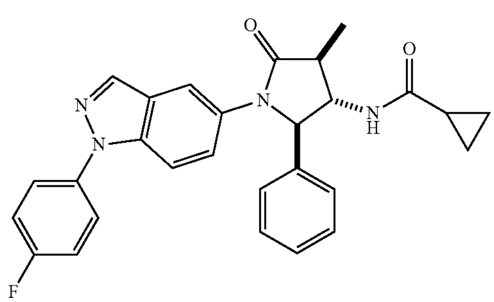 [SMILES: C[C@@H]1C(=O)N(c2ccc3c(cnn3-c3ccc(F)cc3)c2)[C@H](c2ccccc2)[C@H]1NC(=O)C1CC1] | 26 | ¹H NMR (DMSO-$d_6$) δ: 8.57 (d, 1H), 8.29 (t, 1H), 7.78 (d, 1H), 7.77-7.71 (m, 2H), 7.68 (d, 1H), 7.51 (dd, 1H), 7.39 (td, 2H), 7.33 (d, 2H), 7.24 (t, 2H), 7.19-7.11 (m, 1H), 5.19 (d, 1H), 4.04 (td, 1H), 2.78-2.70 (m, 1H), 1.57 (tt, 1H), 1.24 (d, 3H), 0.74-0.58 (m, 4H). |
| 47 | A13-trans | 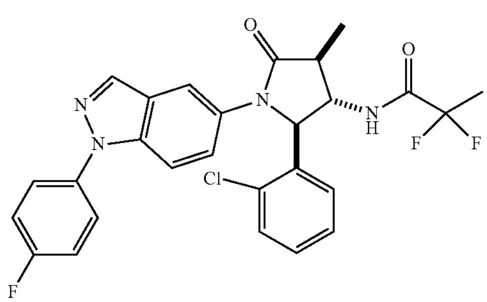 [SMILES: C[C@@H]1C(=O)N(c2ccc3c(cnn3-c3ccc(F)cc3)c2)[C@H](c2ccccc2Cl)[C@H]1NC(=O)C(C)(F)F] | 43 | ¹H NMR (DMSO-$d_6$) δ: 9.21 (s, 1H), 8.33 (s, 1H), 7.73 (dt, 4H), 7.53-7.46 (m, 1H), 7.45-7.32 (m, 3H), 7.27-7.15 (m, 2H), 5.85 (s, 1H), 4.16 (s, 1H), 2.96 (dd, 1H), 2.55 (d, 0H), 1.73 (t, 3H), 1.28 (d, 3H) |

-continued

| Ex. # | Intermediate (INT) | Structure | Yield (%) | ¹H NMR |
|---|---|---|---|---|
| 60 | A9 | 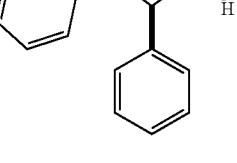 | 30 | ¹H NMR (DMSO-d$_6$) δ: 9.08 (s, 1H), 8.70 (d, 1H), 8.29 (d, 1H), 7.80 (dd, 1H), 7.76-7.72 (m, 2H), 7.68 (dt, 1H), 7.51 (dd, 1H), 7.43-7.34 (m, 4H), 7.28-7.22 (m, 2H), 7.20-7.14 (m, 1H), 5.33 (d, 1H), 4.27 (td, 1H), 2.89 (dq, 1H), 2.56 (s, 3H), 1.31 (d, 3H) |
| 63 | A11-trans | 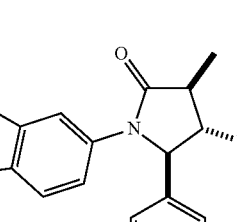 | 55 | ¹H NMR (DMSO-d$_6$) δ: 8.56 (d, 1H), 8.30 (d, 1H), 7.79 (dd, 1H), 7.77-7.71 (m, 2H), 7.69 (dd, 1H), 7.56-7.48 (m, 1H), 7.43-7.36 (m, 2H), 7.17-7.07 (m, 3H), 6.97 (ddt, 1H), 5.15 (d, 1H), 4.01 (td, 1H), 2.76-2.68 (m, 1H), 2.20 (s, 3H), 1.57 (tt, 1H), 1.23 (d, 3H), 0.74 0.58 (m, 4H) |
| 64 | A9 | 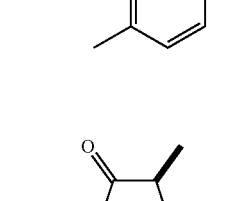 | 28 | ¹H NMR (DMSO-d$_6$) δ: 8.60 (d, 1H), 8.29 (d, 1H), 7.78 (d, 1H), 7.77-7.70 (m, 3H), 7.68 (dt, 1H), 7.46 (dd, 1H), 7.43-7.36 (m, 2H), 7.34-7.29 (m, 2H), 7.21 (dd, 2H), 7.16-7.10 (m, 1H), 6.56 (d, 1H), 5.37 (d, 1H), 4.34 (td, 1H), 3.94 (s, 3H), 2.92 (dq, 1H), 1.26 (d, 3H) |
| 65 | A9 | 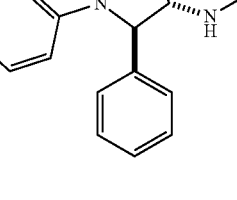 | 44 | ¹H NMR (DMSO-d$_6$) δ: 9.11 (d, 1H), 9.07-8.99 (m, 1H), 8.74 (dd, 1H), 8.30 (d, 1H), 8.23 8.18 (m, 1H), 7.82 (dd, 1H), 7.78-7.71 (m, 2H), 7.70 (dt, 1H), 7.57-7.51 (m, 2H), 7.43-7.36 (m, 4H), 7.24 (dd, 2H), 7.19-7.13 (m, 1H), 5.38 (d, 1H), 4.32 (td, 1H), 2.92 (dq, 1H), 1.32 (d, 3H) |
| 66 | A9 | 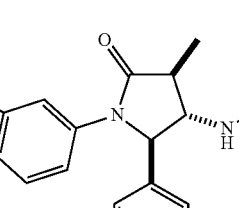 | 35 | ¹H NMR (DMSO-d$_6$) δ: 9.45 (d, 1H), 9.00 (d, 2H), 8.30 (d, 1H), 7.78-7.69 (m, 4H), 7.68 (dd, 1H), 7.48 (dd, 1H), 7.44-7.36 (m, 2H), 7.36-7.32 (m, 2H), 7.24-7.19 (m, 2H), 7.17-7.11 (m, 1H), 5.44 (d, 1H), 4.40 (td, 1H), 3.02-2.94 (m, 1H), 1.30 (d, 3H) |

-continued

| Ex. # | Intermediate (INT) | Structure | Yield (%) | ¹H NMR |
|---|---|---|---|---|
| 67 | A11-trans | 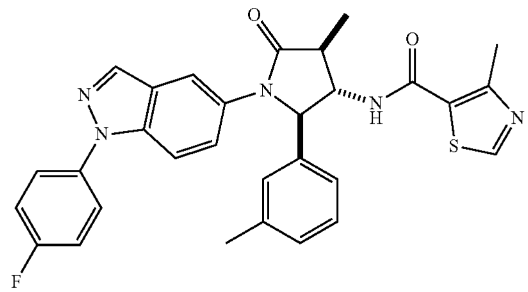 [SMILES: Cc1cccc([C@@H]2[C@@H](NC(=O)c3scnc3C)[C@H](C)C(=O)N2c2ccc3c(cnn3-c3ccc(F)cc3)c2)c1] | 43 | ¹H NMR (DMSO-d₆) δ: 9.08 (s, 1H), 8.70 (d, 1H), 8.30 (d, 1H), 7.80 (d, 1H), 7.77-7.71 (m, 2H), 7.69 (d, 1H), 7.51 (dd, 1H), 7.45-7.36 (m, 2H), 7.18 (d, 1H), 7.17-7.10 (m, 2H), 6.98 (dt, 1H), 5.28 (d, 1H), 4.23 (td, 1H), 2.94-2.78 (m, 1H), 2.57 (s, 3H), 2.20 (s, 3H), 1.31 (d, 3H) |
| 68 | A11-trans | 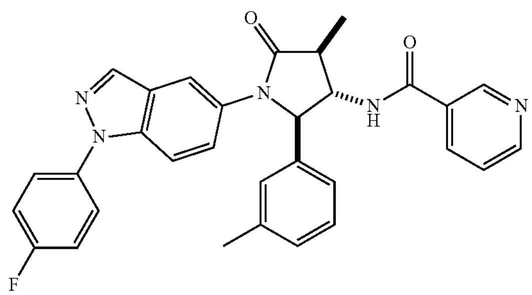 [SMILES: Cc1cccc([C@@H]2[C@@H](NC(=O)c3cccnc3)[C@H](C)C(=O)N2c2ccc3c(cnn3-c3ccc(F)cc3)c2)c1] | 54 | ¹H NMR (DMSO-d₆) δ: 9.10 (d, 1H), 9.04 (d, 1H), 8.74 (dd, 1H), 8.31 (d, 1H), 8.20 (dt, 1H), 7.82 (d, 1H), 7.78-7.72 (m, 2H), 7.71 (dd, 1H), 7.57-7.51 (m, 2H), 7.43-7.36 (m, 2H), 7.21 (t, 1H), 7.19-7.10 (m, 2H), 6.97 (d, 1H), 5.33 (d, 1H), 4.30 (td, 1H), 2.90 (dq, 1H), 2.19 (s, 3H), 1.32 (d, 3H) |
| 69 | A11-trans | 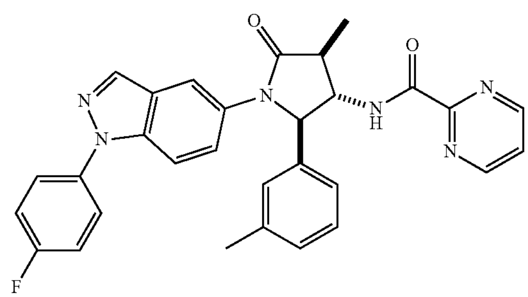 [SMILES: Cc1cccc([C@@H]2[C@@H](NC(=O)c3ncccn3)[C@H](C)C(=O)N2c2ccc3c(cnn3-c3ccc(F)cc3)c2)c1] | 23 | ¹H NMR (DMSO-d₆) δ: 9.47 9.42 (m, 1H), 9.00 (d, 1H), 8.31 (s, 1H), 7.78-7.73 (m, 2H), 7.76-7.69 (m, 2H), 7.69 (d, 1H), 7.48 (dd, 1H), 7.43-7.36 (m, 2H), 7.18-7.07 (m, 4H), 6.95 (d, 1H), 5.39 (d, 1H), 4.39 (td, 1H), 2.97 (dq, 1H), 2.17 (s, 3H), 1.30 (d, 3H) |
| 70 | A11-cis | 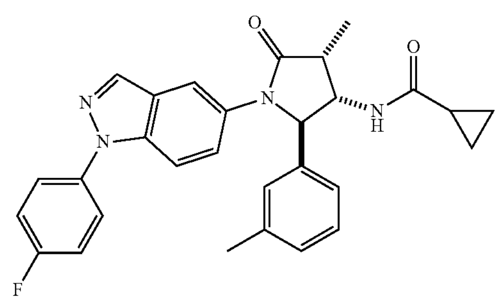 [SMILES: Cc1cccc([C@@H]2[C@@H](NC(=O)C3CC3)[C@@H](C)C(=O)N2c2ccc3c(cnn3-c3ccc(F)cc3)c2)c1] | 52 | ¹H NMR (DMSO-d₆) δ: 8.76 (d, 1H), 8.32 (s, 1H), 7.96 (d, 1H), 7.80 (ddd, 1H), 7.79-7.71 (m, 3H), 7.44-7.37 (m, 2H), 7.22 (t, 1H), 7.18 (d, 1H), 7.14-7.09 (m, 1H), 7.07 (d, 1H), 5.15 (d, 1H), 4.35 (ddd, 1H), 3.04 (p, 1H), 2.27 (s, 3H), 1.78-1.68 (m, 1H), 1.11 (d, 3H), 0.80-0.73 (m, 1H), 0.76-0.70 (m, 2H) |
| 71 | A11-cis | 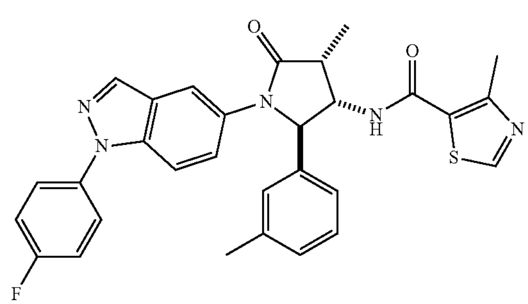 [SMILES: Cc1cccc([C@@H]2[C@@H](NC(=O)c3scnc3C)[C@@H](C)C(=O)N2c2ccc3c(cnn3-c3ccc(F)cc3)c2)c1] | 49 | ¹H NMR (DMSO-d₆) δ: 9.08 (s, 0H), 9.01 (d, 1H), 8.32 (d, 1H), 7.94 (dd, 1H), 7.79-7.71 (m, 4H), 7.44-7.36 (m, 2H), 7.26-7.21 (m, 2H), 7.20-7.15 (m, 1H), 7.08 (ddt, 1H), 5.32 (d, 1H), 4.52 (td, 1H), 3.16 (p, 1H), 2.60 (s, 3H), 2.28 (d, 3H), 2.08 (s, 1H), 1.16 (d, 3H) |

| Ex. # | Intermediate (INT) | Structure | Yield (%) | ¹H NMR |
|---|---|---|---|---|
| 72 | A11-cis | 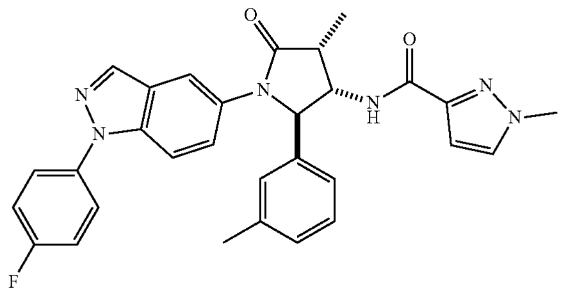 [SMILES: Cc1cccc([C@@H]2[C@@H](NC(=O)c3ccn(C)n3)[C@@H](C)C(=O)N2c2ccc3c(cnn3-c3ccc(F)cc3)c2)c1] | 48 | 1H NMR (DMSO-d$_6$) δ: 8.79 (d, 1H), 8.32 (s, 1H), 7.91 (dd, 1H), 7.81-7.67 (m, 6H), 7.44-7.36 (m, 2H), 7.23-7.13 (m, 3H), 7.07-7.02 (m, 1H), 6.66 (d, 1H), 5.40 (d, 1H), 4.57 (td, 1H), 3.93 (s, 3H), 3.12 (p, 1H), 2.25 (s, 3H), 1.11 (d, 3H) |
| 73 | A11-cis | 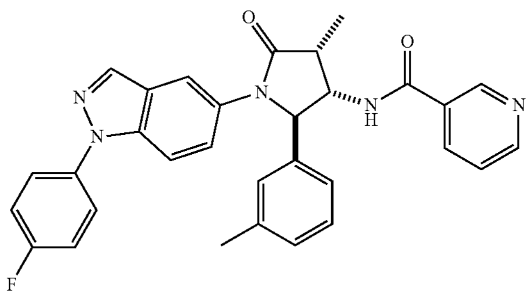 [SMILES: Cc1cccc([C@@H]2[C@@H](NC(=O)c3cccnc3)[C@@H](C)C(=O)N2c2ccc3c(cnn3-c3ccc(F)cc3)c2)c1] | 45 | 1H NMR (DMSO-d$_6$) δ: 9.28 (d, 1H), 9.09 (d, 1H), 8.74 (dd, 1H), 8.32 (t, 1H), 8.27 (dt, 1H), 7.98 (d, 1H), 7.80 (dd, 1H), 7.78-7.71 (m, 3H), 7.54 (ddd, 1H), 7.44-7.37 (m, 2H), 7.27-7.21 (m, 2H), 7.21-7.16 (m, 1H), 7.08 (d, 1H), 5.37 (d, 1H), 4.62 (ddd, 1H), 3.19 (p, 1H), 2.28 (s, 3H), 1.17 (d, 3H) |
| 74 | A11-cis | 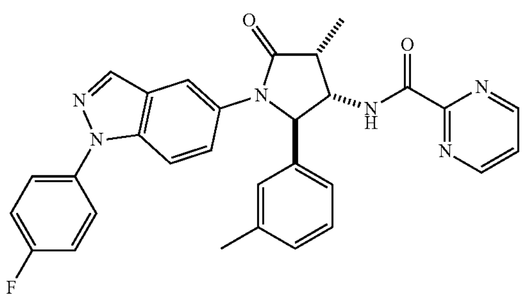 [SMILES: Cc1cccc([C@@H]2[C@@H](NC(=O)c3ncccn3)[C@@H](C)C(=O)N2c2ccc3c(cnn3-c3ccc(F)cc3)c2)c1] | 49 | 1H NMR (DMSO-d$_6$) δ: 9.53 (d, 1H), 9.00 (dd, 1H), 9.90-6.59 (m, 0H), 8.32 (d, 1H), 7.93 (dd, 1H), 7.79-7.69 (m, 6H), 7.44-7.36 (m, 2H), 7.25-7.16 (m, 3H), 7.06 (dd, 1H), 5.45 (d, 1H), 4.62 (td, 1H), 3.24-3.16 (m, 1H), 2.26 (s, 3H), 1.15 (d, 3H) |
| 75 | A11-trans | 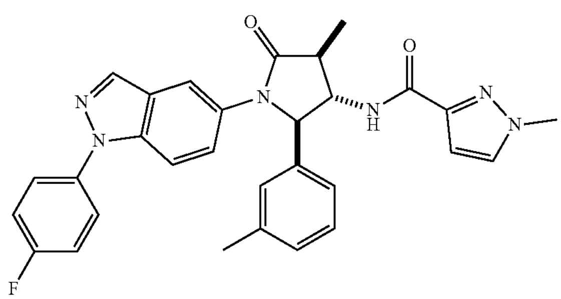 [SMILES: Cc1cccc([C@@H]2[C@@H](NC(=O)c3ccn(C)n3)[C@H](C)C(=O)N2c2ccc3c(cnn3-c3ccc(F)cc3)c2)c1] | 86 | ¹H NMR (DMSO-d$_6$) δ: 8.59 (d, 1H), 8.30 (d, 1H), 7.78 (d, 1H), 7.78-7.71 (m, 3H), 7.69 (dt, 1H), 7.46 (dd, 1H), 7.43-7.31 (m, 2H), 7.16-7.07 (m, 3H), 6.97-6.92 (m, 1H), 6.57 (d, 1H), 5.33 (d, 1H), 4.32 (td, 1H), 3.94 (s, 3H), 2.90 (dq, 1H), 2.17 (s, 3H), 1.26 (d, 3H) |
| 77 | A11-cis | 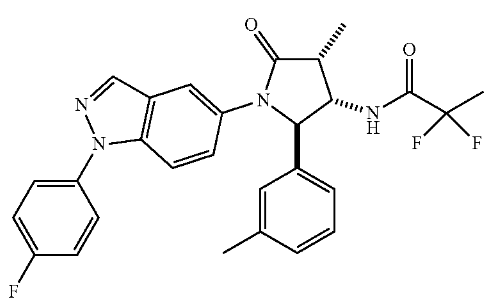 [SMILES: Cc1cccc([C@@H]2[C@@H](NC(=O)C(C)(F)F)[C@@H](C)C(=O)N2c2ccc3c(cnn3-c3ccc(F)cc3)c2)c1] | 54 | ¹H NMR (DMSO-d$_6$) δ: 9.45 (d, 1H), 8.33 (d, 1H), 7.92 (t, 1H), 7.81-7.69 (m, 4H), 7.47-7.35 (m, 2H), 7.29 7.16 (m, 2H), 7.16-7.10 (m, 1H), 7.10-7.03 (m, 1H), 5.28 (d, 1H), 4.41 (td, 1H), 3.16 (p, 1H), 2.26 (s, 3H), 1.81 (t, 3H), 1.08 (d, 3H) |

-continued

| Ex. # | Intermediate (INT) | Structure | Yield (%) | ¹H NMR |
|---|---|---|---|---|
| 78 | A13-cis | 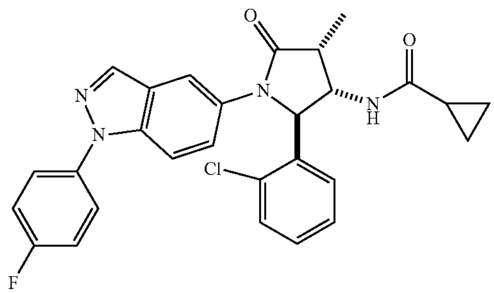 [SMILES: C[C@H]1C(=O)N(c2ccc3c(cnn3-c3ccc(F)cc3)c2)[C@H](c2ccccc2Cl)[C@H]1NC(=O)C1CC1] | 41 | 1H NMR (DMSO-d$_6$) δ: 8.82 (d, 1H), 8.36 (d, 1H), 7.97 (d, 1H), 7.82-7.73 (m, 4H), 7.51 (dd, 1H), 7.44-7.38 (m, 2H), 7.38-7.26 (m, 4H), 5.50 (d, 1H), 4.49 (ddd, 1H), 3.03 (p, 1H), 1.68 (tt, 1H), 1.05 (d, 3H), 0.77-0.67 (m, 4H) |
| 79 | A13-cis | 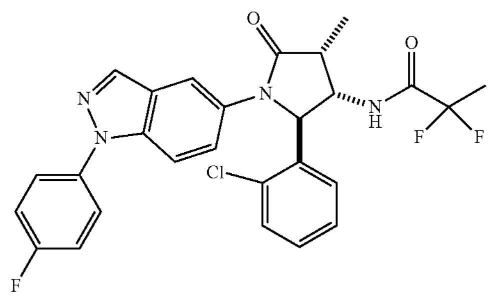 [SMILES: C[C@H]1C(=O)N(c2ccc3c(cnn3-c3ccc(F)cc3)c2)[C@H](c2ccccc2Cl)[C@H]1NC(=O)C(C)(F)F] | 54 | ¹H NMR (DMSO-d$_6$) δ: 9.58 (d, 1H), 8.36 (d, 1H), 7.95 (dd, 1H), 7.83-7.69 (m, 4H), 7.52 (dt, 1H), 7.46-7.35 (m, 2H), 7.38-7.25 (m, 3H), 5.62 (d, 1H), 4.48 (t, 1H), 3.22 3.11 (m, 1H), 1.82 (t, 3H), 1.11-1.01 (m, 4H) |
| 80 | A9 | 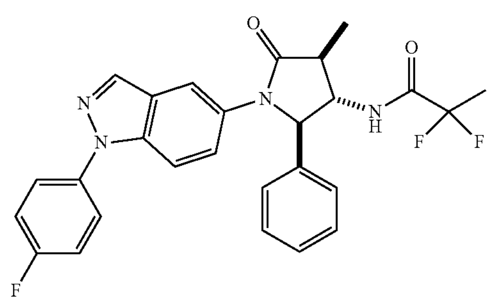 [SMILES: C[C@@H]1C(=O)N(c2ccc3c(cnn3-c3ccc(F)cc3)c2)[C@H](c2ccccc2)[C@H]1NC(=O)C(C)(F)F] | 33 | ¹H NMR (DMSO-d$_6$) δ: 9.17 (d, 1H), 8.29 (s, 1H), 7.79-7.70 (m, 3H), 7.68 (d, 1H), 7.47 (dd, 1H), 7.44-7.35 (m, 2H), 7.35-7.29 (m, 2H), 7.24 (t, 2H), 7.20-7.12 (m, 1H), 5.27 (d, 1H), 4.12 (q, 1H), 2.87 (dq, 1H), 1.73 (t, 3H), 1.26 (d, 3H) |
| 81 | A11-trans | 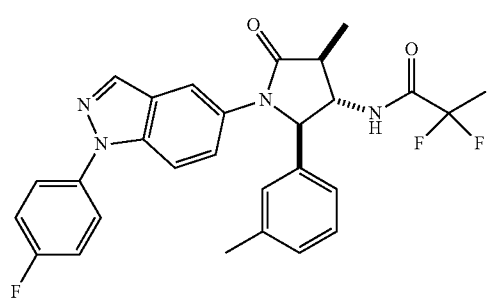 [SMILES: Cc1cccc([C@@H]2[C@@H](NC(=O)C(C)(F)F)[C@H](C)C(=O)N2c2ccc3c(cnn3-c3ccc(F)cc3)c2)c1] | 62 | ¹H NMR (DMSO-d$_6$) δ: 9.16 (d, 1H), 8.30 (d, 1H), 7.78-7.72 (m, 3H), 7.69 (d, 1H), 7.48 (dd, 1H), 7.44-7.35 (m, 2H), 7.15-7.08 (m, 3H), 6.98 (dt, 1H), 5.22 (d, 1H), 4.14-4.04 (m, 1H), 2.85 (dq, 1H), 2.20 (s, 3H), 1.73 (t, 3H), 1.26 (d, 3H) |
| 82 | A15-trans | 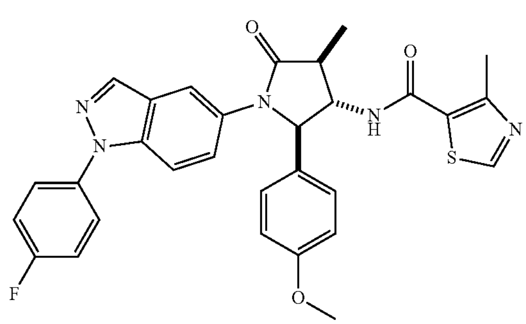 [SMILES: COc1ccc([C@@H]2[C@@H](NC(=O)c3scnc3C)[C@H](C)C(=O)N2c2ccc3c(cnn3-c3ccc(F)cc3)c2)cc1] | 23 | ¹H NMR (DMSO-d$_6$) δ: 9.07 (s, 1H), 8.65 (d, 1H), 8.30 (s, 1H), 7.79-7.71 (m, 3H), 7.68 (d, 1H), 7.48 (dd, 1H), 7.40 (t, 2H), 7.29 (d, 2H), 6.79 (d, 2H), 5.25 (d, 1H), 4.26 (td, 1H), 3.64 (s, 3H), 2.87 (dq, 1H), 2.57 (s, 3H), 1.31 (d, 3H) |

-continued

| Ex. # | Intermediate (INT) | Structure | Yield (%) | ¹H NMR |
|---|---|---|---|---|
| 83 | A15-trans | 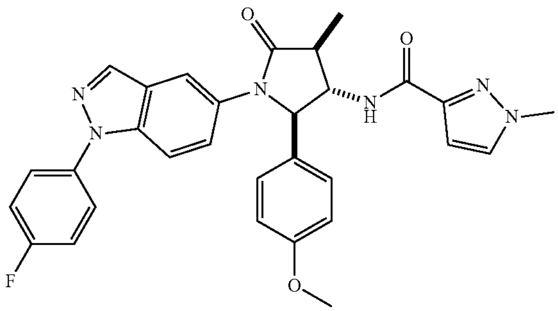 [SMILES: COc1ccc([C@@H]2[C@@H](NC(=O)c3ccn(C)n3)[C@H](C)C(=O)N2c2ccc3c(cnn3-c3ccc(F)cc3)c2)cc1] | 18 | ¹H NMR (DMSO-d₆) δ: 8.54 (d, 1H), 8.29 (d, 1H), 7.79-7.73 (m, 2H), 7.75-7.70 (m, 2H), 7.67 (dt, 1H), 7.43 (dd, 1H), 7.43 7.36 (m, 2H), 7.27-7.21 (m, 2H), 6.79-6.73 (m, 2H), 6.56 (d, 1H), 5.30 (d, 1H), 4.33 (td, 1H), 3.94 (s, 3H), 3.63 (s, 3H), 2.90 (dq, 1H), 1.26 (d, 3H) |
| 84 | A15-trans | 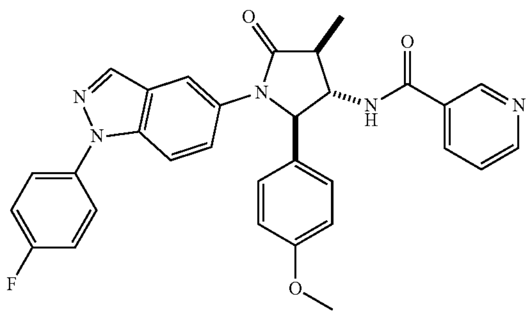 [SMILES: COc1ccc([C@@H]2[C@@H](NC(=O)c3cccnc3)[C@H](C)C(=O)N2c2ccc3c(cnn3-c3ccc(F)cc3)c2)cc1] | 30 | ¹H NMR (DMSO-d₆) δ: 9.08-9.02 (m, 2H), 8.74 (dd, 1H), 8.31 (d, 1H), 8.20 (ddd, 1H), 7.79 (dd, 1H), 7.78-7.72 (m, 2H), 7.69 (dt, 1H), 7.54 (ddd, 1H), 7.50 (dd, 1H), 7.43-7.36 (m, 2H), 7.33-7.28 (m, 2H), 6.81-6.76 (m, 2H), 5.30 (d, 1H), 4.32 (tdd, 1H), 3.64 (s, 3H), 2.89 (dq, 1H), 1.32 (d, 3H) |
| 85 | A15-trans | 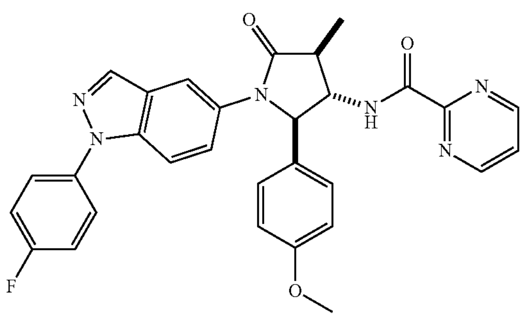 [SMILES: COc1ccc([C@@H]2[C@@H](NC(=O)c3ncccn3)[C@H](C)C(=O)N2c2ccc3c(cnn3-c3ccc(F)cc3)c2)cc1] | 30 | ¹H NMR (DMSO-d₆) δ: 9.39 (d, 1H), 8.99 (dd, 2H), 8.30 (d, 1H), 7.76-7.73 (m, 3H), 7.71 (td, 1H), 7.68 (dd, 1H), 7.44 (dd, 1H), 7.43-7.36 (m, 2H), 7.29-7.24 (m, 2H), 6.79-6.73 (m, 2H), 5.36 (d, 1H), 4.40 (td, 1H), 3.63 (d, 3H), 2.97 (dq, 1H), 1.30 (d, 3H) |
| 87 | A13-cis | 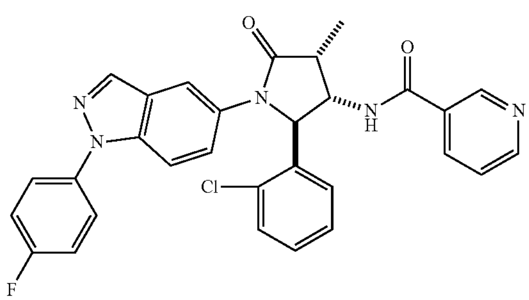 [SMILES: C[C@H]1C(=O)N(c2ccc3c(cnn3-c3ccc(F)cc3)c2)[C@H](c2ccccc2Cl)[C@H]1NC(=O)c1cccnc1] | 42 | ¹H NMR (DMSO-d₆) δ: 9.35 (d, 1H), 9.09 (dd, 1H), 8.75 (dd, 1H), 8.37 (s, 1H), 8.27 (dt, 1H), 8.00 (t, 1H), 7.83-7.74 (m, 4H), 7.58-7.50 (m, 2H), 7.44-7.37 (m, 2H), 7.33 (dtd, 3H), 5.71 (d, 1H), 4.77-4.71 (m, 1H), 3.19 (p, 1H), 1.12 (d, 3H) |
| 88 | A13-cis | 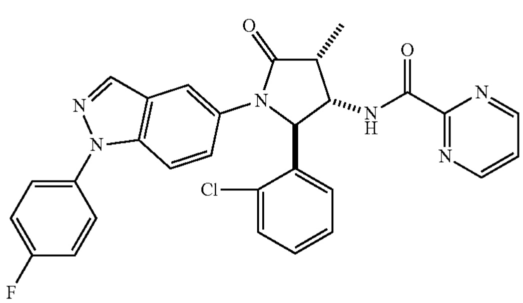 [SMILES: C[C@H]1C(=O)N(c2ccc3c(cnn3-c3ccc(F)cc3)c2)[C@H](c2ccccc2Cl)[C@H]1NC(=O)c1ncccn1] | 41 | ¹H NMR (DMSO-d₆) δ: 9.73 (d, 1H), 9.00 (d, 2H), 8.36 (d, 1H), 7.98 (d, 1H), 7.77 (tq, 4H), 7.71 (t, 1H), 7.53-7.47 (m, 1H), 7.44-7.34 (m, 3H), 7.34-7.28 (m, 2H), 5.80 (d, 1H), 4.72 (s, 1H), 3.24-3.16 (m, 1H), 1.12 (d, 3H) |

-continued

| Ex. # | Intermediate (INT) | Structure | Yield (%) | ¹H NMR |
|---|---|---|---|---|
| 89 | A21 | 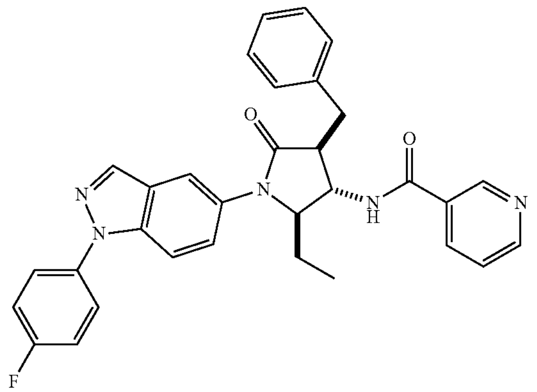 [SMILES: CC[C@@H]1[C@@H](NC(=O)c2cccnc2)[C@H](Cc2ccccc2)C(=O)N1c1ccc2c(cnn2-c2ccc(F)cc2)c1] | 41 | ¹H NMR (DMSO-d$_6$) δ: 8.89 (dd, 1H), 8.82 (d, 1H), 8.72 (dd, 1H), 8.40 (d, 1H), 8.08 (dt, 1H), 7.86-7.78 (m, 4H), 7.51 (ddd, 1H), 7.48-7.41 (m, 3H), 7.39-7.34 (m, 2H), 7.28 (t, 2H), 7.19 7.13 (m, 1H), 4.45 (td, 1H), 4.14 (td, 1H), 3.20-3.09 (m, 2H), 3.05 (dd, 1H), 1.47 (ddd, 1H), 1.24 (dp, 1H), 0.52 (t, 3H) |
| 90 | A21 | 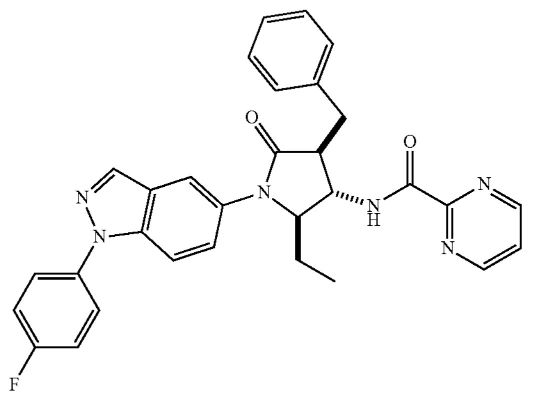 [SMILES: CC[C@@H]1[C@@H](NC(=O)c2ncccn2)[C@H](Cc2ccccc2)C(=O)N1c1ccc2c(cnn2-c2ccc(F)cc2)c1] | 55 | ¹H NMR (DMSO-d$_6$) δ: 9.26 (d, 1H), 8.98 (d, 2H), 8.40 (d, 1H), 7.85-7.79 (m, 3H), 7.76 (dd, 1H), 7.71 (t, 1H), 7.48-7.39 (m, 3H), 7.38-7.33 (m, 2H), 7.29-7.23 (m, 2H), 7.17-7.11 (m, 1H), 4.47 (td, 1H), 4.20 (td, 1H), 3.27-3.20 (m, 1H), 3.09 (dd, 1H), 3.01 (dd, 1H), 1.41 (ddt, 1H), 1.26-1.15 (m, 1H), 0.46 (t, 3H) |
| 92 | A13-trans | 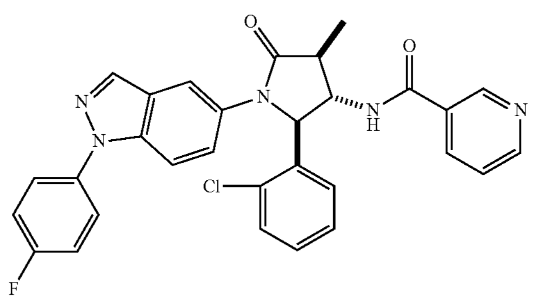 [SMILES: C[C@@H]1C(=O)N(c2ccc3c(cnn3-c3ccc(F)cc3)c2)[C@H](c2ccccc2Cl)[C@H]1NC(=O)c1cccnc1] | 73 | ¹H NMR (DMSO-d$_6$) δ: 9.16 (s, 1H), 9.01 (d, 1H), 8.74 (dd, 1H), 8.34 (s, 1H), 8.17 (dt, 1H), 7.78 (s, 1H), 7.77-7.71 (m, 3H), 7.58-7.50 (m, 2H), 7.46 (s, 1H), 7.43-7.36 (m, 2H), 7.32 (d, 1H), 7.23 (td, 1H), 7.18 (t, 1H), 5.93 (s, 1H), 4.36 (s, 1H), 3.01 (dq, 1H), 1.34 (d, 3H) |
| 94 | A13-cis | 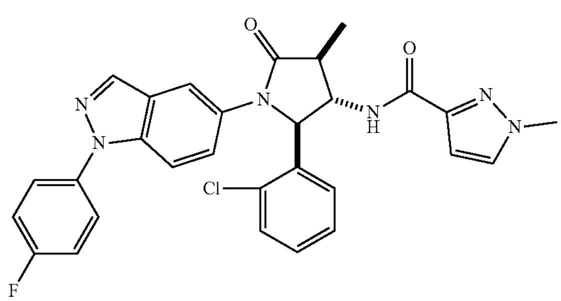 [SMILES: C[C@@H]1C(=O)N(c2ccc3c(cnn3-c3ccc(F)cc3)c2)[C@H](c2ccccc2Cl)[C@H]1NC(=O)c1ccn(C)n1] | 12 | ¹H NMR (DMSO-d$_6$) δ: 8.99 (d, 1H), 8.36 (d, 1H), 7.98-7.95 (m, 1H), 7.81-7.72 (m, 3H), 7.48 (dt, 1H), 7.43-7.38 (m, 2H), 7.35 (dd, 1H), 7.30 (dd, 2H), 6.66 (d, 1H), 5.77 (d, 1H), 4.67 (s, 1H), 3.93 (s, 2H), 3.13 (dd, 1H), 1.08 (d, 3H) |

-continued
| Ex. # | Intermediate (INT) | Structure | Yield (%) | ¹H NMR |
|---|---|---|---|---|
| 97 | A15-cis | 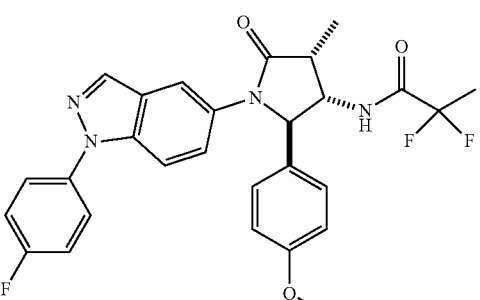 | 60 | 1H NMR (DMSO-$d_6$) δ: 9.39 (d, 1H), 8.32 (d, 1H), 7.89 (d, 1H), 7.81-7.71 (m, 3H), 7.68 (dd, 1H), 7.45-7.35 (m, 2H), 7.32-7.23 (m, 2H), 6.92-6.83 (m, 2H), 5.28 (d, 1H), 4.41 (td, 1H), 3.69 (s, 3H), 3.13 (p, 1H), 1.80 (t, 3H), 1.09 (d, 3H) |
| 98 | A15-trans | 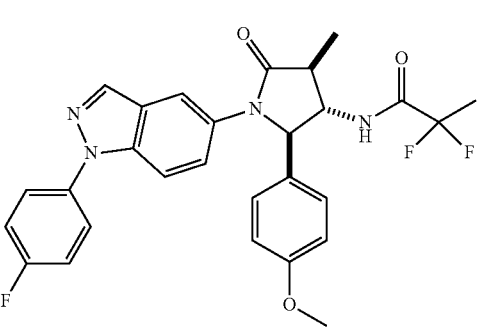 [SMILES: COc1ccc([C@@H]2[C@@H](NC(=O)C(C)(F)F)[C@H](C)C(=O)N2c2ccc3c(cnn3-c3ccc(F)cc3)c2)cc1] | 24 | ¹H NMR (DMSO-$d_6$) δ: 9.11 (d, 1H), 8.29 (d, 1H), 7.78-7.70 (m, 3H), 7.68 (d, 1H), 7.48-7.35 (m, 3H), 7.29-7.20 (m, 2H), 6.83-6.74 (m, 2H), 5.19 (d, 1H), 4.11 (q, 1H), 3.65 (s, 3H), 2.84 (dq, 1H), 1.73 (t, 3H), 1.26 (d, 3H) |
| 104 | A21 | 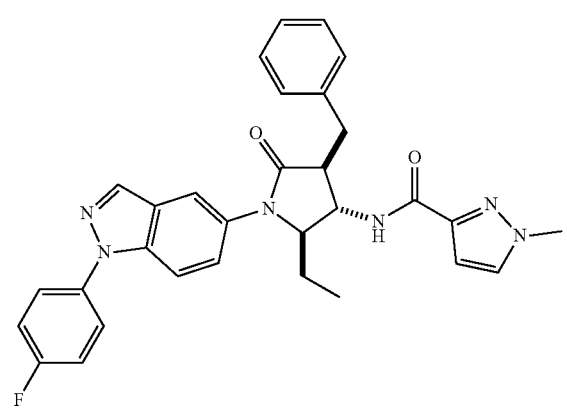 [SMILES: CC[C@@H]1[C@@H](NC(=O)c2ccn(C)n2)[C@H](Cc2ccccc2)C(=O)N1c1ccc2c(cnn2-c2ccc(F)cc2)c1] | 33 | ¹H NMR (DMSO-$d_6$) δ: 8.48 (d, 1H), 8.39 (d, 1H), 7.84-7.77 (m, 4H), 7.73 (d, 1H), 7.44 (t, 2H), 7.40 (dd, 1H), 7.36 (d, 2H), 7.29 (t, 2H), 7.20 (t, 1H), 6.64 (d, 1H), 4.43 (td, 1H), 4.14 (td, 1H), 3.93 (s, 3H), 3.19-3.11 (m, 1H), 3.10 (d, 1H), 2.93 (dd, 1H), 1.38 (dtd, 1H), 1.14 (dp, 1H), 0.41 (t, 3H) |
| 105 | A21 | 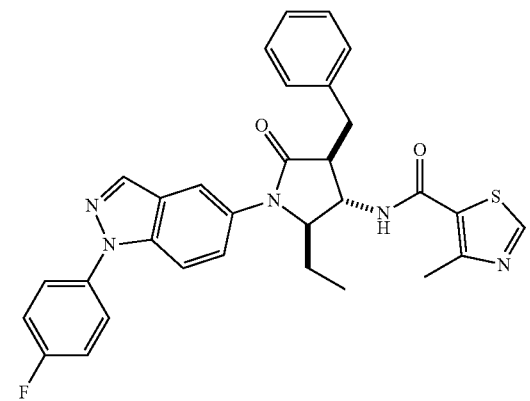 [SMILES: CC[C@@H]1[C@@H](NC(=O)c2scnc2C)[C@H](Cc2ccccc2)C(=O)N1c1ccc2c(cnn2-c2ccc(F)cc2)c1] | 25 | ¹H NMR (DMSO-$d_6$) δ: 9.05 (s, 1H), 8.43 (d, 1H), 8.40 (d, 1H), 7.84-7.80 (m, 3H), 7.79 (d, 1H), 7.48-7.41 (m, 3H), 7.38-7.33 (m, 2H), 7.30 (t, 2H), 7.23-7.17 (m, 1H), 4.40 (td, 1H), 4.12 (td, 1H), 3.14-3.10 (m, 1H), 3.09 (d, 1H), 3.04 (dd, 1H), 2.54 (s, 3H), 1.46 (dtd, 1H), 1.23 (dp, 1H), 0.51 (t, 3H) |

-continued

| Ex. # | Intermediate (INT) | Structure | Yield (%) | ¹H NMR |
|---|---|---|---|---|
| 106 | A21 | 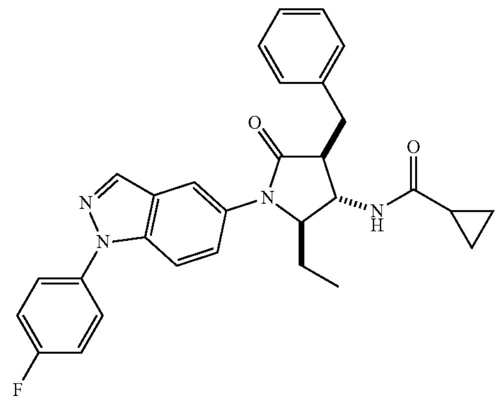 [SMILES: CC[C@@H]1[C@@H](NC(=O)C2CC2)[C@H](Cc2ccccc2)C(=O)N1c1ccc2c(cnn2-c2ccc(F)cc2)c1] | 46 | ¹H NMR (DMSO-d₆) δ: 8.39 (s, 1H), 8.33 (d, 1H), 7.84-7.78 (m, 3H), 7.76 (d, 1H), 7.48-7.38 (m, 3H), 7.34-7.28 (m, 4H), 7.23 (dq, 1H), 4.20 (td, 1H), 3.98 (td, 1H), 3.02 (qd, 2H), 2.92 (dt, 1H), 1.45 (td, 1H), 1.39 (dtd, 1H), 1.18 (dq, 1H), 0.73-0.63 (m, 4H), 0.42 (t, 3H) |
| 107 | A21 | 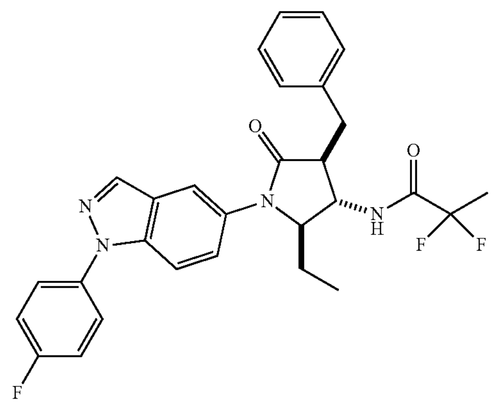 [SMILES: CC[C@@H]1[C@@H](NC(=O)C(C)(F)F)[C@H](Cc2ccccc2)C(=O)N1c1ccc2c(cnn2-c2ccc(F)cc2)c1] | 47 | ¹H NMR (DMSO-d₆) δ: 8.90 (d, 1H), 8.39 (d, 1H), 7.86-7.77 (m, 3H), 7.77 (d, 1H), 7.49-7.38 (m, 3H), 7.31 (d, 4H), 7.23 (tt, 1H), 4.23 (td, 1H), 4.06 (td, 1H), 3.12 (ddd, 1H), 3.06 (dd, 1H), 2.99 (dd, 1H), 1.63 (t, 3H), 1.38 (dtd, 1H), 1.20 (dp, 1H), 0.48 (t, 3H) |
| 108 | A17-trans | 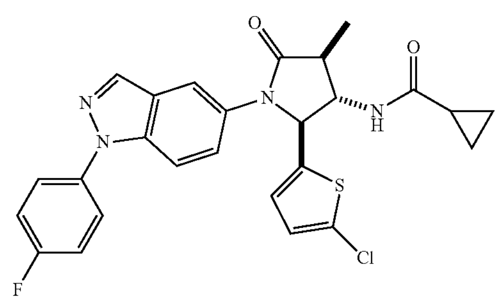 [SMILES: C[C@@H]1C(=O)N(c2ccc3c(cnn3-c3ccc(F)cc3)c2)[C@H](c2ccc(Cl)s2)[C@H]1NC(=O)C1CC1] | 27 | ¹H NMR (DMSO-d₆) δ: 8.56 (d, 1H), 8.34 (s, 1H), 7.81 (d, 1H), 7.78 (ddd, 2H), 7.73 (d, 1H), 7.48 (dd, 1H), 7.44-7.40 (m, 2H), 6.96 (d, 1H), 6.85 (dd, 1H), 5.38 (d, 1H), 4.16 4.09 (m, 1H), 2.76 (dq, 1H), 1.58 (ddd, 1H), 1.24 (d, 3H), 0.75-0.70 (m, 3H), 0.68 (td, 1H) |
| 109 | A17-trans | 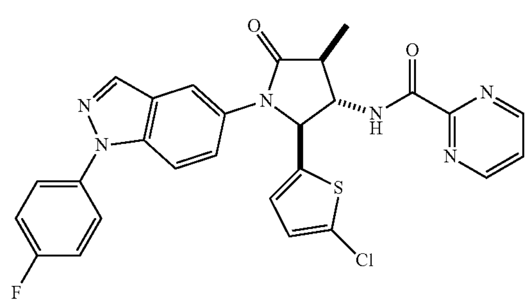 [SMILES: C[C@@H]1C(=O)N(c2ccc3c(cnn3-c3ccc(F)cc3)c2)[C@H](c2ccc(Cl)s2)[C@H]1NC(=O)c1ncccn1] | 33 | ¹H NMR (DMSO-d₆) δ: 9.47 (d, 1H), 9.01 (dd, 2H), 8.35 (d, 1H), 7.80-7.77 (m, 3H), 7.75 (d, 1H), 7.73 (td, 1H), 7.47 (dd, 1H), 7.45-7.39 (m, 2H), 6.98 (d, 1H), 6.83 (d, 1H), 5.63 (d, 1H), 4.48 (td, 1H), 3.02 (dq, 1H), 1.29 (d, 3H) |

-continued

| Ex. # | Intermediate (INT) | Structure | Yield (%) | ¹H NMR |
|---|---|---|---|---|
| 110 | A17-trans | 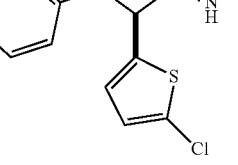 | 31 | ¹H NMR (DMSO-$d_6$) δ: 8.62 (d, 1H), 8.35 (d, 1H), 7.81-7.76 (m, 4H), 7.74 (dt, 1H), 7.45 (dd, 1H), 7.45-7.39 (m, 2H), 6.96 (d, 1H), 6.82 (d, 1H), 6.61 (d, 1H), 5.56 (d, 1H), 4.42 (td, 1H), 3.94 (s, 3H), 2.94 (dq, 1H), 1.25 (d, 3H) |
| 111 | A17-trans | 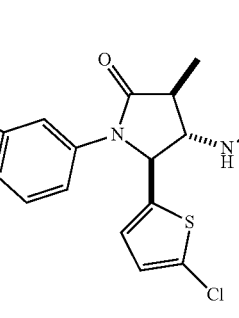 | 36 | ¹H NMR (DMSO-$d_6$) δ: 9.11 (d, 1H), 9.06 (dd, 1H), 8.76 (dd, 1H), 8.36 (d, 1H), 8.22 (dt, 1H), 7.85 (d, 1H), 7.80 7.75 (m, 3H), 7.56 (dd, 1H), 7.52 (dd, 1H), 7.45-7.39 (m, 2H), 7.02 (d, 1H), 6.85 (dd, 1H), 5.57 (d, 1H), 4.40 (td, 1H), 2.95 (dq, 1H), 1.32 (d, 3H) |
| 112 | A13-trans | 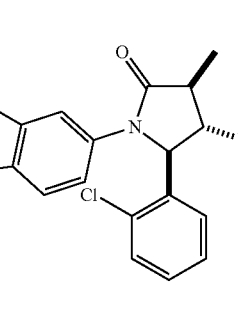 | 32 | ¹H NMR (DMSO-$d_6$) δ: 8.54 (d, 1H), 8.31 (s, 1H), 7.77-7.68 (m, 3H), 7.43 (s, 2H), 7.42-7.35 (m, 2H), 7.33 (d, 1H), 7.19 (dt, 2H), 5.81 (s, 0H), 4.04 (s, 0H), 2.85 (p, 1H), 1.55 (p, 1H), 1.26 (d, 3H), 0.72-0.64 (m, 3H), 0.61 (s, 1H) |
| 113 | A17-trans | 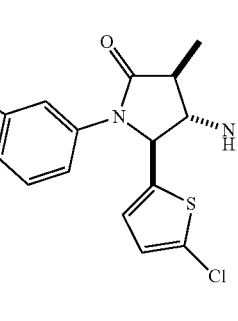 | 28 | ¹H NMR (DMSO-$d_6$) δ: 9.09 (s, 1H), 8.70 (d, 1H), 8.35 (d, 1H), 7.84 (d, 1H), 7.80-7.76 (m, 2H), 7.75 (d, 1H), 7.50 (dd, 1H), 7.45-7.39 (m, 2H), 7.01 (d, 1H), 6.86 (d, 1H), 5.53 (d, 1H), 4.35 (q, 1H), 2.91 (dq, 1H), 2.60 (s, 3H), 1.31 (d, 3H) |
| 115 | A19 | 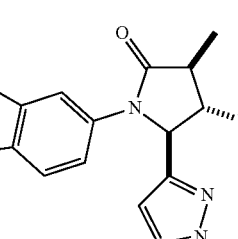 | 51 | ¹H NMR (DMSO-$d_6$) δ: 8.55 (d, 1H), 8.32 (t, 1H), 7.80-7.73 (m, 3H), 7.70 (dd, 1H), 7.48-7.44 (m, 2H), 7.44-7.40 (m, 2H), 6.15 (d, 1H), 5.17 (d, 1H), 4.21 (td, 1H), 3.68 (s, 3H), 2.71 2.63 (m, 1H), 1.56 (ddd, 1H), 1.26 (d, 3H), 0.72-0.65 (m, 4H) |

| Ex. # | Intermediate (INT) | Structure | Yield (%) | ¹H NMR |
|---|---|---|---|---|
| 116 | A19 | 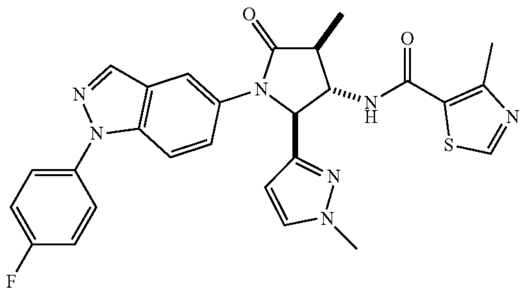 [SMILES: Cc1ncsc1C(=O)N[C@H]1[C@H](C)C(=O)N(c2ccc3c(cnn3-c3ccc(F)cc3)c2)[C@@H]1c1ccn(C)n1] | 35 | ¹H NMR (DMSO-d$_6$) δ: 9.07 (s, 1H), 8.67 (d, 1H), 8.33 (d, 1H), 7.80-7.73 (m, 3H), 7.71 (dt, 1H), 7.50-7.45 (m, 2H), 7.45-7.38 (m, 2H), 6.19 (d, 1H), 5.30 (d, 1H), 4.43 (td, 1H), 3.68 (s, 3H), 2.82 (dq, 1H), 2.59 (s, 3H), 1.33 (d, 3H) |
| 117 | A19 | 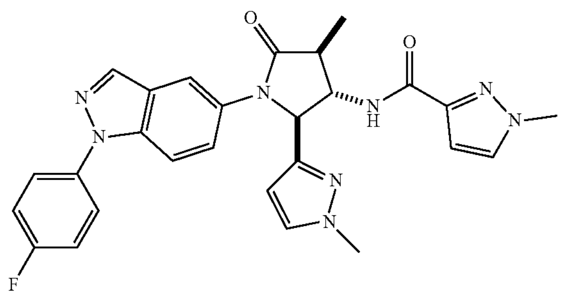 [SMILES: C[C@@H]1C(=O)N(c2ccc3c(cnn3-c3ccc(F)cc3)c2)[C@H](c2ccn(C)n2)[C@H]1NC(=O)c1ccn(C)n1] | 41 | ¹H NMR (DMSO-d$_6$) δ: 8.54 (d, 1H), 8.32 (d, 1H), 7.80-7.74 (m, 3H), 7.73-7.68 (m, 2H), 7.47-7.42 (m, 1H), 7.44-7.38 (m, 3H), 6.59 (dd, 1H), 6.20 (d, 1H), 5.35 (d, 1H), 4.52 (td, 1H), 3.93 (d, 3H), 3.65 (d, 3H), 2.85 (dq, 1H), 1.27 (d, 3H) |
| 118 | A19 | 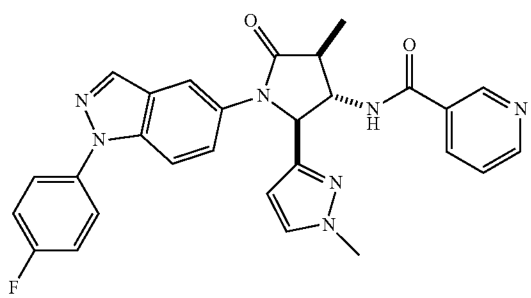 [SMILES: C[C@@H]1C(=O)N(c2ccc3c(cnn3-c3ccc(F)cc3)c2)[C@H](c2ccn(C)n2)[C@H]1NC(=O)c1cccnc1] | 29 | ¹H NMR (DMSO-d$_6$) δ: 9.10 (d, 1H), 9.04 (dd, 1H), 8.74 (dd, 1H), 8.33 (d, 1H), 8.21 (dt, 1H), 7.81-7.74 (m, 3H), 7.74-7.69 (m, 1H), 7.57-7.52 (m, 1H), 7.52-7.46 (m, 2H), 7.45-7.38 (m, 2H), 6.21 (d, 1H), 5.35 (d, 1H), 4.49 (q, 1H), 3.67 (s, 3H), 2.85 (p, 1H), 1.34 (d, 3H) |
| 119 | A19 | 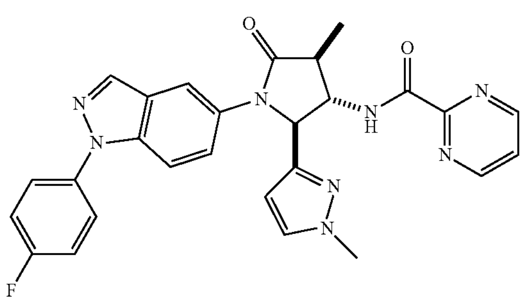 [SMILES: C[C@@H]1C(=O)N(c2ccc3c(cnn3-c3ccc(F)cc3)c2)[C@H](c2ccn(C)n2)[C@H]1NC(=O)c1ncccn1] | 44 | ¹H NMR (DMSO-d$_6$) δ: 9.41 (d, 1H), 8.99 (dd, 2H), 8.33 (d, 1H), 7.80-7.68 (m, 5H), 7.48-7.38 (m, 4H), 6.23 (t, 1H), 5.41 (dd, 1H), 4.59 (td, 1H), 3.64 (d, 3H), 2.98-2.83 (m, 1H), 1.31 (dd, 3H) |
| 120 | A19 | 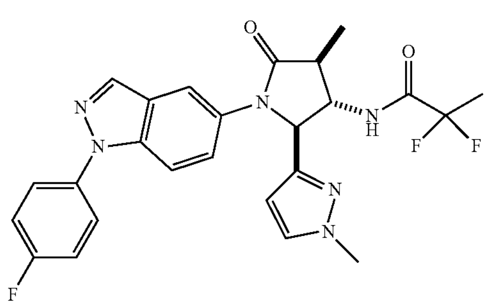 [SMILES: C[C@@H]1C(=O)N(c2ccc3c(cnn3-c3ccc(F)cc3)c2)[C@H](c2ccn(C)n2)[C@H]1NC(=O)C(C)(F)F] | 48 | ¹H NMR (DMSO-d$_6$) δ: 9.14 (d, 1H), 8.32 (d, 1H), 7.81-7.71 (m, 3H), 7.71 (d, 1H), 7.50-7.36 (m, 4H), 6.16 (d, 1H), 5.25 (d, 1H), 4.29 (td, 1H), 3.68 (s, 3H), 2.78 (dq, 1H), 1.75 (t, 3H), 1.31 1.14 (m, 3H) |

-continued

| Ex. # | Intermediate (INT) | Structure | Yield (%) | ¹H NMR |
|---|---|---|---|---|
| 123 | A17-trans | 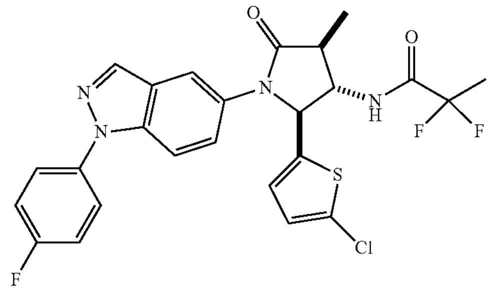 [SMILES: C[C@@H]1C(=O)N(c2ccc3c(cnn3-c3ccc(F)cc3)c2)[C@H](c2ccc(Cl)s2)[C@H]1NC(=O)C(C)(F)F] | 35 | ¹H NMR (DMSO-$d_6$) δ: 9.18 (d, 1H), 8.35 (d, 1H), 7.81-7.76 (m, 3H), 7.74 (d, 1H), 7.46 (dd, 1H), 7.44-7.39 (m, 2H), 7.00 (d, 1H), 6.86 (d, 1H), 5.46 (d, 1H), 4.20 (q, 1H), 2.89 (dq, 1H), 1.77 (t, 3H), 1.26 (d, 3H) |
| 124 | A17-cis | 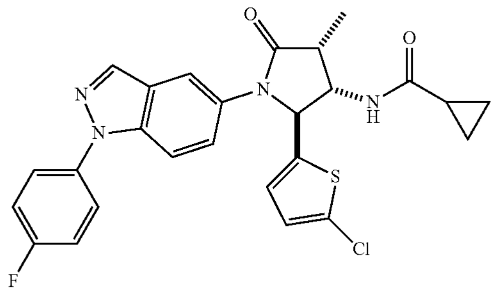 [SMILES: C[C@H]1C(=O)N(c2ccc3c(cnn3-c3ccc(F)cc3)c2)[C@H](c2ccc(Cl)s2)[C@H]1NC(=O)C1CC1] | 24 | ¹H NMR (DMSO-$d_6$) δ: 8.76 (d, 1H), 8.36 (d, 1H), 7.99 (dd, 1H), 7.83-7.76 (m, 3H), 7.72 (dd, 1H), 7.46-7.38 (m, 2H), 6.99-6.92 (m, 2H), 5.42 (d, 1H), 4.51 (ddd, 1H), 3.14 (p, 1H), 1.70 (tt, 1H), 1.11 (d, 3H), 0.80-0.67 (m, 4H) |
| 125 | A17-cis | 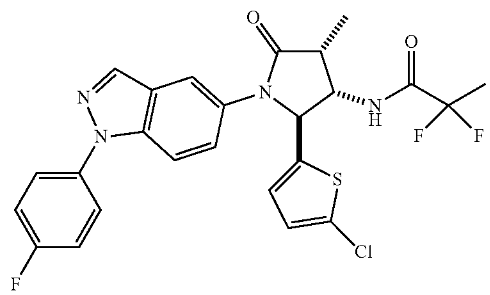 [SMILES: C[C@H]1C(=O)N(c2ccc3c(cnn3-c3ccc(F)cc3)c2)[C@H](c2ccc(Cl)s2)[C@H]1NC(=O)C(C)(F)F] | 19 | ¹H NMR (DMSO-$d_6$) δ: 9.45 (d, 1H), 8.37 (d, 1H), 7.95 (d, 1H), 7.84-7.74 (m, 3H), 7.67 (dd, 1H), 7.47-7.37 (m, 2H), 7.01 (d, 1H), 6.95 (d, 1H), 5.58 (d, 1H), 4.56 (td, 1H), 3.22 (p, 1H), 1.82 (t, 3H), 1.09 (d, 3H) |
| 133 | A15-trans | 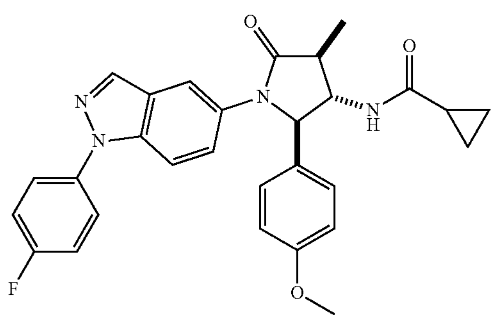 [SMILES: COc1ccc([C@@H]2[C@@H](NC(=O)C3CC3)[C@H](C)C(=O)N2c2ccc3c(cnn3-c3ccc(F)cc3)c2)cc1] | 33 | ¹H NMR (DMSO-$d_6$) δ: 8.54 8.49 (m, 1H), 8.29 (d, 1H), 7.78-7.71 (m, 3H), 7.67 (dd, 1H), 7.47 (dd, 1H), 7.43-7.36 (m, 2H), 7.27-7.21 (m, 2H), 6.81 6.75 (m, 2H), 5.11 (d, 1H), 4.03 (td, 1H), 3.65 (s, 3H), 2.71 (dq, 1H), 1.56 (ft, 1H), 1.24 (d, 3H), 0.73-0.57 (m, 4H) |

Human Glucocorticoid Receptor (hGR) Ligand-Binding Assay

The human lymphoblast cell line IM9 (ATCC, Bethesda, MD) was cultivated in RPMI 1640 media containing 10% fetal bovine serum, penicillin (100 U/ml), streptomycin (100 µg/ml), and 2 mM L-glutamine at 37° and 7% CO2 in a humidified incubator. Cells were centrifuged for 10 minutes at 1500 g and were washed in PBS and repelleted. Cell were then resuspended in homogenization buffer consisting of: 10 mM TES, 10 mM sodium molybdate, 1 mM EDTA, pH 7.4, 20 mM 2-mercaptoethanol, and 10% glycerol. Disruption of the cells was performed by nitrogen cavitation using 2×15 minutes at 600 to 750 psi nitrogen in a N2 cavitator at 0° C. The cell preparation was then centrifuged at 27,000 g for 15 minutes, and the resultant supernatant (=cytosol of IM9 cells) was centrifuged at 103,000 g for 60 minutes at 4° C. The amount of protein in the supernatant fraction was determined using a BCA assay kit and aliquots were snap frozen in a dry ice-acetone bath and stored at −70° C. Competitive binding assays were done in duplicate in homogenization buffer with a total volume of 200 µl. To this end, 1 mg of IM9 cytosol, 0.05 µCi (1.5 nM) of 3H-dexamethasone and unlabeled Example compounds as competitor compounds at 1 µM were mixed. The reaction was stopped after incubation at 0° C. for 16 to 18 hours by the addition of 100 µl of a charcoal-dextran mixture (2% activated charcoal, 0.5% dextran in 10 mM Tris, 1 mM EDTA, pH 7.4). Another incubation step at 0° C. for 10 minutes followed before the samples were centrifuged for 5 minutes at 8200 g. 100 µl of the supernatant) was finally assayed for radioactivity by liquid scintillationspectrometry, and percentage inhibition of 3H-dexamethasone binding was calculated.

GRE Agonist

The reporter cell line CHO-Gal4/GR consisted of a chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of ligand-induced activation of the GR and therefore for the identification of compounds with agonistic properties. The GAL4/UAS reporter was premixed with a vector that constitutively expressed Renilla luciferase, which served as an internal positive control for transfection efficiency.

The complete culture medium for the assay was:
DMEM F-12 (1:1) MIXTURE (LONZA cat. No: BE04-687F/U1) 500 mL
5 mL of 100 mM Sodium Pyruvate (LONZA cat. No: BE12-115E)
25 mL of 7.5% Sodium Bicarbonate (LONZA cat. No BE17-613E)
6.5 mL of 1 M Hepes (LONZA cat. No: BE17-737E)
5 mL of 100× Penicillin/Streptomycin (LONZA cat. No DE17-602E)
50 mL of Fetal Bovine Serum (Euroclone cat. No ECS 0180L)
0.25 mL of 10 mg/mL Puromycin (InvivoGen cat.: ant-pr-1)
0.5 mL of 100 mg/mL Zeocin (InvivoGen cat.: ant-zn-1)

Cryo-preserved CHO-Gal4/GR cells were suspended in complete medium and 5000 cells/25 µl/well were seeded into the wells of 384-well polystyrene assay plates (Thermo Scientific, cat. #4332) and cultured at 37° C., 5% $CO_2$ and 95% humidity. After 24 hours growth medium was carefully removed and replaced by 30 µl Opti-MEM (GIBCO, cat. #31985062) as assay buffer. To test the compounds an 8-point half-log compound dilution curve was generated in 100% DMSO starting from a 2 mM stock and compounds were then diluted 1:50 in Opti-MEM. 10 µl of compounds were then added to the wells containing 30 µl Opti-MEM resulting in a final assay concentration range from 10 µM to 0.003 µM in 0.5% DMSO. Compounds were tested at 8 concentrations in quadruplicate data points. Cells were incubated for 6 hour with compounds and beclometasone (Sigma, cat. #Y0000351) as control compound at 37° C., 5% $CO_2$ and 95% humidity in a total volume of 40 µl. Finally, cells were lysed with 20 µl of Triton/Luciferin solution and the signal of the emitted luminescence was recorded at the FLIPR$^{TETRA}$ for 2 minutes.

The relative efficacy of a compound (% effect) was calculated based on the full effect of the agonist beclometasone:

- % effect = ((compound − min) / (max − min)) × 100
- [min = Opti-MEM only, max = beclometasone]

To calculate $EC_{50}$, max, min and slope factor for each compound a concentration response curve was fitted by plotting % effect versus compound concentration using a 4 parameter logistic equation:

$$y = A + (B - A)/(1 + ((10C)/x)D)$$

- [$A = \text{min}y, B = \text{max}y, C = \log EC_{50}, D = \text{slope}$]

GRE Antagonist

The reporter cell line CHO-Gal4/GR consisted of a chinese hamster ovary (CHO) cell line (Leibniz Institute DSMZ—German Collection of Microorganisms and Cell Cultures GmbH: ACC-110) containing a firefly luciferase gene under the control of the GR ligand binding domain fused to the DNA binding domain (DBD) of GAL4 (GAL4 DBD-GR) stably integrated into CHO cells. This cell line was established by stable transfection of CHO cells with a GAL4-UAS-Luciferase reporter construct. In a subsequent step the ligand binding domain of the GR cloned into pIRES2-EGFP-GAL4 containing the DNA binding domain of GAL4 from pFA-AT2 was transfected. This fusion construct activated firefly luciferase expression under the control of a multimerized GAL4 upstream activation sequence (UAS). The signal of the emitted luminescence was recorded by the FLIPR$^{TETRA}$. This allowed for specific detection of antagonistic properties of compounds by measuring the ligand-induced inhibition of beclometasone-activated GR. The GAL4/UAS reporter was premixed with a vector that constitutively expressed Renilla luciferase, which served as an internal positive control for transfection efficiency.

The complete culture medium for the assay was:
DMEM F-12 (1:1) MIXTURE (LONZA cat. No: BE04-687F/U1) 500 mL
5 mL of 100 mM Sodium Pyruvate (LONZA cat. No: BE12-115E)
25 mL of 7.5% Sodium Bicarbonate (LONZA cat. No BE17-613E)
6.5 mL of 1 M Hepes (LONZA cat. No: BE17-737E)
5 mL of 100× Penicillin/Streptomycin (LONZA cat. No DE17-602E)
50 mL of Fetal Bovine Serum (Euroclone cat. No ECS 0180L)
0.25 mL of 10 mg/mL Puromycin (InvivoGen cat.: ant-pr-1)
0.5 mL of 100 mg/mL Zeocin (InvivoGen cat.: ant-zn-1)

Cryo-preserved CHO-Gal4/GR cells were suspended in complete medium and 5000 cells/25 µl/well were seeded into the wells of 384-well polystyrene assay plates (Thermo Scientific, cat. #4332) and cultured at 37° C., 5% $CO_2$ and 95% humidity. After 24 hours growth medium was carefully removed and replaced by 20 µl Opti-MEM (GIBCO, cat. #31985062) as assay buffer. For testing compounds an 8-point half-log compound dilution curve was generated in 100% DMSO starting from a 2 mM stock and compounds were then diluted 1:50 in Opti-MEM. To test the compounds in the antagonist mode 10 µl of compounds were then added to the wells containing 20 µl Opti-MEM and incubated for 10 min After this pre-incubation 10 µl of the reference agonist beclometasone (Sigma, cat. #Y0000351) at an EC50 of 2.5 nM were added resulting in a final assay concentration range from 10 µM to 0.003 µM in 0.5% DMSO in a total volume of 40 µl. Compounds were tested at 8 concentrations in quadruplicate data points. Cells were incubated for 6 hour with compounds and mifepristone as control compound (Sigma, cat. #M8046) at 37° C., 5% $CO_2$ and 95% humidity. Finally, cells were lysed with 20 µl of Triton/Luciferin solution and the signal of the emitted luminescence was recorded at the FLIPR$^{TETRA}$ for 2 minutes.

The relative efficacy of a compound (% effect) was calculated based on the full effect of the antagonist mifepristone:

$$\% \text{ effect} = ((\text{compund} - \text{min})/(\text{max} - \text{min})) \times -100$$

[min = Opti-MEM only, max = mifepristone]

To calculate $IC_{50}$, max, min and slope factor for each compound a concentration response curve was fitted by plotting % effect versus compound concentration using a 4 parameter logistic equation:

$$y = A + (B - A)/(1 + ((10C)/x)D)$$

[A = miny, B = maxy, C = log$IC_{50}$, D = slope]

Table summarizing biological data:

| cmpd # | IC50 or EC50<br>A < 100 nM,<br>B = 100 nM-1 µM,<br>C = 1 µM-15 µM | % inhibition<br>hGR at 1 µM |
|---|---|---|
| 1 | A | 99 |
| 2 | B | 91 |
| 3 | A | 98 |
| 4 | B | 95 |
| 5 | B | 95 |
| 6 | B | 97 |
| 7 | C | 96 |
| 8 | n.a. | 12 |
| 9 | n.a. | 86 |
| 10 | n.a. | 100 |
| 12 | n.a. | 83 |
| 13 | n.a. | 20 |
| 14 | n.a. | 84 |
| 15 | n.a. | 87 |
| 16 | n.a. | 30 |
| 17 | n.a. | 80 |
| 18 | n.a. | 29 |
| 21 | n.a. | 22 |
| 22 | n.a. | 18 |
| 24 | n.a. | 12 |
| 26 | n.a. | 28 |
| 30 | n.a. | 27 |
| 31 | B | n.d. |
| 33 | C | n.d. |
| 34a | A | n.d. |
| 34b | B | n.d. |
| 35a | A | n.d. |
| 36a | B | n.d. |
| 36b | B | n.d. |
| 37 | A | n.d. |
| 38a | B | n.d. |
| 38b | A | n.d. |
| 39a | A | n.d. |
| 40a | A | n.d. |
| 40b | B | n.d. |
| 41b | C | n.d. |
| 42a | A | n.d. |
| 42b | B | n.d. |
| 43a | A | n.d. |
| 43b | C | n.d. |
| 44a | A | n.d. |
| 44b | B | n.d. |
| 45a | A | n.d. |
| 45b | B | n.d. |
| 46 | A | n.d. |
| 47 | A | n.d. |
| 60 | B | n.d. |
| 61 | B | n.d. |
| 62 | B | n.d. |
| 63 | B | n.d. |
| 64 | A | n.d. |
| 65 | A | n.d. |
| 66 | A | n.d. |
| 67 | A | n.d. |
| 68 | B | n.d. |
| 69 | A | n.d. |
| 70 | A | n.d. |
| 71 | B | n.d. |
| 72 | A | n.d. |
| 73 | A | n.d. |
| 74 | B | n.d. |
| 75 | A | n.d. |
| 76 | A | n.d. |
| 77 | A | n.d. |
| 82 | B | n.d. |
| 83 | A | n.d. |
| 84 | B | n.d. |
| 85 | B | n.d. |
| 86 | A | n.d. |
| 87 | A | n.d. |
| 88 | A | n.d. |
| 90 | C | n.d. |
| 91 | C | n.d. |
| 92 | A | n.d. |
| 93 | A | n.d. |
| 94 | A | n.d. |
| 95 | A | n.d. |
| 96 | A | n.d. |
| 98 | A | n.d. |
| 100 | A | n.d. |
| 101 | B | n.d. |
| 104 | C | n.d. |
| 107 | C | n.d. |
| 108 | A | n.d. |
| 109 | A | n.d. |
| 110 | A | n.d. |
| 111 | A | n.d. |
| 112 | B | n.d. |
| 113 | B | n.d. |
| 114 | B | n.d. |
| 120 | C | n.d. |
| 121 | A | n.d. |
| 123 | A | n.d. |
| 124 | A | n.d. |
| 125 | A | n.d. |
| 126 | A | n.d. |
| 127 | B | n.d. |
| 128 | B | n.d. |
| 129 | A | n.d. |
| 130 | B | n.d. |
| 131 | B | n.d. |
| 132 | A | n.d. |
| 133 | B | n.d. |
| 134 | B | n.d. |
| 135 | A | n.d. |
| 136 | A | n.d. |
| 137 | A | n.d. |
| 138 | B | n.d. |
| 139a | C | n.d. |

149
-continued

Table summarizing biological data:

| cmpd # | IC50 or EC50<br>A < 100 nM,<br>B = 100 nM-1 µM,<br>C = 1 µM-15 µM | % inhibition<br>hGR at 1 µM |
| --- | --- | --- |
| 139b | C | n.d. |
| 148 | A | n.d. |
| 149 | A | n.d. |
| 150 | B | n.d. |
| 151 | B | n.d. |

"n.a.": not active in the GR cell-based assays, neither in the agonistic nor in the antagonistic mode.
"n.d.": not determined.

PROPHETIC EXAMPLES

The prophetic examples summarized in the following table could be synthesized in analogy to Example 7 described above. The person skilled in the art would know how to select suitable intermediates in order to obtain any of the prophetic examples shown in the below table.

| Proph. Ex. # | Structure |
| --- | --- |
| 48 | |
| 49 | |
| 142 | |
| 143 | 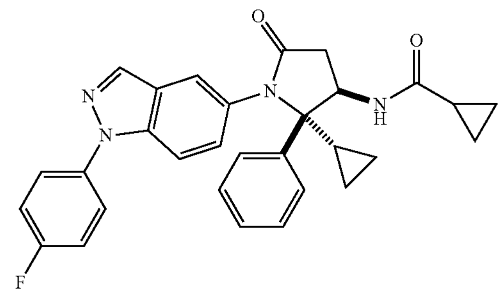 [SMILES: O=C(N[C@@H]1CC(=O)N(c2ccc3c(cnn3-c3ccc(F)cc3)c2)[C@@]1(c1ccccc1)C1CC1)C1CC1] |
| 144 | 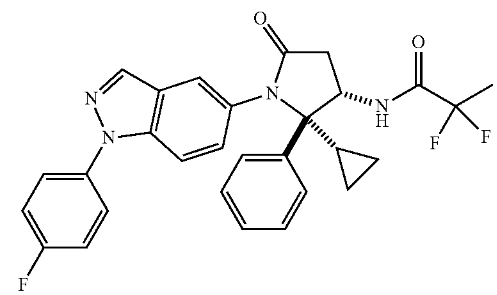 [SMILES: CC(F)(F)C(=O)N[C@H]1CC(=O)N(c2ccc3c(cnn3-c3ccc(F)cc3)c2)[C@@]1(c1ccccc1)C1CC1] |
| 145 | 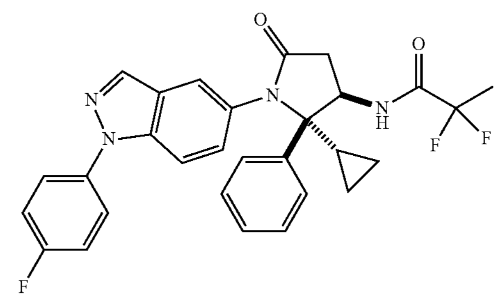 [SMILES: CC(F)(F)C(=O)N[C@@H]1CC(=O)N(c2ccc3c(cnn3-c3ccc(F)cc3)c2)[C@@]1(c1ccccc1)C1CC1] |
| 146 | 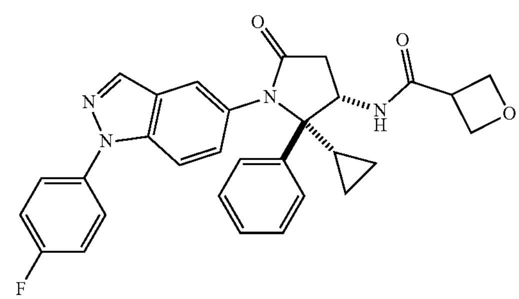 [SMILES: O=C(N[C@H]1CC(=O)N(c2ccc3c(cnn3-c3ccc(F)cc3)c2)[C@@]1(c1ccccc1)C1CC1)C1COC1] |
| 147 | 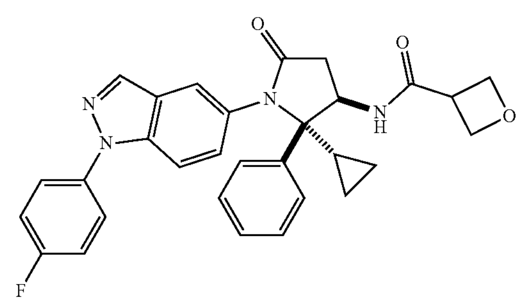 [SMILES: O=C(N[C@@H]1CC(=O)N(c2ccc3c(cnn3-c3ccc(F)cc3)c2)[C@@]1(c1ccccc1)C1CC1)C1COC1] |

In any of the above tables, the example compounds wherein the substituents which are connected to the central pyrrolidone have a different relative orientation, e.g. phenyl moiety and methyl moiety up ("bold bond", ／) and amide moiety down ("hashed bond", ⸝⸌) or vice versa, are the "trans" diastereomer which is a racemic mixture of the two corresponding trans enantiomers.

The invention claimed is:
1. A compound according to general formula (I),

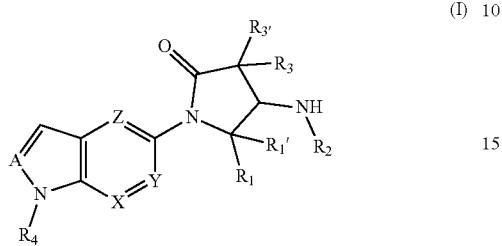

wherein
$R_1$ represents phenyl; —$C_{1-6}$-alkylene-phenyl; 5 or 6-membered heteroaryl; —$C_{1-6}$-alkylene- (5 or 6-membered heteroaryl) or —$C_{1-10}$-alkyl;
$R_{1'}$ represents H; —$C_{1-10}$-alkyl; or —$C_{3-10}$-cycloalkyl;
$R_2$ represents —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-(3 to 7 membered heterocycloalkyl); —C(=O)—$C_{1-6}$-alkylene- (3 to 7 membered heterocycloalkyl); —C(=O)-phenyl; —C(=O)—$C_{1-6}$-alkylene-phenyl; —C(=O)-(5 or 6-membered heteroaryl); —C(=O)—$C_{1-6}$-alkylene- (5 or 6-membered heteroaryl); —S(=O)$_{1-2}$—$C_{1-10}$-alkyl; —S(=O)$_{1-2}$—$C_{3-10}$-cycloalkyl; —S(=O)$_{1-2}$—$C_{1-6}$-alkylene-$C_{3-10}$-cycloalkyl; —S(=O) 1-2-(3 to 7 membered heterocycloalkyl); —S(=O)$_{1-2}$—$C_{1-6}$-alkylene- (3 to 7 membered heterocycloalkyl); —S(=O)$_{1-2}$-phenyl; —S(=O)$_{1-2}$—$C_{1-6}$-alkylene-phenyl; —S(=O)$_{1-2}$—(5 or 6-membered heteroaryl); or —S(=O)$_{1-2}$—$C_{1-6}$-alkylene-(5 or 6-membered heteroaryl);
$R_3$ and $R_{3'}$ independently from one another represent H; F; Cl; —$C_{1-10}$-alkyl; —$C_{3-6}$-cycloalkyl; —$CH_2$—$C_{3-6}$-cycloalkyl; 3 to 7 membered heterocycloalkyl; —$CH_2$-(3 to 7 membered heterocycloalkyl); —$CH_2$-phenyl; or —$CH_2$-(5 or 6-membered heteroaryl);
or $R_3$ and $R_{3'}$ together with the carbon atom to which they are bound form a $C_{3-10}$-cycloalkyl; or 3 to 7 membered heterocycloalkyl;
$R_4$ represents-phenyl; —$C_{1-6}$-alkylene-phenyl; —5 or 6-membered heteroaryl; or —$C_{1-6}$-alkylene-(5 or 6-membered heteroaryl);
A, X, Y and Z independently from one another represent N or CH;
wherein at least one of $R_1$, $R_3$ and $R_{3'}$ is not H;
wherein —$C_{1-10}$-alkyl and —$C_{1-6}$-alkylene- in each case independently from one another is linear or branched, saturated or unsaturated;
wherein —$C_{1-10}$-alkyl, —$C_{1-6}$-alkylene-, —$C_{3-10}$-cycloalkyl and 3 to 7 membered heterocycloalkyl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —C(=O)—$C_{1-6}$-alkyl; —C(=O)—OH; —C(=O)—$OC_{1-6}$-alkyl; —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—C(=O)—$C_{1-6}$-alkyl; —O—C(=O)—O—$C_{1-6}$-alkyl; —O—(CO)—NH($C_{1-6}$-alkyl); —O—C(=O)—N($C_{1-6}$-alkyl)$_2$; —O—S(=O)$_2$—$NH_2$; —O—S(=O)$_2$—NH($C_{1-6}$-alkyl); —O—S(=O)$_2$—N($C_{1-6}$-alkyl)$_2$; —$NH_2$; —NH($C_{1-6}$-alkyl); —N($C_{1-6}$-alkyl)$_2$; —NH—C(=O)—$C_{1-6}$-alkyl; —NH—C(=O)—O—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—$C_{1-6}$-alkyl; —N($C_{1-6}$-alkyl)-C(=O)—O—$C_{1-6}$-alkyl; —N($C_{1-6}$-alkyl)-C(=O)—$NH_2$; —N($C_{1-6}$-alkyl)-C(=O)—NH($C_{1-6}$-alkyl); —N($C_{1-6}$-alkyl)-C(=O)—N($C_{1-6}$-alkyl)$_2$; —NH—S(=O)$_2$OH; —NH—S(=O)$_2$—$C_{1-6}$-alkyl; —NH—S(=O)$_2$—O—$C_{1-6}$-alkyl; —NH—S(=O)$_2$—$NH_2$; —NH—S(=O)$_2$—NH($C_{1-6}$-alkyl); —NH—S(=O)$_2$N($C_{1-6}$-alkyl)$_2$; —N($C_{1-6}$-alkyl)-S(=O)$_2$—OH; —N($C_{1-6}$-alkyl)-S(=O)$_2$—$C_{1-6}$-alkyl; —N($C_{1-6}$-alkyl)-S(=O)$_2$—O—$C_{1-6}$-alkyl; —N($C_{1-6}$-alkyl)-S(=O)$_2$—$NH_2$; —N($C_{1-6}$-alkyl)-S(=O)$_2$—NH($C_{1-6}$-alkyl); —N($C_{1-6}$-alkyl)-S(=O)$_2$—N($C_{1-6}$-alkyl)$_2$; —$SCF_3$; —$SCF_2H$; —$SCFH_2$; —S—$C_{1-6}$-alkyl; —S(=O)—$C_{1-6}$-alkyl; —S(=O)$_2$—$C_{1-6}$-alkyl; —S(=O)$_2$—OH; —S(=O)$_2$—O—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; 3 to 6-membered heterocycloalkyl; phenyl; 5 or 6-membered heteroaryl; —O—$C_{3-6}$-cycloalkyl; —O-(3 to 6-membered heterocycloalkyl); —O-phenyl; —O-(5 or 6-membered heteroaryl); —C(=O)—$C_{3-6}$-cycloalkyl; —C(=O)-(3 to 6-membered heterocycloalkyl); —C(=O)-phenyl; —C(=O)— (5 or 6-membered heteroaryl); —S(=O)$_2$—($C_{3-6}$-cycloalkyl); —S(=O)$_2$—(3 to 6-membered heterocycloalkyl); —S(=O)$_2$- phenyl or —S(=O)$_2$—(5 or 6-membered heteroaryl);
wherein phenyl and 5 or 6-membered heteroaryl in each case independently from one another are unsubstituted or mono- or polysubstituted with one or more substituents selected from —F; —Cl; —Br; —I; —CN; —$C_{1-6}$-alkyl; —$CF_3$; —$CF_2H$; —$CFH_2$; —$CF_2Cl$; —$CFCl_2$; —$C_{1-4}$-alkylene-$CF_3$; —$C_{1-4}$-alkylene-$CF_2H$; —$C_{1-4}$-alkylene-$CFH_2$; —C(=O)—$C_{1-6}$-alkyl; —C(=O)—OH; —C(=O)—$OC_{1-6}$-alkyl; —C(=O)—NH(OH); —C(=O)—$NH_2$; —C(=O)—NH($C_{1-6}$-alkyl); —C(=O)—N($C_{1-6}$-alkyl)$_2$; —OH; =O; —$OCF_3$; —$OCF_2H$; —$OCFH_2$; —$OCF_2Cl$; —$OCFCl_2$; —O—$C_{1-6}$-alkyl; —O—$C_{3-6}$-cycloalkyl; —O-(3 to 6-membered heterocycloalkyl); —$NH_2$; —NH($C_{1-6}$-alkyl); —N($C_{1-6}$-alkyl)$_2$; —NH—C(=O)—$C_{1-6}$-alkyl; —N($C_{1-6}$-alkyl)-C(=O)—$C_{1-6}$-alkyl; —NH—C(=O)—$NH_2$; —NH—C(=O)—NH($C_{1-6}$-alkyl); —NH—C(=O)—N($C_{1-6}$-alkyl)$_2$; —N($C_{1-6}$-alkyl)-C(=O)—NH($C_{1-6}$-alkyl); —N($C_{1-6}$-alkyl)-C(=O)—N($C_{1-6}$-alkyl)$_2$; —NH—S(=O)$_2$—$C_{1-6}$-alkyl; —$SCF_3$; —S—$C_{1-6}$-alkyl; —S(=O)—$C_{1-6}$-alkyl; —S(=O)$_2$—$C_{1-6}$-alkyl; —S(=O)$_2$—$NH_2$; —S(=O)$_2$—NH($C_{1-6}$-alkyl); —S(=O)$_2$—N($C_{1-6}$-alkyl)$_2$; —$C_{3-6}$-cycloalkyl; —$C_{1-4}$-alkylene-$C_{3-6}$-cycloalkyl; 3 to 6-membered heterocycloalkyl; —$C_{1-4}$-alkylene- (3 to 6-membered heterocycloalkyl); phenyl or 5 or 6-membered heteroaryl;
in the form of the free compound or a physiologically acceptable salt thereof;
with the proviso that the following compounds are excluded:
N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-cyclopropanecarboxylic acid amide;

N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-cyclopropanecarboxylic acid amide;

N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-1-methyl-1H-pyrazole-3-carboxylic acid amide;

N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-[1,2,4]oxadiazole-3-carboxylic acid amide;

N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-4-methyl-thiazole-5-carboxylic acid amide;

N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-thiazole-4-carboxylic acid amide; and N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-thiazole-4-carboxylic acid amide.

2. The compound according to claim 1, which has a stereochemistry according to general formula (II) or (VI)

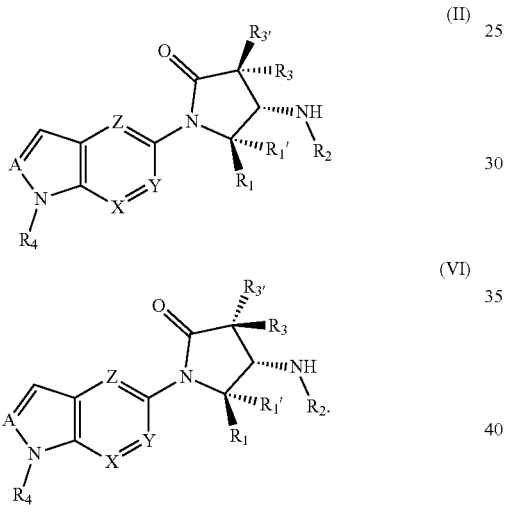

3. The compound according to claim 1, wherein
A represents N, X represents CH, Y represents CH; and Z represents CH; or
A represents N, X represents N, Y represents CH; and Z represents CH; or
A represents N, X represents CH, Y represents N; and Z represents CH; or
A represents N, X represents CH, Y represents CH; and Z represents N; or
A represents N, X represents N, Y represents N; and Z represents CH; or
A represents N, X represents N, Y represents CH; and Z represents N; or
A represents N, X represents CH, Y represents N; and Z represents N; or
A represents N, X represents N, Y represents N; and Z represents N; or
A represents CH, X represents CH, Y represents CH; and Z represents CH; or
A represents CH, X represents N, Y represents CH; and Z represents CH; or
A represents CH, X represents CH, Y represents N; and Z represents CH; or
A represents CH, X represents CH, Y represents CH; and Z represents N; or
A represents CH, X represents N, Y represents N; and Z represents CH; or
A represents CH, X represents N, Y represents CH; and Z represents N; or
A represents CH, X represents CH, Y represents N; and Z represents N; or
A represents CH, X represents N, Y represents N; and Z represents N.

4. The compound according to claim 1, wherein
$R_1$ represents phenyl; and/or
$R_{1'}$ represents H, $CH_3$ or cyclopropyl.

5. The compound according to claim 1, wherein
$R_2$ represents —C(=O)—$C_{1-10}$-alkyl; —C(=O)—$C_{3-10}$-cycloalkyl; —C(=O)—$C_{1-6}$-alkylene-$C_{3-10}$-cycloalkyl; —C(=O)-(3 to 7 membered heterocycloalkyl); —C(=O)-(5 or 6-membered heteroaryl); —S(=O)$_2$—$C_{1-10}$-alkyl; —S(=O)$_2$—$C_{3-10}$-cycloalkyl; —S(=O)$_2$—$C_{1-6}$-alkylene-$C_{3-10}$-cycloalkyl; —S(=O)$_2$—(3 to 7 membered heterocycloalkyl); or —S(=O)$_2$—(5 or 6-membered heteroaryl).

6. The compound according to claim 1, wherein
$R_3$ and $R_{3'}$ both represent-$C_{1-10}$-alkyl.

7. The compound according to claim 1, wherein
$R_4$ represents-phenyl; or 5 or 6-membered heteroaryl.

8. The compound according to claim 1, wherein
$R_1$ represents
phenyl, unsubstituted or mono- or disubstituted with substituents independently of one another selected from the group consisting of —F, —Cl, —Br, —OCH$_3$, —CH$_3$, —CF$_3$, —CN, and cyclopropyl.

9. The compound according to claim 1, wherein
$R_2$ represents
—C(=O)—$C_{1-10}$-alkyl, unsubstituted or mono- or disubstituted with substituents independently of one another selected from the group consisting of —F, —Cl, and —Br;
C(=O)-cyclopropyl, unsubstituted or mono- or disubstituted with substituents independently of one another selected from the group consisting of —F, —Cl, —Br, —CH$_3$, —CF$_3$, —CN, and —OCH$_3$;
—C(=O)-2-tetrahydrofuranyl, unsubstituted;
—C(=O)-(5- to 6-membered heteroaryl), wherein said 5- to 6-membered heteroaryl is selected from the group consisting of thiazolyl, pyrazolyl, oxazolyl, isoxazolyl, 1-oxa-2,4-diazolyl, 1,2,5-oxadiazolyl, and isothiazolyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$;
—S(=O)$_2$—$C_{1-10}$-alkyl, unsubstituted;
—S(=O)$_2$—cyclopropyl, unsubstituted;
—S(=O)$_2$—CH$_2$-cyclopropyl, unsubstituted;
—S(=O)$_2$—2-tetrahydrofuranyl, unsubstituted; or
—S(=O)$_2$—(5- to 6-membered heteroaryl), wherein said 5- to 6-membered heteroaryl is selected from the group consisting of thiazolyl, pyrazolyl, oxazolyl, isoxazolyl, 1-oxa-2,4-diazolyl, 1,2,5-oxadiazolyl, and isothiazolyl, wherein in each case said 5- to 6-membered heteroaryl is unsubstituted or mono- or disubstituted with substituents independently of one another selected from the group consisting of —F, —Cl, —Br, —CH$_3$, —CF$_3$, —CN, =O, and —OCH$_3$.

10. The compound according to claim 1, wherein $R_3$ and $R_{3'}$ both represent —$CH_3$.

11. The compound according to claim 1, wherein $R_4$ represents phenyl, unsubstituted or mono- or disubstituted with substituents independently of one another selected from the group consisting of —F, —Cl, —Br, —$CH_3$, —$CF_3$, —CN, and —$OCH_3$;

5- to 6-membered heteroaryl selected from the group consisting of pyridyl, pyrazolyl, and pyrimidinyl, wherein in each case said 5- to 6-membered heteroaryl is unsubstituted or mono- or disubstituted with substituents independently of one another selected from the group consisting of =O, —F, —Cl, —Br, —$CH_3$, —$CF_3$, —CN, and —$OCH_3$.

12. The compound according to claim 1, wherein $R_1$ represents phenyl, unsubstituted or mono- or disubstituted with substituents independently of one another selected from the group consisting of —F, —Cl, —Br, —$CH_3$, and —$OCH_3$; and/or $R_{1'}$ represents H, $CH_3$, or cyclopropyl; and/or $R_2$ represents —C(=O)—$C_{1-6}$-alkyl; —C(=O)-cyclopropyl; or —C(=O)— (5- to 6-membered heteroaryl), unsubstituted or mono- or disubstituted with substituents independently of one another selected from the group consisting of —F, —Cl, —Br, and —$CH_3$; and/or $R_4$ represents fluoro-phenyl or N-methyl-2-oxo-pyridyl.

13. The compound according to claim 1, which is selected from the group consisting of:

1 N-[(2R,3S)-1-[1-(4-Fluorophenyl)-1H-indazol-5-yl]-4,4-dimethyl-5-oxo-2-phenyl-pyrrolidin-3-yl]-cyclopropanecarboxylic acid amide 2 N-[(2S,3R)-1-[1-(4-Fluorophenyl)-1H-indazol-5-yl]-4,4-dimethyl-5-oxo-2-phenyl-pyrrolidin-3-yl]-cyclopropanecarboxylic acid amide 3 N-[rac-(6R,7S)-5-[1-(4-Fluorophenyl)-1H-indazol-5-yl]-4-oxo-6-phenyl-5-azaspiro[2.4]heptan-7-yl]-cyclopropanecarboxylic acid amide 4 2,2-Difluoro-N-[(2S,3R)-1-[1-(4-fluorophenyl)-1H-indazol-5-yl]-4,4-dimethyl-5-oxo-2-phenyl-pyrrolidin-3-yl]-propionamide 5 N-[rac-(6R,7S)-5-[1-(4-Fluorophenyl)-1H-indol-5-yl]-4-oxo-6-phenyl-5-azaspiro[2.4]heptan-7-yl]-cyclopropanecarboxylic acid amide 6 N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-thiazole-2-carboxylic acid amide 7 N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-isoxazole-3-carboxylic acid amide 8 N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-2,2-difluoro-propionamide 9 N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-2,2-difluoro-propionamide 10 2,2-Difluoro-N-[(2R,3S)-1-[1-(4-fluorophenyl)-1H-indazol-5-yl]-4,4-dimethyl-5-oxo-2-phenyl-pyrrolidin-3-yl]-propionamide 12 N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-1-methyl-1H-pyrazole-3-carboxylic acid amide 13 N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-oxazole-5-carboxylic acid amide 14 N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-[1,2,4]oxadiazole-3-carboxylic acid amide 15 N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-thiazole-5-carboxylic acid amide 16 N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-4-methyl-thiazole-5-carboxylic acid amide 17 N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-thiazole-4-carboxylic acid amide 18 N-[(2R,3S)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-thiazole-4-carboxylic acid amide 21 N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-oxazole-5-carboxylic acid amide 22 N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-isoxazole-3-carboxylic acid amide 24 N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-thiazole-5-carboxylic acid amide 26 N-[(2S,3R)-4,4-Dimethyl-1-[1-(1-methyl-6-oxo-1H-pyridin-3-yl)-1H-indazol-5-yl]-5-oxo-2-phenyl-pyrrolidin-3-yl]-5-methyl-thiazole-2-carboxylic acid amide 30 N-[rac-(6R,7S)-5-[1-(1-Methyl-6-oxo-1H-pyridin-3-yl)-1H-indazol-5-yl]-4-oxo-6-phenyl-5-azaspiro[2.4]heptan-7-yl]-cyclopropanecarboxylic acid amide 31 N-[rac-(6R,7S)-5-[1-(4-Fluorophenyl)-1H-pyrazolo[3,4-b]pyridin-5-yl]-4-oxo-6-phenyl-5-azaspiro[2.4]heptan-7-yl]-cyclopropanecarboxylic acid amide 32 N-[rac-(6R,7S)-5-[1-(4-Fluorophenyl)-1H-pyrazolo[3,4-c]pyridin-5-yl]-4-oxo-6-phenyl-5-azaspiro[2.4]heptan-7-yl]-cyclopropanecarboxylic acid amide 33 N-[rac-(6R,7S)-5-[1-(4-Fluorophenyl)-1H-pyrazolo[4,3-b]pyridin-5-yl]-4-oxo-6-phenyl-5-azaspiro[2.4]heptan-7-yl]-cyclopropanecarboxylic acid amide 34a N-((2R,3S)-1-(1-(4-fluorophenyl)-1H-indazol-5-yl)-4,4-dimethyl-5-oxo-2-phenylpyrrolidin-3-yl)methanesulfonamide 34b N-((2S,3R)-1-(1-(4-fluorophenyl)-1H-indazol-5-yl)-4,4-dimethyl-5-oxo-2-phenylpyrrolidin-3-yl)methanesulfonamide 35a N-((2R,3S)-1-(1-(4-fluorophenyl)-1H-indazol-5-yl)-4,4-dimethyl-5-oxo-2-phenylpyrrolidin-3-yl)cyclopropanesulfonamide 35b N-((2S,3R)-1-(1-(4-fluorophenyl)-1H-indazol-5-yl)-4,4-dimethyl-5-oxo-2-phenylpyrrolidin-3-yl)cyclopropanesulfonamide 36a N-((2R,3S)-1-(1-(4-fluorophenyl)-1H-indazol-5-yl)-4,4-dimethyl-5-oxo-2-phenylpyrrolidin-3-yl)oxazole-5-carboxamide 36b N-((2S,3R)-1-(1-(4-fluorophenyl)-1H-indazol-5-yl)-4,4-dimethyl-5-oxo-2-phenylpyrrolidin-3-yl)oxazole-5-carboxamide 37 N-((2R,3S)-1-(1-(4-fluorophenyl)-1H-indazol-5-yl)-4,4-dimethyl-5-oxo-2-phenylpyrrolidin-3-yl)-1-methyl-1H-pyrazole-3-carboxamide 38a N-((2S,3R)-1-(1-(4-fluorophenyl)-1H-indazol-5-yl)-4,4-dimethyl-5-oxo-2-phenylpyrrolidin-3-yl)-4-methylthiazole-5-carboxamide 38b N-((2R,3S)-1-(1-(4-fluorophenyl)-1H-indazol-5-yl)-4,4-dimethyl-5-oxo-2-phenylpyrrolidin-3-yl)-4-methylthiazole-5-carboxamide 39a N-((2R,3S)-1-(1-(4-fluorophenyl)-1H-indazol-5-yl)-4,4-dimethyl-5-oxo-2-phenylpyrrolidin-3-yl)-5-methylthiazole-4-carboxamide 39b N-((2S,3R)-1-(1-(4-fluorophenyl)-1H-indazol-5-yl)-4,4-dimethyl-5-oxo-2-phenylpyrrolidin-3-yl)-5-methylthiazole-4-carboxamide 40a N-((2R,3S)-1-(1-(4-fluorophenyl)-1H-indazol-5-yl)-4,4-dimethyl-5-oxo-2-phenylpyrrolidin-3-yl)-3-methylisoxazole-4-carboxamide 40b N-((2S,3R)-1-(1-(4-fluorophenyl)-1H-indazol-5-yl)-4,4-dimethyl-5-oxo-2-phenylpyrrolidin-3-yl)-3-methylisoxazole-4-carboxamide 41a N-((2R,3S)-1-(1-(4-fluorophenyl)-1H-indazol-5-yl)-4,4-dimethyl-5-oxo-2-phenylpyrrolidin-3-yl)-1-methyl-1H-pyrazole-4-carboxamide 41b N-((2S,3R)-1-(1-(4-fluorophenyl)-1H-indazol-5-yl)-4,4-dimethyl-5-oxo-2-phenylpyrrolidin-3-yl)-1-methyl-1H-pyrazole-4-carboxamide 42a N-((2R,3S)-1-(1-(4-fluorophenyl)-1H-indazol-5-yl)-4,4-dimethyl-5-oxo-2-phenylpyrrolidin-3-yl)nicotinamide 42b N-((2S,3R)-1-(1-(4-fluorophenyl)-1H-indazol-5-yl)-4,4-dimethyl-5-oxo-2-phenylpyrrolidin-3-yl)nicotinamide 43a N-((2R,3S)-1-(1-(4-fluorophenyl)-1H-indazol-5-yl)-4,4-dimethyl-5-oxo-2-phenylpyrrolidin-3-yl)pyrimidine-2-carboxamide 43b N-((2S,3R)-1-(1-(4-fluorophenyl)-1H-indazol-5-yl)-4,4-dimethyl-5-oxo-2-phenylpyrrolidin-3-yl)pyrimidine-2-carboxamide 44a N-((2R,3S)-1-(1-(4-fluorophenyl)-1H-indazol-5-yl)-4,4-dimethyl-5-oxo-2-phenylpyrrolidin-3-yl)-2-methyloxazole-5-carboxamide 44b N-((2S,3R)-1-(1-(4-fluorophenyl)-1H-indazol-5-yl)-4,4-dimethyl-5-oxo-2-phenylpyrrolidin-3-yl)-2-methyloxazole-5-carboxamide 45a N-((2R,3S)-1-(1-(4-fluorophenyl)-1H-indazol-5-yl)-4,4-dimethyl-5-oxo-2-phenylpyrrolidin-3-yl)-4-methyloxazole-5-carboxamide 45b N-((2S,3R)-1-(1-(4-fluorophenyl)-1H-indazol-5-yl)-4,4-dimethyl-5-oxo-2-phenylpyrrolidin-3-yl)-4-methyloxazole-5-carboxamide 46 N-[rac-(2R,3S,4S)-1-[1-(4-Fluorophenyl)-1H-indazol-5-yl]-4-methyl-5-oxo-2-phenyl-pyrrolidin-3-yl]-cyclopropanecarboxylic acid amide 47 N-[rac-(2R,3S,4S)-2-(2-Chlorophenyl)-1-[1-(4-fluorophenyl)-1H-indazol-5-yl]-4-methyl-5-oxo-pyrrolidin-3-yl]-2,2-difluoro-propionamide 48 N-[rac-(2R,3S,4S)-1-[1-(4-Fluorophenyl)-1H-indazol-5-yl]-2-(3-methoxyphenyl)-4-methyl-5-oxo-pyrrolidin-3-yl]-cyclopropanecarboxylic acid amide 49 N-[rac-(2R,3S,4S)-2-(4-Fluorophenyl)-1-[1-(4-fluorophenyl)-1H-indazol-5-yl]-4-methyl-5-oxo-pyrrolidin-3-yl]-cyclopropanecarboxylic acid amide 60 N-[rac (2R,3S,4S)-1-[1-(4-Fluorophenyl)-1H-indazol-5-yl]-4-methyl-5-oxo-2-phenyl-pyrrolidin-3-yl]-4-methyl-thiazole-5-carboxylic acid amide 61 N-[rac-(2R,3S,4S)-1-[1-(4-Fluorophenyl)-1H-indazol-5-yl]-4-methyl-5-oxo-2-phenyl-pyrrolidin-3-yl]-methanesulfonic acid amide 62 N-[rac-(2R,3S,4S)-1-[1-(4-Fluorophenyl)-1H-indazol-5-yl]-4-methyl-2-m-tolyl-5-oxo-pyrrolidin-3-yl]-methanesulfonic acid amide 63 N-[rac-(2R,3S,4S)-1-[1-(4-Fluorophenyl)-1H-indazol-5-yl]-4-methyl-2-m-tolyl-5-oxo-pyrrolidin-3-yl]-cyclopropanecarboxylic acid amide 64 N-[rac-(2R,3S,4S)-1-[1-(4-Fluorophenyl)-1H-indazol-5-yl]-4-methyl-5-oxo-2-phenyl-pyrrolidin-3-yl]-1-methyl-1H-pyrazole-3-carboxylic acid amide 65 N-[rac-(2R,3S,4S)-1-[1-(4-Fluorophenyl)-1H-indazol-5-yl]-4-methyl-5-oxo-2-phenyl-pyrrolidin-3-yl]-pyridine-3-carboxylic acid amide 66 N-[rac-(2R,3S,4S)-1-[1-(4-Fluorophenyl)-1H-indazol-5-yl]-4-methyl-5-oxo-2-phenyl-pyrrolidin-3-yl]-pyrimidine-2-carboxylic acid amide 67 N-[rac-(2R,3S,4S)-1-[1-(4-Fluorophenyl)-1H-indazol-5-yl]-4-methyl-2-m-tolyl-5-oxo-pyrrolidin-3-yl]-4-methyl-thiazole-5-carboxylic acid amide 68 N-[rac-(2R,3S,4S)-1-[1-(4-Fluorophenyl)-1H-indazol-5-yl]-4-methyl-2-m-tolyl-5-oxo-pyrrolidin-3-yl]-pyridine-3-carboxylic acid amide 69 N-[rac-(2R,3S,4S)-1-[1-(4-Fluorophenyl)-1H-indazol-5-yl]-4-methyl-2-m-tolyl-5-oxo-pyrrolidin-3-yl]-pyrimidine-2-carboxylic acid amide 70 N-[rac-(2R,3S,4R)-1-[1-(4-Fluorophenyl)-1H-indazol-5-yl]-4-methyl-2-m-tolyl-5-oxo-pyrrolidin-3-yl]-cyclopropanecarboxylic acid amide 71 N-[rac-(2R,3S,4R)-1-[1-(4-Fluorophenyl)-1H-indazol-5-yl]-4-methyl-2-m-tolyl-5-oxo-pyrrolidin-3-yl]-4-methyl-thiazole-5-carboxylic acid amide 72 N-[rac-(2R,3S,4R)-1-[1-(4-Fluorophenyl)-1H-indazol-5-yl]-4-methyl-2-m-tolyl-5-oxo-pyrrolidin-3-yl]-1-methyl-1H-pyrazole-3-carboxylic acid amide 73 N-[rac-(2R,3S,4R)-1-[1-(4-Fluorophenyl)-1H-indazol-5-yl]-4-methyl-2-m-tolyl-5-oxo-pyrrolidin-3-yl]-pyridine-3-carboxylic acid amide 74 N-[rac-(2R,3S,4R)-1-[1-(4-Fluorophenyl)-1H-indazol-5-yl]-4-methyl-2-m-tolyl-5-oxo-pyrrolidin-3-yl]-pyrimidine-2-carboxylic acid amide 75 N-[rac-(2R,3S,4S)-1-[1-(4-Fluorophenyl)-1H-indazol-5-yl]-4-methyl-2-m-tolyl-5-oxo-pyrrolidin-3-yl]-1-methyl-1H-pyrazole-3-carboxylic acid amide 76 N-[rac-(2R,3S,4R)-1-[1-(4-Fluorophenyl)-1H-indazol-5-yl]-4-methyl-2-m-tolyl-5-oxo-pyrrolidin-3-yl]-methanesulfonic acid amide 77 2,2-Difluoro-N-[rac-(2R,3S,4R)-1-[1-(4-fluorophenyl)-1H-indazol-5-yl]-4-methyl-2-m-tolyl-5-oxo-pyrrolidin-3-yl]-propionamide 78 N-[rac-(2R,3S,4R)-2-(2-Chlorophenyl)-1-[1-(4-fluorophenyl)-1H-indazol-5-yl]-4-methyl-5-oxo-pyrrolidin-3-yl]-cyclopropanecarboxylic acid amide 79 N-[rac-(2R,3S,4R)-2-(2-Chlorophenyl)-1-[1-(4-fluorophenyl)-1H-indazol-5-yl]-4-methyl-5-oxo-pyrrolidin-3-yl]-2,2-difluoro-propionamide 80 2,2-Difluoro-N-[rac-(2R,3S,4S)-1-[1-(4-fluorophenyl)-1H-indazol-5-yl]-4-methyl-5-oxo-2-phenyl-pyrrolidin-3-yl]-propionamide 81 2,2-Difluoro-N-[rac-(2R,3S,4S)-1-[1-(4-fluorophenyl)-1H-indazol-5-yl]-4-methyl-2-m-tolyl-5-oxo-pyrrolidin-3-yl]-propionamide 82 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-4-methyl-thiazole-5-carboxylic acid amide 83 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-1-methyl-1H-pyrazole-3-carboxylic acid amide 84 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-pyridine-3-carboxylic acid amide
85 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-pyrimidine-2-carboxylic acid amide
86 N-[rac-(2R,3S,4R)-2-(2-Chlorophenyl)-1-[1-(4-fluorophenyl)-1H-indazol-5-yl]-4-methyl-5-oxo-pyrrolidin-3-yl]-methanesulfonic acid amide
87 N-[rac-(2R,3S,4R)-2-(2-Chlorophenyl)-1-[1-(4-fluorophenyl)-1H-indazol-5-yl]-4-methyl-5-oxo-pyrrolidin-3-yl]-pyridine-3-carboxylic acid amide
88 N-[rac-(2R,3S,4R)-2-(2-Chlorophenyl)-1-[1-(4-fluorophenyl)-1H-indazol-5-yl]-4-methyl-5-oxo-pyrrolidin-3-yl]-pyrimidine-2-carboxylic acid amide
89 N-[rac-(2R,3S,4S)-4-Benzyl-2-ethyl-1-[1-(4-fluorophenyl)-1H-indazol-5-yl]-5-oxo-pyrrolidin-3-yl]-pyridine-3-carboxylic acid amide
90 N-[rac-(2R,3S,4S)-4-Benzyl-2-ethyl-1-[1-(4-fluorophenyl)-1H-indazol-5-yl]-5-oxo-pyrrolidin-3-yl]-pyrimidine-2-carboxylic acid amide
91 N-[rac-(2R,3S,4S)-4-Benzyl-2-ethyl-1-[1-(4-fluorophenyl)-1H-indazol-5-yl]-5-oxo-pyrrolidin-3-yl]-methanesulfonic acid amide
92 N-[rac-(2R,3S,4S)-2-(2-Chlorophenyl)-1-[1-(4-fluorophenyl)-1H-indazol-5-yl]-4-methyl-5-oxo-pyrrolidin-3-yl]-pyridine-3-carboxylic acid amide
93 N-[rac-(2R,3S,4S)-2-(2-Chlorophenyl)-1-[1-(4-fluorophenyl)-1H-indazol-5-yl]-4-methyl-5-oxo-pyrrolidin-3-yl]-methanesulfonic acid amide
94 N-[rac-(2R,3S,4R)-2-(2-Chlorophenyl)-1-[1-(4-fluorophenyl)-1H-indazol-5-yl]-4-methyl-5-oxo-pyrrolidin-3-yl]-1-methyl-1H-pyrazole-3-carboxylic acid amide
95 N-((2R,3R,4S)-4-fluoro-1-(1-(4-fluorophenyl)-1H-indazol-5-yl)-5-oxo-2-phenylpyrrolidin-3-yl)cyclopropanecarboxamide
96 N-((2R,3R)-4,4-difluoro-1-(1-(4-fluorophenyl)-1H-indazol-5-yl)-5-oxo-2-phenylpyrrolidin-3-yl)cyclopropanecarboxamide
97 2,2-Difluoro-N-[rac-(2R,3S,4R)-1-[1-(4-fluorophenyl)-1H-indazol-5-yl]-2-(4-methoxyphenyl)-4-methyl-5-oxo-pyrrolidin-3-yl]-propionamide
98 2,2-Difluoro-N-[rac-(2R,3S,4S)-1-[1-(4-fluorophenyl)-1H-indazol-5-yl]-2-(4-methoxyphenyl)-4-methyl-5-oxo-pyrrolidin-3-yl]-propionamide
99 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-methanesulfonic acid amide
100 2,2-Difluoro-N-[rac-(2R,3S)-1-[1-(4-fluorophenyl)-1H-indazol-5-yl]-2-methyl-5-oxo-2-phenyl-pyrrolidin-3-yl]-propionamide
101 N-[rac-(2R,3S)-1-[1-(4-Fluorophenyl)-1H-indazol-5-yl]-2-methyl-5-oxo-2-phenyl-pyrrolidin-3-yl]-cyclopropanecarboxylic acid amide
102 2,2-Difluoro-N-[rac-(2R,3S)-2-methyl-1-[1-(1-methyl-6-oxo-1H-pyridin-3-yl)-1H-indazol-5-yl]-5-oxo-2-phenyl-pyrrolidin-3-yl]-propionamide
103 N-[rac-(2R,3S)-2-Methyl-1-[1-(1-methyl-6-oxo-1H-pyridin-3-yl)-1H-indazol-5-yl]-5-oxo-2-phenyl-pyrrolidin-3-yl]-cyclopropanecarboxylic acid amide
104 N-[rac-(2R,3S,4S)-4-Benzyl-2-ethyl-1-[1-(4-fluorophenyl)-1H-indazol-5-yl]-5-oxo-pyrrolidin-3-yl]-1-methyl-1H-pyrazole-3-carboxylic acid amide
105 N-[rac-(2R,3S,4S)-4-Benzyl-2-ethyl-1-[1-(4-fluorophenyl)-1H-indazol-5-yl]-5-oxo-pyrrolidin-3-yl]-4-methyl-thiazole-5-carboxylic acid amide
106 N-[rac-(2R,3S,4S)-4-Benzyl-2-ethyl-1-[1-(4-fluorophenyl)-1H-indazol-5-yl]-5-oxo-pyrrolidin-3-yl]-cyclopropanecarboxylic acid amide
107 N-[rac-(2R,3S,4S)-4-Benzyl-2-ethyl-1-[1-(4-fluorophenyl)-1H-indazol-5-yl]-5-oxo-pyrrolidin-3-yl]-2,2-difluoro-propionamide
108 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-cyclopropanecarboxylic acid amide
109 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-pyrimidine-2-carboxylic acid amide
110 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-1-methyl-1H-pyrazole-3-carboxylic acid amide
111 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-pyridine-3-carboxylic acid amide
112 N-[rac-(2R,3S,4S)-2-(2-Chlorophenyl)-1-[1-(4-fluorophenyl)-1H-indazol-5-yl]-4-methyl-5-oxo-pyrrolidin-3-yl]-cyclopropanecarboxylic acid amide
113 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-4-methyl-thiazole-5-carboxylic acid amide
114 N-[(2S,3S,4S)-2-(5-Chloro-thiophen-2-yl)-1-[1-(4-fluorophenyl)-1H-indazol-5-yl]-4-methyl-5-oxo-pyrrolidin-3-yl]-methanesulfonic acid amide
115 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-cyclopropanecarboxylic acid amide
116 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-4-methyl-thiazole-5-carboxylic acid amide
117 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-1-methyl-1H-pyrazole-3-carboxylic acid amide
118 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-pyridine-3-carboxylic acid amide
119 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-pyrimidine-2-carboxylic acid amide
120 2,2-Difluoro-N-[rac-(2S,3S,4S)-1-[1-(4-fluorophenyl)-1H-indazol-5-yl]-4-methyl-2-(1-methyl-1H-pyrazol-3-yl)-5-oxo-pyrrolidin-3-yl]-propionamide
121 N-[rac-(2R,3S,4S)-4-(Cyclopropyl-methyl)-1-[1-(4-fluorophenyl)-1H-indazol-5-yl]-5-oxo-2-phenyl-pyrrolidin-3-yl]-cyclopropanecarboxylic acid amide
122 N-[rac-(2S,3S,4S)-1-[1-(4-Fluorophenyl)-1H-indazol-5-yl]-4-methyl-2-(1-methyl-1H-pyrazol-3-yl)-5-oxo-pyrrolidin-3-yl]-methanesulfonic acid amide
123 N-[rac-(2S,3S,4S)-2-(5-Chloro-thiophen-2-yl)-1-[1-(4-fluorophenyl)-1H-indazol-5-yl]-4-methyl-5-oxo-pyrrolidin-3-yl]-2,2-difluoro-propionamide
124 N-[rac-(2S,3S,4R)-2-(5-Chloro-thiophen-2-yl)-1-[1-(4-fluorophenyl)-1H-indazol-5-yl]-4-methyl-5-oxo-pyrrolidin-3-yl]-cyclopropanecarboxylic acid amide
125 N-[rac-(2S,3S,4R)-2-(5-Chloro-thiophen-2-yl)-1-[1-(4-fluorophenyl)-1H-indazol-5-yl]-4-methyl-5-oxo-pyrrolidin-3-yl]-2,2-difluoro-propionamide 126 N-[rac-(2R,3S,4S)-4-Ethyl-1-[1-(4-fluorophenyl)-1H-indazol-5-yl]-5-oxo-2-phenyl-pyrrolidin-3-yl]-cyclopropanecarboxylic acid amide
127 N-((2R,3S)-1-(1-(4-fluorophenyl)-1H-indazol-5-yl)-5-oxo-4-phenethyl-2-phenylpyrrolidin-3-yl)cyclopropanecarboxamide, diastereomer 2
128 N-[rac-(2R,3R,4R)-4-Fluoro-1-[1-(4-fluorophenyl)-1H-indazol-5-yl]-4-methyl-5-oxo-2-phenyl-pyrrolidin-3-yl]-cyclopropanecarboxylic acid amide
129 N-[rac-(2R,3R,4S)-4-Fluoro-1-[1-(4-fluorophenyl)-1H-indazol-5-yl]-4-methyl-5-oxo-2-phenyl-pyrrolidin-3-yl]-cyclopropanecarboxylic acid amide
130 N-((2R,3S)-1-(1-(4-fluorophenyl)-1H-indazol-5-yl)-5-oxo-4-phenethyl-2-phenylpyrrolidin-3-yl)cyclopropanecarboxamide, diastereomer 1
131 N-((2R,3S,4S)-4-(2,2-difluoroethyl)-1-(1-(4-fluorophenyl)-1H-indazol-5-yl)-5-oxo-2-phenylpyrrolidin-3-yl)cyclopropanecarboxamide
132 N-((2R,3S,4R)-4-(2,2-difluoroethyl)-1-(1-(4-fluorophenyl)-1H-indazol-5-yl)-5-oxo-2-phenylpyrrolidin-3-yl)cyclopropanecarboxamide
133 N-[rac-(2R,3S,4S)-1-[1-(4-Fluorophenyl)-1H-indazol-5-yl]-2-(4-methoxyphenyl)-4-methyl-5-oxo-pyrrolidin-3-yl]-cyclopropanecarboxylic acid amide
134 N-(rac-(2R,3S,4R)-4-ethyl-1-(1-(4-fluorophenyl)-1H-indazol-5-yl)-4-methyl-5-oxo-2-phenylpyrrolidin-3-yl)cyclopropanecarboxamide
135 N-((7R,8S)-6-(1-(4-fluorophenyl)-1H-indazol-5-yl)-5-oxo-7-phenyl-6-azaspiro[3.4]octan-8-yl)cyclopropanecarboxamid
136 N-(rac (2R,3S,4S)-4-(2,2-difluoroethyl)-1-(1-(4-fluorophenyl)-1H-indazol-5-yl)-4-methyl-5-oxo-2-phenylpyrrolidin-3-yl)cyclopropanecarboxamide
137 N-(rac-(2R,3R,4S)-4-benzyl-2-ethyl-4-fluoro-1-(1-(4-fluorophenyl)-1H-indazol-5-yl)-5-oxopyrrolidin-3-yl)cyclopropanecarboxamide
138 N-((2R,3S,4S)-1-(1-(4-fluorophenyl)-1H-indazol-5-yl)-4-((3-methyl-1,2,4-oxadiazol-5-yl)methyl)-5-oxo-2-phenylpyrrolidin-3-yl)cyclopropanecarboxamide
139 N-((2R,3S,4S)-1-(1-(4-fluorophenyl)-1H-indazol-5-yl)-4-((1-methyl-1H-pyrazol-4-yl)methyl)-5-oxo-2-phenylpyrrolidin-3-yl)cyclopropanecarboxamide
142 N-(rac-(2R,3S)-2-cyclopropyl-1-(1-(4-fluorophenyl)-1H-indazol-5-yl)-5-oxo-2-phenylpyrrolidin-3-yl)cyclopropanecarboxamide
143 N-(rac-(2R,3R)-2-cyclopropyl-1-(1-(4-fluorophenyl)-1H-indazol-5-yl)-5-oxo-2-phenylpyrrolidin-3-yl)cyclopropanecarboxamide
144 N-(rac-(2R,3S)-2-cyclopropyl-1-(1-(4-fluorophenyl)-1H-indazol-5-yl)-5-oxo-2-phenylpyrrolidin-3-yl)-2,2-difluoropropanamide
145 N-(rac-(2R,3R)-2-cyclopropyl-1-(1-(4-fluorophenyl)-1H-indazol-5-yl)-5-oxo-2-phenylpyrrolidin-3-yl)-2,2-difluoropropanamide
146 N-(rac-(2R,3S)-2-cyclopropyl-1-(1-(4-fluorophenyl)-1H-indazol-5-yl)-5-oxo-2-phenylpyrrolidin-3-yl)oxetane-3-carboxamide
147 N-(rac-(2R,3R)-2-cyclopropyl-1-(1-(4-fluorophenyl)-1H-indazol-5-yl)-5-oxo-2-phenylpyrrolidin-3-yl)oxetane-3-carboxamide
148 N-(rac-(2R,3S,4S)-4-(2,2-difluoroethyl)-1-(1-(4-fluorophenyl)-1H-indazol-5-yl)-4-methyl-5-oxo-2-phenylpyrrolidin-3-yl)cyclopropanecarboxamide
149 N-(rac-(2R,3S,4S)-4-(cyclopropylmethyl)-1-(1-(4-fluorophenyl)-1H-indazol-5-yl)-4-methyl-5-oxo-2-phenylpyrrolidin-3-yl)cyclopropanecarboxamide
150 N-((2R,3S,4R)-1-(1-(4-fluorophenyl)-1H-indazol-5-yl)-5-oxo-2-phenyl-4-(thiazol-2-ylmethyl)pyrrolidin-3-yl)cyclopropanecarboxamide and
151 N-((2S,3S)-2-(5-chlorothiophen-2-yl)-1-(1-(4-fluorophenyl)-1H-indazol-5-yl)-2-methyl-5-oxopyrrolidin-3-yl)cyclopropanecarboxamide in each case in the form of the free compound or a physiologically acceptable salt thereof.

14. A pharmaceutical dosage form comprising a compound according to claim 1.

15. A method of treating and/or preventing pain and/or inflammation comprising administering to a patient in need an effective amount therefor of a compound according to claim 1.

16. The compound according to claim 1, which is N-[(2R,3S)-1-[1-(4-fluorophenyl)-1H-indazol-5-yl]-4,4-dimethyl-5-oxo-2-phenyl-pyrrolidin-3-yl]-cyclopropanecarboxylic acid amide having the formula:

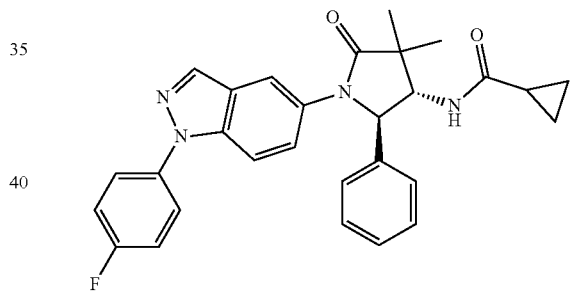

or a physiologically acceptable salt thereof.

17. A pharmaceutical dosage form comprising a compound according to claim 16.

18. A method of treating and/or preventing pain and/or inflammation comprising administering to a patient in need an effective amount therefor of a compound according to claim 16.

* * * * *